(12) United States Patent
Sasmal et al.

(10) Patent No.: US 10,344,031 B2
(45) Date of Patent: *Jul. 9, 2019

(54) SUBSTITUTED PYRAZOLO[1,5-A] PYRIDINE AS TROPOMYOSIN RECEPTOR KINASE (TRK) INHIBITORS

(71) Applicant: Dr. Reddy's Laboratories Ltd., Hyderabad (IN)

(72) Inventors: Pradip Kumar Sasmal, Hyderabad (IN); Shahadat Ahmed, Bangalore (IN); Ashok Tehim, Ridgewood, NJ (US); Vidyadhar Paradkar, Branchburg, NJ (US); Prasanna M. Dattatreya, Hyderabad (IN); Nanjegowda Jagadeesh Mavinahalli, Bangalore (IN)

(73) Assignee: Dr. Reddy's Laboratories Ltd. (IN)

(*) Notice: Subject to any disclaimer, the term of this patent is extended or adjusted under 35 U.S.C. 154(b) by 0 days.

This patent is subject to a terminal disclaimer.

(21) Appl. No.: 16/101,753

(22) Filed: Aug. 13, 2018

(65) Prior Publication Data

US 2018/0354951 A1    Dec. 13, 2018

Related U.S. Application Data

(60) Continuation of application No. 15/611,203, filed on Jun. 1, 2017, now Pat. No. 10,047,087, which is a continuation of application No. 15/164,430, filed on May 25, 2016, now Pat. No. 9,670,207, which is a continuation of application No. 14/725,683, filed on May 29, 2015, now Pat. No. 9,402,833, which is a division of application No. 14/364,451, filed as application No. PCT/IB2012/003012 on Dec. 12, 2012, now Pat. No. 9,045,478.

(30) Foreign Application Priority Data

Dec. 12, 2011 (IN) .......................... 4329/CHE/2011

(51) Int. Cl.

| A61K 31/437 | (2006.01) |
|---|---|
| C07D 471/04 | (2006.01) |
| C07D 519/00 | (2006.01) |
| A61K 31/4545 | (2006.01) |
| A61K 31/4725 | (2006.01) |
| A61K 31/496 | (2006.01) |
| A61K 31/4985 | (2006.01) |
| A61K 31/4995 | (2006.01) |
| A61K 31/506 | (2006.01) |
| A61K 31/5377 | (2006.01) |
| A61K 31/55 | (2006.01) |
| A61K 31/635 | (2006.01) |
| A61K 31/444 | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/4725* (2013.01); *A61K 31/496* (2013.01); *A61K 31/4985* (2013.01); *A61K 31/4995* (2013.01); *A61K 31/506* (2013.01); *A61K 31/5377* (2013.01); *A61K 31/55* (2013.01); *A61K 31/635* (2013.01); *C07D 519/00* (2013.01); *Y02A 50/414* (2018.01)

(58) Field of Classification Search
CPC .......................... A61K 401/02; A61K 401/10
USPC ........................................................ 514/300
See application file for complete search history.

(56) References Cited

U.S. PATENT DOCUMENTS

| 6,465,485 B1 | 10/2002 | Branch et al. | |
| 9,045,478 B2* | 6/2015 | Sasmal | A61K 31/437 |
| 9,670,207 B2* | 6/2017 | Sasmal | A61K 31/437 |
| 2011/0195948 A1 | 8/2011 | Haas et al. | |

FOREIGN PATENT DOCUMENTS

| JP | 2003231687 A | 8/2003 |
| JP | 2005533040 A | 11/2005 |
| JP | 2009518340 A | 5/2009 |
| WO | 2004011461 A1 | 2/2004 |
| WO | 2005005427 A1 | 1/2005 |
| WO | 2007065664 A2 | 6/2007 |
| WO | 2009008748 A1 | 1/2009 |
| WO | 2010048314 A1 | 4/2010 |
| WO | 2012116217 A1 | 8/2012 |

OTHER PUBLICATIONS

Alvares et al., "Building blocks of pain: the regulation of key molecules in spinal sensory neurones during development and following peripheral axotomy", Pain Supplement, 6, 1999, pp. S71-S85.

Belvisi et al., "The nerve growth factor and its receptors in airway inflammatory diseases", Pharmacology & Therapeutics, ScienceDirect, 2008, 117(1), 52-76.

Boyd et al., Journal of the Chemical Society [Section] C: Organic (1971 ), (2), 225-9.

Delafoy et al., "Role of nerve growth factor in the trinitrobenzene sulfonic acid-induced colonic hypersensitivity", Pain, 2003, 105, pp. 489-497.

Dou et al., "Increased nerve growth factor and its receptors in atopic dermatitis: an immunohistochemical study", Arch Dermatol Res, 2006, 298, 31-37.

Ghilardi et al., "Sustained blockade of neurotrophin receptors TrkA, TrkB and TrkC reduces non-malignant skeletal pain but not the maintenance of sensory and sympathetic nerve fibers", Bone, 48, 2011, pp. 389-398.

(Continued)

*Primary Examiner* — Niloofar Rahmani
(74) *Attorney, Agent, or Firm* — Lerner, David, Littenberg, Krumholz & Mentlik, LLP

(57) ABSTRACT

The present application relates to a series of substituted pyrazolo[1,5-a]pyridine compounds, their use as tropomyosin receptor kinase (Trk) family protein kinase inhibitors, method of making and pharmaceutical compositions comprising such compounds.

19 Claims, No Drawings

(56) References Cited

OTHER PUBLICATIONS

Gwak et al., "Attenuation of mechanical hyperalgesia following spinal cord injury by administration of antibodies to nerve growth factor in the rat", Neuroscience Letters, 336, 2003, pp. 117-120_.
Hayashi et al., "Involvement of NGF in the Rat Model of Persistent Muscle Pain Associated With Taut Band", The Jouranl of Pain, vol. 12, No. 10, Oct. 2011, pp. 1059-1068.
Hu et al., "Decrease in Bladder Overactivity with REN1820 in Rats with Cyclophosphamide Induced Cystitis", The Journal of Urology, vol. 173, 1016-1021, Mar. 2005.
International Search Report for Application No. PCT/IB2012/003012 dated May 7, 2013.
International Search Report for Application No. PCT/IB2012/003022 dated May 7, 2013.
Legault et al., "Highly Efficient Synthesis of O-(2,4-Dinitrophenyl)hydroxylamine. Application to the Synthesis of Substituted N-Benzoyliminopyridinium Ylides", J. Org. Chem., 2003, 68, pp. 7119-7122.
Matayoshi et al., "Actions of brain-derived neurotrophic factor on spinal nociceptive transmission during inflammation in the rat", J Physiol, 569.2, 2005. pp. 685-695.
McMahon et al., "The bioloical effects of endogenous nerve growth factor on adult sensory neurons revealed by a trkA-IgG fusion molecule", Nature Medicine, vol. 1, No. 8, Aug. 1995, pp. 774-780.
Mola et al., "Nerve growth factor and Trk high affinity receptor (TrkA) gene expression in inflammatory bowel disease", Gut, 2000, 46(5), 670-678.
Nwosu, Lilian N., et al., Blocking the tropomyosin receptor kinase A (TrkA) receptor inhibits pain behaviour in two rat models of osteoarthritis, Ann Rheum Dis 2015, 2015, doi:10.1136/annrheumdis-2014-207203.

Patapoutian et al., "Trk receptors: mediators of neurotrophin action", Current Opinion Neurobiology, 2001, 11, 272-280.
Ramer et al., "Adrenergic innervation of rat sensory ganglia following proximal or distal painful sciatic neuropathy: distinct mechanisms revealed by anti-NGF treatment", European Journal of Neuroscience, vol. 11, pp. 837-846, 1999.
Raychaudhuri et al., "K252a, a High-Affinity Nerve Growth Factor Receptor Blocker, Improves Psoriasis: An In Vivo Study Using the Severe Combined Immunodeficient Mouse-Human Skin Model", J.Invest Dermatol., 2004, 122(3), 312-819.
Ro et al., "Effect of NGF and anti-NGF on neuropathic pain in rats following chronic constriction injury of the sciatic nerve", Pain, 1999, 79, 265-274.
Roblin, David, et al., Topical TrkA Kinase Inhibitor CT327 is an Effective, Novel Thereapy for the Treatment of Pruritus due to Psoriasis: Results from Experimental Studies, and Efficacy and Safety of CT327 in Phase 2b Clinical Trial in Patients with Psoriasis, Acta Derm Vereal 95, pp. 542-548, 2015.
Shelton et al., "Nerve growth factor mediates hyperalgesia and cachexia in auto-immune arthritis", Pain, 2005, 116, pp. 8-16.
Thompson et al., "Brain-derived neurotrophic factor is an endogenous modulator of nociceptive responses in the spinal cord", Proc. Natl. Acad. Sci. USA 1999, vol. 96, pp. 7714-7718.
Wang et al., "Trk kinase inhibitors as new treatments for cancer and pain", Expert Opinion Ther. Patents, 2009, 19(3):305-319.
Wei et al., "Activation of Erk in the anterior cingulate cortex during the induction and expression of chronic pain", Molecular Pain, 2008, 4(28), pp. 1-6.
Woolf et al., "Nerve Growth Factor Contributes to the Generation of Inflammatory Sensory Hypersensitivity", Neuroscience, vol. 62, No. 2, pp. 327-331, 1994.
Zahn et al., "Effect of Blockade of Nerve Growth Factor and Tumor Necrosis Factor on Pain Behaviors After Plantar Incision", The Journal of Pain, vol. 5, No. 3, Apr. 2004, pp. 157-163.

* cited by examiner

SUBSTITUTED PYRAZOLO[1,5-A] PYRIDINE AS TROPOMYOSIN RECEPTOR KINASE (TRK) INHIBITORS

CROSS-REFERENCE TO RELATED APPLICATIONS

The present application is a continuation of U.S. patent application Ser. No. 15/611,203, filed on Jun. 1, 2017, which is a continuation of U.S. patent application Ser. No. 15/164,430, filed on May 25, 2016, issued as U.S. Pat. No. 9,670,207, which is a continuation of U.S. patent application Ser. No. 14/725,683, filed on May 29, 2015, issued as U.S. Pat. No. 9,402,833, which is a divisional of U.S. patent application Ser. No. 14/364,451, filed on Jun. 11, 2014, issued as U.S. Pat. No. 9,045,478, which application is a national phase entry under 35 U.S.C. § 371 of International Application No. PCT/IB2012/003012 filed on Dec. 12, 2012, published in English, which claims the priority from Indian Patent Application No. 4329/CHE/2011, filed on Dec. 12, 2011, the disclosures of which are incorporated herein by reference.

TECHNICAL FIELD

The present application relates to a series of substituted pyrazolo[1,5-a]pyridine compounds. The present application is further directed to use such compounds as tropomyosin receptor kinase (Trk) family protein kinase inhibitors. The present application also describes method of making such compounds and pharmaceutical compositions comprising such compounds.

BACKGROUND

TrkA, TrkB and TrkC, which make up the Trk receptor family, are high affinity receptor tyrosine kinases activated by a group of soluble growth factors called neurotrophins (NT) (Curr Opin Neurobiol, 2001, 11, 272-280).

Inhibitors of the Trk/neurotrophin pathway have been demonstrated to be effective in numerous animal models of pain. For example, sustained blockade of neurotrophin receptors TrkA, TrkB and TrkC reduces non-malignant skeletal pain (Bone, 2011, 48(2), 389-398). Administration of NGF receptor (TrkA) inhibitor K252a showed significant suppression of mechanical hyperalgesia (relevant to the pathogenesis of myofascial pain syndrome (MPS)) in animal models (J. Pain, Article in Press, 2011, 12(10), 1059-1068). Antagonistic NGF and TrkA antibodies have been shown to be efficacious in inflammatory and neuropathic pain animal models (Neuroscience, 1994, 62, 327-331; J. Pain, 2004, 5, 157-163; Nat. Med., 1995, 1, 774-780; Pain, 2005, 116, 8-16; Pain, 2003, 105, 489-497) and neuropathic pain animal models (Eur. J. Neurosci., 1999, 11, 837-846; Pain, 1999, 79, 265-274; Pain, 1999, 81, 245-255; Neurosci. Lett., 2003, 336, 117-120).

NGF secreted by tumor cells and tumor invading macrophages has been shown to directly stimulate TrkA located on peripheral pain fibers. It has also been demonstrated in various tumor models in both mice and rats that neutralizing NGF with a monoclonal antibody inhibits cancer related pain. Further, activation of the BDNF/TrkB pathway has been implicated in numerous studies as a modulator of various types of pain including inflammatory pain (J. Physiol. 2005, 569:685-95), neuropathic pain (Proc. Natl. Acad. Sci. USA 1999, 96:7714-18) and surgical pain (Molecular Pain, 2008, 4(28), 1-11). Since TrkA kinase has been demonstrated to serve as a mediator of NGF driven biological responses, inhibitors of TrkA and/or other Trk kinases may provide an effective treatment for various pain conditions.

Inhibition of the neurotrophin/Trk pathway with NGF antibodies or non-selective small molecule inhibitors of Trk A, B and C has been shown to be effective in treatment of pre-clinical models of inflammatory diseases such as asthma (Pharmacol. Therapeut., 2008, 117(1), 52-76), interstitial cystitis (J. Urology, 2005, 173(3), 1016-21), inflammatory bowel diseases including ulcerative colitis and Crohn's disease (Gut, 2000, 46(5), 670-678) and inflammatory skin diseases such as atopic dermatitis (Arc Dermatol Res., 2006, 298(1), 31-37), eczema and psoriasis (J. Investig Dermatol., 2004, 122(3), 812-819).

The current treatment regimes for pain conditions utilize several classes of compounds. The opiates apart from being potentially addictive have several adverse effects such as emesis, constipation, dose-related respiratory depression. Nonsteroidal anti-inflammatory analgesics (NSAID) also have drawbacks such as gastric ulceration, dyspepsia and insufficient efficacy in treating severe pain. Accordingly, there is a continuing need for new and more effective treatments for the relief of pain, especially chronic pain. Several classes of small molecule inhibitors of Trk kinases said to be useful for treating pain or cancer are known (Expert Opin. Ther. Patents, 2009, 19(3), 305-319).

U.S. Publication No. 20110195948 describes substituted pyrazolo[1,5-a]pyrimidine compounds as Trk kinase inhibitors.

JP Publication No. 2003231687 describes a series of pyrazolyl condensed cyclic compounds as Trk inhibitors.

PCT Publication No. 200505427 describes compounds containing a 1,4,5,6-tetrahydropyrrolo[3,4-c]pyrazole bicyclic scaffold as TrkA inhibitors.

PCT Publication No. 2004011461 describes a series of isothiazole derivatives as Trk inhibitors.

SUMMARY

The present applications relates to pyrazolo[1,5-a]pyridine compounds of formula (I),

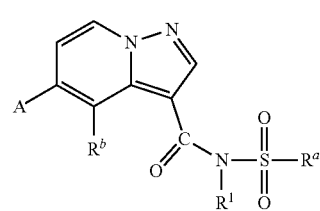

(I)

their pharmaceutically acceptable salts, pharmaceutically acceptable solvates or stereoisomers thereof, wherein A is

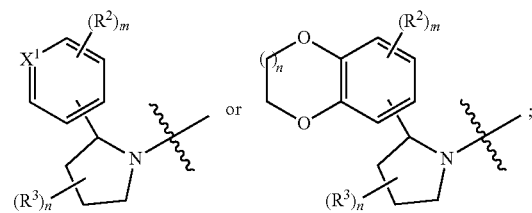

$X^1$ is CH or N;

$R^1$ represents hydrogen or —$(C_1-C_6)$alkyl;

$R^2$ is independently selected from hydrogen, halogen, cyano, —$(C_1-C_6)$alkyl, -halo$(C_1-C_6)$alkyl, -halo$(C_1-C_6)$alkoxy, phenyl optionally substituted with 1 to 3 halogens or an optionally substituted —O-heterocyclyl wherein the optional substituent is selected from alkyl, —$OR^i$ or —$C(O)N(R^i)_2$;

when $X^1$ is CH, optionally two $R^2$s present on any two adjacent carbon atoms combine to form a 5 to 7 membered heterocyclic ring;

$R^3$ is independently selected from halogen, cyano, —$OR^i$, —$C(O)N(R^i)_2$ or two $R^3$s together with the carbon atom they are attached form a $(C_3-C_7)$cycloalkyl group spiro attached to pyrrolidine; or two $R^3$ when they are attached to adjacent carbon atoms form a $(C_3-C_7)$ cycloalkyl ring fused to the pyrrolidine;

$R^a$ is selected from
  (i) a group selected from optionally substituted —$(C_1-C_6)$alkyl, -hydroxy$(C_1-C_6)$alkyl or —$(C_1-C_6)$alkyl-$(C_1-C_6)$alkoxy wherein the optional susbstituent is selected from cyano, halogen or —$(C_6-C_{12})$aryl,
  (ii) an optionally substituted —$(C_3-C_{10})$cycloalkyl wherein the optional substituent is selected from cyano, —$(C_1-C_6)$alkyl, hydroxyl, halogen or —$R^s$,
  (iii) an optionally substituted —$(C_6-C_{12})$aryl wherein the optional substituent is selected from cyano, hydroxyl, halogen, —$(C_1-C_6)$alkyl or —$R^r$,
  (iv) an optionally substituted 5 to 10 membered heterocyclyl wherein the optional substituent is selected from cyano, hydroxyl, halogen or —$(C_1-C_6)$alkyl,
  (v) an optionally substituted 5 to 10 membered heteroaryl wherein the optional substituent is selected from cyano, oxo (=O), hydroxyl, halogen, —$(C_1-C_6)$alkyl, —$(C_1-C_6)$alkoxy, —$NR^cR^d$ or —$R^r$,
  (vi) —$NR^4R^5$,
  (vii) —$(C_1-C_6)$alkyl-$(C_6-C_{12})$aryl;

$R^b$ represents hydrogen or halogen;

$R^4$ is selected from hydrogen, —$(C_1-C_6)$alkyl, —$(C_3-C_{10})$cycloalkyl, -hydroxy$(C_1-C_6)$alkyl, -alkoxy$(C_1-C_6)$alkyl, -halogen$(C_1-C_6)$alkyl or —$(C_1-C_6)$alkyl-$(C_3-C_{10})$cycloalkyl;

$R^5$ is selected from hydrogen or —$(C_1-C_6)$alkyl or —$(C_1-C_6)$alkyl-$(C_3-C_{10})$cycloalkyl;

Alternatively $R^4$ and $R^5$ together with the nitrogen atom to which they are attached may form an optionally substituted 5 to 10 membered heterocyclic ring optionally containing 1-2 additional heteroatoms or groups selected from —O—, —S—, —N—, —C(=O)—, —S(=O)— or —S(=O)$_2$—, wherein the optional substituent is selected from hydroxyl, —$(C_1-C_6)$alkyl, —C(=O)—$(C_1-C_6)$alkyl, mesyl or $COOR^e$;

$R^c$ and $R^d$ are independently selected from hydrogen or —$(C_1-C_6)$alkyl;

$R^e$ is selected from hydrogen or alkyl;

$R^i$ is hydrogen, —$(C_1-C_6)$alkyl, -halo$(C_1-C_6)$alkyl, —$(C_1-C_6)$alkyl-$(C_1-C_6)$alkoxy, —$(C_3-C_{10})$cycloalkyl, optionally substituted —$(C_1-C_6)$alkyl-$(C_3-C_{10})$cycloalkyl wherein the optional substituent is halogen or —$(C_1-C_6)$alkyl substituted with 1 to 3 hydroxy groups;

$R^r$ is independently selected from a 5 to 10 membered heterocyclyl or a 5 to 10 membered heteroaryl, wherein optional substituent is selected from hydroxyl, halogen, —$(C_1-C_6)$alkyl or —$(C_1-C_6)$alkoxy;

$R^s$ is an optionally substituted —$(C_1-C_6)$alkyl-$(C_6-C_{10})$ aryl, wherein the optional substituent is halogen;

m is independently represents 0, 1, 2, 3 or 4; and n is independently represents 0, 1, 2, or 3.

The present application further relates to methods of treating or preventing conditions, diseases and/or disorders associated with abnormal or deregulated Trk kinase activity by administereing effective amount of a compound of formula (I), to a patient in need thereof.

One aspect of the present application provides methods of treating or preventing conditions, diseases and/or disorders associated with abnormal or deregulated TrkA kinase activity by administereing effective amount of a compound of formula (I), to a patient in need thereof.

One aspect of the present application provides conditions. diseases and/or disorders treatable or preventable by inhibition of Trk kinase activity, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative disease or a disease, disorder or injury relating to dysmyelination or demyelination by administering a therapeutically effective amount of compound of formula (I), to a patient in need thereof.

The present application also relates to pharmaceutical compositions comprising effective amount of a compound of formula (I), and a pharmaceutically acceptable carrier or diluent, and the use of such compositions in the treatment and/or prevention of diseases associated with inhibiting TrkA in a patient in need thereof, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative disease, a disease, disorder, or injury relating to dysmyelination or demyelination or certain infectious diseases such as *Trypanosoma cruzi* infection

DETAILED DESCRIPTION

As used herein, 'halogen or halo' group refers to fluorine, chlorine, bromine or iodine.

As used herein, '$(C_1-C_6)$alkyl' refers to linear or branched alkyl group with 1 to 6 carbon atoms. Exemplary $(C_1-C_6)$ alkyl group includes, but is not limited to, methyl, ethyl, n-propyl, iso-propyl, n-butyl, iso-butyl, t-butyl, n-pentyl, iso-pentyl and the like. $(C_1-C_3)$alkyl refers to linear or branched alkyl group having one to three carbon atoms such as methyl, ethyl propyl or iso-propyl.

As used herein, 'hydroxy$(C_1-C_6)$alkyl' refers to a group wherein at least one hydrogen atom of an $(C_1-C_6)$alkyl group is replaced by a hydroxyl group. $(C_1-C_6)$alkyl group is as defined above. Representative examples of hydroxy $(C_1-C_6)$alkyl groups include one or more of, but are not limited to hydroxymethyl, hydroxyethyl and the like. Unless otherwise specified, a hydroxy$(C_1-C_6)$alkyl group is having 1 to 6 carbon atoms. As used herein, 'halo$(C_1-C_6)$alkyl', in each occurrence, independently means at least one hydrogen atom of an $(C_1-C_6)$alkyl group is replaced by a halogen group. Halogen and $(C_1-C_6)$alkyl group are as defined above. Representative examples of halo$(C_1-C_6)$alkyl groups include one or more of, but are not limited to fluoromethyl, difluoromethyl, fluroethyl, difluroethyl, trifluloethyl, fluoropropyl, difluoropropyl, trifluoropropyl and the like.

As used herein '$(C_3-C_{10})$cycloalkyl' refers to a cyclic alkyl group which may be mono, bicyclic, polycyclic, or a fused/bridged ring system having 3 to 10 carbon atoms. Exemplary cycloalkyl groups include, but are not limited to, cyclopropyl, cyclobutyl, cyclopentyl, cyclohexyl, cycloheptyl, cyclooctyl, and the like. Typical bridged cycloalkyls include, but are not limited to adamantyl, noradamantyl, bicyclo[1.1.0]butanyl, norbornyl(bicyclo[2.2.1]heptanyl), and the like.

As used herein, two $R^3$s when they are attached two adjacent carbon atoms form $(C_3-C_7)$cycloalkyl spiro attached to pyrrolidine are selected from cyclopropyl, cyclobutyl and the like.

As used herein, '$(C_1-C_6)$alkyl-$(C_3-C_{10})$cycloalkyl' refers to a group wherein $(C_1-C_6)$alkyl group is optionally substituted with at least one $(C_3-C_{10})$cycloalkyl, wherein $(C_1-C_6)$ alkyl and $(C_3-C_{10})$cycloalkyl are as defined above. Exemplary $(C_1-C_6)$alkyl-$(C_3-C_{10})$cycloalkyl groups include methyl-cyclobutyl, ethyl-clcobutyl and the like.

As used herein, '$(C_1-C_6)$alkoxy' refers to an —O—$(C_1-C_6)$alkyl group, wherein $(C_1-C_6)$alkyl group is as defined above. Exemplary $(C_1-C_6)$alkoxy groups include methoxy, ethoxy, n-propoxy, iso-propoxy, n-butoxy, iso-butoxy, t-butoxy, and the like. $(C_1-C_3)$alkoxy refers to an alkoxy group having one to three carbon atoms, such as methoxy, ethoxy, propoxy or isopropoxy.

As used herein, 'halo$(C_1-C_6)$alkoxy' refers to a group wherein at least one hydrogen atom of an $(C_1-C_6)$alkoxy group is replaced by a halogen group. Halogen and $(C_1-C_6)$ alkoxy group are as defined above. Representative examples of halo$(C_1-C_6)$alkoxy groups include one or more of, but are not limited to fluoromethoxy, difluoromethoxy, fluroethoxy, difluroethoxy, trifluloethoxy, fluoropropoxy, difluoropropoxy, trifluoropropoxy and the like.

As used herein, '$(C_6-C_{12})$aryl' refers to a monocyclic or polycyclic aromatic ring system having 6 to 12 carbon atoms. Exemplary aryl groups include, but are not limited to, phenyl, naphthyl, and the like.

As used herein, 'aralkyl' refers to an $(C_1-C_6)$alkyl group substituted with at least one $(C_6-C_{12})$aryl group, wherein $(C_1-C_6)$alkyl and $(C_6-C_{12})$aryl groups are as defined above. Exemplary aralkyl groups include, but are not limited to, benzyl, ethyl-phenyl and the like. $(C_1-C_3)$alkyl-$(C_6-C_{12})$aryl groups refers to an $(C_1-C_3)$alkyl group substituted with at least one $(C_6-C_{12})$aryl group, wherein $(C_1-C_3)$ represents an alkyl group having 1 to 3 carbon atoms and $(C_6-C_{12})$aryl group is as defined above. Exemplary $(C_1-C_3)$alkyl-$(C_6-C_{12})$ aryl groups include methyl-phenyl, ethyl-phenyl and the like.

As used herein, '5 to 10 membered heterocyclyl' or '5 to 10 membered heterocyclic ring' refers to a monocyclic or polycyclic ring system, having at least one heteroatom or heterogroup selected from O, N, S, SO, $SO_2$, or CO. Exemplary heterocyclyl or heterocyclic ring groups include, but not limited to, azetidinyl, pyrrolidinyl, piperidinyl, piperazinyl, tetrahydrofuranyl, tetrahydro-2H-pyranyl, morpholinyl, thiomorpholinyl, thiomorpholine-1,1-dioxide, tetrahydro-2H-thiopyranyl, thiazolidinyl, 1,3-dioxolanyl, 1,4-dioxanyl, 1-oxidotetrahydro-2H-thiopyranyl, 1,1-dioxidotetrahydro-2H-thiopyranyl, hexahydropyrrolo[3,4-c]pyrrol-2(1H)-yl, 2,5-diazabicyclo[2.2.1]heptan-2-yl, azepanyl and the like.

As used herein, '5 to 7 membered heterocyclyl' or '5 to 7 membered heterocyclic ring' refers to a monocyclic ring system, having at least one heteroatom or heterogroup selected from O, N, S, SO, $SO_2$, or CO. Exemplary heterocyclyl or heterocyclic ring groups include, but not limited to, 1,4-dioxane, 1,4-dioxepane and the like.

As used herein, '5 to 10 membered heteroaryl group' refers to a monocyclic or polycyclic ring system, unsaturated, aromatic or non-aromatic; having at least one heteroatom or heterogroup selected from —O—, —N—, —S—, —S(=O)—, —S(=O)$_2$, or —C(=O)—. Exemplary heteroaryl ring groups, aromatic or non-aromatic rings, include, but not limited to, furanyl, oxazolyl, isoxazole, imidazolyl, triazolyl, thiophenyl, thiazolyl, pyridinyl, thiazinyl, pyrazinyl, pyrazolyl, tetrazolyl, imidazothiazolyl, furanyl, oxazolyl, isoxazole, imidazolyl, oxadiazolyl, triazolyl, thiazolyl, pyridinyl, thiazinyl, pyrazinyl, pyrazolyl, tetrazolyl, imidazothiazolyl, indolizidinyl, indolinyl, oxoindolinyl, indolyl, oxoindolyl, quinolinyl, 3,4-dihydroisoquinolin-2 (1H)-yl, quinoxalinyl, benzoxazolyl, benzo[d]isoxazolyl, benzo[d]thiazolyl, benzo[d][1,3]dioxolyl, 1H-benzo[d][1,2,3]triazolyl, 2H-indazolyl, 1H-indazolyl, quinoxalin-2-yl, 1H-benzo[d]imidazolyl, pyrazolo[1,5-a]pyridinyl, dihydrobenzo[b][1,4]dioxinyl, (5,6,7,8-tetrahydroimidazo[1,2-a]pyridin-7-yl), 4,5,6,7-tetrahydropyrazolo[1,5-a]pyrazinyl, 5,6-dihydroimidazo[1,2-a]pyrazin-7(8H)-yl), 5,6,7,8-tetrahydroimidazo[1,2-a]pyrazinyl, Hexahydropyrrolo[1,2-a]pyrazin-2(1H)-yl, 5,6-dihydro-[1,2,4]triazolo[4,3-a]pyrazinyl, pyrazolo[1,5a]pyridinyl and the like.

The Trk's are made up of three family members TrkA, TrkB and TrkC that bind to and mediate the the signal transduction derived from the Neurotrophins. Inhibitors of the Trk/neutrophin pathway have been demonstrated to be highly effective in numerous pre-clinical animal models of pain. The compounds of the invention are modulators of the Trk receptors, particularly TrkA.

As used herein, the term TrkA refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5).

'Optionally substituted' means that the substitution is optional and therefore it is possible for the designated atom or group to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is oxo (i.e., =O), then two hydrogens on the atom are replaced and when the substitution is fluoro, then one hydrogen on the atom is replaced and the like. When more than one substituent is present on an atom or group, the chosen substituents are independent of each other (i.e same or different).

As used herein and in the appended claims, the singular forms "a", "an", and "the" include plural reference unless the context clearly indicates otherwise.

As used herein, the term 'subject' or 'patient' means mammals, such as humans and other animals, including horses, dogs, cats, rats, mice, sheep, pigs, monkeys, chimpanzees or other apes or primates. In exemplary embodiments, the subject may include subjects for which treatment and/or prevention of the conditions described herein would be beneficial.

For ease of reference, in this application it will be described in terms of administration to human subjects. It will be understood, however, that such descriptions are not limited to administration to humans, but will also include administration to other animals unless explicitly stated otherwise.

A 'therapeutically effective amount' is the amount of compound of the present application that is effective in generating biological or medical response of a subject, for example, reduction or inhibition of an enzyme or a protein activity, or ameliorate symptoms, alleviate conditions, slow or delay disease progression, or prevent a disease.

In one embodiment, the term 'a therapeutically effective amount' refers to the amount of the compound of the present application that, when administered to a subject, is effective in (i) at least partially alleviating, inhibiting, preventing and/or ameliorating a condition, or a disorder or a disease mediated by TrkA, TrkB and/or TrkC, associated with TrkA, TrkB and/or TrkC activity or characterized by activity (normal or abnormal) of TrkA, TrkB and/or TrkC; (ii) reducing or inhibiting the activity of TrkA, TrkB and/or TrkC; or (iii) reducing or inhibiting the expression of TrkA, TrkB and/or TrkC.

In another embodiment, the term "a therapeutically effective amount" refers to the amount of the compound of the present invention that, when administered to a cell, or a tissue, or a non-cellular biological material, or a medium, is effective to at least partially reducing or inhibiting the activity of TrkA, TrkB and/or TrkC; or at least partially reducing or inhibiting the expression of TrkA, TrkB and/or TrkC.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful in producing at least one physiological response in a subject to which such pharmaceutical composition is administered.

The term 'substantially pure' means that the isolated material is at least 80% pure, preferably 90% pure, more preferably 95% pure, and even more preferably 99% pure as measured by a suitable analytical techniques known in the art.

Unless defined otherwise, all technical and scientific terms used herein have the same meaning as commonly understood to one of ordinary skill in the art.

One or more compounds of formula (I) can be supplied in the form of a therapeutic composition that is within the scope of the present application.

The term 'Pharmaceutically acceptable salts' refers to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the application. The preparation of salts can be carried out using known methods.

For example, pharmaceutically acceptable salts of compound of formula (I) contemplated refers to salts prepared from acids or bases including inorganic or organic acids and inorganic or organic bases by conventional chemical methods using a compound of formula (I). Generally, such salts may be prepared, for example, by making free base of the compounds and reacting with a stoichiometric quantity of the appropriate acid and vice-versa in water or in an organic solvent, or in a mixture of the two. The comounds of the present applications may form mono, di or tris salts.

When the compound of formula (I) is basic, salts may be prepared from acids, including inorganic or organic acids (acid addition salts). Examples of such acids include, but not limited toformic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), nitric, hydrochloride, hydrobromide, isoethionic, hydroiodide, phosphoric, sulfuric, succinic, tartaric, methanesulfonic, ethanesulfonic, benzenesulfonic, benzoic, mucic, pantothenic, p-toluenesulfonic, camphorsulfonic, 2-hydroxyethanesulfonic, sulfanilic, cyclohexylaminosulfonic, algenic, β-hydroxybutyric, galactaric, and galacturonic acid, and the like.

Salts formed from inorganic bases include sodium, potassium, lithium, calcium, copper, magnesium, manganic salts, manganous, zinc, aluminum, ammonium, ferric, ferrous and the like.

Salts derived from organic bases include salts of primary, secondary, and tertiary amines, substituted amines including naturally occurring substituted amines, cyclic amines, and basic ion exchange resins, such as arginine, betaine, caffeine, choline, N,N-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylgiucamine, morpholine, piperazine, piperid e, polyamine resins, procaine, purines, theobromine, triethylamine, trimethylamine, tripropylamine, tromethamine, and the like.

'Pharmaceutically acceptabl salts' in the solid form may exist in more than one crystal structure, and may also be in the form of hydrates.

The term 'stereoisomers' is a general term used for all isomers of an individual molecule that differ only in the orientation of their atoms in space. Where the compounds according to the present application possess one or more asymmetric centers and compounds with asymmetric centers give rise to enantiomers, diastereomers or both as pure or partially purified compounds. It is to be understood that all stereoisomeric forms of the compounds of the invention, including but not limited to, diastereomers, enantiomers and atropsiomers, as well as mixtures thereof such as forms, are included in the scope of the present application. Preparation of such stereoisomeric forms of compound of formula (I), may be achieved by appropriate modification of the methodology known in the art. Their absolute stereochemistry may be determined by the suitable methods. If required, racemic mixtures of the compound of formula (I) may be separated to isolate individual enantiomers or diastereomers. Such separation can be carried out by methods known in the art, such as the coupling of a racemic mixture of compound of formula (I) to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer or diastereomer of a compound may be obtained by stereoselective synthesis using optically pure starting materials or known reagents.

For any particular compound disclosed herein, wherein the stereochemistry of any particular chiral atom is not specified, then all stereoisomers are contemplated and included as the compounds of the application. Where stereochemistry is specified by a solid wedge or a dashed wedge bond or dashed line representing a particular configuration then that stereoisomer is so specified and defined.

Following the standard chemical literature description practice and as used herein, a full wedge bond means above the ring plane, and a dashed wedge bond or dashed line means below the ring plane.

Pharmaceutically acceptable solvates of compound of formula (I) may be hydrates or comprising other solvents of crystallization such as alcohols. Pharmaceutically acceptable solvates of compound of formula (I) may be prepared by conventional methods such as dissolving the compounds of formula (I) in solvents such as water, methanol, ethanol etc., preferably water and recrystallizing by using different crystallization techniques.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

Reference will now be made in detail to the embodiments of the invention, one or more examples of which are set forth below. Each example is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present application.

Thus in accordance of this application there is provided a series of substituted pyrazolo[1,5-a]pyridine derivatives having the general formula (I),

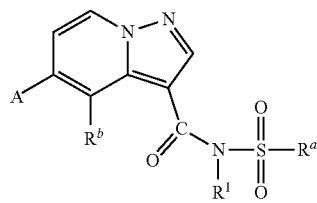

(I)

their pharmaceutically acceptable salts, pharmaceutically acceptable solvates or stereoisomers thereof, wherein

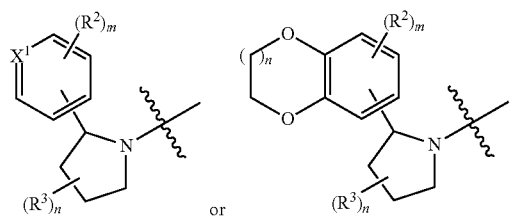

$X^1$ is CH or N;

$R^1$ represents hydrogen or —($C_1$-$C_6$)alkyl;

$R^2$ is independently selected from hydrogen, halogen, cyano, —($C_1$-$C_6$)alkyl, -halo($C_1$-$C_6$)alkyl, -halo($C_1$-$C_6$)alkoxy, phenyl optionally substituted with 1 to 3 halogens or an optionally substituted —O-heterocyclyl wherein the optional substituent is selected from alkyl, —$OR^i$ or —$C(O)N(R^i)_2$;

when $X^1$ is CH, optionally two $R^2$s present on any two adjacent carbon atoms combine to form a 5 to 7 membered heterocyclic ring;

$R^3$ is independently selected from halogen, cyano, —$OR^i$, —$C(O)N(R^i)_2$ or two $R^3$s together with the carbon atom they are attached form a ($C_3$-$C_7$)cycloalkyl group spiro attached to pyrrolidine; or two $R^3$ when they are attached to adjacent carbon atoms form a ($C_3$-$C_7$) cycloalkyl ring fused to the pyrrolidine;

$R^a$ is selected from
(i) a group selected from optionally substituted —($C_1$-$C_6$)alkyl, -hydroxy($C_1$-$C_6$)alkyl or —($C_1$-$C_6$)alkyl-($C_1$-$C_6$)alkoxy wherein the optional susbstituent is selected from cyano, halogen or —($C_6$-$C_{12}$)aryl,
(ii) an optionally substituted —($C_3$-$C_{10}$)cycloalkyl wherein the optional substituent is selected from cyano, —($C_1$-$C_6$)alkyl, hydroxyl, halogen or —$R^s$,
(iii) an optionally substituted —($C_6$-$C_{12}$)aryl wherein the optional substituent is selected from cyano, hydroxyl, halogen, —($C_1$-$C_6$)alkyl or —$R^r$,
(iv) an optionally substituted 5 to 10 membered heterocyclyl wherein the optional substituent is selected from cyano, hydroxyl, halogen or —($C_1$-$C_6$)alkyl,
(v) an optionally substituted 5 to 10 membered heteroaryl wherein the optional substituent is selected from cyano, oxo (=O), hydroxyl, halogen, —($C_1$-$C_6$)alkyl, —($C_1$-$C_6$)alkoxy, —$NR^cR^d$ or —$R^r$,
(vi) —$NR^4R^5$,
(vii) —($C_1$-$C_6$)alkyl-($C_6$-$C_{12}$)aryl;

$R^b$ represents hydrogen or halogen;

$R^4$ is selected from hydrogen, —($C_1$-$C_6$)alkyl, —($C_3$-$C_{10}$)cycloalkyl, -hydroxy($C_1$-$C_6$)alkyl, -alkoxy($C_1$-$C_6$)alkyl, -halogen($C_1$-$C_6$)alkyl or —($C_1$-$C_6$)alkyl-($C_3$-$C_{10}$)cycloalkyl;

$R^5$ is selected from hydrogen or —($C_1$-$C_6$)alkyl or —($C_1$-$C_6$)alkyl-($C_3$-$C_{10}$)cycloalkyl;

Alternatively $R^4$ and $R^5$ together with the nitrogen atom to which they are attached may form an optionally substituted 5 to 10 membered heterocyclic ring optionally containing 1-2 additional heteroatoms or groups selected from —O—, —S—, —N—, —C(=O)—, —S(=O)— or —S(=O)$_2$—, wherein the optional substituent is selected from hydroxyl, —($C_1$-$C_6$)alkyl, —C(=O)—($C_1$-$C_6$)alkyl, mesyl or $COOR^e$;

$R^c$ and $R^d$ are independently selected from hydrogen or —($C_1$-$C_6$)alkyl;

$R^e$ is selected from hydrogen or alkyl;

$R^i$ is hydrogen, —($C_1$-$C_6$)alkyl, -halo($C_1$-$C_6$)alkyl, —($C_1$-$C_6$)alkyl-($C_1$-$C_6$)alkoxy, —($C_3$-$C_{10}$)cycloalkyl, optionally substituted —($C_1$-$C_6$)alkyl-($C_3$-$C_{10}$)cycloalkyl wherein the optional substituent is halogen or —($C_1$-$C_6$)alkyl substituted with 1 to 3 hydroxy groups;

$R^r$ is independently selected from a 5 to 10 membered heterocyclyl or a 5 to 10 membered heteroaryl, wherein optional substituent is selected from hydroxyl, halogen, —($C_1$-$C_6$)alkyl or —($C_1$-$C_6$)alkoxy;

$R^s$ is an optionally substituted —($C_1$-$C_6$)alkyl-($C_6$-$C_{10}$) aryl, wherein the optional substituent is halogen;

m is independently represents 0, 1, 2, 3 or 4; and n is independently represents 0, 1, 2, or 3.

In one embodiment, there is provided a compound of formula (I),

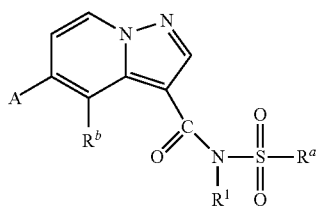
(I)

their pharmaceutically acceptable salts, pharmaceutically acceptable solvates or stereoisomers thereof, wherein
A is

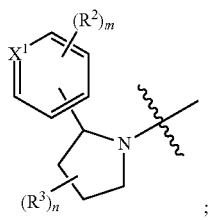
;

$X^1$ is CH or N;
$R^1$ represents hydrogen or —($C_1$-$C_6$)alkyl;
$R^2$ is independently selected from hydrogen, halogen, cyano, —($C_1$-$C_6$)alkyl, -halo($C_1$-$C_6$)alkyl, -halo($C_1$-$C_6$)alkoxy, phenyl optionally substituted with 1 to 3 halogens or an optionally substituted —O-heterocyclyl wherein the optional substituent is selected from alkyl, —$OR^i$ or —C(O)N($R^i$)$_2$;
when $X^1$ is CH, optionally two $R^2$s present on any two adjacent carbon atoms combine to form a 5 to 7 membered heterocyclic ring;
$R^3$ is independently selected from halogen, cyano, —$OR^i$, —C(O)N($R^i$)$_2$ or two $R^3$s together with the carbon atom they are attached form a ($C_3$-$C_7$)cycloalkyl group spiro attached to pyrrolidine; or two $R^3$ when they are attached to adjacent carbon atoms form a ($C_3$-$C_7$) cycloalkyl ring fused to the pyrrolidine;
$R^a$ is selected from
(i) a group selected from optionally substituted —($C_1$-$C_6$)alkyl, -hydroxy($C_1$-$C_6$)alkyl or —($C_1$-$C_6$)alkyl-($C_1$-$C_6$)alkoxy wherein the optional susbstituent is selected from cyano, halogen or —($C_6$-$C_{12}$)aryl,
(ii) an optionally substituted —($C_3$-$C_{10}$)cycloalkyl wherein the optional substituent is selected from cyano, —($C_1$-$C_6$)alkyl, hydroxyl, halogen or —$R^s$,
(iii) an optionally substituted —($C_6$-$C_{12}$)aryl wherein the optional substituent is selected from cyano, hydroxyl, halogen, —($C_1$-$C_6$)alkyl or —$R^r$
(iv) an optionally substituted 5 to 10 membered heterocyclyl wherein the optional substituent is selected from cyano, hydroxyl, halogen or —($C_1$-$C_6$)alkyl,
(v) an optionally substituted 5 to 10 membered heteroaryl wherein the optional substituent is selected from cyano, oxo (=O), hydroxyl, halogen, —($C_1$-$C_6$)alkyl, —($C_1$-$C_6$)alkoxy, —$NR^cR^d$ or —$R^r$,
(vi) —$NR^4R^5$,
(vii) —($C_1$-$C_6$)alkyl-($C_6$-$C_{12}$)aryl;
$R^b$ represents hydrogen or halogen;

$R^4$ is selected from hydrogen, —($C_1$-$C_6$)alkyl, —($C_3$-$C_{10}$)cycloalkyl, -hydroxy($C_1$-$C_6$)alkyl, -alkoxy($C_1$-$C_6$) alkyl, -halogen($C_1$-$C_6$)alkyl or —($C_1$-$C_6$)alkyl-($C_3$-$C_{10}$)cycloalkyl;
$R^5$ is selected from hydrogen or —($C_1$-$C_6$)alkyl or —($C_1$-$C_6$)alkyl-($C_3$-$C_{10}$)cycloalkyl;
Alternatively $R^4$ and $R^5$ together with the nitrogen atom to which they are attached may form an optionally substituted 5 to 10 membered heterocyclic ring optionally containing 1-2 additional heteroatoms or groups selected from —O—, —S—, —N—, —C(=O)—, —S(=O)— or —S(=O)$_2$—, wherein the optional substituent is selected from hydroxyl, —($C_1$-$C_6$)alkyl, —C(=O)—($C_1$-$C_6$)alkyl, mesyl or $COOR^e$;
$R^c$ and $R^d$ are independently selected from hydrogen or —($C_1$-$C_6$)alkyl;
$R^e$ is selected from hydrogen or alkyl;
$R^i$ is hydrogen, —($C_1$-$C_6$)alkyl, -halo($C_1$-$C_6$)alkyl, —($C_1$-$C_6$)alkyl-($C_1$-$C_6$)alkoxy, —($C_3$-$C_{10}$)cycloalkyl, optionally substituted —($C_1$-$C_6$)alkyl-($C_3$-$C_{10}$)cycloalkyl wherein the optional substituent is halogen or —($C_1$-$C_6$)alkyl substituted with 1 to 3 hydroxy groups;
$R^r$ is independently selected from a 5 to 10 membered heterocyclyl or a 5 to 10 membered heteroaryl, wherein optional substituent is selected from hydroxyl, halogen, —($C_1$-$C_6$)alkyl or —($C_1$-$C_6$)alkoxy;
$R^s$ is an optionally substituted —($C_1$-$C_6$)alkyl-($C_6$-$C_{10}$) aryl, wherein the optional substituent is halogen;
m is independently represents 0, 1, 2, 3 or 4; and
n is independently represents 0, 1, 2, or 3.
In another embodiment, the compounds of formula (I) are represented as compounds of formula (Ia),

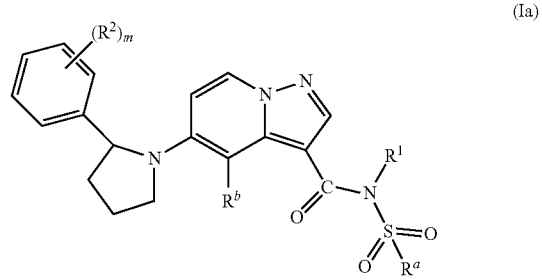
(Ia)

their pharmaceutically acceptable salts, pharmaceutically acceptable solvates or stereoisomers thereof, wherein the values of all the variables are as described for compound of formula (I).
In another embodiment, compounds of formula (I) are represented as compounds of formula (Ib),

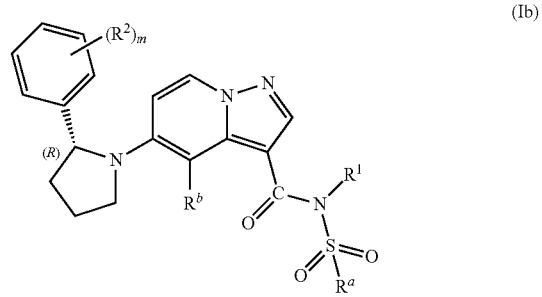
(Ib)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Ic),

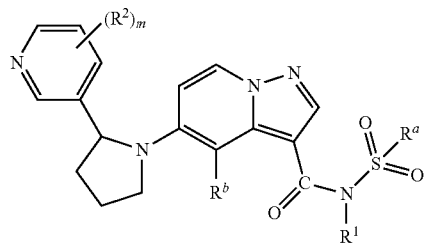

(Ic)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Id),

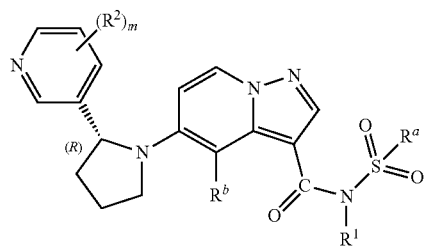

(Id)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Ie),

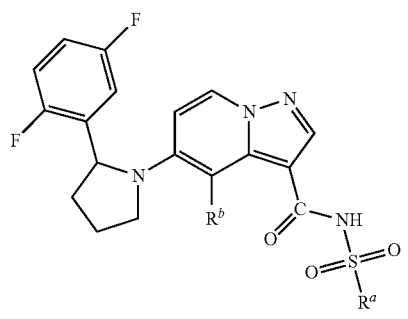

(Ie)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (If),

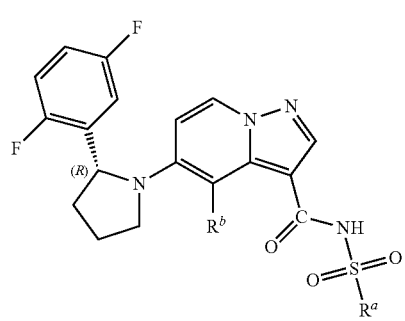

(If)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Ig),

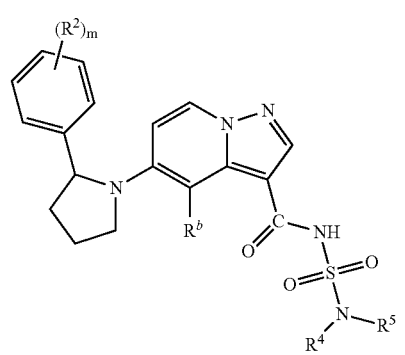

(Ig)

wherein the values of all the variables are as described for compound of formula (I).

In another embodiment, compounds of formula (I) are represented as compounds of formula (Ih),

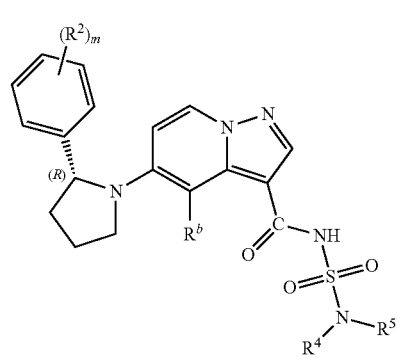

(Ih)

wherein the values of all the variables are as described for compound of formula (I).

In another embodiment, compounds of formula (I) are represented as compounds of formula (Ii),

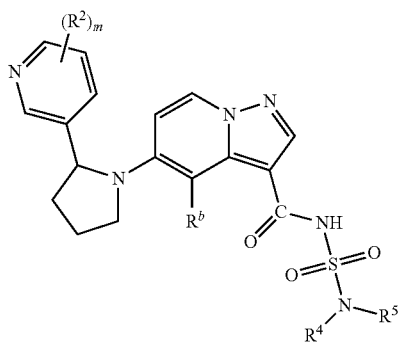

(Ii)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Ij),

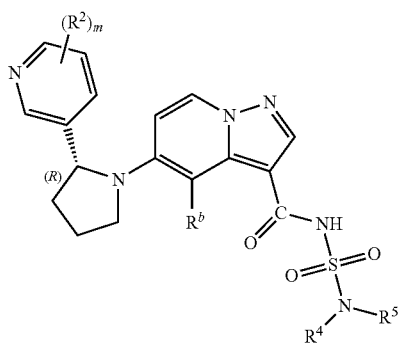

(Ij)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Ik),

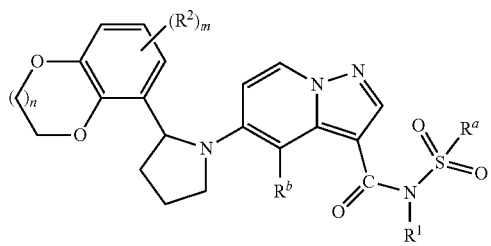

(Ik)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Ikk),

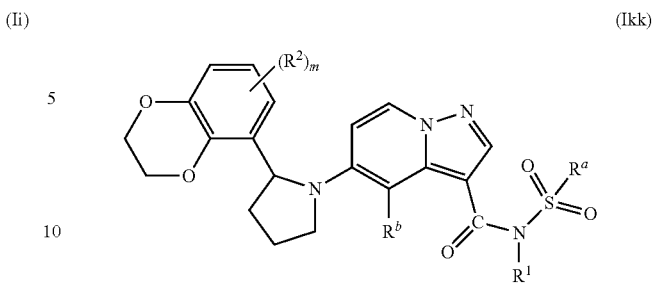

(Ikk)

their pharmaceutically acceptable salts, pharmaceutically acceptable solvates or stereoisomers thereof, wherein the values of all the variables are as described for compound of formula (I).

In another embodiment, compounds of formula (I) are represented as compounds of formula (Il),

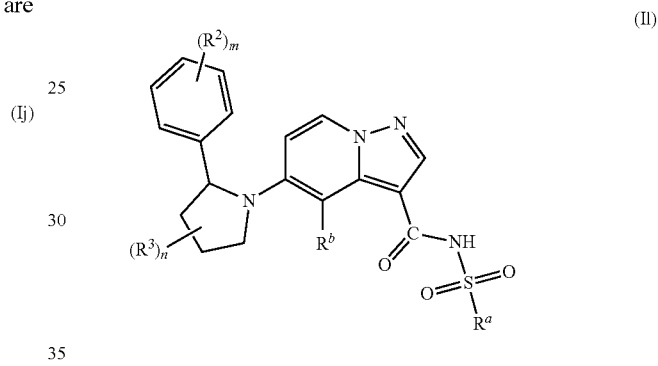

(Il)

their pharmaceutically acceptable salts, pharmaceutically acceptable solvates or stereoisomers thereof, wherein $R^3$ is fluorine, n is 1 or 2, and the values of all other variables are as described for compound of formula (I).

In another embodiment, compounds of formula (I) are represented as compounds of formula (Im),

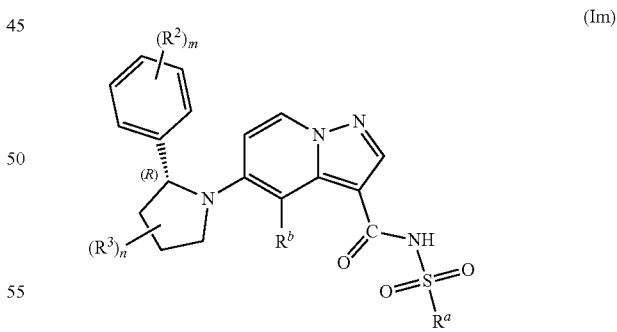

(Im)

their pharmaceutically acceptable salts, pharmaceutically acceptable solvates or stereoisomers thereof, wherein $R^3$ is fluorine, n is 1 or 2, and the values of all other variables are as described for compound of formula (I).

In one embodiment of formula (Ia), $R^1$ is hydrogen, $R^a$ is —$(C_1$-$C_6)$alkyl or an optionally substituted —$(C_3$-$C_{10})$cycloalkyl group, wherein the optional substituent independently selected from cyano, —$(C_1$-$C_6)$alkyl, hydroxyl, halogen or —$R^s$.

In one embodiment of formula (Ia), $R^1$ is hydrogen, $R^a$ is an optionally substituted —($C_6$-$C_{12}$)aryl, wherein the optional substituent is selected from cyano, hydroxyl, halogen, —($C_1$-$C_6$)alkyl or —$R^r$.

In one embodiment of formula (Ia), $R^1$ is hydrogen, $R^a$ is an optionally substituted 5 to 10 membered heterocyclyl optionally substituted with 1 to 3 substituents independently selected from cyano, hydroxyl, halogen or —($C_1$-$C_6$)alkyl.

In one embodiment of formula (Ia), $R^1$ is hydrogen, $R^a$ is —$NR^4R^5$.

In one embodiment of formula (Ia), $R^a$ is an optionally substituted 5 to 10 membered heteroaryl, wherein the optional substituent is selected from cyano, oxo (=O), hydroxyl, halogen, —($C_1$-$C_6$)alkyl, —($C_1$-$C_6$)alkoxy, —$NR^cR^d$ or —$R^t$.

In another embodiment, the compound of formula (Ia) of the above embodiments is defined as compound of formula (Ib).

In certain embodiments of formula (Ib), as defined above, $R^2$, in each occurrence, independently represents halogen, cyano or haloalkyl; m is 1 or 2.

In certain embodiments of formula (Ib), as defined above, $R^1$ is hydrogen.

In certain embodiment of formula (Ib), $R^4$ and $R^5$, independently represents methyl, ethyl or propyl.

In certain embodiment of formula (Ib), $R^a$, independently represents methyl, ethyl, propyl, isopropyl, butyl or tert-butyl.

In one embodiment of formula (Ic), $R^1$ is hydrogen, $R^a$ is —($C_1$-$C_6$)alkyl or optionally substituted —($C_3$-$C_{10}$)cycloalkyl, wherein the optional substituent is independently selected from selected from cyano, —($C_1$-$C_6$)alkyl, hydroxyl, halogen or —$R^s$.

In one embodiment of formula (Ic), $R^1$ is hydrogen, $R^a$ is optionally substituted —($C_6$-$C_{12}$)aryl, wherein the optional substituent is selected from cyano, hydroxyl, halogen, —($C_1$-$C_6$)alkyl or —$R^r$.

In one embodiment of formula (Ic), $R^1$ is hydrogen, $R^a$ is an optionally substituted 5 to 10 membered heterocyclyl, wherein the optional substituent is selected from cyano, hydroxyl, halogen or —($C_1$-$C_6$)alkyl.

In one embodiment of formula (Ic), $R^1$ is hydrogen, $R^a$ is —$NR^4R^5$.

In one embodiment of formula (Ic), $R^a$ is an optionally substituted 5 to 10 membered heteroaryl, wherein the optional substituent is selected from cyano, oxo (=O), hydroxyl, halogen, —($C_1$-$C_6$)alkyl, —($C_1$-$C_6$)alkoxy, —$NR^cR^d$ or —$R^t$.

In another embodiment, the compound of formula (Ic) of the above embodiments is defined as compound of formula (Id).

In certain embodiments of formula (Id), as defined above, $R^2$, in each occurrence, independently represents halogen, cyano or haloalkyl; m is 1 or 2.

In certain embodiments of formula (Id), as defined above, $R^1$ is hydrogen.

In certain embodiment of formula (Id), $R^4$ and $R^5$, independently represents methyl, ethyl or propyl.

In certain embodiment of formula (Id), $R^a$, independently represents methyl, ethyl, propyl, isopropyl, butyl or tert-butyl.

In one embodiment of formula (Ic), $R^1$ is hydrogen, $R^a$ is —($C_1$-$C_6$)alkyl or optionally substituted —($C_3$-$C_{10}$)cycloalkyl, wherein the optional substituent is independently selected from lected from cyano, —($C_1$-$C_6$)alkyl, hydroxyl, halogen or —$R^s$.

In one embodiment of formula (Ic), $R^1$ is hydrogen, $R^a$ is optionally substituted —($C_6$-$C_{12}$)aryl, wherein the optional substituent is selected from cyano, hydroxyl, halogen, —($C_1$-$C_6$)alkyl or —$R^r$.

In one embodiment of formula (Ie), $R^1$ is hydrogen, $R^a$ is an optionally substituted 5 to 10 membered heterocyclyl, wherein the optional substituent is selected from cyano, hydroxyl, halogen or —($C_1$-$C_6$)alkyl.

In one embodiment of formula (Ie), $R^1$ is hydrogen and $R^a$ is —$NR^4R^5$.

In one embodiment of formula (Ie), $R^a$ is an optionally substituted 5 to 10 membered heteroaryl, wherein the optional substitutent is selected from cyano, oxo (=O), hydroxyl, halogen, —($C_1$-$C_6$)alkyl, —($C_1$-$C_6$)alkoxy, —$NR^cR^d$ or —$R^t$.

In another embodiment, the compound of formula (Ie) of the above embodiments is defined as compound of formula (If).

In certain embodiments of formula (If), as defined above, $R^2$, in each occurrence, independently represents halogen, cyano or haloalkyl; m is 1 or 2.

In certain embodiments of formula (If), as defined above, $R^1$ is hydrogen.

In certain embodiment of formula (If), $R^4$ and $R^5$, independently represents methyl, ethyl or propyl.

In certain embodiment of formula (If), $R^a$, independently represents methyl, ethyl, propyl, isopropyl, butyl or tert-butyl.

In another embodiment, the compound of formula (Ig) of the above embodiment is defined as compound of formula (Ih).

In certain embodiments of formula (Ih), as defined above, $R^2$, in each occurrence, independently represents halogen, cyano or haloalkyl and m is 1 or 2.

In certain embodiments of formula (Ih), as defined above, $R^1$ is hydrogen.

In certain embodiment of formula (Ih), $R^4$ and $R^5$, independently represents methyl, ethyl or propyl.

In another embodiment, the compound of formula (Ii) of the above embodiments is defined as compound of formula (Ij).

In certain embodiments of formula (Ij), as defined above, $R^2$, in each occurrence, independently represents halogen, cyano or haloalkyl and m is 1 or 2.

In certain embodiments of formula (Ij), as defined above, $R^1$ is hydrogen.

In certain embodiment of formula (Ij), $R^4$ and $R^5$, independently represents methyl, ethyl or propyl.

In certain embodiments of formula (I), (Ia), (Ib), (Ic), (Id), (Ie), (If), (Ig), (Ih), (Ii), (Ij) and (Ik), $R^b$ is hydrogen.

In certain embodiments of formula (I), (Ia), (Ib), (Ic), (Id), (Ie), (If), (Ig), (Ih), (Ii), (Ij) and (Ik), $R^b$ is fluorine.

In certain embodiments of formula (I), (Ia), (Ib), (Ic), (Id), (Ie), (If), (Ig), (Ih), (Ii), (Ij) and (Ik), wherein $R^2$, in each occurrence, indepenty represents fluorine.

In certain embodiments of formula (I), (Ia), (Ib), (Ic), (Id), (Ie), (If), (Ig), (Ih), (Ii), (Ij) and (Ik), wherein $R^3$, in each occurrence, indepenty represents fluorine.

The compounds of formula (I) can also exist in the form of pharmaceutically acceptable salts, pharmaceutically acceptable solvates or stereoisomers thereof In another embodiment, the present application provides compounds of formula (9i),

(9i)

or its stereoisomers thereof, wherein the values of all the variables are as described for compound of formula (I).

In another embodiment, the present application provides compounds of formula (9ii),

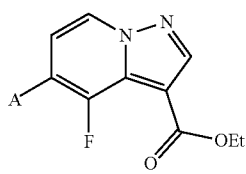

(9ii)

or its stereoisomers thereof, wherein A represents

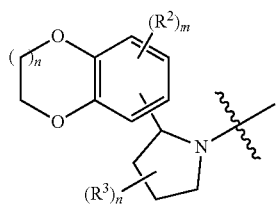

and values of all other variables are as described for compound of formula (I).

In another embodiment, the present application provides compounds of formula (10i),

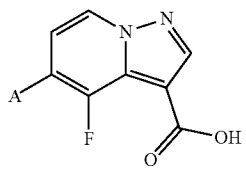

(10i)

or its stereoisomers thereof, wherein the values of all the variables are as described for compound of formula (I).

In another embodiment, the present application provides compounds of formula (10ii),

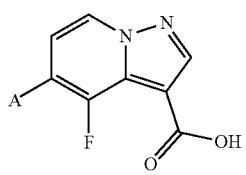

(10ii)

or its stereoisomers thereof, wherein A represents

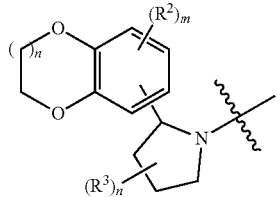

and values of all other variables are as described for compound of formula (I).

In another embodiment, the present application provides compounds of formula (13),

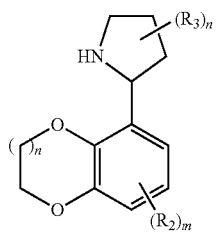

(13)

or its stereoisomers thereof, wherein the values of all variables are as described for compound of formula (I).

The present application relates to the compounds of formula (I), which are inhibitrs of TrkA, TrkB and/or TrkC kinase activity, for the treatment or prevention of diseases or conditions or disorders associated with TrkA, TrkB and/or TrkC kinase activity.

One embodiment of the present application further provides methods of treating or preventing conditions, diseases and/or disorders associated TrkA, TrkB and/or TrkC kinase activity, wherein the method includes administration of a therapeutically effective amount of a compound formula (I), to a patient in need thereof.

One embodiment of the present application provides conditions. diseases and/or disorders treatable or preventable by inhibition of Trk kinase activity, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative; a disease, disorder or injury relating to dysmyelination or demyelination or infectious diseases such as *Trypanosoma cruzi* infection by administering a therapeutically effective amount of compound of formula (I), to a patient in need thereof.

One embodiment of the present application further provides methods of treating or preventing conditions, diseases and/or disorders associated TrkA, wherein the method includes administration of a therapeutically effective amount of a compound formula (I), to a patient in need thereof.

In another embodiment, there is provided a method of treating or preventing pain or pain disorder in a patient in need of such a treatment comprising the administration of a therapeutically effective amount of the compound of formula (I), to said patient.

In another embodiment, pain includes chronic and acute pain but is not limited to, pain related to cancer, surgery, bone fracture, skeletal pain caused by tumor metastasis, osteoarthritis, psoriatic arthritis, rheumatoid arthritis, interstitial cystitits, chronic pancreatitis, visceral pain, inflammatory pain, migraine, chronic lower back pain, bladder pain syndrome and neuropathic pain.

In one embodiment, there is provided a method of binding TrkA protein in a patient in need of such a treatment comprising the administration of a therapeutically effective amount of the compound of formula (I) to said patient.

The present application further relates to use of compound of formula (I) for treating or preventing conditions, diseases and/or disorders associated with abnormal or deregulated Trk kinase activity.

One aspect of the present application provides use of compound of formula (I) for treating or preventing conditions, diseases and/or disorders associated with abnormal or deregulated TrkA kinase activity, in a patient in need thereof.

In another embodiment, there is provided an use of the compound for formula (I) for treating or preventing pain or pain disorder in a patient in need of such a treatment, comprising the administration of a therapeutically effective amount of the compound of formula (I), to said patient.

In another embodiment of the present application, pain includes chronic and acute pain but is not limited to, pain related to cancer, surgery, bone fracture, skeletal pain caused by tumor metastasis, osteoarthritis, visceral pain, inflammatory pain and neuropathic pain.

In yet another embodiment, the compounds of the present application may be useful for the pain disorders include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, denial pain, cancer pain, myofascial pain (muscular injury, fibromyalgia); perioperative pain (general surgery, gynecological), chronic pain, dysmenorrhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

In another embodiment of the above aspect, there is provided a method of treating or preventing pain which comprises administering to said subject a pharmaceutical composition comprising an effective amount of a compound of formula (I).

Another embodiment of the application provides the use of such compositions in the treatment and/or prevention of diseases associated with inhibition of TrkA, such as pain, cancer, restenosis, atherosclerosis, psoriasis, thrombosis, neurodegenerative disease, a disease, disorder, or injury relating to dysmyelination or demyelination or certain infectious diseases such as *Trypanosoma crurzi* infection.

In another embodiment, the compounds of formula (I) are useful in treating or preventing neurodegenerative disease.

In one embodiment, neurodegenerative disease is Parkinson's disease or Alzheimer's disease.

In another aspect, the present application provides a method of treating or preventing neurodegenerative disease.

In one embodiment, neurodegenerative disease, as described above, is Parkinson's disease or Alzheimer's disease.

In another embodiment, the present application provides method of treating or preventing certain infectious diseases, for example *Trypanosoma cruzi* infection, by administering effective amount of compound of formula (I) to a patient in need thereof.

In another embodiment, the present application provides method of treating or preventing *Trypanosoma cruzi* infection by administering effective amount of compound of formula (I), to a patient in need thereof.

In another embodiment, certain compounds of formula (I) posseses Rat liver microsome (RLM) stability (half life in minutes) >30, specifically >60, more specifically >80, still further more specifically >90.

In another embodiment, certain compounds of formula (I) posseses Human liver microsome (HLM) stability (half life in minutes) >30, specifically >60, more specifically >80, still further more specifically >90.

In one embodiment of the present application, there is provided a pharmaceutical composition comprising a therapeutically effective amount of one or more compounds of formula (I) and pharmaceutically acceptable carrier.

Another embodiment of the present application provides a method of administering TrkA inhibitors in a subject (i.e., a patient), which comprises administering to said subject (i.e., a patient) a pharmaceutical composition comprising a therapeutically effective amount of a compound of formula (I). As used herein the term "subject" and "patient" can be the same and can be used interchangeably.

In another embodiment, there is provided a method of inhibiting TrkA comprising administering to said subject a pharmaceutical composition comprising an effective amount of a compound of formula (I).

In an embodiment, specific compounds of formula (I) without any limitation are enumerated below (List-1):
(R)-5-(2-(2,5-difluorophenyl)pyrrolidin-1-yl)-N-((4-fluorophenyl)sulfonyl)pyrazolo[1,5-a]pyridine-3-carboxamide,
(R)—N-(tert-butylsulfonyl)-5-(2-(2,5-difluorophenyl) pyrrolidin-1-yl)pyrazolo[1,5-a] pyridine-3-carboxamide,
(R)-5-(2-(2,5-difluorophenyl)pyrrolidin-1-yl)-N-(ethylsulfonyl)pyrazolo[1,5-a] pyridine-3-carboxamide,
(R)—N-((3-cyanophenyl)sulfonyl)-5-(2-(2,5-difluorophenyl)pyrrolidin-1-yl)pyrazolo [1,5-a] pyridine-3-carboxamide,
(R)—N-(cyclopropylsulfonyl)-5-(2-(2,5-difluorophenyl) pyrrolidin-1-yl)pyrazolo[1,5-a]pyridine-3-carboxamide,
(R)-5-(2-(2,5-difluorophenyl)pyrrolidin-1-yl)-N-(methylsulfonyl)pyrazolo[1,5-a] pyridine-3-carboxamide,
(R)-5-(2-(2,5-difluorophenyl)pyrrolidin-1-yl)-N-(isopropylsulfonyl)pyrazolo[1,5-a] pyridine-3-carboxamide,
5-((R)-2-(2,5-difluorophenyl)pyrrolidin-1-yl)-N-((4-((S)-3-hydroxypyrrolidin-1-yl) phenyl) sulfonyl)pyrazolo[1,5-a]pyridine-3-carboxamide,
(R)—N-((3-cyanophenyl)sulfonyl)-5-(2-(2,5-difluorophenyl)pyrrolidin-1-yl)-N-methyl pyrazolo[1,5-a]pyridine-3-carboxamide,
(R)-5-(2-(2,5-difluorophenyl)pyrrolidin-1-yl)-N-(propylsulfonyl)pyrazolo[1, 5-a] pyridine-3-carboxamide,
(R)-5-(2-(2,5-difluorophenyl)pyrrolidin-1-yl)-N-((3,5-dimethylisoxazol-4-yl) sulfonyl)pyrazolo [1, 5-a] pyridine-3-carboxamide,
(R)—N-(cyclohexylsulfonyl)-5-(2-(2,5-difluorophenyl)pyrrolidin-1-yl)pyrazolo[1,5-a] pyridine-3-carboxamide,
(R)—N-(cyclopentylsulfonyl)-5-(2-(2, 5-difluorophenyl) pyrrolidin-1-yl)pyrazolo[1,5-a]pyridine-3-carboxamide,
(R)-5-(2-(2,5-difluorophenyl)pyrrolidin-1-yl)-N-(isobutylsulfonyl)pyrazolo[1, 5-a] pyridine-3-carboxamide,
(R)-5-(2-(2,5-difluorophenyl) pyrrolidin-1-yl)-N-((1,2-dimethyl-1H-imidazol-4-yl) sulfonyl) pyrazolo [1, 5-a] pyridine-3-carboxamide, (R)-5-(2-(2,5-difluorophenyl) pyrrolidin-1-yl)-N-((1,2-dimethyl-1H-imidazol-5-yl) sulfonyl) pyrazolo [1, 5-a] pyridine-3-carboxamide, (R)-5-(2-(2, 5-difluorophenyl) pyrrolidin-1-yl)-N-(piperidin-4-ylsulfonyl)pyrazolo[1, 5-a] pyridine-3-carboxamide, (R)-5-(2-(2, 5-difluorophenyl) pyrrolidin-1-yl)-N-((1-methyl-1H-imidazol-4-yl) sulfonyl)pyrazolo [1, 5-a] pyridine-3-carboxamide, (R)-5-(2-(2, 5-difluorophenyl) pyrrolidin-1-yl)-N-((1-methyl-1H-pyrazol-5-yl) sulfonyl)pyrazolo [1, 5-a] pyridine-3-carboxamide, (R)-5-(2-(2, 5-difluorophenyl) pyrrolidin-1-yl)-N-((2,4-dimethylthiazol-5-yl) sulfonyl)pyrazolo [1, 5-a] pyridine-3-carboxamide, (R)-5-(2-(2, 5-difluorophenyl) pyrrolidin-1-yl)-N-((1-methyl-2-oxoindolin-5-yl) sulfonyl)pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, (R)-5-(2-(2, 5-difluorophenyl) pyrrolidin-1-yl)-N-((6-(dimethylamino) pyridin-3-yl) sulfonyl)pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, (R)-5-(2-(2, 5-difluorophenyl) pyrrolidin-1-yl)-N-((6-methoxypyridin-3-yl) sulfonyl) pyrazolo [1, 5-a] pyridine-3-carboxamide, (R)—N-((6-(1H-1,2,4-triazol-1-yl)pyridin-3-yl)sulfonyl)-5-(2-(2,5-difluorophenyl) pyrrolidin-1-yl)pyrazolo [1, 5-a] pyridine-3-carboxamide, (R)-5-(2-(2, 5-difluorophenyl) pyrrolidin-1-yl)-N-((1-methyl-1H-pyrazol-4-yl) sulfonyl)pyrazolo [1, 5-a] pyridine-3-carboxamide, (R)-5-(2-(2, 5-difluorophenyl) pyrrolidin-1-yl)-N-((4-morpholinophenyl)sulfonyl) pyrazolo [1, 5-a] pyridine-3-carboxamide, (R)-5-(2-(2,5-difluorophenyl)pyrrolidin-1-yl)-N-(pyridin-3-ylsulfonyl)pyrazolo[1,5-a]pyridine-3-carboxamide, (R)—N-((5-chlorothiophen-2-yl) sulfonyl)-5-(2-(2, 5-difluorophenyl) pyrrolidin-1-yl) pyrazolo [1, 5-a] pyridine-3-carboxamide, (R)—N-((2,5-dichlorothiophen-3-yl) sulfonyl)-5-(2-(2, 5-difluorophenyl) pyrrolidin-1-yl)pyrazolo [1, 5-a] pyridine-3-carboxamide, (R)—N-(cyclobutylsulfonyl)-5-(2-(2, 5-difluorophenyl) pyrrolidin-1-yl)pyrazolo [1, 5-a]pyridine-3-carboxamide, (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide, (R)—N-(benzo[d][1,3]dioxol-5-ylsulfonyl)-5-(2-(2,5-difluorophenyl)pyrrolidin-1-yl) pyrazolo[1,5-a]pyridine-3-carboxamide, (R)-5-(2-(2,5-difluorophenyl)pyrrolidin-1-yl)-N-((1-ethylcyclopropyl)sulfonyl) pyrazolo[1,5-a]pyridine-3-carboxamide, (R)-5-(2-(2,5-difluorophenyl)pyrrolidin-1-yl)-N-(neopentylsulfonyl)pyrazolo[1,5-a]pyridine-3-carboxamide, (R)-5-(2-(2,5-difluorophenyl)pyrrolidin-1-yl)-N-((1-methylcyclopropyl)sulfonyl) pyrazolo[1,5-a]pyridine-3-carboxamide, (R)-5-(2-(2,5-difluorophenyl)pyrrolidin-1-yl)-N-(o-tolylsulfonyl)pyrazolo[1,5-a] pyridine-3-carboxamide, (R)—N-(benzylsulfonyl)-5-(2-(2,5-difluorophenyl)pyrrolidin-1-yl)pyrazolo[1,5-a] pyridine-3-carboxamide, (R)-5-(2-(2,5-difluorophenyl)pyrrolidin-1-yl)-N-((1-(4-fluorobenzyl)cyclopropyl) sulfonyl)pyrazolo[1,5-a]pyridine-3-carboxamide, (R)—N-(tert-butylsulfonyl)-5-(2-(5-fluoro-2-methoxyphenyl) pyrrolidin-1-yl) pyrazolo [1, 5-a] pyridine-3-carboxamide, (R)—N-(tert-butylsulfonyl)-5-(2-(3-(difluoromethoxy)-5-fluorophenyl) pyrrolidin-1-yl)pyrazolo [1, 5-a] pyridine-3-carboxamide, (R)—N-(tert-butylsulfonyl)-5-(2-(5-fluoropyridin-3-yl) pyrrolidin-1-yl)pyrazolo [1, 5-a]pyridine-3-carboxamide, (R)—N-(tert-butylsulfonyl)-5-(2-(2-ethoxy-5-fluorophenyl) pyrrolidin-1-yl)pyrazolo[1,5-a]pyridine-3-carboxamide, (R)—N-(tert-butylsulfonyl)-5-(2-(2-(cyclopropylmethoxy)-5-fluorophenyl) pyrrolidin-1-yl)pyrazolo[1,5-a]pyridine-3-carboxamide, (R)—N-(tert-butylsulfonyl)-5-(2-(2-chloro-5-fluorophenyl) pyrrolidin-1-yl) pyrazolo[1,5-a]pyridine-3-carboxamide, N-(tert-butylsulfonyl)-5-((2R,4R)-2-(2,5-difluorophenyl)-4-hydroxypyrrolidin-1-yl) pyrazolo[1,5-a]pyridine-3-carboxamide, (R)—N-(tert-butylsulfonyl)-5-(2-(5-fluoro-2-(2,2,2-trifluoroethoxy)phenyl) pyrrolidin-1-yl)pyrazolo[1,5-a]pyridine-3-carboxamide, N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide (Isomer-I), N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide (Isomer-II), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-I), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-II), (R)—N-(tert-butylsulfonyl)-5-(2-(4,4'-difluoro-[1,1'-biphenyl]-2-yl)pyrrolidin-1-yl)pyrazolo[1,5-a]pyridine-3-carboxamide, (S)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(5-fluoro-2-(2-fluoroethoxy)phenyl)pyrrolidin-1-yl)pyrazolo[1,5-a]pyridine-3-carboxamide, N-(tert-butylsulfonyl)-5-((2R,4R)-2-(2,5-difluorophenyl)-4-fluoropyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, (R)—N-(tert-butylsulfonyl)-5-(2-(2, 5-difluorophenyl) pyrrolidin-1-yl)-4-fluoro pyrazolo[1, 5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide, (R)—N-(tert-butylsulfonyl)-5-(2-(2-(difluoromethoxy)-5-fluorophenyl) pyrrolidin-1-yl)pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl)pyrazolo [1, 5-a] pyridine-3-carboxamide, (R)—N-(tert-butylsulfonyl)-5-(2-(3,5-difluorophenyl) pyrrolidin-1-yl)pyrazolo[1,5-a]pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a]pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a] pyridine-3-carboxamide, (R)-5-(2-(3,5-difluorophenyl) pyrrolidin-1-yl)-N-((4-fluorophenyl)sulfonyl) pyrazolo [1, 5-a] pyridine-3-carboxamide, 5-((R)-2-(3,5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, (R)-5-(2-(3,5-difluorophenyl) pyrrolidin-1-yl)-N-(isopropylsulfonyl)pyrazolo [1, 5-a] pyridine-3-carboxamide, (R)—N-((6-(1H-1,2,4-triazol-1-yl)pyridin-3-yl) sulfonyl)-5-(2-(3,5-difluorophenyl) pyrrolidin-1-yl)pyrazolo [1, 5-a] pyridine-3-carboxamide, 5-((R)-2-(3,5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, 5-((2R,4S)-2-(2,5-difluorophenyl)-4-fluoropyrrolidin-1-yl)-N-((1-methyl cyclopropyl)sulfonyl)pyrazolo[1,5-a]pyridine-3-carboxamide, (R)-5-(2-(2, 5-difluorophenyl) pyrrolidin-1-yl)-4-fluoro-N-(isopropylsulfonyl) pyrazolo [1, 5-a] pyridine-3-carboxamide, (R)-5-(2-(2, 5-difluorophenyl) pyrrolidin-1-yl)-N—(N,N-dimethylsulfamoyl) pyrazolo [1, 5-a] pyridine-3-carboxamide, (R)-5-(2-(2,5-difluorophenyl)pyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl)pyrazolo[1,5-a]pyridine-3-carboxamide, 5-((2R,4S)-2-(2,5-difluorophenyl)-4-fluoropyrrolidin-1-yl)-N—(N-ethyl-N-methyl sulfamoyl)pyrazolo[1,5-a]pyridine-3-carboxamide, (R)—N—(N-(cyclopropylmethyl)-N-methylsulfamoyl)-5-(2-(2,5-difluorophenyl) pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl)pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methyl sulfamoyl) pyrazolo[1,5-a]pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl) pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo[1,5-a]pyridine-3-carboxamide, (R)—N—(N,N-diethylsulfamoyl)-5-(2-(5-fluoro-2-methoxyphenyl)pyrrolidin-1-yl) pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl)pyrazolo[1,5-a]pyridine-3-carboxamide, (R)-5-(2-(2,5-difluorophenyl)pyrrolidin-1-yl)-N-(piperidin-1-ylsulfonyl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy) phenyl)pyrrolidin-1-yl)pyrazolo[1,5-a]pyridine-3-carboxamide, 5-((R)-2-(2,5-difluorophenyl)pyrrolidin-1-yl)-N—(((S)-3-hydroxypyrrolidin-1-yl) sulfonyl)pyrazolo[1,5-a]pyridine-3-carboxamide, (R)-5-(2-(2,5-difluorophenyl)pyrrolidin-1-yl)-N-sulfamoylpyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo[1,5-a]pyridine-3-carboxamide, N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1, 5-a]pyridine-3-carboxamide (Diastereomer-I), N—(N-ethyl-N-methylsulfamoyl)-5-(2-(7-fluoro-2,3-dihydrobenzo[b][1,4]dioxin-5-yl)pyrrolidin-1-yl)pyrazolo[1, 5-a]pyridine-3-carboxamide (Diastereomer-II), N—(N-ethyl-N-methylsulfamoyl)-4-fluoro-5-((2R,4S)-4-fluoro-2-(3-fluorophenyl)pyrrolidin-1-yl)pyrazolo[1,5-a]pyridine-3-carboxamide, N—(N-ethyl-N-methylsulfamoyl)-5-((R)-2-(3-fluoro-5-(((S)-tetrahydrofuran-3-yl)oxy)phenyl)pyrrolidin-1-yl) pyrazolo[1,5-a]pyridine-3-carboxamide, (R)-5-(2-(3,5-difluoro-2-((tetrahydro-2H-pyran-4-yl)oxy) phenyl)pyrrolidin-1-yl)-N—(N-ethyl-N-methylsulfamoyl)pyrazolo[1,5-a]pyridine-3-carboxamide, (R)-5-(2-(3,5-difluoro-2-((tetrahydro-2H-pyran-4-yl)oxy) phenyl)pyrrolidin-1-yl)-N—(N,N-dimethylsulfamoyl) pyrazolo[1,5-a]pyridine-3-carboxamide, N—(N-ethyl-N-methylsulfamoyl)-5-((R)-2-(3-fluoro-5-(((R)-tetrahydrofuran-3-yl)oxy)phenyl)pyrrolidin-1-yl) pyrazolo[1,5-a]pyridine-3-carboxamide, 4-fluoro-5-((2R,4S)-4-fluoro-2-(3-fluorophenyl)pyrrolidin-1-yl)-N-sulfamoyl pyrazolo[1,5-a]pyridine-3-carboxamide, N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I), N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2);

(R)-5-(2-(2,5-difluorophenyl)pyrrolidin-1-yl)-N—(N-isobutyl-N-methyl sulfamoyl)pyrazolo[1,5-a]pyridine-3-carboxamide, (R)—N—(N-ethyl-N-methylsulfamoyl)-4-fluoro-5-(2-(3-fluorophenyl)pyrrolidin-1-yl)pyrazolo[1,5-a]pyridine-3-carboxamide, (R)—N—(N,N-dimethylsulfamoyl)-4-fluoro-5-(2-(3-fluorophenyl)pyrrolidin-1-yl) pyrazolo[1,5-a]pyridine-3-carboxamide, (R)—N—(N,N-dimethylsulfamoyl)-4-fluoro-5-(2-(3-fluorophenyl)pyrrolidin-1-yl) pyrazolo[1,5-a]pyridine-3-carboxamide, (R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, 5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide, (R)—N—(N,N-bis(cyclopropylmethyl) sulfamoyl)-5-(2-(2,5-difluorophenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide (Diastereomer-II), N-(tert-butylsulfonyl)-5-(2-(2,5-difluorophenyl)pyrrolidin-1-yl)pyrazolo[1,5-a] pyridine-3-carboxamide (Racemic mixture);

(R)—N-(tert-butylsulfonyl)-5-(2-(3,5-difluoro-2-methoxyphenyl)pyrrolidin-1-yl) pyrazolo[1,5-a]pyridine-3-carboxamide, N-(tert-butylsulfonyl)-4-fluoro-5-((2R,4S)-4-fluoro-2-(3-fluorophenyl)pyrrolidin-1-yl)pyrazolo[1,5-a]pyridine-3-carboxamide, 4-fluoro-5-((2R,4S)-4-fluoro-2-(3-fluorophenyl)pyrrolidin-1-yl)-N-(isopropyl sulfonyl)pyrazolo[1,5-a]pyridine-3-carboxamide, (R)—N-(tert-butylsulfonyl)-5-(2-(3,5-difluoro-2-((tetrahydro-2H-pyran-4-yl)oxy) phenyl)pyrrolidin-1-yl)pyrazolo[1,5-a]pyridine-3-carboxamide, (R)—N-(tert-butylsulfonyl)-5-(2-(5-fluoro-2-((tetrahydro-2H-pyran-4-yl)oxy) phenyl)pyrrolidin-1-yl)pyrazolo[1,5-a]pyridine-3-carboxamide, (R)-5-(2-(3,5-difluoro-2-((tetrahydro-2H-pyran-4-yl)oxy) phenyl)pyrrolidin-1-yl)-N-(isopropylsulfonyl)pyrazolo[1,5-a]pyridine-3-carboxamide, (R)-4-fluoro-5-(2-(3-fluorophenyl)pyrrolidin-1-yl)-N-(isopropylsulfonyl)pyrazolo[1,5-a]pyridine-3-carboxamide, (R)—N-(tert-butylsulfonyl)-4-fluoro-5-(2-(5-fluoro-2-((tetrahydro-2H-pyran-4-yl) oxy)phenyl)pyrrolidin-1-yl)pyrazolo[1,5-a]pyridine-3-carboxamide, Sodium (tert-butylsulfonyl)(5-((2R,4S)-2-(2,5-difluorophenyl)-4-fluoropyrrolidin-1-yl)pyrazolo[1,5-a]pyridine-3-carbonyl)amide, Sodium(R)-(tert-butylsulfonyl)(5-(2-(2,5-difluorophenyl) pyrrolidin-1-yl)pyrazolo [1,5-a] pyridine-3-carbonyl) amide, Sodium (R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide, Sodium (tert-butylsulfonyl)(5-((2R,4R)-2-(2,5-difluorophenyl)-4-fluoropyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl) (N,N-dimethylsulfamoyl)amide, Sodium (tert-butylsulfonyl)(5-(2-(2,5-difluorophenyl)-4,4-difluoropyrrolidin-1-yl)pyrazolo [1,5-a]pyridine-3-carbonyl)amide, Sodium (R)-(5-(2-(2,5-difluorophenyl) pyrrolidin-1-yl) pyrazolo[1,5-a]pyridine-3-carbonyl)((1-methylcyclopropyl)sulfonyl)amide, Sodium (tert-butylsulfonyl)(5-((2R)-2-(2,5-difluorophenyl)-4-fluoropyrrolidin-1-yl)pyrazolo [1,5-a]pyridine-3-carbonyl)amide, Sodium (5-((2R,4S)-2-(2,5-difluorophenyl)-4-fluoropyrrolidin-1-yl)pyrazolo[1,5-a]pyridine-3-carbonyl)(N,N-dimethylsulfamoyl)amide, Sodium (tert-butylsulfonyl)(4-fluoro-5-((2R,4S)-4-fluoro-2-(3-fluorophenyl) pyrrolidin-1-yl)pyrazolo[1,5-a]pyridine-3-carbonyl)amide, Sodium (R)—(N,N-dimethylsulfamoyl)(4-fluoro-5-(2-(3-fluorophenyl)pyrrolidin-1-yl)pyrazolo [1,5-a]pyridine-3-carbonyl)amide, Sodium (N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl)(o-tolylsulfonyl) amide, Sodium (4-fluoro-5-((2R,4S)-4-fluoro-2-(3-fluorophenyl) pyrrolidin-1-yl) pyrazolo[1,5-a]pyridine-3-carbonyl) (isopropylsulfonyl)amide, Sodium (5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, or Sodium (R)-(5-(2-(2,5-difluorophenyl) pyrrolidin-1-yl) pyrazolo[1,5-a]pyridine-3-carbonyl)(piperidin-1-ylsulfonyl)amide;

or a pharmaceutically acceptable salt thereof, a pharmaceutically acceptable solvate thereof or a stereoisomer thereof.

In one embodiment, compounds of formula (I) are represented as (R)-5-(2-(2,5-difluorophenyl)pyrrolidin-1-yl)-N-((4-fluorophenyl)sulfonyl)pyrazolo[1,5-a]pyridine-3-carboxamide, (R)—N-((3-cyanophenyl)sulfonyl)-5-(2-(2,5-difluorophenyl)pyrrolidin-1-yl)pyrazolo [1,5-a] pyridine-3-carboxamide, 5-((R)-2-(2,5-difluorophenyl) pyrrolidin-1-yl)-N-((4-((S)-3-hydroxypyrrolidin-1-yl) phenyl) sulfonyl) pyrazolo [1,5-a] pyridine-3-carboxamide, (R)—N-((3-cyanophenyl)sulfonyl)-5-(2-(2,5-difluorophenyl) pyrrolidin-1-yl)-N-methylpyrazolo [1, 5-a] pyridine-3-carboxamide, (R)-5-(2-(2,5-difluorophenyl) pyrrolidin-1-yl)-N-((4-morpholinophenyl) sulfonyl) pyrazolo [1, 5-a] pyridine-3-carboxamide, (R)-5-(2-(2,5-difluorophenyl)pyrrolidin-1-yl)-N-(o-tolylsulfonyl)pyrazolo[1,5-a]pyridine-3-carboxamide, (R)-5-(2-(3,5-difluorophenyl) pyrrolidin-1-yl)-N-((4-fluorophenyl) sulfonyl) pyrazolo [1, 5-a] pyridine-3-carboxamide, 5-((R)-2-(3,5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide,
Sodium(R)-(5-(2-(2,5-difluorophenyl)pyrrolidin-1-yl)pyrazolo[1,5-a]pyridine-3-carbonyl) (piperidin-1-ylsulfonyl) amide, or
Sodium(R)-(5-(2-(2,5-difluorophenyl)pyrrolidin-1-yl)pyrazolo[1,5-a]pyridine-3-carbonyl) (o-tolylsulfonyl)amide;
or a pharmaceutically acceptable salt thereof, a pharmaceutically acceptable solvate thereof
or a stereoisomer thereof.

In one embodiment, compounds of formula (I) are represented as (R)—N-(tert-butylsulfonyl)-5-(2-(2, 5-difluorophenyl) pyrrolidin-1-yl) pyrazolo [1, 5-a] pyridine-3-carboxamide,
(R)-5-(2-(2,5-difluorophenyl)pyrrolidin-1-yl)-N-(ethylsulfonyl)pyrazolo[1,5-a]pyridine-3-carboxamide,
(R)-5-(2-(2,5-difluorophenyl)pyrrolidin-1-yl)-N-(methylsulfonyl)pyrazolo[1,5-a] pyridine-3-carboxamide,
(R)-5-(2-(2, 5-difluorophenyl) pyrrolidin-1-yl)-N-(isopropylsulfonyl)pyrazolo [1, 5-a] pyridine-3-carboxamide,
(R)-5-(2-(2, 5-difluorophenyl) pyrrolidin-1-yl)-N-(propylsulfonyl)pyrazolo [1, 5-a] pyridine-3-carboxamide,
(R)-5-(2-(2, 5-difluorophenyl) pyrrolidin-1-yl)-N-(isobutylsulfonyl)pyrazolo[1, 5-a] pyridine-3-carboxamide,
(R)-5-(2-(2,5-difluorophenyl)pyrrolidin-1-yl)-N-(neopentylsulfonyl)pyrazolo[1,5-a]pyridine-3-carboxamide,
(R)—N-(benzylsulfonyl)-5-(2-(2,5-difluorophenyl)pyrrolidin-1-yl)pyrazolo[1,5-a]pyridine-3-carboxamide,
(R)—N-(tert-butylsulfonyl)-5-(2-(5-fluoro-2-methoxyphenyl) pyrrolidin-1-yl) pyrazolo [1, 5-a] pyridine-3-carboxamide,
(R)—N-(tert-butylsulfonyl)-5-(2-(3-(difluoromethoxy)-5-fluorophenyl) pyrrolidin-1-yl) pyrazolo [1, 5-a] pyridine-3-carboxamide,
(R)—N-(tert-butylsulfonyl)-5-(2-(5-fluoropyridin-3-yl) pyrrolidin-1-yl) pyrazolo [1, 5-a] pyridine-3-carboxamide,
(R)—N-(tert-butylsulfonyl)-5-(2-(2-ethoxy-5-fluorophenyl) pyrrolidin-1-yl)pyrazolo[1,5-a] pyridine-3-carboxamide,
(R)—N-(tert-butylsulfonyl)-5-(2-(2-(cyclopropylmethoxy)-5-fluorophenyl)pyrrolidin-1-yl) pyrazolo[1,5-a]pyridine-3-carboxamide,
(R)—N-(tert-butylsulfonyl)-5-(2-(2-chloro-5-fluorophenyl) pyrrolidin-1-yl)pyrazolo[1,5-a]pyridine-3-carboxamide,
N-(tert-butylsulfonyl)-5-((2R,4R)-2-(2,5-difluorophenyl)-4-hydroxypyrrolidin-1-yl)pyrazolo[1,5-a]pyridine-3-carboxamide,
N-(tert-butylsulfonyl)-5-((2R,4S)-2-(2,5-difluorophenyl)-4-fluoropyrrolidin-1-yl)pyrazolo [1,5-a]pyridine-3-carboxamide,
(R)—N-(tert-butylsulfonyl)-5-(2-(4,4'-difluoro-[1,1'-biphenyl]-2-yl)pyrrolidin-1-yl)pyrazolo[1,5-a]pyridine-3-carboxamide,
(R)—N-(tert-butylsulfonyl)-5-(2-(5-fluoro-2-(2-fluoroethoxy)phenyl)pyrrolidin-1-yl)pyrazolo[1,5-a]pyridine-3-carboxamide,
N-(tert-butylsulfonyl)-5-((2R)-2-(5-fluoro-2-((tetrahydrofuran-3-yl)oxy)phenyl) pyrrolidin-1-yl)pyrazolo[1,5-a] pyridine-3-carboxamide,
N-(tert-butylsulfonyl)-5-((2R)-2-(5-fluoro-2-((tetrahydrofuran-3-yl)oxy)phenyl) pyrrolidin-1-yl)pyrazolo[1,5-a] pyridine-3-carboxamide,
(R)—N-(tert-butylsulfonyl)-5-(2-(2, 5-difluorophenyl) pyrrolidin-1-yl)-4-fluoro pyrazolo[1, 5-a] pyridine-3-carboxamide,
(R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide,
(R)—N-(tert-butylsulfonyl)-5-(2-(2-(difluoromethoxy)-5-fluorophenyl) pyrrolidin-1-yl) pyrazolo [1, 5-a] pyridine-3-carboxamide,
(R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide,
(R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide,
(R)—N-(tert-butylsulfonyl)-5-(2-(3,5-difluorophenyl) pyrrolidin-1-yl) pyrazolo [1, 5-a] pyridine-3-carboxamide,
(R)—N-(tert-butylsulfonyl)-5-(2-(3-fluoro-5-(2-methoxyethoxy)phenyl)pyrrolidin-1-yl)pyrazolo[1,5-a]pyridine-3-carboxamide,
N-(tert-butylsulfonyl)-5-((2R)-2-(3-fluoro-5-((tetrahydrofuran-3-yl)oxy)phenyl) pyrrolidin-1-yl)pyrazolo[1,5-a] pyridine-3-carboxamide,
(R)-5-(2-(3,5-difluorophenyl) pyrrolidin-1-yl)-N-(isopropylsulfonyl)pyrazolo [1, 5-a] pyridine-3-carboxamide,
N-(tert-butylsulfonyl)-5-(2-(2,5-difluorophenyl)pyrrolidin-1-yl)pyrazolo[1,5-a]pyridine-3-carboxamide (Racemic mixture);
(R)—N-(tert-butylsulfonyl)-5-(2-(3,5-difluoro-2-methoxyphenyl)pyrrolidin-1-yl)pyrazolo[1,5-a]pyridine-3-carboxamide,
(R)—N-(tert-butylsulfonyl)-5-(2-(3,5-difluoro-2-((tetrahydro-2H-pyran-4-yl)oxy)phenyl)pyrrolidin-1-yl)pyrazolo[1,5-a]pyridine-3-carboxamide,
(R)—N-(tert-butylsulfonyl)-5-(2-(5-fluoro-2-((tetrahydro-2H-pyran-4-yl)oxy)phenyl)pyrrolidin-1-yl)pyrazolo[1,5-a]pyridine-3-carboxamide,
(R)-5-(2-(3,5-difluoro-2-((tetrahydro-2H-pyran-4-yl)oxy) phenyl)pyrrolidin-1-yl)-N-(isopropylsulfonyl)pyrazolo [1,5-a]pyridine-3-carboxamide,
(R)-4-fluoro-5-(2-(3-fluorophenyl)pyrrolidin-1-yl)-N-(isopropylsulfonyl)pyrazolo[1,5-a]pyridine-3-carboxamide,
(R)—N-(tert-butylsulfonyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
Sodium(tert-butylsulfonyl)(5-((2R,4R)-2-(2,5-difluorophenyl)-4-fluoropyrrolidin-1-yl)pyrazolo[1,5-a]pyridine-3-carbonyl)amide,
Sodium(tert-butylsulfonyl)(5-((2R,4S)-2-(2,5-difluorophenyl)-4-fluoropyrrolidin-1-yl)pyrazolo[1,5-a]pyridine-3-carbonyl)amide,
Sodium(R)-(tert-butylsulfonyl)(5-(2-(2,5-difluorophenyl) pyrrolidin-1-yl)pyrazolo[1,5-a] pyridine-3-carbonyl) amide, or
Sodium(R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide;
or a pharmaceutically acceptable salt thereof, a pharmaceutically acceptable solvate thereof
or a stereoisomer thereof.

In one embodiment, compounds of formula (I) are represented as (R)—N-(cyclopropylsulfonyl)-5-(2-(2,5-difluorophenyl) pyrrolidin-1-yl)pyrazolo[1,5-a]pyridine-3-carboxamide,
(R)—N-(cyclohexyl sulfonyl)-5-(2-(2, 5-difluorophenyl) pyrrolidin-1-yl)pyrazolo [1, 5-a] pyridine-3-carboxamide,
(R)—N-(cyclopentyl sulfonyl)-5-(2-(2, 5-difluorophenyl) pyrrolidin-1-yl)pyrazolo [1, 5-a] pyridine-3-carboxamide,
(R)—N-(cyclobutylsulfonyl)-5-(2-(2, 5-difluorophenyl) pyrrolidin-1-yl)pyrazolo [1, 5-a] pyridine-3-carboxamide, (R)-5-(2-(2,5-difluorophenyl)pyrrolidin-1-yl)-N-((1-ethyl-cyclopropyl)sulfonyl) pyrazolo[1,5-a]pyridine-3-carboxamide, (R)-5-(2-(2,5-difluorophenyl)pyrrolidin-1-yl)-N-((1-methylcyclopropyl)sulfonyl)pyrazolo[1,5-a]pyridine-3-carboxamide, (R)-5-(2-(2,5-difluorophenyl)pyrrolidin-1-yl)-N-((1-(4-fluorobenzyl)cyclopropyl)sulfonyl) pyrazolo[1,5-a]pyridine-3-carboxamide, (R)-5-(2-(2, 5-difluorophenyl) pyrrolidin-1-yl)-4-fluoro-N-(isopropylsulfonyl)pyrazolo[1, 5-a]pyridine-3-carboxamide, or Sodium(R)-(5-(2-(2,5-difluorophenyl)pyrrolidin-1-yl)pyrazolo[1,5-a]pyridine-3-carbonyl)((1-methylcyclopropyl)sulfonyl)amide;

or a pharmaceutically acceptable salt thereof, a pharmaceutically acceptable solvate thereof
or a stereoisomer thereof.

In one embodiment, compounds of formula (I) are represented as (R)-5-(2-(2,5-difluorophenyl)pyrrolidin-1-yl)-N-((3,5-dimethylisoxazol-4-yl) sulfonyl) pyrazolo [1, 5-a] pyridine-3-carboxamide, (R)-5-(2-(2,5-difluorophenyl) pyrrolidin-1-yl)-N-((1,2-dimethyl-1H-imidazol-4-yl) sulfonyl) pyrazolo [1, 5-a] pyridine-3-carboxamide, (R)-5-(2-(2,5-difluorophenyl)pyrrolidin-1-yl)-N-((1,2-dimethyl-1H-imidazol-5-yl) sulfonyl) pyrazolo [1, 5-a] pyridine-3-carboxamide, (R)-5-(2-(2,5-difluorophenyl) pyrrolidin-1-yl)-N-((1-methyl-1H-imidazol-4-yl) sulfonyl) pyrazolo [1, 5-a] pyridine-3-carboxamide, (R)-5-(2-(2,5-difluorophenyl) pyrrolidin-1-yl)-N-((1-methyl-1H-pyrazol-5-yl) sulfonyl) pyrazolo [1, 5-a] pyridine-3-carboxamide, (R)-5-(2-(2, 5-difluorophenyl) pyrrolidin-1-yl)-N-((2,4-dimethylthiazol-5-yl) sulfonyl) pyrazolo [1, 5-a] pyridine-3-carboxamide, (R)-5-(2-(2,5-difluorophenyl)pyrrolidin-1-yl)-N-((1-methyl-2-oxoindolin-5-yl)sulfonyl) pyrazolo [1, 5-a] pyridine-3-carboxamide, (R)-5-(2-(2, 5-difluorophenyl) pyrrolidin-1-yl)-N-((6-(dimethylamino) pyridin-3-yl) sulfonyl)pyrazolo [1, 5-a] pyridine-3-carboxamide, 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, (R)-5-(2-(2, 5-difluorophenyl) pyrrolidin-1-yl)-N-((6-methoxypyridin-3-yl) sulfonyl) pyrazolo [1, 5-a] pyridine-3-carboxamide, (R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide, (R)-5-(2-(2,5-difluorophenyl) pyrrolidin-1-yl)-N-((1-methyl-1H-pyrazol-4-yl) sulfonyl) pyrazolo [1, 5-a] pyridine-3-carboxamide, (R)-5-(2-(2,5-difluorophenyl)pyrrolidin-1-yl)-N-(pyridin-3-ylsulfonyl)pyrazolo[1,5-a]pyridine-3-carboxamide;

(R)—N-((5-chlorothiophen-2-yl) sulfonyl)-5-(2-(2, 5-difluorophenyl) pyrrolidin-1-yl) pyrazolo [1, 5-a] pyridine-3-carboxamide, (R)—N-((2,5-dichlorothiophen-3-yl) sulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide, (R)—N-(benzo[d][1,3]dioxol-5-ylsulfonyl)-5-(2-(2,5-difluorophenyl)pyrrolidin-1-yl)pyrazolo[1,5-a]pyridine-3-carboxamide, (R)—N-((6-(1H-1,2,4-triazol-1-yl)pyridin-3-yl) sulfonyl)-5-(2-(3,5-difluorophenyl) pyrrolidin-1-yl) pyrazolo [1, 5-a] pyridine-3-carboxamide, or 5-((R)-2-(3,5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide;

or a pharmaceutically acceptable salt thereof, a pharmaceutically acceptable solvate thereof
or a stereoisomer thereof.

In one embodiment, compounds of formula (I) are represented as (R)-5-(2-(2, 5-difluorophenyl) pyrrolidin-1-yl)-N-(piperidin-4-ylsulfonyl) pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl) pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo [1,5-a]pyridine-3-carboxamide, (R)-5-(2-(2,5-difluorophenyl)pyrrolidin-1-yl)-N-(piperidin-1-ylsulfonyl)pyrazolo[1,5-a]pyridine-3-carboxamide, or 5-((R)-2-(2,5-difluorophenyl)pyrrolidin-1-yl)-N—(((S)-3-hydroxypyrrolidin-1-yl) sulfonyl) pyrazolo[1,5-a]pyridine-3-carboxamide;

or a pharmaceutically acceptable salt thereof, a pharmaceutically acceptable solvate thereof
or a stereoisomer thereof.

In one embodiment, compounds of formula (I) are represented as (R)—N-(tert-butylsulfonyl)-5-(2-(5-fluoro-2-(2,2,2-trifluoroethoxy)phenyl)pyrrolidin-1-yl) pyrazolo[1,5-a]pyridine-3-carboxamide, N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide, N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide, N-(tert-butylsulfonyl)-5-((2R,4S)-2-(2,5-difluorophenyl)-4-fluoropyrrolidin-1-yl)pyrazolo[1,5-a]pyridine-3-carboxamide, N-(tert-butylsulfonyl)-5-((2R,4R)-2-(2,5-difluorophenyl)-4-fluoropyrrolidin-1-yl)pyrazolo[1,5-a]pyridine-3-carboxamide, 5-((2R,4S)-2-(2,5-difluorophenyl)-4-fluoropyrrolidin-1-yl)-N-((1-methyl cyclopropyl) sulfonyl)pyrazolo[1,5-a]pyridine-3-carboxamide, 5-((2R,4S)-2-(2,5-difluorophenyl)-4-fluoropyrrolidin-1-yl)-N—(N,N-dimethylsulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethylsulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, N—(N-ethyl-N-methylsulfamoyl)-4-fluoro-5-((2R,4S)-4-fluoro-2-(3-fluorophenyl)pyrrolidin-1-yl) pyrazolo[1,5-a]pyridine-3-carboxamide, N-(tert-butylsulfonyl)-4-fluoro-5-((2R,4S)-4-fluoro-2-(3-fluorophenyl)pyrrolidin-1-yl)pyrazolo [1,5-a]pyridine-3-carboxamide, 4-fluoro-5-((2R,4S)-4-fluoro-2-(3-fluorophenyl)pyrrolidin-1-yl)-N-(isopropylsulfonyl) pyrazolo[1,5-a]pyridine-3-carboxamide, Sodium(4-fluoro-5-((2R,4S)-4-fluoro-2-(3-fluorophenyl)pyrrolidin-1-yl)pyrazolo[1,5-a]pyridine-3-carbonyl) (isopropylsulfonyl)amide, Sodium(5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, Sodium(tert-butylsulfonyl)(5-((2R)-2-(2,5-difluorophenyl)-4-fluoropyrrolidin-1-yl)pyrazolo[1,5-a]pyridine-3-carbonyl)amide, Sodium(5-((2R,4S)-2-(2,5-difluorophenyl)-4-fluoropyrrolidin-1-yl)pyrazolo[1,5-a]pyridine-3-carbonyl)(N,N-dimethylsulfamoyl)amide, Sodium(tert-butylsulfonyl)(4-fluoro-5-((2R,4S)-4-fluoro-2-(3-fluorophenyl)pyrrolidin-1-yl)pyrazolo[1,5-a]pyridine-3-carbonyl)amide, or Sodium (tert-butylsulfonyl)(5-(2-(2,5-difluorophenyl)-4,4-difluoropyrrolidin-1-yl)pyrazolo[1,5-a]pyridine-3-carbonyl)amide;

or a pharmaceutically acceptable salt thereof, a pharmaceutically acceptable solvate thereof
or a stereoisomer thereof.

In one embodiment, compounds of formula (I) are represented as (R)-5-(2-(2,5-difluorophenyl) pyrrolidin-1-yl)-N—(N, N-dimethylsulfamoyl)pyrazolo[1,5-a] pyridine-3-carboxamide, (R)-5-(2-(2,5-difluorophenyl)pyrrolidin-1-yl)-N—(N-ethyl-N-methylsulfamoyl)pyrazolo[1,5-a]pyridine-3-carboxamide, (R)—N—(N-(cyclopropylmethyl)-N-methylsulfamoyl)-5-(2-(2,5-difluorophenyl)pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl)pyrazolo[1,5-a]pyridine-3-carboxamide, (R)—N—(N,N-diethylsulfamoyl)-5-(2-(5-fluoro-2-methoxyphenyl)pyrrolidin-1-yl)pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy)phenyl)pyrrolidin-1-yl)pyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo[1,5-a]pyridine-3-carboxamide, (R)-5-(2-(2,5-difluorophenyl)pyrrolidin-1-yl)-N-sulfamoylpyrazolo[1,5-a]pyridine-3-carboxamide, N—(N-ethyl-N-methylsulfamoyl)-5-((R)-2-(3-fluoro-5-(((S)-tetrahydrofuran-3-yl)oxy) phenyl)pyrrolidin-1-yl)pyrazolo[1,5-a]pyridine-3-carboxamide, (R)-5-(2-(3,5-difluoro-2-((tetrahydro-2H-pyran-4-yl)oxy) phenyl)pyrrolidin-1-yl)-N—(N-ethyl-N-methylsulfamoyl)pyrazolo[1,5-a]pyridine-3-carboxamide, (R)-5-(2-(3,5-difluoro-2-((tetrahydro-2H-pyran-4-yl)oxy) phenyl)pyrrolidin-1-yl)-N—(N,N-dimethylsulfamoyl) pyrazolo[1,5-a]pyridine-3-carboxamide, N—(N-ethyl-N-methylsulfamoyl)-5-((R)-2-(3-fluoro-5-(((R)-tetrahydrofuran-3-yl)oxy)phenyl)pyrrolidin-1-yl) pyrazolo[1,5-a]pyridine-3-carboxamide, 4-fluoro-5-((2R,4S)-4-fluoro-2-(3-fluorophenyl)pyrrolidin-1-yl)-N-sulfamoylpyrazolo[1,5-a]pyridine-3-carboxamide, N—(N,N-dimethylsulfamoyl)-5-(2-(8-fluoro-3,4-dihydro-2H-benzo[b][1,4]dioxepin-6-yl)pyrrolidin-1-yl)pyrazolo [1,5-a]pyridine-3-carboxamide (Diastereomer-I), (R)-5-(2-(2,5-difluorophenyl)pyrrolidin-1-yl)-N—(N-isobutyl-N-methylsulfamoyl)pyrazolo[1,5-a]pyridine-3-carboxamide, (R)—N—(N-ethyl-N-methylsulfamoyl)-4-fluoro-5-(2-(3-fluorophenyl)pyrrolidin-1-yl)pyrazolo[1,5-a]pyridine-3-carboxamide, (R)—N—(N,N-dimethylsulfamoyl)-4-fluoro-5-(2-(3-fluorophenyl)pyrrolidin-1-yl)pyrazolo[1,5-a]pyridine-3-carboxamide, (R)—N—(N,N-dimethylsulfamoyl)-4-fluoro-5-(2-(3-fluorophenyl)pyrrolidin-1-yl)pyrazolo[1,5-a]pyridine-3-carboxamide, (R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, 5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide, (R)—N—(N,N-bis(cyclopropylmethyl) sulfamoyl)-5-(2-(2,5-difluorophenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, Sodium(R)—(N,N-dimethylsulfamoyl)(4-fluoro-5-(2-(3-fluorophenyl)pyrrolidin-1-yl)pyrazolo[1,5-a]pyridine-3-carbonyl)amide, Sodium(N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide, or Sodium (R)-(5-(2-(2,5-difluorophenyl) pyrrolidin-1-yl) pyrazolo[1,5-a]pyridine-3-carbonyl)(N,N-dimethylsulfamoyl)amide;

or a pharmaceutically acceptable salt thereof, a pharmaceutically acceptable solvate thereof
or a stereoisomer thereof.

In one embodiment, compounds of formula (I) are represented as

N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-I), N—(N-ethyl-N-methylsulfamoyl)-5-(2-(8-fluoro-3,4-di-hydro-2H-benzo[b][1,4]dioxepin-6-yl)pyrrolidin-1-yl)pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), or N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2);

or a pharmaceutically acceptable salt thereof, a pharmaceutically acceptable solvate thereof
or a stereoisomer thereof.

In another embodiment, there is provided a method of treating or preventing pain or pain disorder in a patient in need of such a treatment comprising the administration of a therapeutically effective amount of the compound of formula (I) enlisted in List-1, or a stereoisomer thereof or a pharmaceutically acceptable salt thereof to said patient.

The present application further relates to methods of treating a patient for diseases or disorders in which the nerve growth factor (NGF) receptor are involved, in particular TrkA, such as such as pain, cancer, restenosis, atherosclerosis, psoriasis, thrombosis, or a disease, disorder, or injury relating to dysmyelination or demyelination, by administering a therapeutically effective amount of compound of formula (I), as enlisted in List-1, to said patient.

In another embodiment, there is provided a method of treating or preventing pain or pain disorder in a patient in need of such a treatment comprising the administration of a therapeutically effective amount of the compound of formula (I), as enlisted in List-1, to said patient.

In another embodiment, pain includes chronic and acute pain but is not limited to, pain related to cancer, surgery, bone fracture, skeletal pain caused by tumor metastasis, osteoarthritis, visceral pain, inflammatory pain and neuropathic pain.

In one embodiment, there is provided a method of binding NGF receptor TrkA protein in a patient in need of such a treatment comprising the administration of a therapeutically effective amount of the compound of formula (I), as enlisted in List-1, to said patient.

The present application further relates to use of compound of formulation (I) for treating a patient for diseases or disorders in which the NGF receptor are involved, in particular TrkA, such as such as pain, cancer, restenosis, atherosclerosis, psoriasis, thrombosis, or a disease, disorder, or injury relating to dysmyelination or demyelination, by administering a therapeutically effective amount of compound of formula (I), as enlisted in List-1, to said patient.

In another embodiment, there is provided an use of the compound for formula (I) for treating or preventing pain or pain disorder in a patient in need of such a treatment, comprising the administration of a therapeutically effective amount of the compound of formula (I), as enlisted in List-1, to said patient.

In another embodiment, pain includes chronic and acute pain but is not limited to, pain related to cancer, surgery, bone fracture, skeletal pain caused by tumor metastasis, osteoarthritis, visceral pain, inflammatory pain and neuropathic pain.

In another embodiment of the above aspect, there is provided a method of treating or preventing pain which comprises administering to said subject a pharmaceutical composition comprising an effective amount of a compound of formula (I), as enlisted in List-1.

Another embodiment of the application provides the use of such compositions in the treatment or prevention of diseases associated with inhibiting NGF receptor TrkA, such as pain, cancer, restenosis, atherosclerosis, psoriasis, thrombosis, or a disease, disorder, or injury relating to dysmyelination or demyelination.

One embodiment of the present application provides intermediates as 2-(7-fluoro-2, 3-dihydrobenzo[b] [1, 4]dioxin-5-yl)pyrrolidine, Ethyl 5-(2-(7-fluoro-2, 3-dihydrobenzo [b] [1, 4] dioxin-5-yl) pyrrolidin-1-yl) pyrazolo[1, 5-a]pyridine-3-carboxylate (Isomer-I), 5-(2-(7-fluoro-2, 3-dihydrobenzo [b] [1, 4] dioxin-5-yl) pyrrolidin-1-yl) pyrazolo [1, 5-a] pyridine-3-carboxylic acid (Isomer-I)

Ethyl 5-(2-(7-fluoro-2, 3-dihydrobenzo [b] [1, 4] dioxin-5-yl) pyrrolidin-1-yl) pyrazolo [1, 5-a]pyridine-3-carboxylate (Isomer-II)

5-(2-(7-fluoro-2, 3-dihydrobenzo [b] [1, 4] dioxin-5-yl) pyrrolidin-1-yl) pyrazolo [1, 5-a] pyridine-3-carboxylic acid (Isomer-II)

The pharmaceutical composition of a compound of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present invention may be administered in a wide variety of different dosage forms. For example, they may be combined with various pharmaceutically acceptable inert carriers in the form of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include solid diluents or fillers, sterile aqueous media, and various nontoxic organic solvents, etc. Moreover, oral pharmaceutical compositions may be sweetened and/or flavored. In general, the compounds of the invention may be present in such dosage forms at concentration levels ranging from about 0.1% to about 90% by weight.

In general, compounds of the present invention for treatment may be administered to a subject in a suitable effective dose in the range of from about 0.01 to about 100 mg per kilogram of body weight of recipient per day, in some embodiments, in the range of from about 0.5 to about 50 mg per kilogram body weight of recipient per day, in still other embodiments, in the range of from about 0.1 to about 20 mg per kilogram body weight of recipient per day. The exemplary dose may be suitably administered once daily, or several sub-doses, e.g. 2 to 5 sub-doses, may be administered at appropriate intervals through the day, or on other appropriate schedules.

An embodiment of the present invention provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention claimed herein. All temperatures are in degrees Celsius (° C.) unless otherwise noted.

The following acronyms, abbreviations, terms and definitions have been used throughout the reaction scheme and experimental section.

ACN (Acetonitrile), BINAP (2,2'-bis(diphenylphosphino)-1,1'-binaphthyl), CDCl$_3$ (Deuterated chloroform), CD$_3$OD (Deuterated methanol), Cs$_2$CO$_3$ (Caesium Carbonate) DCM (Dichloromethane), DIPEA [(N,N-diisopropylethylamine) (Hünig's base)], DMF (N,N-dimethylformamide), DMSO (Dimethyl sulfoxide), DMAP (Dimethyl amino pyridine), EtOH (Ethanol), EtOAc (Ethyl acetate), Et$_3$N (Triethylamine), EDCl (1-ethyl-3-(3-dimethylaminopropyl)carbodiimide hydrochloride, HOBt (1-hydroxybenzotriazole), HCl (hydrochloric acid), HATU [O-(-7-azabenzotriazol-1-yl)-N,N,N',N'-tetramethyluronium hexafluorophosphate], MeOH (Methanol), LiHMDS (Lithium bis(trimethylsilyl)amide), LiOH (Lithium hydroxide), K$_2$CO$_3$ (Potassium Carbonate), KOBu$_t$ (Potassium tert-butoxide), Pd (Palladium), Pd(OAc)$_2$ (Palladium (II) acetate), Pd$_2$(dba)$_3$ (Tris(dibenzylideneacetone)dipalladium (0)), POCl$_3$ (Phosphorus oxychloride), NaHCO$_3$ (Sodium Bicarbonate), NaOH (Sodium hydroxide), Na$_2$SO$_4$ (Sodium Sulfate), NaBH$_4$ (Sodium borohydride), NH$_4$Cl (Ammonium chloride), TFA (Trifluoroacetic acid), THF (Tetrahydrofuran), H$_2$O (Water).

Another embodiment of the present invention provides a process for the preparation of compounds of formulae (Ii)-(Iix) represent respectively a sub-group of a compound of formula (I), wherein all symbols/variables are as defined earlier unless otherwise stated. The process is represented by Scheme-1:

Scheme 1

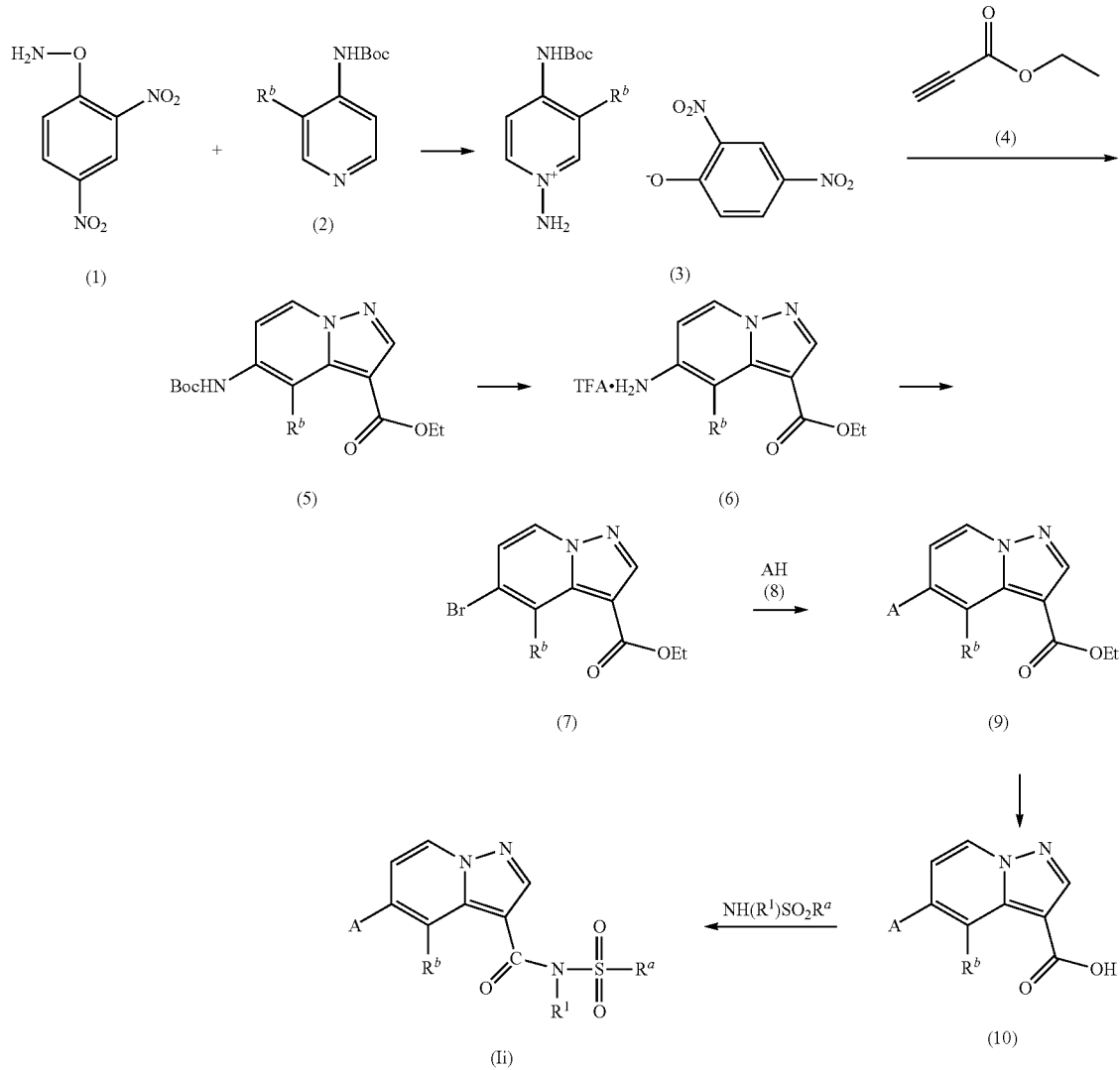

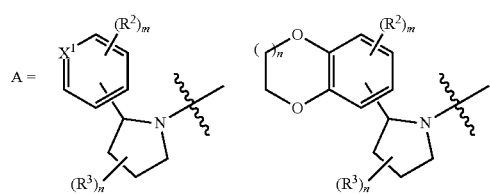

Compound of formula (3) obtained from compound (1) (prepared according to the procedure described in J. Org. Chem. 2003, 68, 7119-7122) and (2) was reacted with compound (4) to obtain of formula (5) where $R^b$ is as defined as before.

A compound of formula (6) can be obtained by reacting a compound of formula (5) with trifluoroacetic acid in dichloromethane at room temperature.

A compound of formula (7) was obtained from compound of formula (6) by standard Sandmeyer reaction protocol.

DMAP or EDCI, HOBt, NaH and the like in presence of a suitable solvent such as DMF, DCM and the like at a temperature of about 20 to about 65° C. for about 15 to about 18 h.

Another embodiment of the present invention provides a process for the preparation of compounds of formulae (10i), (11i) and (1i), wherein all symbols/variables are as defined earlier unless otherwise stated. The process is represented by Scheme-2:

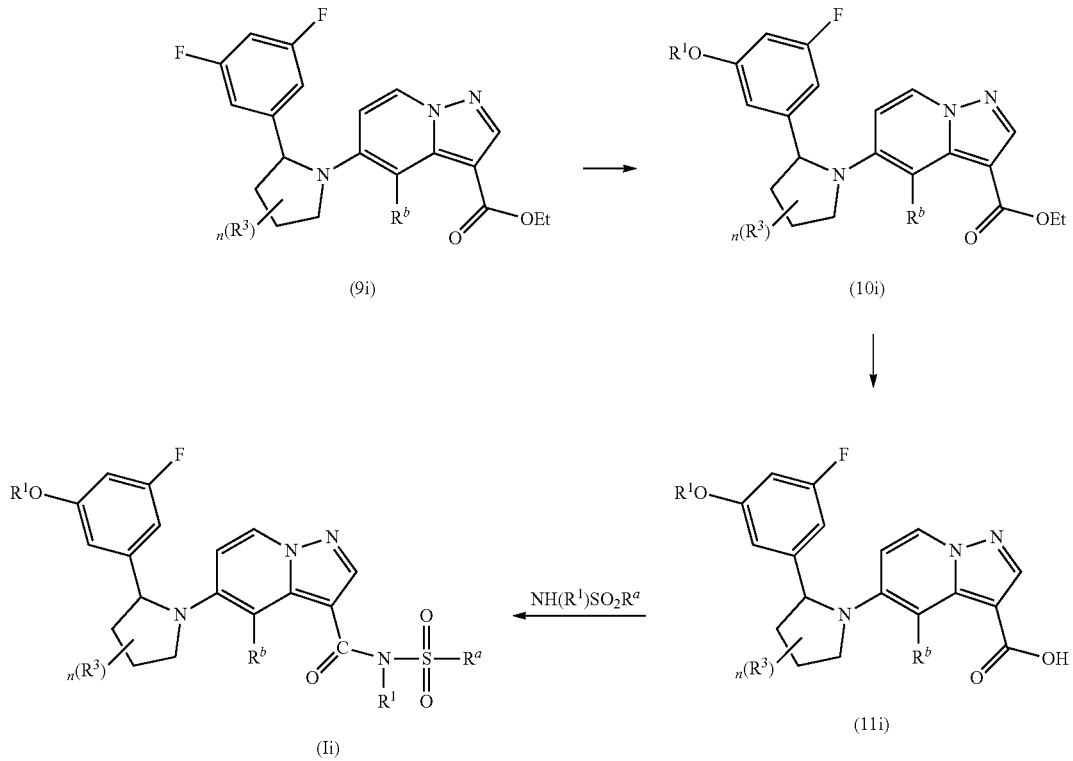

A compound of formula (9) was obtained from compound of formula (7) by reaction with compound of formula (8) in the presence of $Pd_2dba_3$, BINAP, $Et_3N$ and $Cs_2CO_3$, in a solvent such as 1,4-dioxane and the like at a temperature of about 60 to about 80° C. for about 12 to about 16 h where A is as defined before A compound of formula (9) to formula (10) can be converted using reagents such as 3M LiOH solution, 5N NaOH solution and the like in presence of a suitable solvent such as THF, THF-MeOH and the like.

A compound of formula (10) to formula (I) can be converted by using suitable reagents such as HATU, DIPEA or HATU, HOBt, DIPEA or EDCI, HOBt, DIPEA or EDCI, A compound of formula (10i) can be obtained from compound of formula (9i) by reacting with hydroxyl containing compounds like R'OH where Ri is defined as before under suitable conditions.

A compound of formula (10i) can be converted to the compound of formula (11i) and subsequently to compound of formula (1i) using conditions as mentioned under Scheme-1.

Another embodiment of the present invention provides a process for the preparation of compounds of formulae (10ii), (11ii), (12i) and (1iii), wherein all symbols/variables are as defined earlier unless otherwise stated. The process is represented by Scheme-3:

Scheme-3

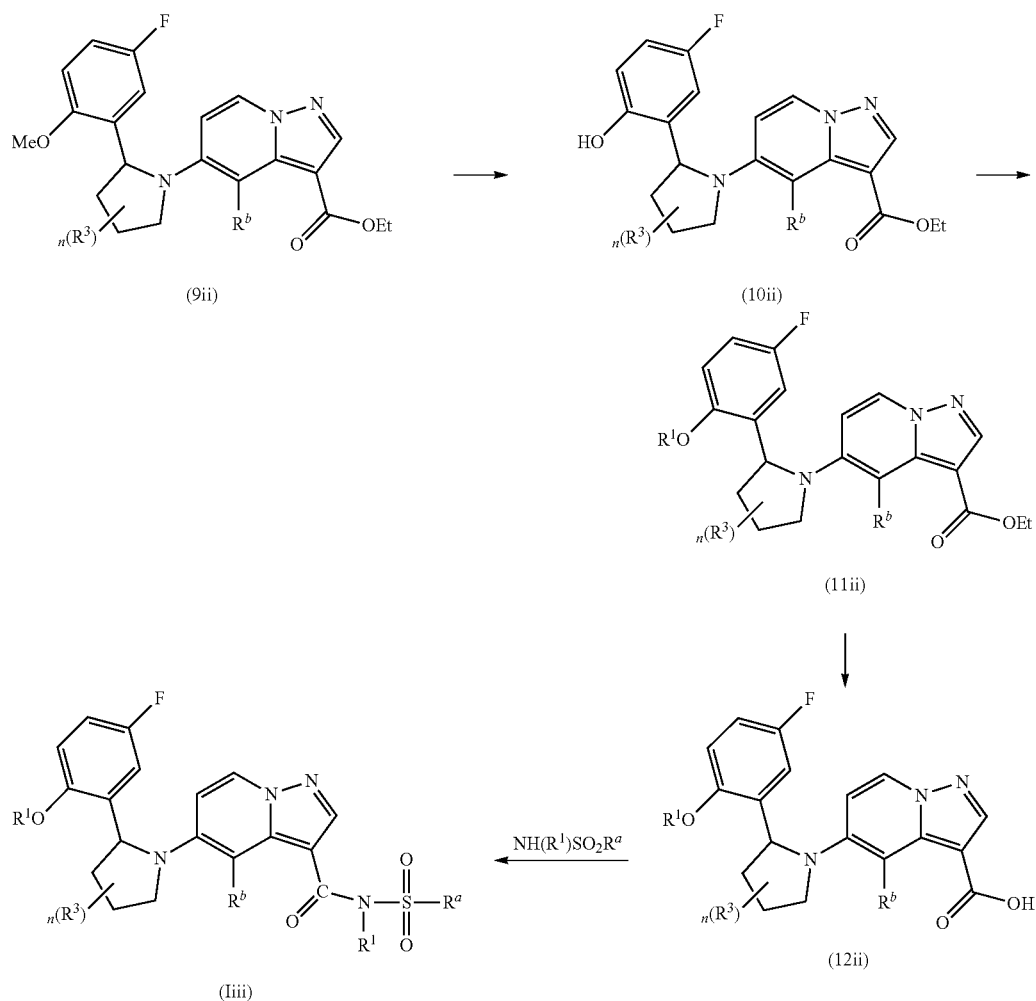

A compound of formula (10ii) can be obtained from compound of formula (9ii) by reacting with BBr$_3$ in a suitable solvent like dichloromethane.

A compound of formula (10ii) can be converted to the compound of formula (11ii) using suitable reaction conditions known in the art.

A compound of formula (11ii) can be converted to the compound of formula (12ii) and subsequently to compound of formula (1ii) using conditions as mentioned under Scheme-1.

Another embodiment of the present invention provides a process for the preparation of compounds of formula (13), wherein all symbols/variables are as defined earlier unless otherwise stated. The process is represented by Scheme-4:

Scheme-4

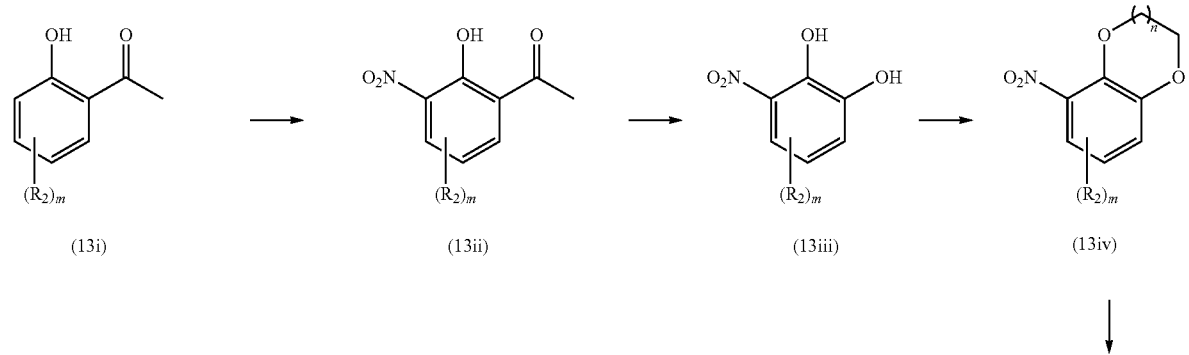

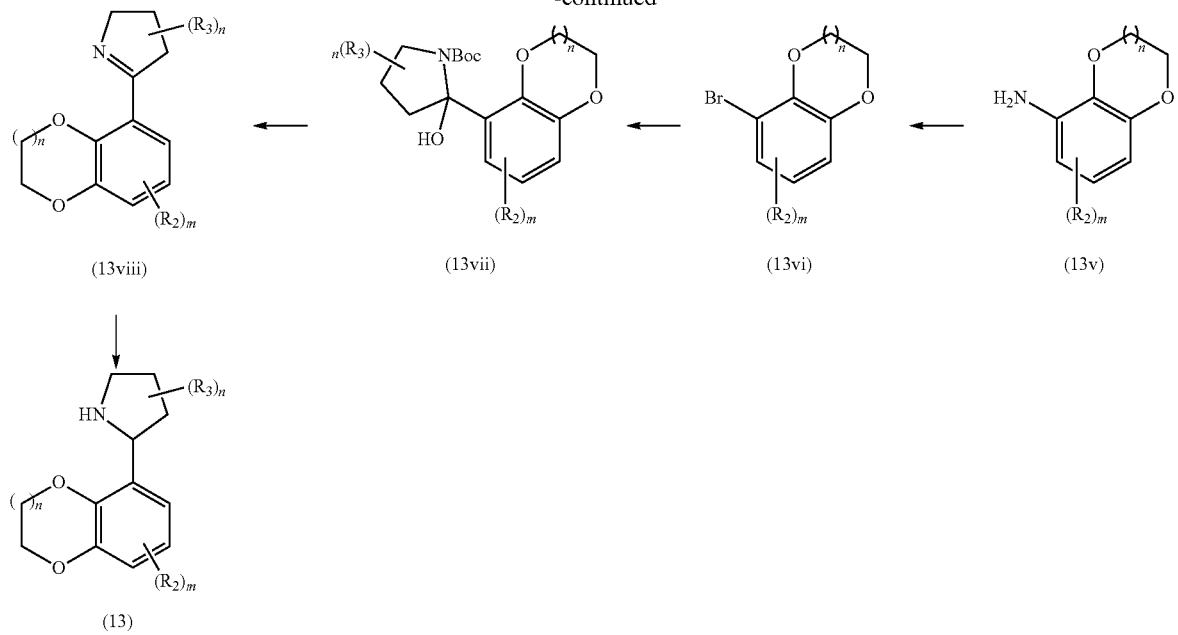

A compound of formula (13ii) can be obtained from compound of formula (13i) by nitration in presence of fuming nitric acid/acetic acid or a similar nitrating reagent.

Nitration of the compounds (13ii) on Dakin oxidation resulted compound of formula (13iii), which can be cyclized to compound (13iv) by reacting with a dihalo alkyl in presence of a suitable base and solvent.

Compound of formula (13v) can be obtained by reduction of (13iv) in presence of a suitable reducing agent, which can then be converted to a compound of formula (13vi) by Sandmeyer reaction with a suitable copper halide.

Compound of formula (13vi) can be converted to a compound of formula (13vii) by magnesium metal mediated reaction with Boc protected pyrrolidin-2-one derivatives.

Compound of formula (13vii) on TFA de-protection followed by NaBH₄ or a suitable reducing agent mediated reduction afforded compound of formula (13).

As used in the examples and preparations that follow, the terms used therein shall have the meanings indicated: "g" or "gm" refers to grams, "mg" refers to milligrams, "g" refers to micrograms, "mol" refers to moles, "mmol" refers to millimoles, "L" refers to liters, "mL" or "ml" refers to milliliters, "μL" refers to microliters, "mp" or "m.p." refers to melting point, "mm of Hg" refers to pressure in millimeters of mercury, "cm" refers to centimeters, "nm" refers to nanometers, "conc." refers to concentrated, "M" refers to molar, "mM" refers to millimolar, "μM" refers to micromolar, "nM" refers to nanomolar, "TLC" refers to thin layer chromatography, "HPLC" refers to high performance liquid chromatography, "anhyd" refers to anhydrous; "aq" refers to aqueous; "min" refers to minute; "mins" refers to minutes; "h" or "hr" refers to hour; "d" refers to day; "atm" refers to atmosphere; "sat." refers to saturated; "s" refers to singlet, "d" refers to doublet; "t" refers to triplet; "q" refers to quartet; "m" refers to multiplet; "dd" refers to "doublet of doublets"; "br" refers to broad; "bs" refers to broad singlet, "LC" refers to liquid chromatograph; "MS" refers to mass spectroscopy; "ESI" refers to electrospray ionization; "CI" refers to chemical ionization; "RT" refers to retention time; "M" refers to molecular ion; "NMR" refers to nuclear magnetic resonance spectroscopy; "MHz" refers to megahertz.

EXAMPLES

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

Synthesis of Intermediates

Int-6: (R)-2-(2,5-difluorophenyl)pyrrolidine hydrochloride

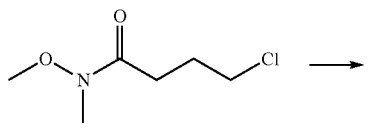

Int-1

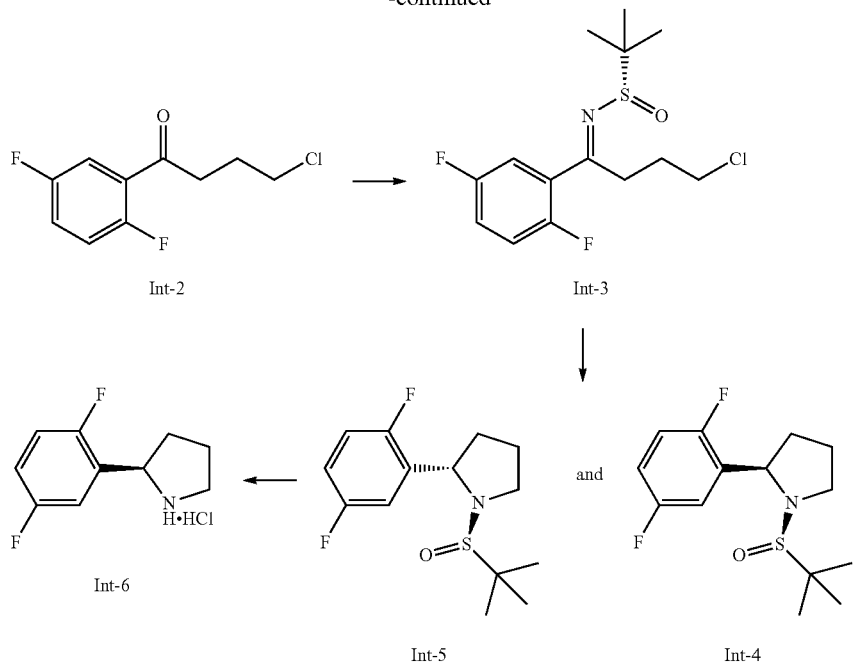

Int-1: 4-chloro-N-methoxy-N-methylbutanamide

Pyridine (101.28 g, 106.6 mL 1281.79 mmol) was added to a solution of N,O-dimethylhydroxylamine hydrochloride (50 g, 512.72 mmol) in DCM (800 mL) at 0° C. and stirring was continued for 15 min. Chlorobutyrylchloride (72.29 g, 512.72 mmol) was then added to this mixture and was stirred continuously at 0° C. for 2 h. The reaction mixture was diluted with DCM and the organic layer was washed with water followed by brine. The organic layer was separated; dried over anhydrous sodium sulphate and concentrated under reduced pressure to afford 79 g of the title compound as a pale brown liquid.

MS (ESI): m/z 166.1 (M+H)

Int-2: 4-chloro-1-(2,5-difluorophenyl)butan-1-one

2-Bromo-1,4-difluorobenzene (53.6 g, 277.74 mmol) in THF cooled to −50° C. was added to isopropyl magnesium chloride (2M in THF)(133 mL, 266 mmol). The reaction mixture thus obtained was warmed to 0° C. and stirred for 1 h. The reaction mixture was cooled again to −50° C. 4-chloro-N-methoxy-N-methylbutanamide (40 g, 241.52 mmol) in THF (200 mL) was added dropwise to this reaction mixture with stirring and the stirring was continued at 0° C. for 1 h. The reaction mixture was quenched with saturated aqueous NH$_4$Cl solution, extracted with ethylacetate. The organic layer collected was washed with water (500 mL) and then with brine solution, dried over anhydrous sodium sulfate and concentrated under reduced pressure to afford a crude liquid residue. The residue thus obtained was purified by column chromatography (using 60-120 silica gel and 5% EtOAc in Hexane as eluent) to afford 35 g of the title compound as a colourless liquid.

$^1$H NMR (300 MHz, CDCl$_3$) δ ppm 7.6-7.53 (1H, m), 7.26-7.09 (2H, m), 3.7 (2H, t) 3.22-3.14 (2H, m), 2.28-2.16 (2H, m).

Int-3: (S, E)-N-(4-chloro-1-(2, 5-difluorophenyl) butylidene)-2-methylpropane-2-sulfinamide Titanium (IV) ethoxide (54.77 g, 240.13 mmol) was added to a solution of 4-chloro-1-(2,5-difluorophenyl)butan-1-one (35 g, 160.09 mmol) and (S)-2-methylpropane-2-sulfinamide (29.1 g, 240.13 mmol) in THF (400 mL) with stirring. The mixture was stirred continuously at 70° C. for 16 h. Reaction mixture was then cooled to a temperature of 20-35° C., quenched with saturated aqueous NH$_4$Cl solution, diluted with ethylacetate and filtered. The filtrate was washed with water followed by brine solution. The organic layer was separated, dried over anhydrous sodium sulfate and concentrated under reduced pressure to afford 44.5 g of the title compound as a colourless liquid.

MS (ESI): m/z 322.3 (M+H)

Int-4: (R)-1-((S)-tert-butylsulfinyl)-2-(2, 5-difluorophenyl) pyrrolidine and Int-5: (S)-1-((S)-tert-butyl-sulfinyl)-2-(2, 5-difluorophenyl) pyrrolidine (S,E)-N-(4-chloro-1-(2,5-difluorophenyl)butylidene)-2-methylpropane-2-sulfinamide (44 g, 136.72 mmol) in THF (500 mL) was cooled to −78° C. and to which was added cold (−78° C.) Lithium triethylborohydride (1M in THF) (17.38 g, 165 mL, and 134.67 mmol) dropwise and stirring was continued at −78° C. for 3 h. LiHMDS (1M in THF) (25.26 g, 150 mL, 150 mmol) was then added and stirring was continued at −78° C. to 0° C. for 2 h. The resultant reaction mixture was quenched with saturated NH$_4$Cl solution, diluted with ethylacetate. The ethylacetate layer separated was washed with water followed by brine solution, dried over anhydrous sodium sulphate and concentrated under reduce pressure to afford the crude residue. The residue thus obtained was purified by column chromatography twice (using initially with 60-120 silicagel and 15% EtOAC in Hexane as eluent and again with 230-400 silicagel and 12-14% EtOAc in Hexane as eluent) to afford 14.5 g of the title compound (R)-1-((S)-tert-butylsulfinyl)-2-(2, 5-difluorophenyl) pyrrolidine as a pale brown liquid.

$^1$H NMR (300 MHz, CDCl$_3$) δ ppm 7.1-6.85 (3H, m), 5.0 (1H, t) 3.93-3.85 (1H, m), 3.02-2.94 (1H, m), 2.32-2.2 (1H, m), 2.0-1.72 (3H, m), 1.16 (9H, s)

and 4 g of the title compound (S)-1-((S)-tert-butylsulfinyl)-2-(2, 5-difluorophenyl) pyrrolidine.

H NMR (300 MHz, CDCl$_3$) $^1$H NMR (300 MHz, CDCl$_3$) δ ppm 7.1-6.8 (3H, m), 5.42-5.2 (1H, d, J=7.5 Hz), 2.3-2.05 (1H, m), 2.0-1.65 (4H, m), 1.1 (9H, s).

Int-6: (R)-2-(2,5-difluorophenyl) pyrrolidine hydrochloride

4M HCl solution (in Dioxane) (75 mL) was added to stirred solution of (R)-1-((S)-tert-butylsulfinyl)-2-(2, 5-difluorophenyl) pyrrolidine (15 g, 52.19 mmol) in Dioxane (25 mL) and stirring was continued at 20-35° C. for 4 h. After which the reaction mixture was concentrated under reduced pressure to afford the crude product. The crude product was purified by washing with diethyl ether to afford 7.5 g of the title compound as a white solid.

MS (ESI): m/z 184 (M+H)

Int-10: 2-(2,5-difluorophenyl)pyrrolidine

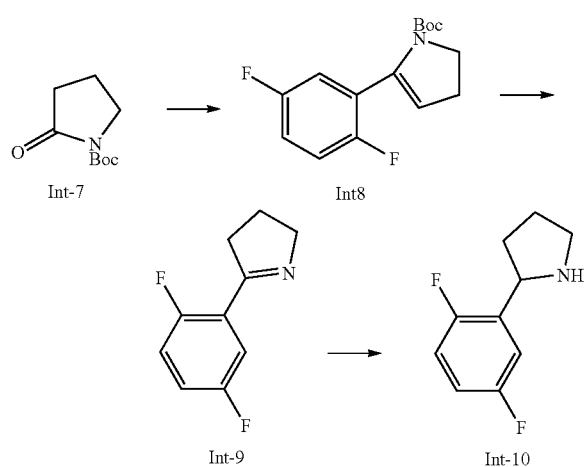

Int-7: tert-butyl 2-oxopyrrolidine-1-carboxylate

Di-tert-butyldicarbonate (154 g, 154 mL, 704 mmol) was added to solution of 2-Pyrrolidinone (50 g, 587 mmol) and DMAP (36 g, 293.7 mmol) in acetonitrile (500 mL) at 0-5° C. and stirring was continued at 20-35° C. for 2 h. Reaction mixture was concentrated under reduced pressure to afford the residue, which was diluted with EtOAc, washed it with water, dried over anhydrous sodium sulphate and concentrated under reduced pressure to afford 73 g of the title compound.

Int-8: tert-butyl 5-(2,5-difluorophenyl)-2,3-dihydro-1H-pyrrole-1-carboxylate 2.0 M Isopropyl magnesium chloride solution in THF (163 mL, 324.3 mmol) was added to a solution of 2-bromo-1,4-difluorobenzene (62.5 g, 324.3 mmol) in THF (350 mL) at −40° C. and stirring was continued at 5° C. for 1 h. tert-Butyl 2-oxopyrrolidine-1-carboxylate (Step-1)(73 g, 392 mmol) in THF (150 mL) was added dropwise to above reaction mixture at −40° C. and stirring was continued at 10° C. for 2 h. Reaction mixture was quenched with saturated NH$_4$Cl solution, extracted with EtOAc, dried over anhydrous sodium sulphate and concentrated under reduced pressure to afford 76 g of the title compound.

Int-9: 5-(2,5-difluorophenyl)-3,4-dihydro-2H-pyrrole

TFA (108 g, 940 mmol) was added to a solution of tert-butyl 5-(2,5-difluorophenyl)-2,3-dihydro-1H-pyrrole-1-carboxylate (53 g, 188 mmol) in DCM (300 mL) at 0° C. and stirring was continued at 20-35° C. for 2 h. The reaction mixture was concentrated under reduced pressure to afford the crude, which was diluted with EtOAc, washed with saturated NaHCO$_3$ solution, dried over anhydrous sodium sulphate to afford 28.5 g of the title compound.

MS (ESI): m/z 181.9 (M+H)

Int-10: 2-(2,5-difluorophenyl)pyrrolidine

NaBH$_4$(12 g, 314.9 mmol) was added to a solution of 5-(2,5-difluorophenyl)-3,4-dihydro-2H-pyrrole (28.5 g, 157.4 mmol) in a mixture of MeOH:H$_2$O (4:1, 250 mL) and stirring was continued at 25-35° C. for 2 h. The reaction mixture was quenched with 1N aqueous HCl solution and basified with 2N aqueous NaOH solution, extracted with DCM, dried over anhydrous sodium sulphate and concentrated under reduced pressure to afford 23 g of the title compound.

MS (ESI): m/z 184 (M+H)

Synthesis of ethyl 5-bromo-4-fluoropyrazolo[1,5-a]pyridine-3-carboxylate (Int-14)

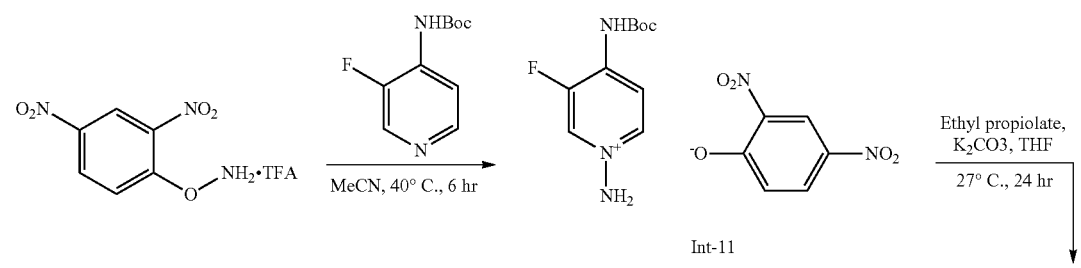

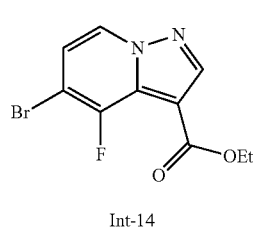 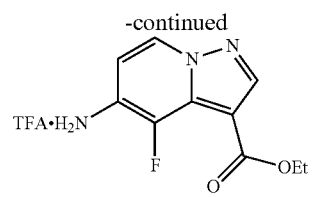 

Int-14 ← (NaNO₂, CuBr, Aq. HBr) ← Int-13 ← (TFA, DCM, RT, 12 hr) ← Int-12

Int-11: 1-amino-4-((tert-butoxycarbonyl)amino)-3-fluoropyridin-1-ium-2,4-dinitrophenolate Int-13: 3-(ethoxycarbonyl)-4-fluoropyrazolo[1,5-a]pyridin-5-aminium 2,2,2-trifluoroacetate

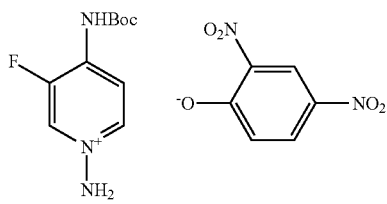

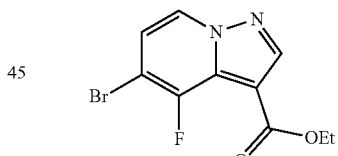

A solution of tert-butyl (3-fluoropyridin-4-yl)carbamate (25.0 g, 125 mmol) in MeCN (200 ml), was added O-(2,4-dinitrophenyl) hydroxylamine (26.64 g, 125 mmol) in MeCN (200 ml), drop wise over 30 min at RT, reaction mass was stirred at 40° C. for 12 hrs, reaction mass was concentrated at temperature below 40° C. under reduced pressure to afford Int-11 (50 g) which was used in the next step without further purification.

To a solution of ethyl 5-((tert-butoxycarbonyl)amino)-4-fluoropyrazolo[1,5-a]pyridine-3-carboxylate (7 g, 21 mmol) in DCM (60 mL), TFA (12 g, 108 mmol) was added at 0-5° C. drop wise over a period of 30 min, then stirred at room temperature for 2 hrs, reaction mass was concentrated at temperature below 40° C. under reduced pressure to afford the title compound (7 g) which was used in the next step without further purification, MS m/z 223.2 (M+)

Int-12: Ethyl 5-((tert-butoxycarbonyl)amino)-4-fluoropyrazolo[1,5-a]pyridine-3-carboxylate Int-14: Ethyl 5-bromo-4-fluoropyrazolo[1,5-a]pyridine-3-carboxylate

K₂CO₃ (36.96 g, 267 mmol) was added to a solution of 1-amino-4-((tert-butoxycarbonyl)amino)-3-fluoropyridin-1-ium 2,4-dinitrophenolate (50 g, 121 mmol) in THF (500 mL) at 28° C. and continued stirring at same temperature for 30 min. Ethyl propiolate (14.3 g, 145 mmol) was added to above solution and stirring was continued at 28° C. for 16 hr. Reaction mixture was filtered to remove the salt, filtrate collected was diluted with EtOAc washed it with water followed by brine, dried over anhydrous sodium sulphate and concentrated under reduced pressure to afford crude. The crude obtained was purified by column purification (using 60-120 silicagel and 10% EtOAc in Hexane as eluant) to afford the title compound.

MS m/z 323.9 (M+H)

NaNO₂ (2.26 g, 32.89 mmol) in water (7 mL) was added dropwise at 0° C. to a solution of 3-(ethoxycarbonyl)-4-fluoropyrazolo[1,5-a]pyridin-5-aminium 2,2,2-trifluoroacetate (7 g, 97.5 mmol) in aq. 47% HBr (56 mL) and continued stirring at same temperature for 30 min. CuBr (6.29 g, 44 mmol) in aq. 47% HBr (56 mL) was added dropwise to above solution at 0° C. and stirring was continued at 28° C. for 1 hr. Reaction mixture was quenched with ice water, extracted into EtOAc, washed it with water followed by brine, dried over anhydrous sodium sulphate and concentrated under reduced pressure to afford crude. The crude obtained was purified by column purification (using 60-120 silicagel and 5% EtOAc in Hexane as eluant) to afford ethyl 5-bromo-4-fluoropyrazolo[1,5-a]pyridine-3-carboxylate. NMR (300 MHz, DMSO-d₆) δ 9.45-9.43 (d, 1H), 8.51 (s, 1H), 8.33-8.30 (d, 1H), 4.35-4.28 (m, 2H), 1.36-1.31 (t, 3H).

Int-15: 2-methylpropane-2-sulfonamide

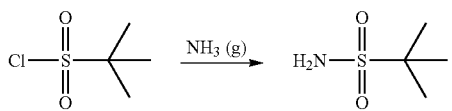

Ammonia gas was purged into t-butylsulfonyl chloride (500 mg, 3.2 mmol) in THF (5 mL) at −50° C. for 15 minutes and stirring was continued at 20-35° C. for 16 h. The solid precipitate obtained was filtered; the filtrate collected was concentrated under reduced pressure to afford 350 mg of the title compound. $^1$H NMR (400 MHz, DMSO-$d_6$) δ ppm 6.71 (2H, bs), 1.38 (9H, s).

The following sulfonamides (Int-16 to Int-19) are prepared following the similar procedure as mentioned in Int-15 using the appropriate sulfonyl chloride.

| Intermediate | Structure | IUPAC name | ESMS (M + H) |
|---|---|---|---|
| Int-16 | 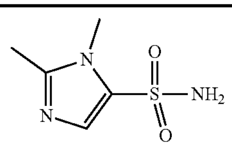 | 1,2-dimethyl-1H-imidazole-5-sulfonamide | m/z 176 |
| Int-17 | 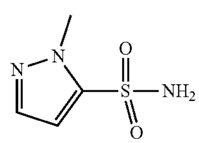 | 1-methyl-1H-pyrazole-5-sulfonamide | m/z 162 |
| Int-18 | | benzyl 4-sulfamoyl-piperidine-1-carboxylate | m/z 299 |
| Int-19 | | 6-methoxy-pyridine-3-sulfonamide | m/z 189 |

Int-20: 4-(3-hydroxypyrrolidin-1-yl) benzene sulfonamide

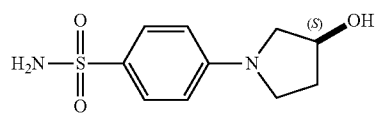

A solution of 4-fluorobenzene sulfonamide (0.39 g, 2.22 mmol) and S(−)-3-hydroxypyrrolidine (0.32 g, 2.67 mmol) in DMSO (2 mL) was heated to 100° C. for 20 h. Reaction was cooled to 25° C. and quenched with cold water. The separated solid was filtered and washed with water and dried to afford 4-(3-hydroxypyrrolidin-1-yl) benzene sulfonamide (Int-20) as a white solid. MS (ESI): m/z 243.1 (M+H).

The sulfonamides Int-21 to Int-23 are synthesized following the procedure as mentioned in Int-20 using the appropriate aryl halides and amines.

| Intermediate | Structure | IUPAC name | ESMS (M + H) |
|---|---|---|---|
| Int-21 | 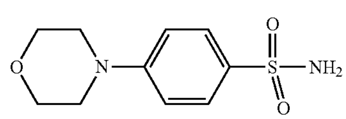 [SMILES: NS(=O)(=O)c1ccc(N2CCOCC2)cc1] | 4-morpholinobenzene-sulfonamide | m/z 243 |
| Int-22 | 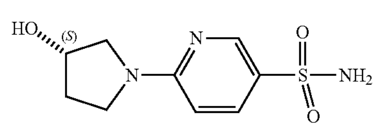 | (S)-6-(3-hydroxypyrrolidin-1-yl)pyridine-3-sulfonamide | m/z 244 |
| Int-23 | 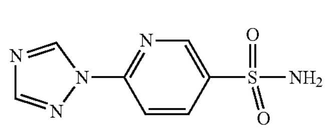 [SMILES: NS(=O)(=O)c1ccc(-n2cncn2)nc1] | 6-(1H-1,2,4-triazol-1-yl)pyridine-3-sulfonamide | m/z 226 |

Int-24: Benzyl cyclopropanesulfonate

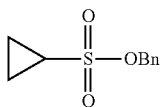

Cyclopropyl sulfonyl chloride (2 g, 14.2 mmol) was added drop-wise at 0° C. to a solution of Benzyl alcohol (2.1 g, 28.4 mmol) and Pyridine (2.35 g, 29.8 mmol) in DCM (20 mL) and continued stirring at 25° C. for 16 h. The reaction mixture was diluted with DCM (100 mL), washed with 1N aq.HCl solution followed by water and brine; Organic layer collected was dried over anhydrous sodium sulphate and concentrated under reduced pressure to afford the Benzyl cyclopropanesulfonate. $^1$H NMR (300 MHz, CD$_3$OD) δ ppm 4.3-4.1 (2H, t), 2.7-2.6 (1H, m), 1.8-1.6 (2H, m), 1.6-1.4 (2H, m), 1.2-1.1 (4H, m), 1.0-0.9 (3H, t).

Int-25: Benzyl 1-methylcyclopropane-1-sulfonate

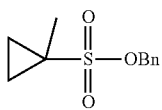

n-BuLi (0.78 g, 12.25 mmol) was added drop-wise at −78° C. to a solution of Benzylcyclopropane sulfonate (2.0 g, 11.2 mmol) in THF (20 mL) and continued stirring at the same temperature for 10 min. CH$_3$I (3.98 g, 28.0 mmol) was added at −78° C., allowed the reaction to warm to 0° C. with stirring for 30 min. The reaction mixture was quenched with ice cold water, diluted with ethylacetate (100 mL), organic layer collected was dried over anhydrous sodium sulphate and concentrated under reduced pressure to afford the crude. The crude was purified by column chromatography (using silica gel and 4% ethyl acetate in Hexane as eluent) to afford benzyl 1-methylcyclopropane-1-sulfonate (Int-25). $^1$H NMR (300 MHz, CD$_3$OD) δ ppm 4.2-4.1 (2H, t), 1.7-1.6 (2H, m), 1.4 (3H, s), 1.5-1.3 (2H, m), 1.3-1.2 (2H, m), 1.0-0.9 (2H, m), 0.9 (3H, t).

Int-26: Potassium 1-methylcyclopropane-1-sulfonate

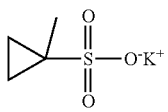

KSCN (2.48 g, 25.5 mmol) was added to a solution of Benzyl 1-methylcyclopropane-1-sulfonate (4.9 g, 25.5 mmol) in DME/H$_2$O (1:1, 120 mL) and continued stirring at 100° C. for 16 h. Reaction mixture was concentrated under reduced pressure and the residue was washed with n-Pentane and dried to afford Potassium 1-methylcyclopropane-1-sulfonate (Int-26) which was used in the next step without further purification.

Int-27: 1-Methylcyclopropane-1-sulfonamide

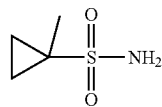

To a solution of Potassium 1-methylcyclopropane-1-sulfonate (4.44 g, 25.5 mmol) in THF (50 mL) at 0° C. was added POCl$_3$ (11.7 g, 76.5 mmol) with stirring maintaining the same temperature for 30 min. DIPEA (9.8 g, 76.5 mmol) was added to above mixture and continued stirring at 25° C. for 2 h. Reaction mixture was quenched with ice cold water, extracted into diethyl ether (3×100 mL), dried over anhydrous sodiumsulphate to afford 1-methylcyclopropane-1-sulfonylchloride in diethyl ether. The above dried ethereal solution of 1-methylcyclopropane-1-sulfonylchloride was cooled to −78° C. and purged in with NH$_3$ gas for 30 min. and slowly allowed the reaction mixture to warm to 25° C. with stirring for 16 h. Reaction mixture was filtered through celite bed and the filtrate was concentrated under reduced pressure and the crude thus obtained was washed with n-pentane to afford 1-methylcyclopropane-1-sulfonamide (Int-27) as pale brown solid. $^1$H NMR (300 MHz, DMSO-d6) δ ppm 6.7 (2H, s), 1.4 (3H, s), 1.1-1.0 (2H, m) 0.7-0.6 (2H, m).

Int-28: 1-(4-Fluorobenzyl)cyclopropane-1-sulfonamide

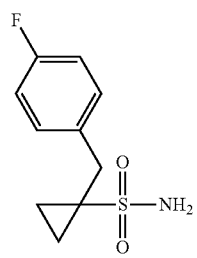

The title compound Int-28 was prepared by the similar method as mentioned in Int-27 except in Int-25, 4-Fluoro benzyl bromide was used in place of CH$_3$I to afford 1.1 g of Int-28 as pale brown solid. $^1$H NMR (300 MHz, DMSO-d6) δ ppm 7.3-7.2 (5H, m), 6.9 (2H, s), 3.3 (2H, s) 1.2-1.1 (2H, m), 0.5-0.4 (2H, m).

Int-29: 1-ethylcyclopropane-1-sulfonamide

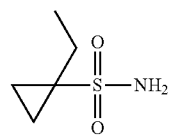

The title compound Int-29 was prepared by the similar method as mentioned in Int-27 except in Int-25, ethyl iodide was used in place of CH₃I to afford 0.9 g of Int-29 as pale brown solid.

Int-30: N-Ethyl-N-methyl sulfamide

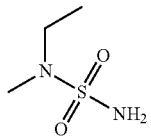

Int-30

N-Ethyl-N-methyl amine (2.95 g, 50 mmol) was added to a solution of Sulfamide (4 g, 41.6 mmol) in 1,4-Dioxane (40 mL) and continued stirring at 110° C. for 16 h. Reaction mass was concentrated under reduced pressure to afford the crude, which was purified by column purification (using neutral alumina and 10-70% ethyl acetate in Hexane as eluent) to afford N-Ethyl-N-methyl sulfamide (Int-30) as pale yellow oil. ¹H NMR (300 MHz, DMSO-d6) δ ppm 6.7 (2H, s), 3.1-2.3 (2H, m), 2.6 (3H, s), 1.2-1.0 (3H, t).

Following sulfamides Int-31 and Int-35 were made using above method except changing the amine

| Intermediate | Structure | IUPAC name | MS (ESI) (M + H) |
|---|---|---|---|
| 31 | 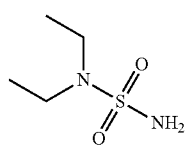 | N,N-Diethylsulfamide | m/z 153.07 |
| 32 | 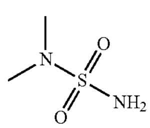 | N,N-Dimethyl-sulfamide | m/z 125.03 |
| 33 | 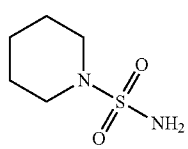 | Piperidine-1-sulfonamide | m/z 165.07 |
| 34 | 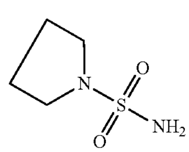 | Pyrrolidine-1-sulfonamide | m/z 151.03 |
| 35 | 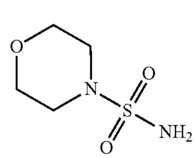 | Morpholine-4-sulfonamide | m/z 167.03 |

Int-39: N-Ethyl-N-cyclopropyl sulfamide

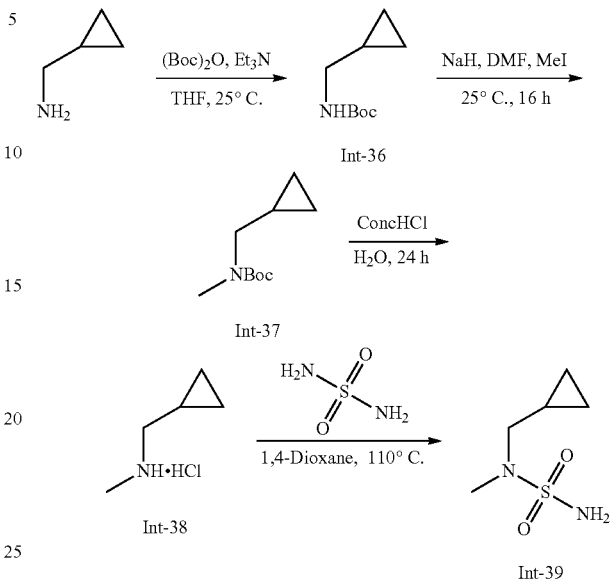

Int-36: Tert-butyl (cyclopropylmethyl) carbamate

Int-36

Di-tert-butyldicarbonate (6.13 g, 6.46 mL, 28.08 mmol) was added to solution of Cyclopropyl methyl amine (2 g, 28.1 mmol), Et₃N (2.84 g, 28.1 mmol) and DMAP (0.34 g, 2.8 mmol) in THF (20 mL) at 0-5° C. and stirring was continued at 25° C. for 3 h. Reaction mixture was diluted with ethyl acetate and the organic layer was washed with brine, followed by water, dried over anhydrous sodium sulphate and concentrated under reduced pressure to afford tert-butyl (cyclopropylmethyl) carbamate (Int-36) as pale yellow oil. ¹H NMR (300 MHz, DMSO-d6) δ ppm 7.0-6.7 (2H, bs), 2.9-2.7 (2H, t), 1.3 (9H, s), 0.9-0.8 (1H, bs), 0.4-0.3 (2H, m), 0.1-0.05 (2H, m).

Int-37: Tert-butyl (cyclopropylmethyl) (methyl) carbamate

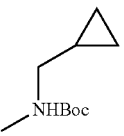

Int-37

A solution of tert-butyl (cyclopropylmethyl)carbamate (4 g, 23.4 mmol) in DMF (35 mL) was added to a suspension of NaH (60% suspension in mineral oil) (0.58 g, 25.7 mmol)

in DMF (5 mL) at 0-5° C., to it was added Iodomethane (2.5 mL, 40 mmol) and stirring was continued at 25° C. for 16 h. Reaction mixture was quenched with cold water, extracted with ethyl acetate (3×50 mL), dried over anhydrous sodium sulphate and concentrated under reduced pressure to afford the crude, which was purified by flash chromatography (Biotage, Column: silica gel 12 g pack size, solid load, Mobile Phase: EtOAc in n-Hexane: 0 to 5% as eluent) to afford tert-butyl (cyclopropylmethyl)(methyl)carbamate (Int-37) as pale yellow oil. $^1$H NMR (300 MHz, DMSO-d6) δ ppm 3.0-2.9 (2H, d), 2.85 (3H, s), 1.4 (9H, s), 0.9-0.7 (1H, bs), 0.5-0.3 (2H, m), 0.2-0.05 (2H, m).

Int-38:1-Cyclopropyl-N-methylmethanamine hydrochloride

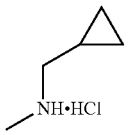

Int-38

Conc.HCl (0.6 mL) was added to a solution of tert-butyl (cyclopropylmethyl)(methyl)carbamate (2 g, 10.8 mmol) in H$_2$O (20 mL) at 0-5° C. and stirring was continued at 25° C. for 48 h. Reaction mixture was concentrated under reduced pressure to afford 1-Cyclopropyl-N-methylmethanamine hydrochloride (Int-38) (1.24 g cr.). $^1$H NMR (300 MHz, DMSO-d6) δ ppm 2.9-2.8 (2H, d), 2.7 (3H, s), 1.1-1.0 (1H, m), 0.7-0.6 (2H, m), 0.5-0.3 (2H, m), 0.4-0.3 (2H, m).

Int-39: N-Ethyl-N-cyclopropyl sulfamide

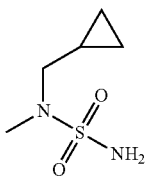

Int-39

The title compound Int-39 was synthesized by a similar method as that of Int-30 except Int-38 was used in place of N-Ethyl-N-methyl amine to afford N-Ethyl-N-cyclopropyl sulfamide (Int-39) as pale yellow oil. $^1$H NMR (300 MHz, DMSO-d6) δ ppm 6.7 (2H, s), 2.8-2.7 (2H, d), 2.7 (3H, s), 1.0-0.9 (1H, m), 0.5-0.4 (2H, m), 0.2-0.1 (2H, m).

Int-40: (R)-2-(2-Chloro-5-fluorophenyl) pyrrolidine hydrochloride (Int-40)

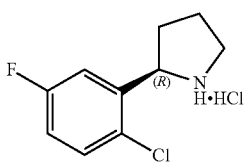

Int-40

The title compound was prepared by the method similar to that mentioned for Int-6 using 2-chloro-5-fluoro-1-bromobenzene in place of 2,5-dilfuoro-1-bromobenzene to afford the title compound (Int-40) as pale pink solid. MS (ESI): m/z 200.1 (M+H).

Int-41: (R)-2-(5-Fluoro-2-methoxyphenyl) pyrrolidine hydrochloride

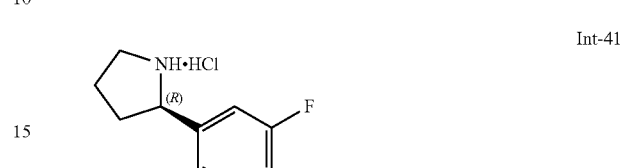

The title compound was prepared by the method similar to that mentioned for Int-6 using 2-Bromo-4-fluoro-anisole in place of 2,5-dilfuoro-1-bromobenzene to afford the title compound Int-41 as white solid. MS (ESI): m/z 195.9 (M+H).

Int-42: 2-Bromo-4-fluoro-1-(2-methoxyethoxy) benzene

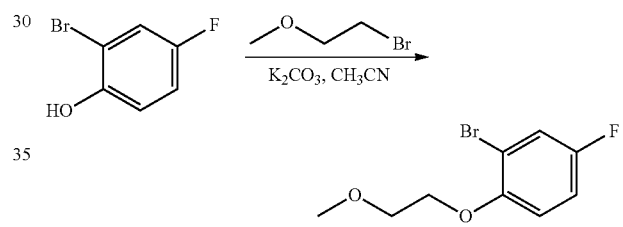

Int-42

1-bromo-2-methoxyethane (5.49 g, 39.5 mmol) was added to a mixture of 2-bromo-4-fluoro phenol (5 g, 26.18 mmol) and K$_2$CO$_3$ (11.5 g, 83.25 mmol) in CH$_3$CN (41.5 mL) and continued stirring at 80° C. for 16 hr. The reaction mixture was quenched with 1M aq.NaOH solution, extracted with diethyl ether (3×100 mL), dried over anhydrous sodium sulphate and concentrated under reduced pressure to afford the crude, which was purified by column chromatography (using silica gel and 2% ethyl acetate in hexane as eluent) to afford the desired compound (Int-42). $^1$H NMR (300 MHz, CDCl$_3$) δ ppm 7.3 (1H, m), 6.9 (1H, m), 6.7 (1H, m), 4.1 (2H, t), 3.8 (2H, t), 3.5 (3H, s).

Int-43: (R)-2-(5-Fluoro-2-(2-methoxyethoxy) phenyl) pyrrolidine hydrochloride

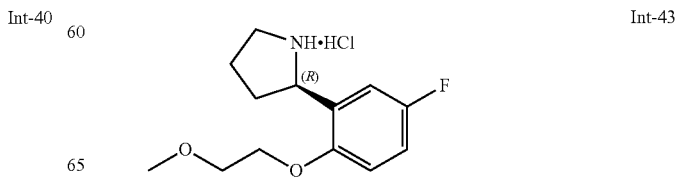

Int-43

The title compound (Int-43) was prepared by the method similar to that mentioned for Int-6 using 2-bromo-4-fluoro-1-(2-methoxyethoxy)benzene (Int-42) in place of 2,5-dilfuoro-1-bromobenzene to afford the desired compound (Int-43) as a solid. MS (ESI): m/z 240.2 (M+H).

Int-44: (R)-2-(3,5-Difluorophenyl) pyrrolidine hydrochloride

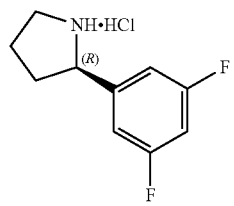

The title compound (Int-44) was prepared by the method similar to that mentioned for Int-6 using 3,5-difluoro-1-bromobenzene in place of 2,5-dilfuoro-1-bromobenzene to afford the title compound (Int-44) as white solid. MS (ESI): m/z 184 (M+H).

Int-46: (R)-2-(3-(difluoromethoxy)-5-fluorophenyl) pyrrolidine hydrochloride

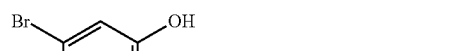
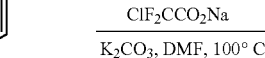
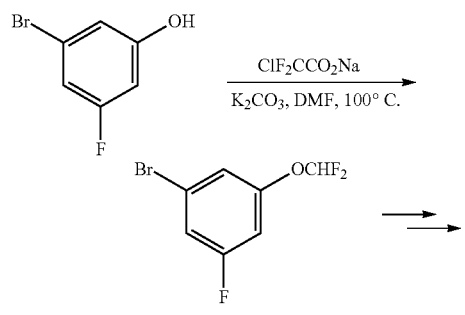

Int-45: 1-Bromo-3-(difluoromethoxy)-5-fluorobenzene

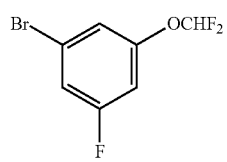

To a solution of 3-bromo-5-fluorophenol (0.5 g, 2.6 mmol) in DMF (4.5 mL) was added K₂CO₃ (0.9 g, 6.54 mmol) and stirred at 25° C. for 10 min. Water (0.5 mL) was added to the above mixture followed by addition of 2-Chloro-2,2,-difluoroacetic acid sodium salt (0.6 g, 3.93 mmol) and stirring was continued at 100° C. for 3 h. The reaction mixture was cooled to 25° C. and diluted with ethyl acetate, washed with brine, dried over anhydrous sodium sulphate and concentrated under reduced pressure to afford the crude, which was purified by column chromatography (using silica gel and 2% ethyl acetate in Hexane as eluent) to afford the desired compound (Int-45). ¹H NMR (400 MHz, CDCl₃) δ ppm 7.2-6.9 (2H, m), 6.8-6.7 (1H, d), 6.7-6.2 (1H, m).

Int-46: (R)-2-(3-(Difluoromethoxy)-5-fluorophenyl) pyrrolidine hydrochloride

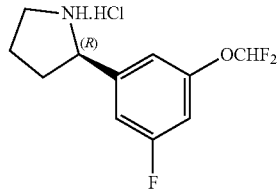

The title compound (Int-46) was prepared by the method similar to that mentioned for Int-6, using 1-bromo-3-(difluoromethoxy)-5-fluorobenzene (Int-45) in place of 2,5-dilfuoro-1-bromobenzene to afford the title compound (Int-46) as a thick brown liquid. MS (ESI): m/z 232.2 (M+H).

Int-47: Synthesis of (2R,4S)-2-(2, 5-difluorophenyl)-4-fluoropyrrolidine hydrochloride

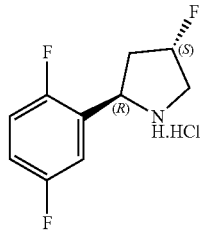

The title compound was prepared by the method similar to that mentioned in WO2009140128 to afford Int-47 as off white solid. MS (ESI): m/z 202.1 (M+H).

Int-48: Synthesis of (R)-2-(2, 5-difluorophenyl)-4, 4-difluoropyrrolidine hydrochloride

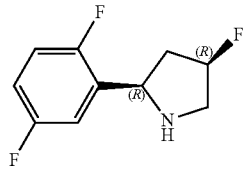

The title compound Int-48 was prepared by following the method similar to that mentioned in WO2009140128. MS (ESI): m/z 220.4 (M+H).

Int-56: Synthesis of 2-(7-fluoro-2, 3-dihydrobenzo[b][1, 4]dioxin-5-yl)pyrrolidine

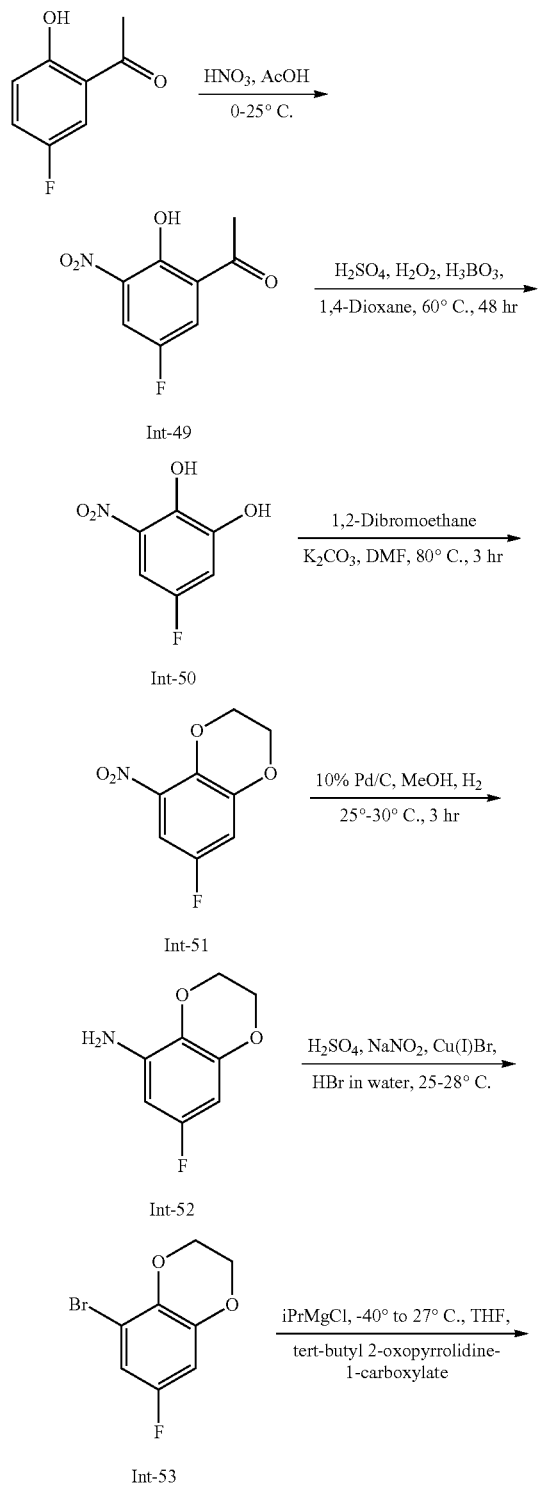

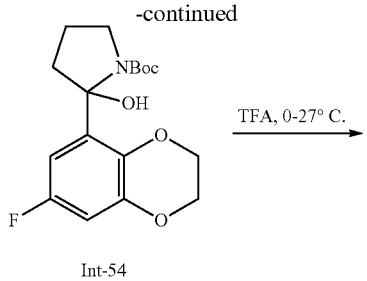

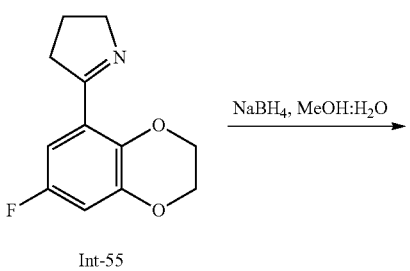

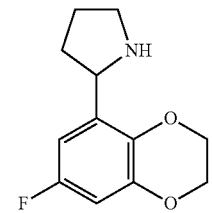

Int-49: 1-(5-Fluoro-2-hydroxy-3-nitrophenyl)ethanone

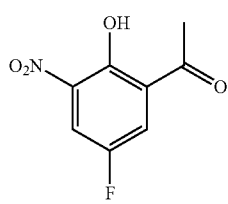

Conc. $HNO_3$ (22.49 g, 357 mmol) was added to a solution 1-(5-fluoro-2-hydroxyphenyl) ethanone (50 g, 325 mmol) in acetic acid (300 mL) at 0° C. and stirring was continued at 20° C. for 3 h. The reaction mixture was quenched with ice cold water. The separated solid was filtered and washed with cold water and dried to afford 1-(5-fluoro-2-hydroxy-3-nitrophenyl) ethanone (Int-49) as pale yellow solid. $^1$H NMR (400 MHz, DMSO-d6) δ ppm 12.6 (1H, s), 8.3-8.2 (1H, dd), 8.2-8.1 (1H, dd), 2.7 (3H, s).

Int-50: 5-Fluoro-3-nitrobenzene-1,2-diol

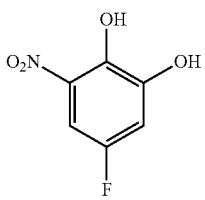

Int-50

$H_2SO_4$ (50 mL) was added to a solution of $H_3BO_3$ (89.3 g, 1.4 mol) in 1,4-Dioxane (300 mL) at 0° C. and stirred at 28° C. for 1 h. 1-(5-fluoro-2-hydroxy-3-nitrophenyl) ethanone (50 g, 289 mmol) was added portion wise to the above solution over 1 h, maintaining the temperature at 0° C., after addition was complete, the reaction mixture was warmed to 25° C. and stirred for 16 h. Reaction mixture was quenched with cold water, solid separated was collected by filtration. The solid was suspended in diethyl ether (500 mL) and filtered to remove insoluble inorganic mass, ether layer was washed with cold water (2 to 3 times) followed by brine, dried over anhydrous sodium sulphate and concentrated under reduced pressure to afford the crude sticky solid. The crude solid was triturated over n-Hexane and filtered to afford 5-fluoro-3-nitrobenzene-1,2-diol (Int-50) as pale yellow solid. MS (ESI): m/z 171.9 (M-1).

Int-51: 7-Fluoro-5-nitro-2, 3-dihydrobenzo[b] [1, 4] dioxine

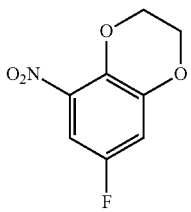

Int-51

$K_2CO_3$ (15.27 g, 110.6 mmol) was added to a solution of 5-fluoro-3-nitrobenzene-1,2-diol (5 g, 28.9 mmol) in DMF (35 mL) followed by the addition of 1,2-Dibromoethane (13.63 g, 6.25 mL, 72.5 mmol) and stirring was continued at 80° C. for 2 h. Reaction mixture was diluted with ethyl acetate, washed with cold water, dried over anhydrous sodium sulphate and concentrated under reduced pressure to afford the crude, which was purified by MPLC (silica gel, Mobile Phase: ethyl acetate in n-Hexane 0 to 5% as eluant) to afford 7-fluoro-5-nitro-2,3-dihydrobenzo[b] [1,4]dioxine (Int-51) as pale yellow solid. $^1$H NMR (300 MHz, CDCl$_3$) δ ppm 7.3-7.2 (1H, dd), 6.9-6.8 (1H, dd), 4.4 (4H, s).

Int-52: 7-Fluoro-2, 3-dihydrobenzo[b] [1, 4] dioxin-5-amine

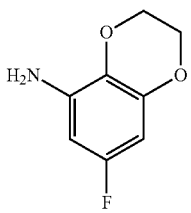

Int-52

10% Pd/C (400 mg) was added to a solution of 7-fluoro-5-nitro-2,3-dihydrobenzo[b][1,4]dioxine (2.0 g, 10 mmol) in methanol (50 mL) and stirring was continued at 25° C. under H$_2$ atmosphere for 3 h. The reaction mixture was filtered over celite bed and washed with methanol. The filtrate and the washings were concentrated under reduced pressure to afford 7-fluoro-2,3-dihydrobenzo[b][1,4]dioxin-5-amine (Int-52) as pale brown liquid. MS (ESI): m/z 170.1 (M+H).

Int-53: 5-Bromo-7-fluoro-2, 3-dihydrobenzo[b] [1, 4] dioxine

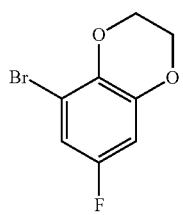

Int-53

NaNO$_2$ (2.69 g, 39.9 mmol) in water (20 mL) was added slowly at 0° C. to a solution of 7-fluoro-2,3-dihydrobenzo[b][1,4]dioxin-5-amine (4.5 g, 26 mmol) in aq. 47% HBr (20 mL) and continued stirring at same temperature for 30 min. The above diazonium salt solution was added slowly to a solution of CuBr (5.7 g, 39.9 mmol) in aq. 47% HBr (25 mL) at 0° C. and stirred at 25° C. for 30 min. Reaction mixture was quenched with ice water, extracted with ethyl acetate (3×50 mL), washed it with water followed by brine, dried over anhydrous sodium sulphate and concentrated under reduced pressure to afford crude. The crude was purified by column purification (using silica gel and 0-5% ethyl acetate in Hexane as eluent) to afford 5-bromo-7-fluoro-2,3-dihydrobenzo[b] [1,4] dioxine (Int-53) (5.9 g). $^1$H NMR (300 MHz, CDCl$_3$) δ ppm 6.9-6.84 (1H, dd), 6.6-6.5 (1H, dd), 4.3-4.3 (4H, m).

Int-54: Tert-butyl-2-(7-fluoro-2,3-dihydrobenzo[b] [1,4]dioxin-5-yl)-2-hydroxypyrrolidine-1-carboxylate

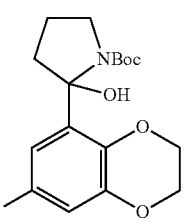

Int-54

A solution of isopropyl magnesium chloride in THF (2M, 5.39 mL, 10.78 mmol) was added to a solution of 5-bromo-7-fluoro-2, 3-dihydrobenzo[b] [1,4] dioxine (Int-53) (1 g, 4.31 mmol) in THF (10 mL) at −45° C. drop-wise and then allowed it to warm up to 5° C. over a period of 1 h. The reaction mixture was cooled again to −45° C. and a solution of tert-butyl 2-oxopyrrolidine-1-carboxylate (1.6 g, 8.62 mmol) in THF (10 mL) was added drop-wise maintaining the temperature at −45° C. The reaction mixture was warmed to 25° C. and stirred for 1 h and then quenched with saturated NH₄Cl solution (100 mL). The reaction mixture was extracted with ethyl acetate (3×30 mL) and the organic layer was dried over anhydrous sodium sulphate and concentrated under reduced pressure and purified by column chromatography (using silica gel and 20% ethyl acetate Hexane as eluent) to afford tert-butyl 5-(7-fluoro-2,3-dihydrobenzo[b][1,4]dioxin-5-yl)-2,3-dihydro-1H-pyrrole-1-carboxylate (Int-54). MS (ESI) m/z 340 (M-+1).

Int-55: 5-(7-Fluoro-2, 3-dihydrobenzo[b] [1, 4] dioxin-5-yl)-3,4-dihydro-2H-pyrrole

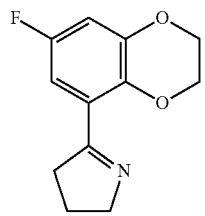

Int-55

TFA (0.09 mL, 1.18 mmol) was added to a solution of tert-butyl 5-(7-fluoro-2,3-dihydrobenzo[b][1,4]dioxin-5-yl)-2,3-dihydro-1H-pyrrole-1-carboxylate (0.04 g, 0.117 mmol) in DCM (5 mL) at 0° C. and stirring was continued at 25° C. for 3 h. Reaction mixture was concentrated under reduced pressure to afford the crude, which was diluted with ethyl acetate, washed with saturated NaHCO₃ solution, dried over anhydrous sodium sulphate to afford 5-(7-fluoro-2,3-dihydrobenzo[b][1,4]dioxin-5-yl)-3,4-dihydro-2H-pyrrole (Int-55). MS (ESI) m/z 222 (M+H)

Int-56: 2-(7-Fluoro-2, 3-dihydrobenzo[b][1,4]dioxin-5-yl)pyrrolidine

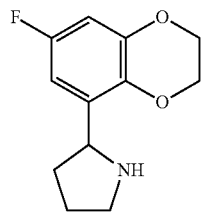

Int-56

NaBH₄ (0.25 g, 6.69 mmol) was added to a solution of 5-(7-fluoro-2,3-dihydrobenzo [b][1,4]dioxin-5-yl)-3,4-dihydro-2H-pyrrole (Int-55) (0.8 g, 3.34 mmol) in a mixture of MeOH and H₂O (3:1, 20 mL) and was stirred at 25° C. for 2 h. Reaction mixture was quenched with 1N aqueous HCl solution (50 mL) and basified with 2N aqueous NaOH solution to pH 8 and extracted with DCM (3×20 mL). The organic layer was dried over anhydrous sodium sulphate and concentrated under reduced pressure to afford 2-(7-fluoro-2, 3-dihydrobenzo[b] [1,4]dioxin-5-yl)pyrrolidine (Int-56). MS (ESI) m/z 224.5 (M+H).

Above enatiomeric mixture was separated in a prerprative chiral HPLC column (Chiral pak IC (10 mm×250 mm×5 u) flow: 7 mL/min; 95:5:Hexane:0.1% ethanolamine in EtOH (isocratic) to afford two isomer, 240 mg (Int-56A) and 233 mg (Int-56B)

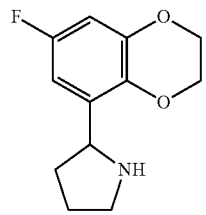

Int-56A Isomer-I

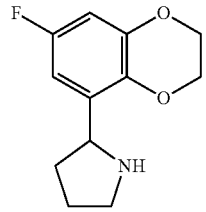

Int-56B Isomer-II

Int-57: (4R)-4-((tert-butyldimethylsilyl) oxy)-2-(2, 5-difluorophenyl) pyrrolidine hydrochloride

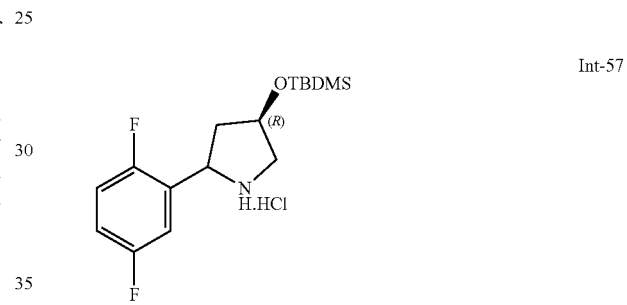

Int-57

TFA (0.27 mL, 0.414 g, 3.63 mmol) was added to a solution of (4R)-tert-butyl 4-((tert-butyldimethylsilyl) oxy)-2-(2, 5-difluorophenyl) pyrrolidine-1-carboxylate (0.5 g, 1.21 mmol) in DCM (10 mL) at 0° C. and stirring was continued at 28° C. for 2 hr. Reaction mixture was concentrated under reduced pressure to afford (4R)-4-((tert-butyldimethylsilyl) oxy)-2-(2, 5-difluorophenyl) pyrrolidine hydrochloride (Int-57). MS(ESI) m/z 200 (M-TBDMS+1, free base)

Int-58: Ethyl 5-((4R)-2-(2, 5-difluorophenyl)-4-hydroxypyrrolidin-1-yl) pyrazolo [1, 5-a] pyridine-3-carboxylate

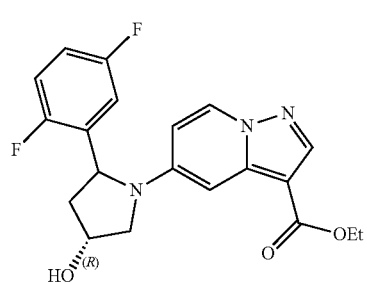

Int-58

The title compound (Int-58) was prepared by the method similar to that mentioned for Int-84, by using ethyl 5-bromopyrazolo [1, 5a] pyridine-3-carboxylate and (4R)-4-((tert-butyldimethylsilyl) oxy)-2-(2, 5-difluorophenyl) pyrrolidine hydrochloride (Int-57) to afford (0.26 g, crude) as white solid after in situ deprotection of OTBDMS group to hydroxyl moiety. MS (ESI) m/z 388.1 (M+H)

Int-59: Ethyl 5-((4R)-4-((tert-butyldimethylsilyl) oxy)-2-(2, 5-difluorophenyl) pyrrolidin-1-yl) pyrazolo [1, 5-a] pyridine-3-carboxylate

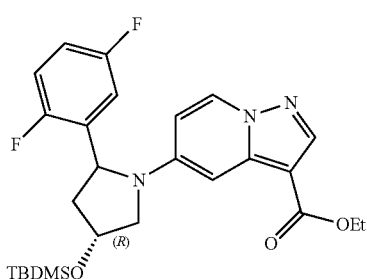

TBDMSCl (0.093 g, 0.62 mmol) was added at 0° C. to a solution of Ethyl 5-((4R)-2-(2,5-difluorophenyl)-4-hydroxypyrrolidin-1-yl) pyrazolo[1, 5-a] pyridine-3-carboxylate (Int-58) (0.2 g, 0.52 mmol) in DMF (5 mL) followed by Imidazole (0.1 g, 1.55 mmol) and continued stirring at 28° C. for 1 hr. The reaction mixture quenched with ice water, extracted into DCM, dried over anhydrous sodium sulfate and concentrated under reduced pressure to afford 5-((4R)-4-((tert-butyldimethylsilyl) oxy)-2-(2, 5-difluorophenyl) pyrrolidin-1-yl) pyrazolo [1, 5-a] pyridine-3-carboxylate (Int-59) (0.28 g, Crude) as Brown oil.

Int-60: Ethyl 5-((2R, 4R)-4-((tert-butyldimethylsilyl) oxy)-2-(2, 5-difluorophenyl) pyrrolidin-1-yl) pyrazolo [1, 5-a] pyridine-3-carboxylate (Isomer-I)

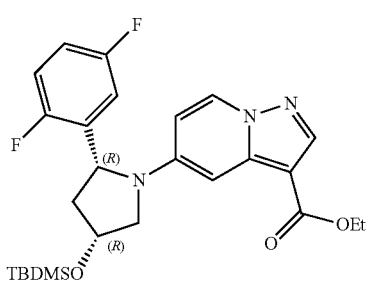

The diastereomeric mixture (Int-59) obtained was purified by Flash Chromatography (Biotage, Column: Silicagel 25 g pack size, Mobile Phase: EtOAc in n-Hexane: 0 to 12% as eluant) to afford ethyl 5-((2R, 4R)-4-((tert-butyldimethylsilyl) oxy)-2-(2, 5-difluorophenyl) pyrrolidin-1-yl) pyrazolo [1, 5-a] pyridine-3-carboxylate (Isomer-I) (Int-60) as yellow solid. MS(ESI) m/z 502.2 (M+H) and Int-61: Ethyl 5-((2S, 4R)-4-((tert-butyldimethylsilyl) oxy)-2-(2, 5-difluorophenyl) pyrrolidin-1-yl) pyrazolo [1, 5-a] pyridine-3-carboxylate (Isomer-II)

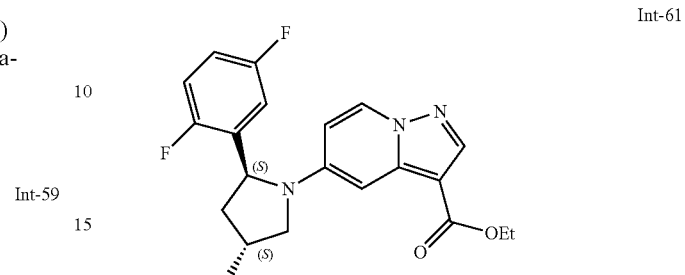

as yellow solid. MS(ESI) m/z 502 (M+H)

Int-62: 5-((2R, 4R)-2-(2, 5-difluorophenyl)-4-hydroxypyrrolidin-1-yl)pyrazolo [1, 5-a] pyridine-3-carboxylic acid

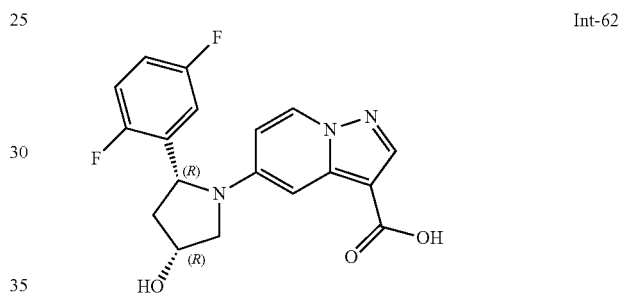

1M aq. solution of LiOH.H₂O (0.4 mL) was added to a stirred solution of ethyl 5-((2R, 4R)-4-((tert-butyldimethylsilyl) oxy)-2-(2, 5-difluorophenyl) pyrrolidin-1-yl) pyrazolo [1, 5-a] pyridine-3-carboxylate (Isomer-I) (Int-60) (0.07 g, 0.14 mmol) in EtOH (5 mL) and the stirring was continued at 90° C. for 8 h. The reaction mixture was concentrated under reduced pressure to afford the crude product. The crude product thus obtained was diluted with cold water, acidified with citric acid solution, filtered the solid precipitated to afford 5-((2R, 4R)-2-(2, 5-difluorophenyl)-4-hydroxypyrrolidin-1-yl) pyrazolo [1, 5-a] pyridine-3-carboxylic acid (Int-62) as yellow solid. MS (ESI): m/z 360 (M+H).

Int-63: Ethyl 5-(2-(7-fluoro-2, 3-dihydrobenzo [b] [1, 4] dioxin-5-yl) pyrrolidin-1-yl) pyrazolo [1, 5-a] pyridine-3-carboxylate (Isomer-I)

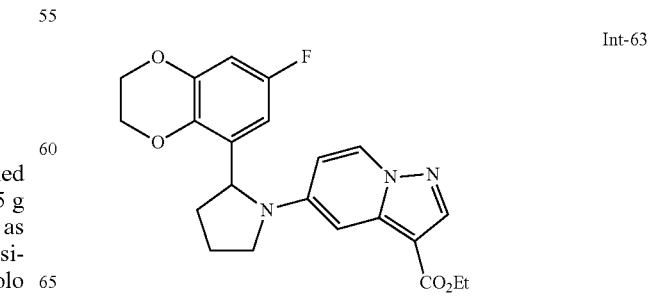

The title compound (Int-63) was prepared by the method similar to that for Int-84 using 2-(7-fluoro-2, 3-dihydrobenzo[b] [1, 4] dioxin-5-yl)pyrrolidine ((Int-56A) and Ethyl 5-bromopyrazolo [1, 5-a] pyridine-3-carboxylate to afford as pale brown solid. LCMS (ESI): m/z 412.85 (M+H).

Int-64: 5-(2-(7-fluoro-2, 3-dihydrobenzo [b] [1, 4] dioxin-5-yl) pyrrolidin-1-yl) pyrazolo[1, 5-a] pyridine-3-carboxylic acid (Isomer-I)

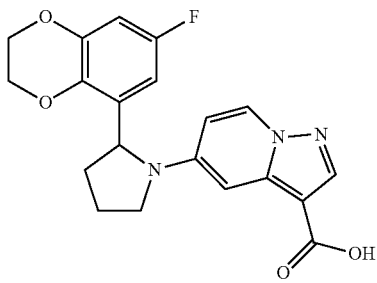

The title compound (Int-64) was prepared by the method similar to that of Int-85 employing Int-63 to afford as white solid. LCMS (ESI): m/z 384.2 (M+H).

Int-65: Ethyl 5-(2-(7-fluoro-2, 3-dihydrobenzo [b] [1, 4] dioxin-5-yl) pyrrolidin-1-yl) pyrazolo [1, 5-a] pyridine-3-carboxylate (Isomer-II)

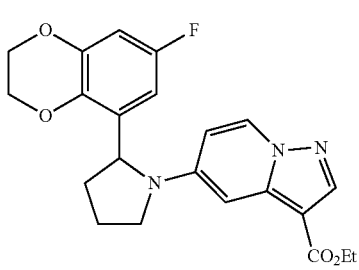

The title compound (Int-65) was prepared by the method similar to that of Int-84 using 2-(7-fluoro-2, 3-dihydrobenzo [b] [1, 4] dioxin-5-yl) pyrrolidine (Int-56B)) and Ethyl 5-bromopyrazolo [1, 5-a] pyridine-3-carboxylate to afford as pale brown solid. LCMS (ESI): m/z 412.85 (M+H).

Int-66: 5-(2-(7-fluoro-2, 3-dihydrobenzo [b] [1, 4] dioxin-5-yl) pyrrolidin-1-yl)pyrazolo[1, 5-a] pyridine-3-carboxylic acid (Isomer-II)

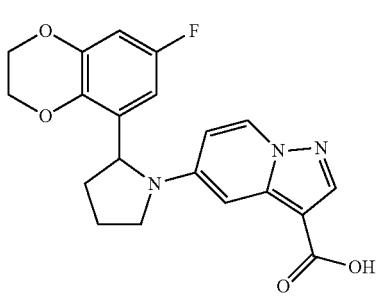

The title compound (Int-66) was prepared by the method similar to that of Int-64 employing Int-65 to afford as white solid. LCMS (ESI): m/z 384.2 (M+H).

Int-67: Ethyl 5-((2R, 4S)-2-(2, 5-difluorophenyl)-4-fluoropyrrolidin-1-yl)pyrazolo [1, 5-a] pyridine-3-carboxylate

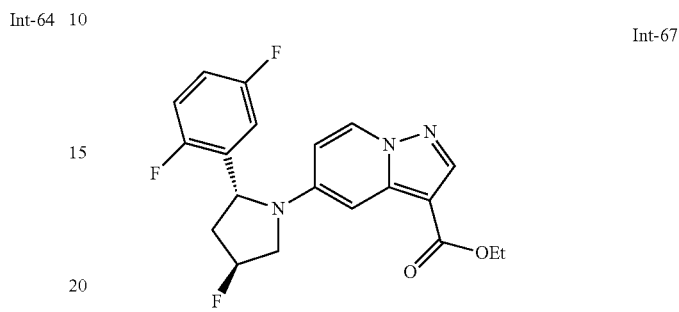

The title compound (Int-67) was prepared by the method similar to that for Int-84 using (2R,4S)-2-(2,5-difluorophenyl)-4-fluoropyrrolidine hydrochloride (Int-47) and Ethyl 5-bromopyrazolo [1, 5-a] pyridine-3-carboxylate to afford as yellow solid. LCMS (ESI): m/z 390.8 (M+H).

Int-68: 5-((2R, 4S)-2-(2, 5-difluorophenyl)-4-fluoropyrrolidin-1-yl) pyrazolo [1, 5-a] pyridine-3-carboxylic acid

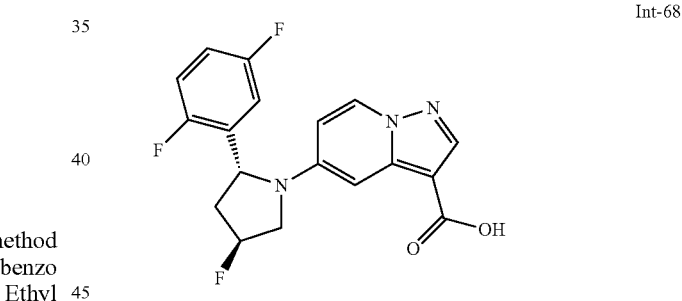

The title compound (Int-68) was prepared by the method similar to that of Int-85 employing Int-67 to afford as white solid. LCMS (ESI): m/z 362.8 (M+H).

Int-69: (R)-Ethyl 5-(2-(2-chloro-5-fluorophenyl) pyrrolidin-1-yl) pyrazolo [1, 5-a] pyridine-3-carboxylate

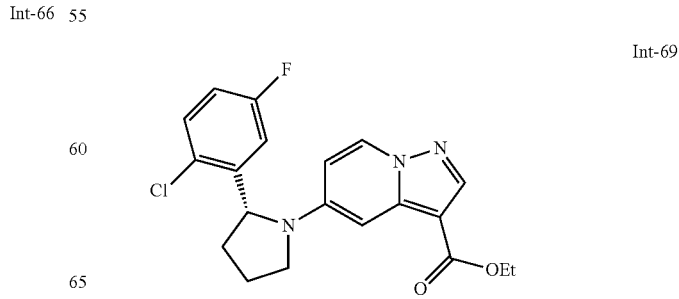

A mixture of ethyl 5-bromopyrazolo[1,5a]pyridine-3-carboxylate (1.3 g, 4.85 mmol), (R)-2-(2-chloro-5-fluorophenyl) pyrrolidine hydrochloride (Int-40) (1.13 g, 4.85 mmol) and K₃PO₄ (3.08 g, 14.5 mmol) in 1,4-Dioxane (20 mL) was degassed with argon gas for 15 min. Pd₂(dba)₃ (0.313 g, 0.34 mmol) and BINAP (0.24 g, 0.39 mmol) were added to the above mixture and stirring was continued at 100° C. for 2 h. After completion of the reaction, the reaction mixture was cooled and filtered over a celite bed. The celite bed was washed with ethylacetate. The filtrate thus obtained was further washed with water, dried over anhydrous sodium sulphate and concentrated under reduced pressure to afford the crude product, which was purified by column chromatography (using silica gel and 20% EtOAc in Hexane as eluant) to afford (R)-Ethyl 5-(2-(2-chloro-5-fluorophenyl) pyrrolidin-1-yl)pyrazolo[1,5-a]pyridine-3-carboxylate (Int-69) as a white solid. MS (ESI): m/z 388.1 (M+H).

Int-70: (R)-Ethyl 5-(2-(4,4'-difluoro-[1,1'-biphenyl]-2-yl)pyrrolidin-1-yl)pyrazolo[1,5-a]pyridine-3-carboxylate

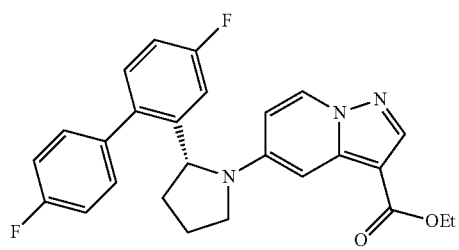

Cs₂CO₃ (0.75 g, 2.32 mmol) in 1,4-Dioxane (10 mL) was degassed with argon gas for 15 min. Pd(OAc)₂ (0.052 g, 0.23 mmol) and X-Phos (0.22 g, 0.45 mmol) were added to the above mixture and degassed with argon gas for 15 min. (R)-Ethyl 5-(2-(2-chloro-5-fluorophenyl) pyrrolidin-1-yl) pyrazolo [1, 5-a] pyridine-3-carboxylate (Int-69) (0.3 g, 0.77 mmol) followed by 4-Fluorophenylboronic acid (0.54 g, 3.87 mmol) and again degassed with argon gas for 15 min. KI (0.025 g, 0.25 mmol) was added to the above mixture and stirring was continued at 100° C. for 20 h. The reaction mixture was cooled to 28° C., diluted with EtOAc, filtered through whatman filter paper filtrate collected was washed with water, dried the organic layer over anhydrous sodium sulphate and concentrated under reduced pressure to afford the crude product, which was purified by Flash Chromatography (Biotage, Column: Silicagel 12 g pack size, Mobile Phase: EtOAc in n-Hexane: 0 to 15% as eluant) to afford (R)-Ethyl 5-(2-(4, 4'-difluoro-[1, 1'-biphenyl]-2-yl) pyrrolidin-1-yl) pyrazolo [1, 5-a] pyridine-3-carboxylate (Int-70) as off white sticky mass. MS (ESI): m/z 448.8 (M+H).

Int-71: (R)-5-(2-(4, 4'-difluoro-[1, 1'-biphenyl]-2-yl) pyrrolidin-1-yl) pyrazolo [1, 5-a] pyridine-3-carboxylic acid

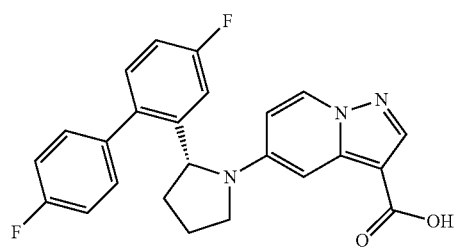

The title compound (Int-71) was prepared by the method similar that of Int-85 employing Int-70 to afford as white solid. MS (ESI): m/z 420.2 (M+H).

Int-72: Ethyl 5-(2-(2, 5-difluorophenyl)-4, 4-difluoropyrrolidin-1-yl) pyrazolo [1, 5-a] pyridine-3-carboxylate

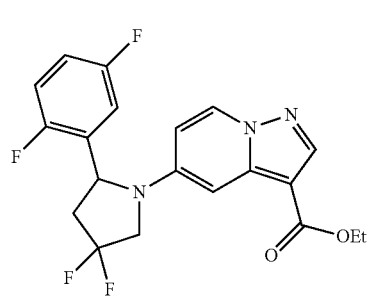

The title compound (Int-72) was prepared by the method similar to that for Int-84 using (R)-2-(2,5-difluorophenyl)-4,4-difluoropyrrolidine hydrochloride and Ethyl 5-bromopyrazolo [1, 5-a] pyridine-3-carboxylate to afford as yellow solid. LCMS (ESI): m/z 408.1 (M+H).

Int-73: 5-(2-(2, 5-difluorophenyl)-4, 4-difluoropyrrolidin-1-yl) pyrazolo [1, 5-a] pyridine-3-carboxylic acid

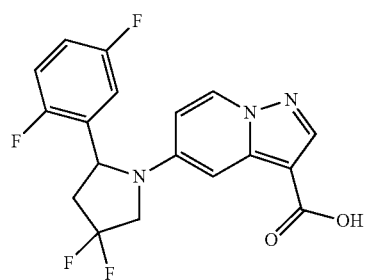

The title compound (Int-73) was prepared by the method similar to that of Int-85 employing Int-72 to afford as white solid. LCMS (ESI): m/z 379.8 (M+H).

Int-74: Ethyl 5-((2R, 4R)-2-(2, 5-difluorophenyl)-4-fluoropyrrolidin-1-yl) pyrazolo [1, 5-a] pyridine-3-carboxylate

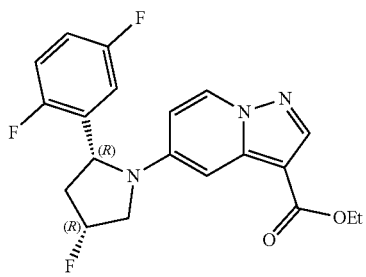

Int-74

The title compound (Int-74) was prepared by the method similar to that for Int-84 using (2R, 4R)-2-(2,5-difluorophenyl)-4-fluoropyrrolidine hydrochloride (Int-48) and Ethyl 5-bromopyrazolo [1,5-a] pyridine-3-carboxylate to afford as yellow liquid. LCMS (ESI): m/z 390.2 (M+H).

Int-75: 5-((2R, 4R)-2-(2, 5-difluorophenyl)-4-fluoropyrrolidin-1-yl) pyrazolo [1, 5-a] pyridine-3-carboxylic acid

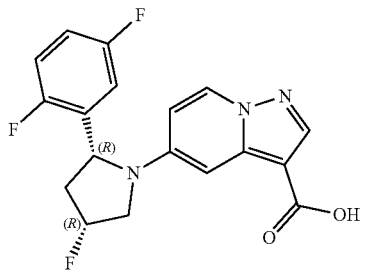

Int-75

The title compound (Int-75) was prepared by the method similar to that of Int-85 using Int-74 to afford as off white solid. LCMS (ESI): m/z 362.2 (M+H).

Int-76: (R)-ethyl 5-(2-(5-fluoro-2-hydroxyphenyl) pyrrolidin-1-yl) pyrazolo [1, 5-a] pyridine-3-carboxylate

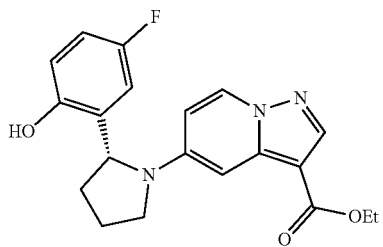

Int-76

To a stirred solution of (R)-ethyl 5-(2-(5-fluoro-2-methoxyphenyl)pyrrolidin-1-yl)pyrazolo[1,5-a]pyridine-3-carboxylate (synthesized similar to that of Int-84 using intermediate 41) (1.2 g, 3.13 mmol) in 25 mL of DCM, 1.0M Borontribromide (15.6 ml, 39.2 g, 15.65 mmol) was added at −70° C. and stirred at −70° C. to room temperature during 16 h. Reaction mass was quenched with 5 mL of ice cooled water and stirred for 15 min. The reaction mixture was diluted with DCM (50 mL) and the organic layer was washed with water followed by brine. The organic layer was dried over anhydrous sodium sulphate and concentrated under reduced pressure to afford of the title compound (Int-76) as off white solid. MS (ESI): m/z 370.3 (M+H).

Int-78: (R)-5-(2-(2-ethoxy-5-fluorophenyl)pyrrolidin-1-yl)pyrazolo[1,5-a]pyridine-3-carboxylic acid

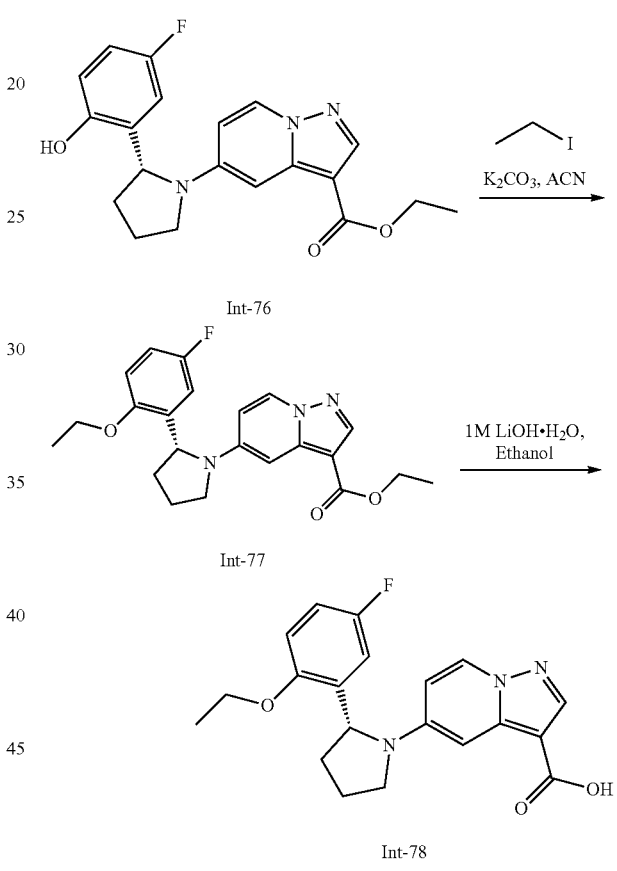

Int-77: (R)-ethyl5-(2-(2-ethoxy-5-fluorophenyl)pyrrolidin-1-yl)pyrazolo[1,5-a]pyridine-3-carboxylate Iodoethane (0.17 g, 1.08 mmol) was added to a mixture of (R)-ethyl 5-(2-(5-fluoro-2-hydroxyphenyl)pyrrolidin-1-yl) pyrazolo[1,5-a]pyridine-3-carboxylate (Int-76) (0.2 g, 0.54 mmol) and $K_2CO_3$ (0.23 g, 1.62 mmol) in $CH_3CN$ (10 mL) and continued stirring at 80° C. for 16 h. The reaction mixture was diluted with ethyl acetate (100 mL), washed with water and dried over anhydrous sodium sulphate and concentrated under reduced pressure to afford the crude, which was purified by column chromatography (using silica gel and 2% ethyl acetate in hexane as eluent) to afford the desired compound (Int-77). MS (ESI): m/z 398.1 (M+H).

Int-78: (R)-5-(2-(2-ethoxy-5-fluorophenyl)pyrrolidin-1-yl)pyrazolo[1,5-a]pyridine-3-carboxylic acid 1M aq. solution of LiOH.H₂O (0.4 mL) was added to a stirred solution of (R)-ethyl 5-(2-(2-ethoxy-5-fluorophenyl)pyrrolidin-1-yl)pyrazolo[1,5-a]pyridine-3-carboxylate (Int-77) (0.12 g, 0.32 mmol) in ethanol (5 mL) and the stirring was continued at 90° C. for 8 h. The reaction mixture was concentrated under reduced pressure to afford the crude, which was diluted with cold water (20 mL) and acidified with 2N HCl solution to pH=2, solid precipitated out was filtered and dried to afford the desired compound (Int-78) as yellow solid. MS (ESI): m/z 370.3 (M+H).

The following intermediates (Int-79 to Int-83) were prepared by a method substantially similar to that mentioned for Int-78 except a suitable alky halides or O-mesylates was used in place of ethyl iodide in Int-77.

| Intermediate | Structure | IUPAC name | MS (ESI) (M + H) |
| --- | --- | --- | --- |
| Int-79 | 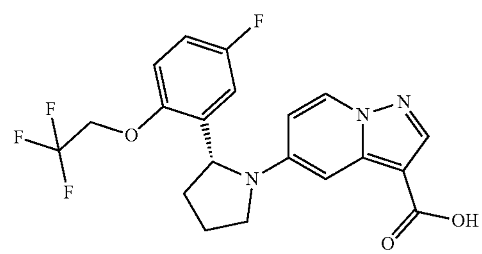 [SMILES: O=C(O)c1cnn2ccc(N3CCC[C@@H]3c3cc(F)ccc3OCC(F)(F)F)cc12] | (R)-5-(2-(5-fluoro-2-(2,2,2-trifluoroethoxy)phenyl)pyrrolidin-1-yl)pyrazolo[1,5-a]pyridine-3-carboxylic acid | m/z 424.1 |
| Int-80 | 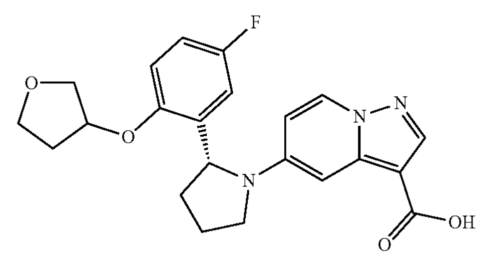 [SMILES: O=C(O)c1cnn2ccc(N3CCC[C@@H]3c3cc(F)ccc3OC3CCOC3)cc12] | 5-((2R)-2-(5-fluoro-2-((tetrahydrofuran-3-yl)oxy)phenyl)pyrrolidin-1-yl)pyrazolo[1,5-a]pyridine-3-carboxylic acid | m/z 412.1 |
| Int-81 | 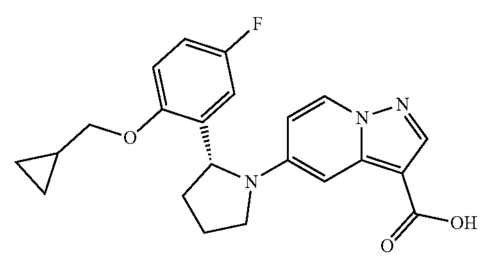 [SMILES: O=C(O)c1cnn2ccc(N3CCC[C@@H]3c3cc(F)ccc3OCC3CC3)cc12] | (R)-5-(2-(2-(cyclopropylmethoxy)-5-fluorophenyl)pyrrolidin-1-yl)pyrazolo[1,5-a]pyridine-3-carboxylic acid | m/z 396.1 |
| Int-82 | 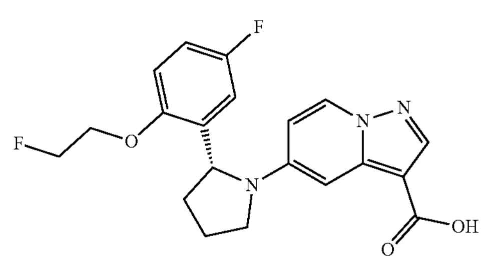 [SMILES: O=C(O)c1cnn2ccc(N3CCC[C@@H]3c3cc(F)ccc3OCCF)cc12] | (R)-5-(2-(5-fluoro-2-(2-fluoroethoxy)phenyl)-pyrrolidin-1-yl)pyrazolo[1,5-a]pyridine-3-carboxylic acid | m/z 388.1 |
| Int-83 | 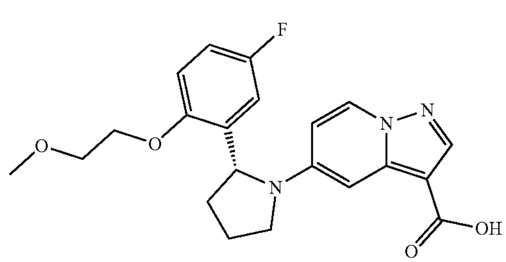 [SMILES: COCCOc1ccc(F)cc1[C@H]1CCCN1c1ccn2ncc(C(=O)O)c2c1] | (R)-5-(2-(5-fluoro-2-(2-methoxyethoxy)phenyl)-pyrrolidin-1-yl)pyrazolo[1,5-a]pyridine-3-carboxylic acid | m/z 400.1 |

Int-84: (R)-ethyl 5-(2-(2, 5-difluorophenyl) pyrrolidin-1-yl)pyrazolo[1,5a]pyridine-3-carboxylate

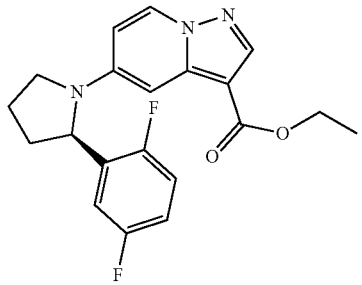

A mixture of ethyl 5-bromopyrazolo[1,5a]pyridine-3-carboxylate (2 g, 7.49 mmol), (R)-2-(2, 5-difluorophenyl) pyrrolidine hydrochloride (Int-6) (1.65 g, 7.49 mmol) and $Cs_2CO_3$ (7.3 g, 22.47 mmol) in 1,4-Dioxane (35 mL) was degassed with argon gas for 15 min. $Pd_2(dba)_3$ (480 mg, 0.52 mmol) and BINAP (380 mg, 0.59 mmol) were added to the above mixture and stirring was continued at 100° C. for 2 h. After completion of the reaction, the reaction mixture was cooled and filtered over a celite bed. The celite bed was washed with ethylacetate. The filtrate thus obtained was further washed with water, dried over anhydrous sodium sulphate and concentrated under reduced pressure to afford the crude product, which was purified by column chromatography (using silica gel 60-120, and 30% EtOAc in Hexane as eluent) to afford 1.8 g of the title compound as a yellow solid.

$^1$H NMR (300 MHz, $CDCl_3$) δ ppm 8.21-8.18 (2H, m), 7.12-7.02 (1H, m), 6.98-6.86 (1H, m), 6.74-6.66 (1H, m), 6.28-6.2 (1H, m), 5.15 (1H, d, J=8 Hz), 6.16-6.13 (1H, m), 5.11 (1H, d, J=8.1 Hz), 4.34-4.27 (2H, m), 3.84 (1H, t) 3.60-3.5 (1H, m), 2.52-2.4 (1H, m), 2.2-2.0 (3H, m), 1.38-1.3 (3H, m).

MS (ESI): m/z 372 (M+H).

Int-85: (R)-5-(2-(2, 5-difluorophenyl) pyrrolidin-1-yl)pyrazolo[1,5a]pyridine-3-carboxylic acid

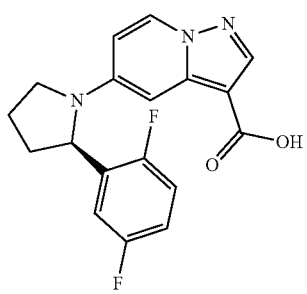 [SMILES: O=C(O)c1cnn2ccc(N3CCC[C@@H]3c3cc(F)ccc3F)cc12]

$LiOH.H_2O$ (0.679 mg, 16.2 mmol) in water (5 mL) was added to a stirred solution of Int-84 (1.8 g, 4.85 mmol) in EtOH (30 mL) and the stirring was continued at reflux temperature for 12-16 h. The reaction mixture was concentrated under reduced pressure to afford the crude product. The crude product thus obtained was diluted with cold water, acidified with 2N aqueous HCl solution, filtered the solid precipitate to afford 1.2 g of the title compound as an off white solid.

MS (ESI): m/z 344 (M+H).

Int 87: 5-(2-(2, 5-difluorophenyl) pyrrolidin-1-yl)pyrazolo[1,5a]pyridine-3-carboxylic acid

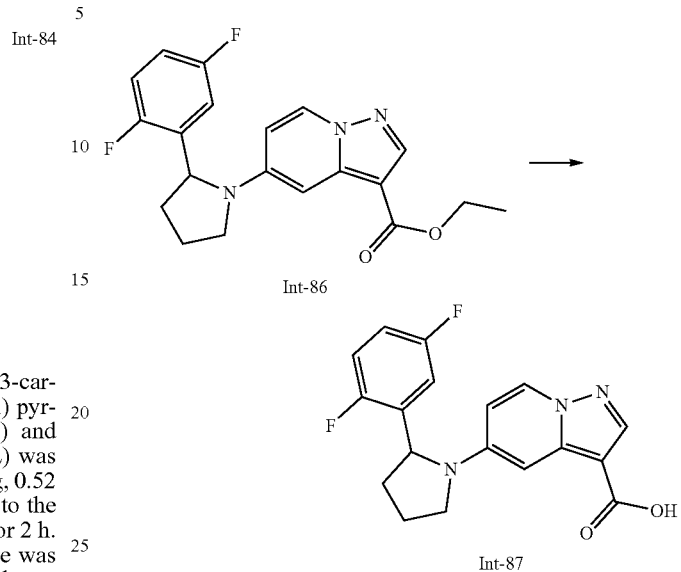

Int-86: Ethyl 5-(2-(2,5-difluorophenyl)pyrrolidin-1-yl)pyrazolo[1,5-a]pyridine-3-carboxylate The title compound was prepared by a procedure substantially similar as for Int-84, using Int-10 in place of Int-6 to afford the crude. The crude compound was purified by column chromatography (using silica gel 60-120, and 5% EtOAc in Hexane as eluent) to afford 135 mg of the title compound.

$^1$H NMR (400 MHz, DMSO-$d_6$) δ ppm 8.52-8.50 (1H, d, J=7.6 Hz), 8.12 (1H, s), 7.4-7.3 (1H, m), 7.2-7.1 (1H, m), 6.95-6.9 (1H, m), 6.7 (1H, s), 6.55 (1H, bs), 5.12 (1H, d, J=7.6 Hz), 4.2-4.27 (2H, m), 3.94-3.84 (1H, t), 3.55-3.40 (1H, m), 2.52-2.40 (1H, m), 2.15-1.85 (3H, m), 1.3-1.15 (3H, m),

MS (ESI): 372 (M+H).

Int-87: 5-(2-(2, 5-difluorophenyl) pyrrolidin-1-yl)pyrazolo[1,5a]pyridine-3-carboxylic acid 5N aqueous solution of NaOH (2 mL) was added to stirred solution of Int-86 (50 mg, 0.134 mmol) in a mixture of MeOH (4 mL) and THF (4 mL) and continued stirring at 80° C. for 4 h. The reaction mixture was concentrated under reduced pressure to afford the crude product. The crude product thus obtained was diluted with cold water, acidified with concentrated HCl solution to obtain a solid precipitate. This solid precipitate was filtered and dried well to afford 18 mg of 5-(2-(2,5-difluorophenyl)pyrrolidin-1-yl)pyrazolo[1,5-a]pyridine-3-carboxylic acid as off white solid.

$^1$H NMR (400 MHz, DMSO-$d_6$) δ ppm 11.82 (1H, s), 8.46 (1H, d, J=7.6 Hz), 8.08 (1H, s), 7.40-7.30 (1H, m), 7.20-7.10 (1H, m), 6.95-6.88 (1H, m), 6.67 (1H, s), 6.39 (1H, s), 5.15 (1H, d, J=8 Hz), 3.80-3.70 00 (1H, t, J=8 Hz), 3.50-3.30 (1H, m), 2.44 (1H, m), 2.10-1.85 (3H, m).

MS (ESI): m/z 344.2 (M+H).

Int-89: (R)-5-(2-(5-(difluoromethoxy)-2-fluorophenyl)pyrrolidin-1-yl)pyrazolo[1,5-a]pyridine-3-carboxylic acid

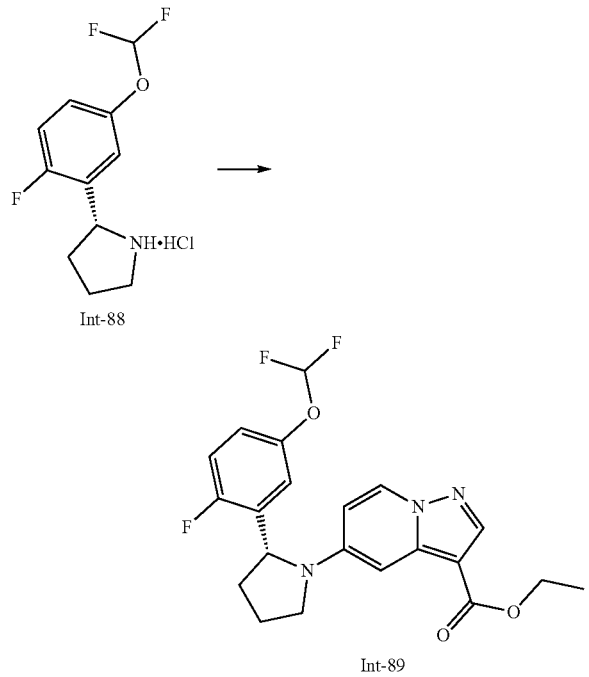

Int-88: (R)-2-(5-(difluoromethoxy)-2-fluorophenyl) pyrrolidine hydrochloride

This compound was prepared by the method substantially similar to the preparation of Int-6 using 2-bromo-4-(difluoromethoxy)-1-fluorobenzene (*J. Med. Chem.* 2003, 46, 1016-1030).

Int-89: (R)-Ethyl 5-(2-(5-(difluoromethoxy)-2-fluorophenyl) pyrrolidin-1-yl)pyrazolo[1,5-a]pyridine-3-carboxylate The title compound was prepared by the method substantially similar to that for Int-84, to afford the crude, which was purified by column chromatography (using silica gel 60-120, and 5% EtOAc in Hexane as eluent) to afford 140 mg of the title compound.
MS (ESI): m/z 420 (M+H).

Int-90: (R)-5-(2-(5-(difluoromethoxy)-2-fluorophenyl)pyrrolidin-1-yl)pyrazolo[1,5-a]pyridine-3-carboxylic acid

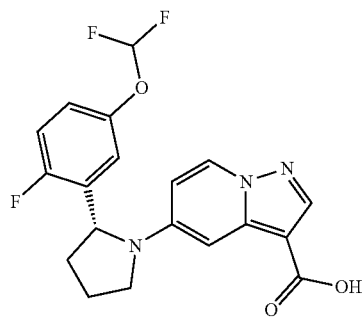 [SMILES: O=C(O)c1cnn2ccc(N3CCC[C@@H]3c3cc(OC(F)F)ccc3F)cc12]

The title compound was prepared by the method substantially similar to that for Int-85, to afford 85 mg of the title compound.
$^1$H NMR (300 MHz, DMSO-d$_6$) δ ppm 11.9 (1H, bs,), 8.47-8.45 (1H, d, J=7.5 Hz), 8.08 (1H, s), 7.37-7.30 (1H, t), 7.20-7.10 (1H, m), 6.87-6.85 (1H, m), 7.33-6.87 (1H, t, OCHF$_2$) 6.76 (1H, bs), 6.45-6.35 (1H, m), 5.16-5.14 (1H, d, J=7.5 Hz), 3.90-3.80 (1H, t), 3.55-3.45 (2H, m), 2.08-1.85 (3H, m).
MS (ESI): m/z 392.1 (M+H).

Int-91 (R)-5-(2-(3,5-difluorophenyl)pyrrolidin-1-yl) pyrazolo[1,5-a]pyridine-3-carboxylic acid

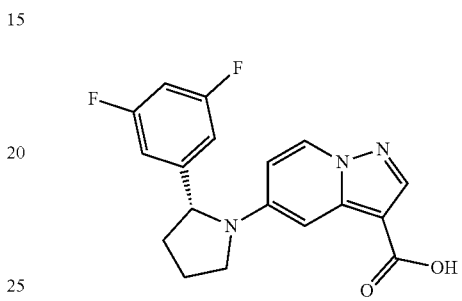

Title compound was prepared by a method substantially similar to that of Int-84 using ethyl 5-bromopyrazolo[1,5a]pyridine-3-carboxylate and (R)-2-(3,5-Difluorophenyl) pyrrolidine hydrochloride (Int-44), followed by hydrolysis similar to that of Int-85 to afford a white solid.
MS (ESI): m/z 344.2 (M+H).

Synthesis of Compounds of Formula I

Example-1: (R)-5-(2-(2,5-difluorophenyl)pyrrolidin-1-yl)-N-((4-fluorophenyl)sulfonyl) pyrazolo[1,5-a]pyridine-3-carboxamide

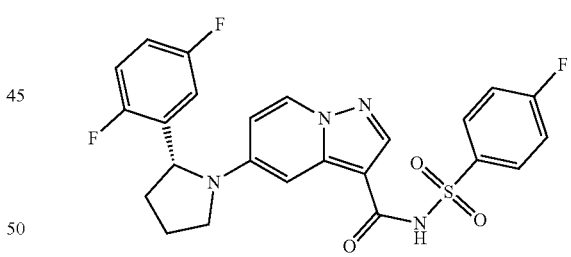

EDCI (111 mg, 0.5 mmol) was added to a solution of (R)-5-(2-(2,5-difluorophenyl)pyrrolidin-1-yl)pyrazolo[1,5-a]pyridine-3-carboxylic acid (100 mg, 0.29 mmol) in DCM (4 mL) followed by DMAP (36 mg, 0.29 mmol) and 4-fluorobenzenesulfonamide (56 mg, 0.31 mmol) and stirring was continued at 20-35° C. for 20 h. Reaction mixture was quenched with water, extracted into EtOAc, dried over anhydrous sodium sulphate and concentrated under reduced pressure to afford the crude. The crude compound was purified by Preparative HPLC [Column: 21.2×150×5 um, Zorbax, Eclipse, C-18, Mobile phase-A: Water, B:ACN, Gradient(Time/% B): 0/30, 2/40, 10/80 and Flow rate:20 mL/min] to afford 9.3 mg of the title compound.
$^1$H NMR (400 MHz, CDCl$_3$) δ ppm 8.29 (1H, bs), 8.22-8.20 (2H, m), 8.12 (1H, d, J=7.6 Hz), 8.00 (1H, s), 7.26-7.20 (2H, m), 7.14-7.04 (2H, m), 6.96-6.88 (1H, m), 6.61 (1H, m), 6.18 (1H, d, J=7.6 Hz), 5.12-5.11 (1H, d, J=8 Hz), 3.80-3.74 (1H, m), 3.6-3.5 (1H, m), 2.5-2.4 (1H, m), 2.15-2.0 (3H, m).

MS (ESI): m/z 501.8 (M+H).

Example-2: (R)—N-(tert-butylsulfonyl)-5-(2-(2, 5-difluorophenyl) pyrrolidin-1-yl) pyrazolo [1, 5-a] pyridine-3-carboxamide

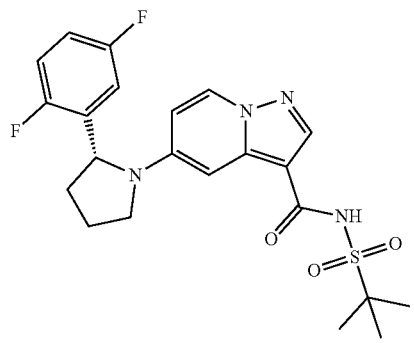 [SMILES: CC(C)(C)S(=O)(=O)NC(=O)c1cnn2ccc(N3CCC[C@@H]3c3cc(F)ccc3F)cc12]

To a stirred solution of (R)-5-(2-(2, 5-difluorophenyl) pyrrolidin-1-yl)pyrazolo[1,5-a]pyridine-3-carboxylic acid (170 mg, 0.49 mmol) in dry DCM (10 mL) was added EDCI (288 mg, 1.5 mmol) followed by DMAP (0.18 g, 1.4 mmol) and stirring was continued at 25° C. for 2 h. To the reaction mixture was added tert-butyl sulfonamide (67 mg, 0.49 mmol) and the stirring was continued at 25° C. for 72 h. Reaction mixture was diluted with DCM (50 mL) and the organic layer was washed with saturated aqueous KHSO₄ solution followed by brine, dried over anhydrous sodium sulphate and concentrated under reduced pressure to afford the crude, which was purified by combiflash chromatography followed by re-crystalisaiton from EtOH to afford (R)—N-(tert-butylsulfonyl)-5-(2-(2, 5-difluorophenyl) pyrrolidin-1-yl)pyrazolo [1, 5-a] pyridine-3-carboxamide as white solid. MS (ESI): m/z 463.2 (M+H).

Example-3: (R)-5-(2-(2, 5-difluorophenyl)pyrrolidin-1-yl)-N-(ethylsulfonyl)pyrazolo[1,5-a]pyridine-3-carboxamide

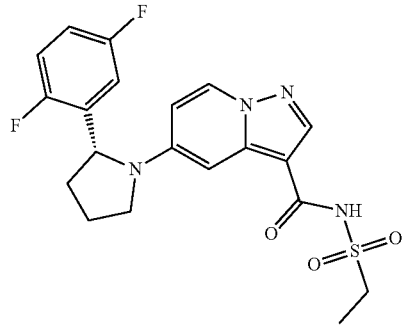 [SMILES: CCS(=O)(=O)NC(=O)c1cnn2ccc(N3CCC[C@@H]3c3cc(F)ccc3F)cc12]

The title compound was prepared by the method substantially similar to that mentioned in Example-2 using Ethanesulfonamide to afford the crude. The crude compound was purified by Preparative HPLC [Column: 21.2×150×5 um, Zorbax, Eclipse, C-18, Mobile phase-A: 0.1% TFA in Water, B:ACN, Gradient(Time/% B): 0/30, 2/40, 5/80 and Flow rate:20 mL/min] to afford 12 mg of the title compound.

¹H NMR (300 MHz, CD₃OD) δ ppm 8.32-8.29 (2H, m), 7.22-7.12 (1H, m), 7.08-6.96 (2H, m), 6.8-6.72 (1H, m), 6.50 (1H, m), 5.2-5.18 (1H, d, J=6.8 Hz), 3.9-3.82 (1H, m), 3.6-3.48 (3H, m), 2.5 (1H, m), 2.18-2.0 (3H, m), 1.4-1.3 (3H, t).

MS (ESI): m/z 434.8 (M+H).

Example-4: (R)—N-((3-cyanophenyl)sulfonyl)-5-(2-(2,5-difluorophenyl)pyrrolidin-1-yl)pyrazolo [1,5-a] pyridine-3-carboxamide

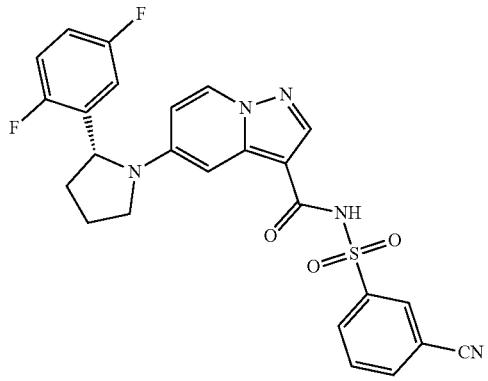 [SMILES: N#Cc1cccc(S(=O)(=O)NC(=O)c2cnn3ccc(N4CCC[C@@H]4c4cc(F)ccc4F)cc23)c1]

The title compound was prepared by the similar coupling method as mentioned in Example-2, using 3-cyanobenzenesulfonamide to afford the crude. The crude was purified by Preparative HPLC [Column: 21.2×150×5 um, Zorbax, XDB, C-18(#22), Mobile phase-A: 0.1% TFA in water, B:ACN, Gradient (Time/% B): 0/30, 5/40, 6/80 and flow rate: 20 mL/min] to afford 46 mg of the title compound.

¹H NMR (400 MHz, DMSO-d₆) δ ppm 12.05 (1H, s), 8.51 (1H, s), 8.42-8.45 (1H, d, J=7.6 Hz), 8.37 (1H, s), 8.30-8.18 (2H, m), 7.89-7.85 (1H, t), 7.36-7.28 (1H, m), 7.18-7.10 (1H, m), 6.90-6.75 (2H, m), 6.39 (1H, bs), 5.14-5.13 (1H, d, J=7.2 Hz), 3.83-3.81 (1H, t), 3.48-3.38 (1H, m), 2.50-2.42 (1H, m), 2.10-1.85 (3H, m).

MS (ESI): m/z 507.8 (M+H).

Example-5: (R)—N-(cyclopropylsulfonyl)-5-(2-(2, 5-difluorophenyl)pyrrolidin-1-yl)pyrazolo[1,5-a] pyridine-3-carboxamide

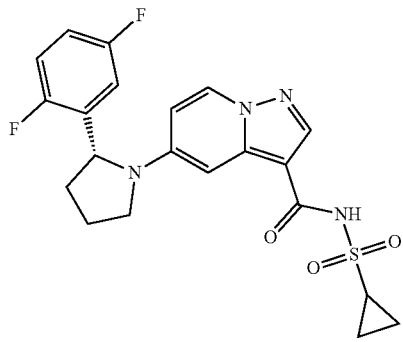 [SMILES: O=C(NS(=O)(=O)C1CC1)c1cnn2ccc(N3CCC[C@@H]3c3cc(F)ccc3F)cc12]

The title compound was prepared by a coupling method substantially similar to that mentioned in Example-2 using cyclopropane sulfonamide in place of 4-fluorobenzenesulfonamide to afford the crude. The crude was purified by Preparative HPLC [Column: 19×150×5 um, Zorbax, XDB, C-18(#22), Mobile phase-A: 0.1% TFA in water, B:ACN, Gradient (Time/% B): 0/30, 2/40, 10/80 and flow rate: 20 mL/min] to afford 8 mg of the title compound.

$^1$H NMR (400 MHz, DMSO-d$_6$) δ ppm 8.51-8.49 (2H, m), 7.40-7.30 (1H, m), 7.20-7.12 (1H, m), 6.95-6.85 (2H, m), 6.46-6.40 (1H, bs), 5.20-5.15 (1H, d, J=7.6 Hz), 3.92-3.85 (1H, m), 3.50-3.42 (1H, m), 3.18-3.10 (1H, m), 2.50-2.41 (1H, m), 2.10-1.85 (3H, m), 1.14-1.02 (4H, m).

MS (ESI): m/z 446.8 (M+H).

Example-6: (R)-5-(2-(2,5-difluorophenyl)pyrrolidin-1-yl)-N-(methylsulfonyl)pyrazolo[1,5-a]pyridine-3-carboxamide

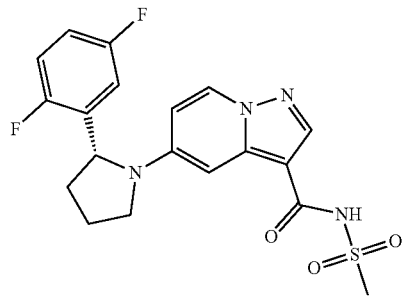 [SMILES: CS(=O)(=O)NC(=O)c1cnn2ccc(N3CCC[C@@H]3c3cc(F)ccc3F)cc12]

The title compound was prepared by the similar coupling method as mentioned in Example-2, using Methane sulfonamide to afford the crude. The crude was purified by Preparative HPLC [Column: 19×150×5 um, Xbridge, C-18 (#22), Mobile phase-A: 0.1% TFA in water, B:ACN, Gradient (Time/% B): 0/40, 2/40, 7/60 and flow rate: 15 mL/min] to afford 16 mg of the title compound.

$^1$H NMR (400 MHz, DMSO-d$_6$) δ ppm 8.54-8.46 (2H, m), 7.38-7.30 (1H, m), 7.20-7.12 (1H, m), 6.96-6.64 (2H, m), 6.48-6.40 (1H, bs), 5.17-5.16 (1H, d, J=8.4 Hz), 3.89-7.81 (1H, t), 3.50-3.40 (1H, m), 3.33 (3H, s), 2.50-2.45 (1H, m), 2.10-1.88 (3H, m).

MS (ESI): m/z 421.2 (M+H).

Example-7 to Example-41 were synthesized following a procedure substantially similar to Example-2 except appropriate sulfonamide was used in place of tert-butyl sulfonamide to afford the desired product.

| Example No. | Structure | IUPAC name | MS(ESI) M + H |
|---|---|---|---|
| 7 | 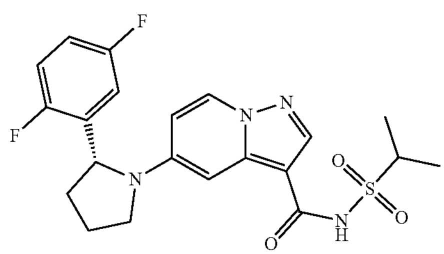 [SMILES: CC(C)S(=O)(=O)NC(=O)c1cnn2ccc(N3CCC[C@@H]3c3cc(F)ccc3F)cc12] | (R)-5-(2-(2,5-difluorophenyl)pyrrolidin-1-yl)-N-(isopropylsulfonyl)pyrazol[1,5-a]pyridine-3-carboxamide | m/z 449.3 |
| 8 | 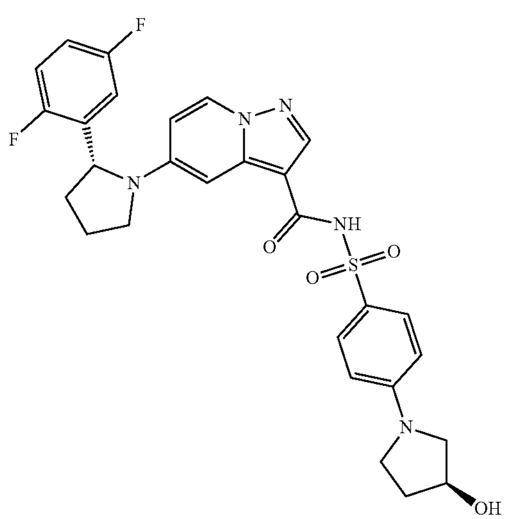 [SMILES: O=C(NS(=O)(=O)c1ccc(N2CC[C@H](O)C2)cc1)c1cnn2ccc(N3CCC[C@@H]3c3cc(F)ccc3F)cc12] | 5-((R)-2-(2,5-difluorophenyl)pyrrolidin-1-yl)-N-((4-((S)-3-hydroxypyrrolidin-1-yl)phenyl)sulfonyl)pyrazolo[1,5-a]pyridine-3-carboxamide | m/z 568.2 |

-continued

| Example No. | Structure | IUPAC name | MS(ESI) M + H |
|---|---|---|---|
| 9 | 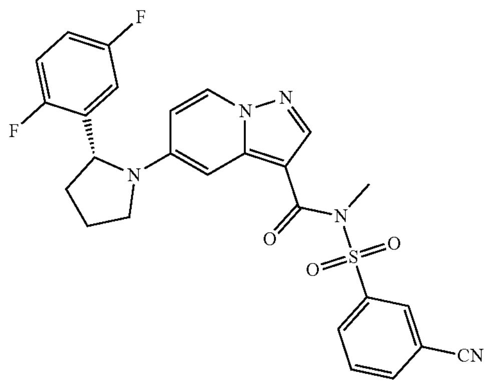 [SMILES: CN(C(=O)c1cnn2ccc(N3CCC[C@@H]3c3cc(F)ccc3F)cc12)S(=O)(=O)c1cccc(C#N)c1] | (R)-N-((3-cyanophenyl)sulfonyl)-5-(2-(2,5-difluorophenyl)-pyrrolidin-1-yl)-N-methylpyrazolo[1,5-a]pyridine-3-carboxamide | m/z 522.2 |
| 10 | 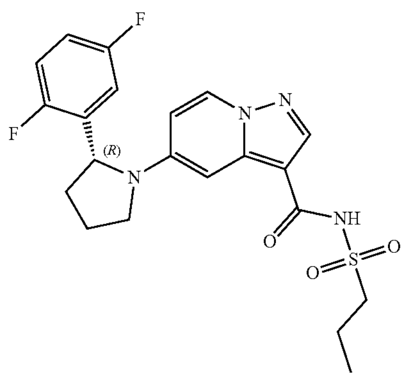 | (R)-5-(2-(2,5-difluorophenyl)pyrrolidin-1-yl)-N-(propylsulfonyl)pyrazolo[1,5-a]pyridine-3-carboxamide | m/z 449.1 |
| 11 | 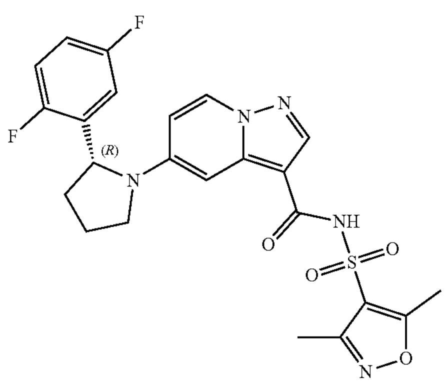 | (R)-5-(2-(2,5-difluorophenyl)pyrrolidin-1-yl)-N-((3,5-dimethylisoxazol-4-yl)sulfonyl)pyrazolo[1,5-a]pyridine-3-carboxamide | m/z 502.2 |
| 12 | 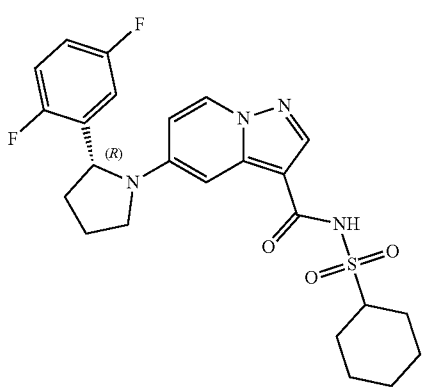 | (R)-N-(cyclohexylsulfonyl)-5-(2-(2,5-difluorophenyl)pyrrolidin-1-yl)pyrazolo[1,5-a]pyridine-3-carboxamide | m/z 489.3 |

-continued

| Example No. | Structure | IUPAC name | MS(ESI) M + H |
|---|---|---|---|
| 13 | 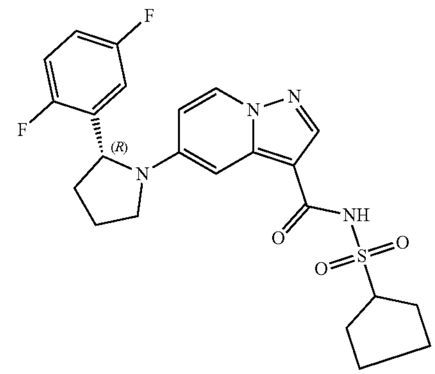 | (R)-N-(cyclopentylsulfonyl)-5-(2-(2,5-difluorophenyl)pyrrolidin-1-yl)pyrazolo[1,5-a]pyridine-3-carboxamide | m/z 475.1 |
| 14 | 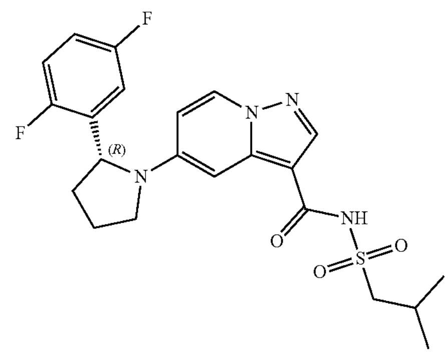 | (R)-5-(2-(2,5-difluorophenyl)pyrrolidin-1-yl)-N-(isobutylsulfonyl)pyrazolo[1,5-a]pyridine-3-carboxamide | m/z 463.1 |
| 15 | 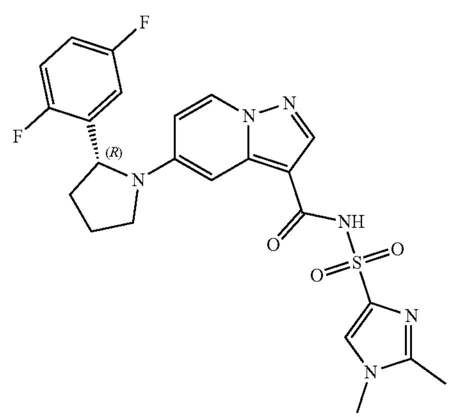 | (R)-5-(2-(2,5-difluorophenyl)pyrrolidin-1-yl)-N-((1,2-dimethyl-1H-imidazol-4-yl)sulfonyl)-pyrazolo[1,5-a]pyridine-3-carboxamide | m/z 501.1 |
| 16 | 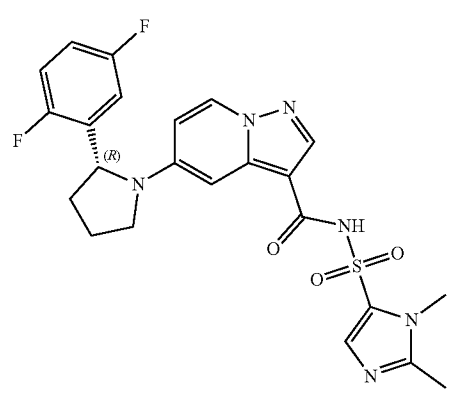 | (R)-5-(2-(2,5-difluorophenyl)pyrrolidin-1-yl)-N-((1,2-dimethyl-1H-imidazol-5-yl)sulfonyl)pyrazolo[1,5-a]pyridine-3-carboxamide | m/z 501.1 |

-continued

| Example No. | Structure | IUPAC name | MS(ESI) M + H |
|---|---|---|---|
| 17 | 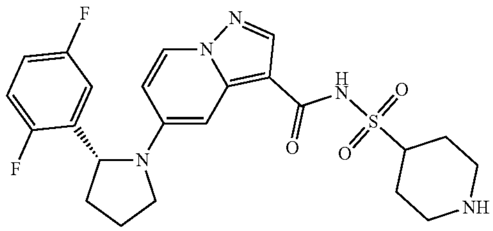 [SMILES: O=C(NS(=O)(=O)C1CCNCC1)c1cnn2ccc(N3CCC[C@@H]3c3cc(F)ccc3F)cc12] | (R)-5-(2-(2,5-difluorophenyl)pyrrolidin-1-yl)-N-(piperidin-4-ylsulfonyl)pyrazolo[1,5-a]pyridine-3-carboxamide | m/z 490.1 |
| 18 | 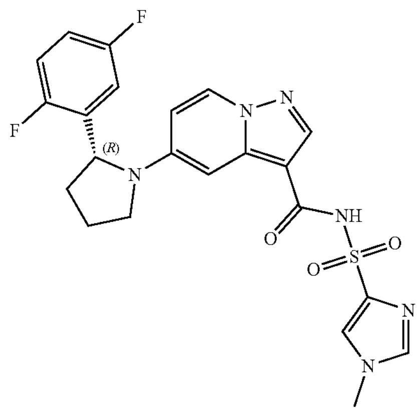 | (R)-5-(2-(2,5-difluorophenyl)pyrrolidin-1-yl)-N-((1-methyl-1H-imidazol-4-yl)sulfonyl)pyrazolo[1,5-a]pyridine-3-carboxamide | m/z 487.3 |
| 19 | 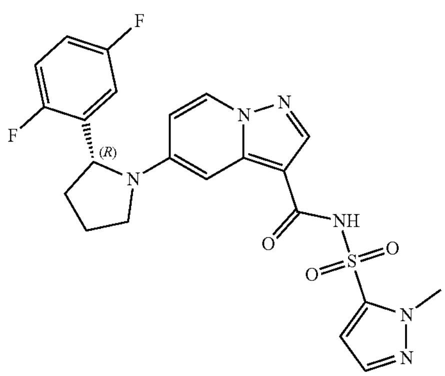 | (R)-5-(2-(2,5-difluorophenyl)pyrrolidin-1-yl)-N-((1-methyl-1H-pyrazol-5-yl)sulfonyl)pyrazolo[1,5-a]pyridine-3-carboxamide | m/z 487.4 |
| 20 | 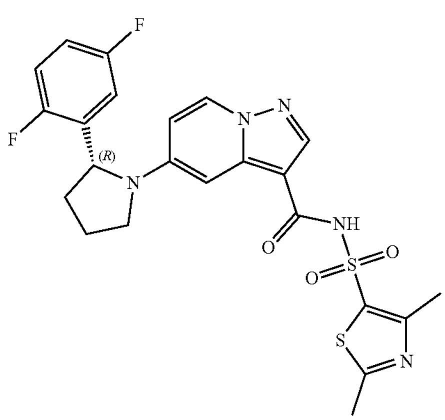 | (R)-5-(2-(2,5-difluorophenyl)pyrrolidin-1-yl)-N-((2,4-dimethylthiazol-5-yl)sulfonyl)pyrazolo[1,5-a]pyridine-3-carboxamide | m/z 518.0 |

-continued

| Example No. | Structure | IUPAC name | MS(ESI) M + H |
|---|---|---|---|
| 21 | 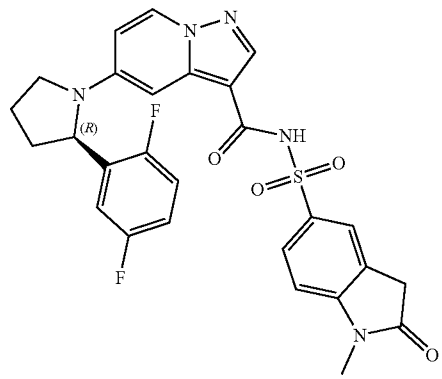 | (R)-5-(2-(2,5-difluorophenyl) pyrrolidin-1-yl)-N-((1-methyl-2-oxoindolin-5-yl)sulfonyl) pyrazolo[1,5-a]pyridine-3-carboxamide | m/z 552.1 |
| 22 | 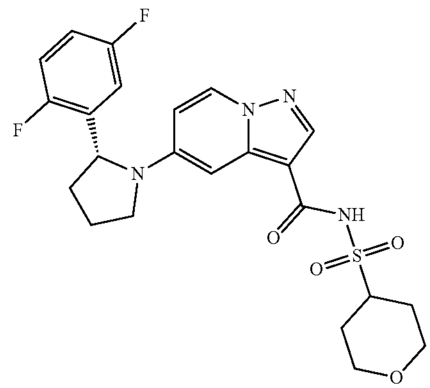 [SMILES: O=C(NS(=O)(=O)C1CCOCC1)c1cnn2ccc(N3CCC[C@@H]3c3cc(F)ccc3F)cc12] | (R)-5-(2-(2,5-difluorophenyl) pyrrolidin-1-yl)-N-((tetrahydro-2H-pyran-4-yl)sulfonyl) pyrazolo[1,5-a]pyridine-3-carboxamide | m/z 491.2 |
| 23 | 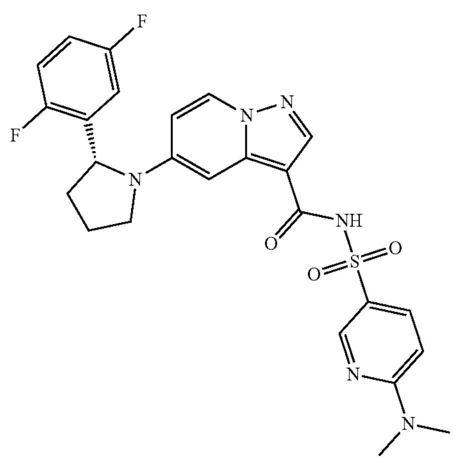 [SMILES: CN(C)c1ccc(S(=O)(=O)NC(=O)c2cnn3ccc(N4CCC[C@@H]4c4cc(F)ccc4F)cc23)cn1] | (R)-5-(2-(2,5-difluorophenyl) pyrrolidin-1-yl)-N-((6-(dimethylamino)pyridin-3-yl) sulfonyl)pyrazolo[1,5-a]pyridine-3-carboxamide | m/z 527.1 |
| 24 | 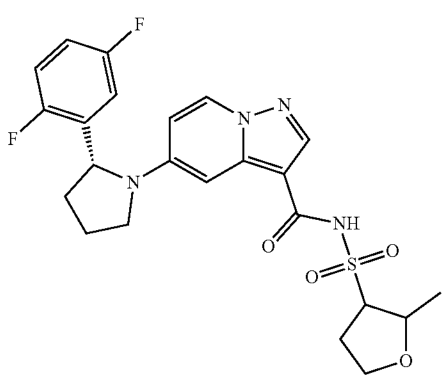 [SMILES: CC1OCCC1S(=O)(=O)NC(=O)c1cnn2ccc(N3CCC[C@@H]3c3cc(F)ccc3F)cc12] | 5-((R)-2-(2,5-difluorophenyl) pyrrolidin-1-yl)-N-((2-methyltetrahydrofuran-3-yl) sulfonyl)pyrazolo[1,5-a]pyridine-3-carboxamide | m/z 491.1 |

| Example No. | Structure | IUPAC name | MS(ESI) M + H |
|---|---|---|---|
| 25 | 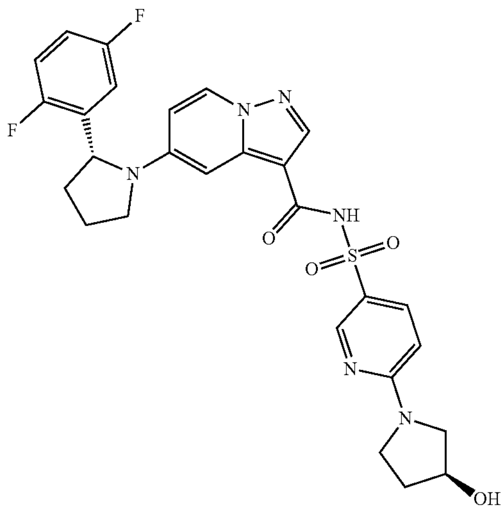 [SMILES: O=C(NS(=O)(=O)c1ccc(N2CC[C@H](O)C2)nc1)c1cnn2ccc(N3CCC[C@@H]3c3cc(F)ccc3F)cc12] | 5-((R)-2-(2,5-difluorophenyl)pyrrolidin-1-yl)-N-((6-((S)-3-hydroxypyrrolidin-1-yl)pyridin-3-yl)sulfonyl)pyrazolo[1,5-a]pyridine-3-carboxamide | m/z 569.1 |
| 26 | 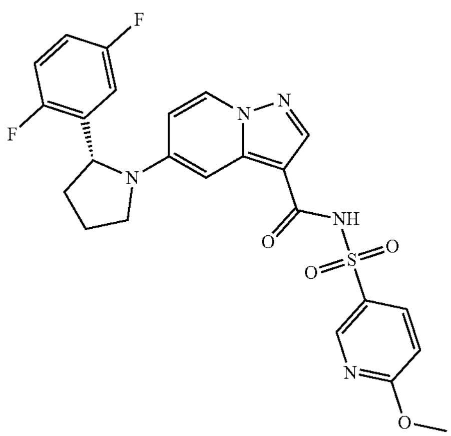 [SMILES: COc1ccc(S(=O)(=O)NC(=O)c2cnn3ccc(N4CCC[C@@H]4c4cc(F)ccc4F)cc23)cn1] | (R)-5-(2-(2,5-difluorophenyl)pyrrolidin-1-yl)-N-((6-methoxypyridin-3-yl)sulfonyl)pyrazolo[1,5-a]pyridine-3-carboxamide | m/z 514.1 |
| 27 | 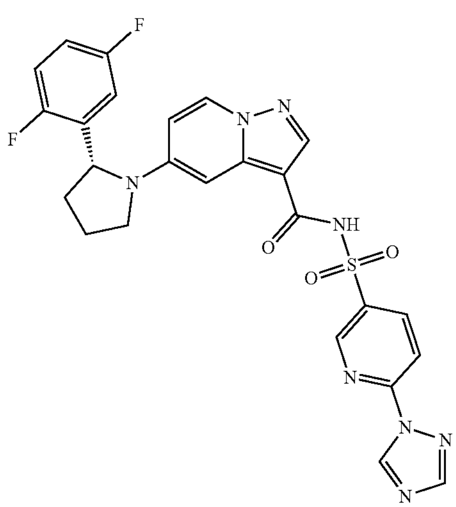 [SMILES: O=C(NS(=O)(=O)c1ccc(-n2cncn2)nc1)c1cnn2ccc(N3CCC[C@@H]3c3cc(F)ccc3F)cc12] | (R)-N-((6-(1H-1,2,4-triazol-1-yl)pyridin-3-yl)sulfonyl)-5-(2-(2,5-difluorophenyl)pyrrolidin-1-yl)pyrazolo[1,5-a]pyridine-3-carboxamide | m/z 551.2 |

-continued

| Example No. | Structure | IUPAC name | MS(ESI) M + H |
|---|---|---|---|
| 28 | 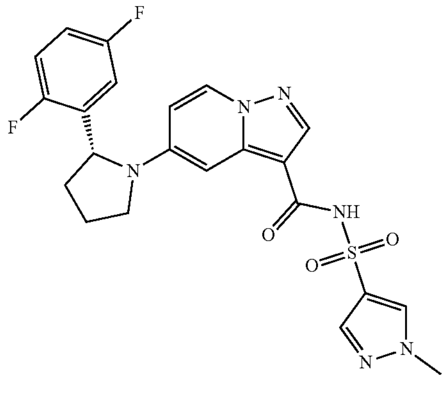 [SMILES: Cn1cc(S(=O)(=O)NC(=O)c2cnn3ccc(N4CCC[C@@H]4c4cc(F)ccc4F)cc23)cn1] | (R)-5-(2-(2,5-difluorophenyl)pyrrolidin-1-yl)-N-((1-methyl-1H-pyrazol-4-yl)sulfonyl)pyrazolo[1,5-a]pyridine-3-carboxamide | m/z 487.1 |
| 29 | 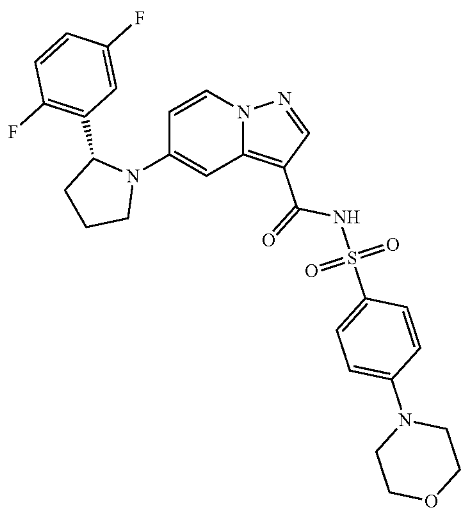 [SMILES: O=C(NS(=O)(=O)c1ccc(N2CCOCC2)cc1)c1cnn2ccc(N3CCC[C@@H]3c3cc(F)ccc3F)cc12] | (R)-5-(2-(2,5-difluorophenyl)pyrrolidin-1-yl)-N-((4-morpholinophenyl)sulfonyl)pyrazolo[1,5-a]pyridine-3-carboxamide | m/z 568.0 |
| 30 | 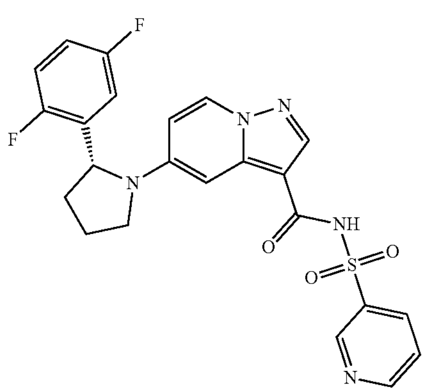 [SMILES: O=C(NS(=O)(=O)c1cccnc1)c1cnn2ccc(N3CCC[C@@H]3c3cc(F)ccc3F)cc12] | (R)-5-(2-(2,5-difluorophenyl)pyrrolidin-1-yl)-N-(pyridin-3-ylsulfonyl)pyrazolo[1,5-a]pyridine-3-carboxamide | m/z 484.1 |

-continued

| Example No. | Structure | IUPAC name | MS(ESI) M + H |
|---|---|---|---|
| 31 | 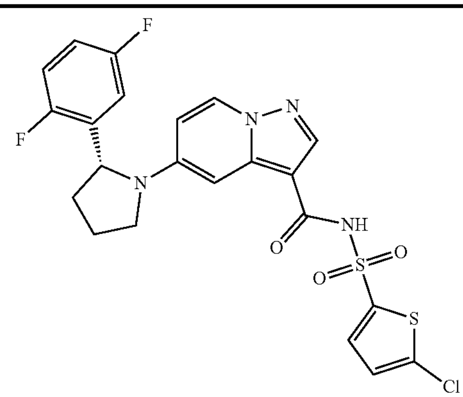 | (R)-N-((5-chlorothiophen-2-yl)sulfonyl)-5-(2-(2,5-difluorophenyl)pyrrolidin-1-yl)-pyrazolo[1,5-a]pyridine-3-carboxamide | m/z 523.0 |
| 32 | 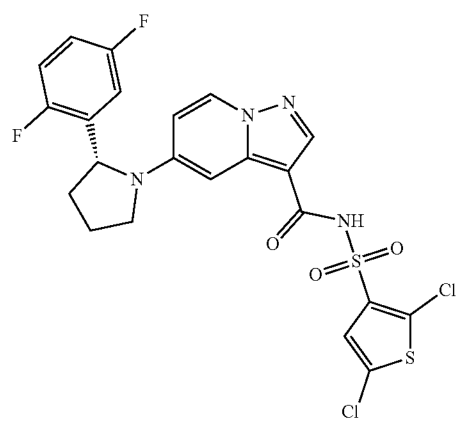 [SMILES: O=C(NS(=O)(=O)c1cc(Cl)sc1Cl)c1cnn2ccc(N3CCC[C@@H]3c3cc(F)ccc3F)cc12] | (R)-N-((2,5-dichlorothiophen-3-yl)sulfonyl)-5-(2-(2,5-difluorophenyl)pyrrolidin-1-yl)pyrazolo[1,5-a]pyridine-3-carboxamide | m/z 556.7 |
| 33 | 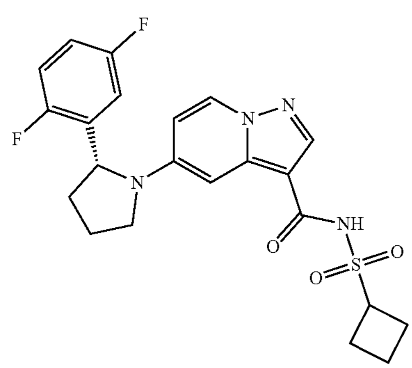 [SMILES: O=C(NS(=O)(=O)C1CCC1)c1cnn2ccc(N3CCC[C@@H]3c3cc(F)ccc3F)cc12] | (R)-N-(cyclobutylsulfonyl)-5-(2-(2,5-difluorophenyl)pyrrolidin-1-yl)pyrazolo[1,5-a]pyridine-3-carboxamide | m/z 461.1 |
| 34 | 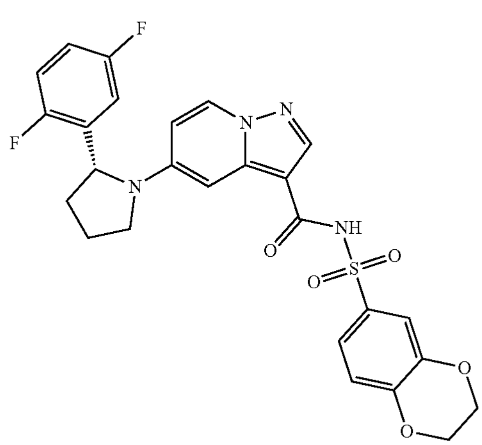 [SMILES: O=C(NS(=O)(=O)c1ccc2c(c1)OCCO2)c1cnn2ccc(N3CCC[C@@H]3c3cc(F)ccc3F)cc12] | (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide | m/z 541.1 |

| Example No. | Structure | IUPAC name | MS(ESI) M + H |
|---|---|---|---|
| 35 | 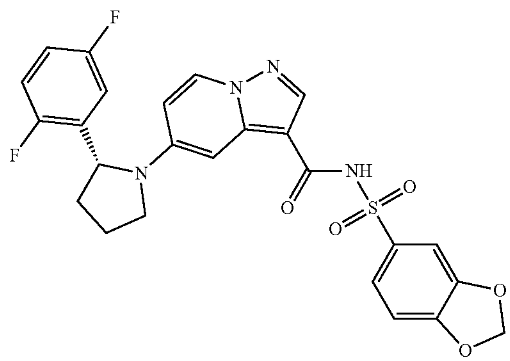 [SMILES: O=C(NS(=O)(=O)c1ccc2c(c1)OCO2)c1cnn2ccc(N3CCC[C@@H]3c3cc(F)ccc3F)cc12] | (R)-N-(benzo[d][1,3]dioxol-5-ylsulfonyl)-5-(2-(2,5-difluorophenyl)pyrrolidin-1-yl)pyrazolo[1,5-a]pyridine-3-carboxamide | m/z 527.1 |
| 36 | 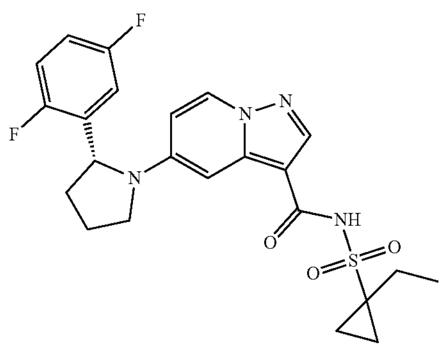 [SMILES: CCC1(S(=O)(=O)NC(=O)c2cnn3ccc(N4CCC[C@@H]4c4cc(F)ccc4F)cc23)CC1] | (R)-5-(2,5-difluorophenyl)pyrrolidin-1-yl)-N-((1-ethylcyclopropyl)sulfonyl)pyrazolo[1,5-a]pyridine-3-carboxamide | m/z 475.4 |
| 37 | 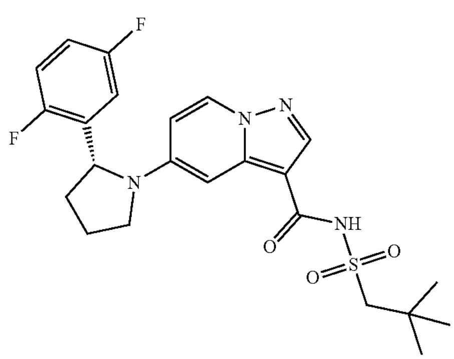 [SMILES: CC(C)(C)CS(=O)(=O)NC(=O)c1cnn2ccc(N3CCC[C@@H]3c3cc(F)ccc3F)cc12] | (R)-5-(2-(2,5-difluorophenyl)pyrrolidin-1-yl)-N-(neopentylsulfonyl)pyrazolo[1,5-a]pyridine-3-carboxamide | m/z 477.4 |
| 38 | 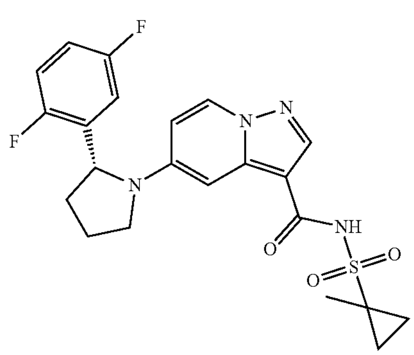 [SMILES: CC1(S(=O)(=O)NC(=O)c2cnn3ccc(N4CCC[C@@H]4c4cc(F)ccc4F)cc23)CC1] | (R)-5-(2-(2,5-difluorophenyl)-pyrrolidin-1-yl)-N-((1-methylcyclopropyl)sulfonyl)-pyrazolo[1,5-a]pyridine-3-carboxamide | m/z 461.1 |

-continued

| Example No. | Structure | IUPAC name | MS(ESI) M + H |
|---|---|---|---|
| 39 | 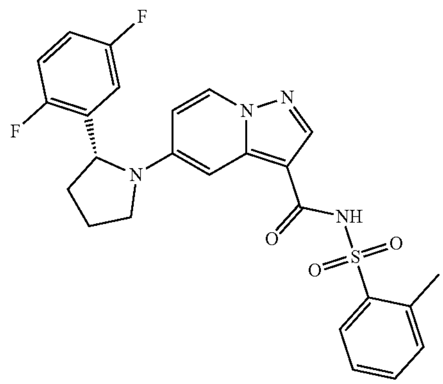 [SMILES: Cc1ccccc1S(=O)(=O)NC(=O)c1cnn2ccc(N3CCC[C@@H]3c3cc(F)ccc3F)cc12] | (R)-5-(2-(2,5-difluorophenyl) pyrrolidin-1-yl)-N-(o-tolylsulfonyl)pyrazolo[1,5-a]pyridine-3-carboxamide | m/z 498.05 |
| 40 | 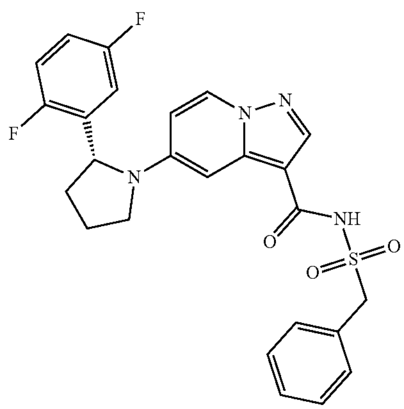 [SMILES: O=C(NS(=O)(=O)Cc1ccccc1)c1cnn2ccc(N3CCC[C@@H]3c3cc(F)ccc3F)cc12] | (R)-N-(benzylsulfonyl)-5-(2-(2,5-difluorophenyl)pyrrolidin-1-yl)pyrazolo[1,5-a]pyridine-3-carboxamide | m/z 497.2 |
| 41 | 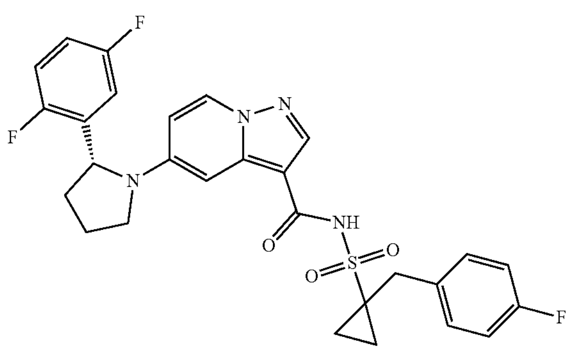 [SMILES: O=C(NS(=O)(=O)C1(Cc2ccc(F)cc2)CC1)c1cnn2ccc(N3CCC[C@@H]3c3cc(F)ccc3F)cc12] | (R)-5-(2-(2,5-difluorophenyl)pyrrolidin-1-yl)-N-((1-(4-fluorobenzyl)cyclopropyl)sulfonyl) pyrazolo[1,5-a]pyridine-3-carboxamide | m/z 555.4 |
| 42 | 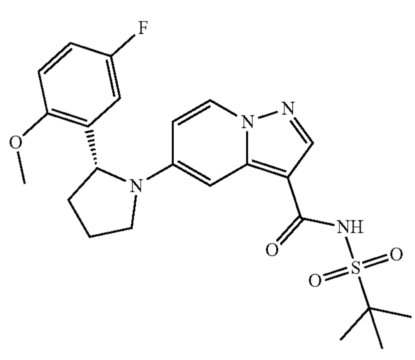 [SMILES: COc1ccc(F)cc1[C@H]1CCCN1c1ccn2ncc(C(=O)NS(=O)(=O)C(C)(C)C)c2c1] | (R)-N-(tert-butylsulfonyl)-5-(2-(5-fluoro-2-methoxyphenyl)pyrrolidin-1-yl)pyrazolo[1,5-a]pyridine-3-carboxamide | m/z 475.0 |

-continued

| Example No. | Structure | IUPAC name | MS(ESI) M + H |
|---|---|---|---|
| 43 | 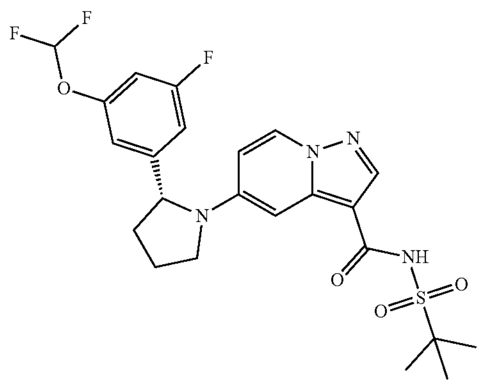 [SMILES: CC(C)(C)S(=O)(=O)NC(=O)c1cnn2ccc(N3CCC[C@@H]3c3cc(F)cc(OC(F)F)c3)cc12] | (R)-N-(tert-butylsulfonyl)-5-(2-(3-(difluoromethoxy)-5-fluorophenyl)pyrrolidin-1-yl)pyrazolo[1,5-a]pyridine-3-carboxamide | m/z 510.9 |
| 44 | 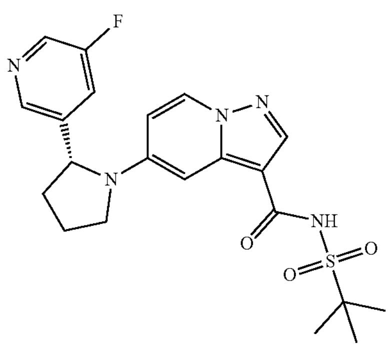 [SMILES: CC(C)(C)S(=O)(=O)NC(=O)c1cnn2ccc(N3CCC[C@@H]3c3cncc(F)c3)cc12] | (R)-N-(tert-butylsulfonyl)-5-(2-(5-fluoropyridin-3-yl)pyrrolidin-1-yl)pyrazolo[1,5-a]pyridine-3-carboxamide | m/z 446.1 |
| 45 | 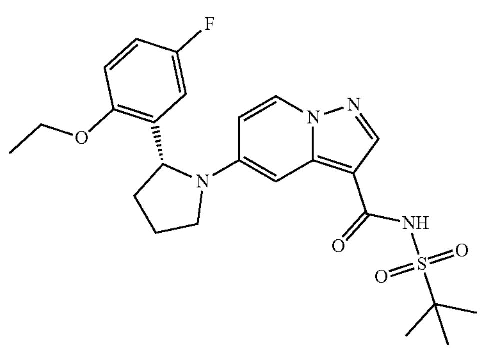 [SMILES: CCOc1ccc(F)cc1[C@H]1CCCN1c1ccn2ncc(C(=O)NS(=O)(=O)C(C)(C)C)c2c1] | (R)-N-(tert-butylsulfonyl)-5-(2-(2-ethoxy-5-fluorophenyl)pyrrolidin-1-yl)pyrazolo[1,5-a]pyridine-3-carboxamide | m/z 488.9 |
| 46 | 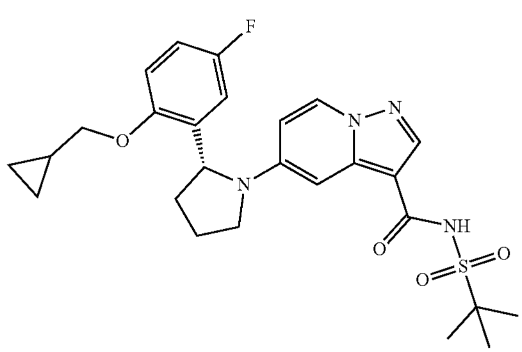 [SMILES: CC(C)(C)S(=O)(=O)NC(=O)c1cnn2ccc(N3CCC[C@@H]3c3cc(F)ccc3OCC3CC3)cc12] | (R)-N-(tert-butylsulfonyl)-5-(2-(2-(cyclopropylmethoxy)-5-fluorophenyl)pyrrolidin-1-yl)pyrazolo[1,5-a]pyridine-3-carboxamide | m/z 514.8 |

-continued

| Example No. | Structure | IUPAC name | MS(ESI) M + H |
|---|---|---|---|
| 47 | 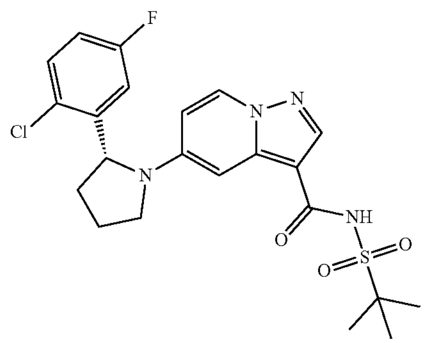 [SMILES: CC(C)(C)S(=O)(=O)NC(=O)c1cnn2ccc(N3CCC[C@@H]3c3cc(F)ccc3Cl)cc12] | (R)-N-(tert-butylsulfonyl)-5-(2-(2-chloro-5-fluorophenyl)pyrrolidin-1-yl)pyrazolo[1,5-a]pyridine-3-carboxamide | m/z 479.1 |
| 48 | 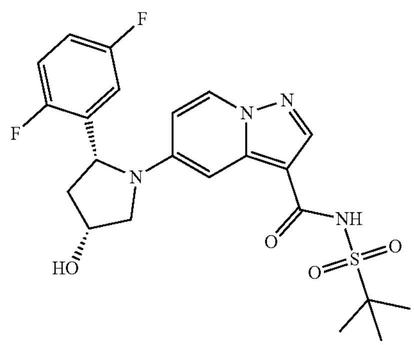 [SMILES: CC(C)(C)S(=O)(=O)NC(=O)c1cnn2ccc(N3C[C@H](O)C[C@@H]3c3cc(F)ccc3F)cc12] | N-(tert-butylsulfonyl)-5-((2R,4R)-2-(2,5-difluorophenyl)-4-hydroxypyrrolidin-1-yl)pyrazolo[1,5-a]pyridine-3-carboxamide | m/z 478.9 |
| 49 | 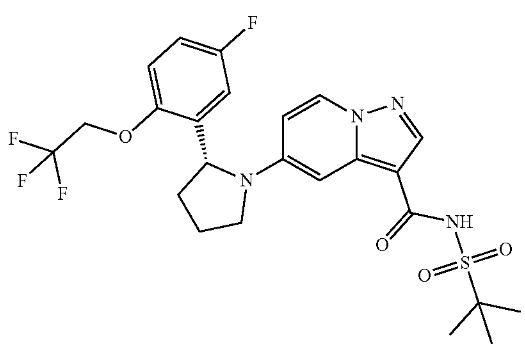 [SMILES: CC(C)(C)S(=O)(=O)NC(=O)c1cnn2ccc(N3CCC[C@@H]3c3cc(F)ccc3OCC(F)(F)F)cc12] | (R)-N-(tert-butylsulfonyl)-5-(2-(5-fluoro-2-(2,2,2-trifluoroethoxy)phenyl)pyrrolidin-1-yl)pyrazolo[1,5-a]pyridine-3-carboxamide | m/z 542.7 |
| 50 (Isomer-I) | 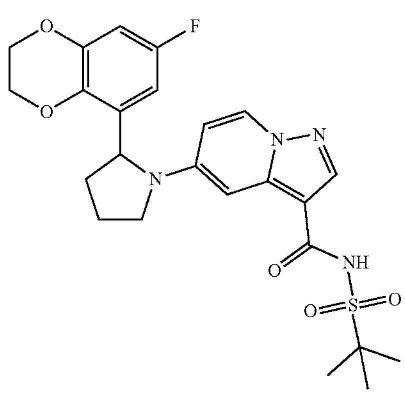 [SMILES: CC(C)(C)S(=O)(=O)NC(=O)c1cnn2ccc(N3CCCC3c3cc(F)cc4c3OCCO4)cc12] | N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide | m/z 503.4 |

-continued

| Example No. | Structure | IUPAC name | MS(ESI) M + H |
|---|---|---|---|
| 51 (Isomer-II) | 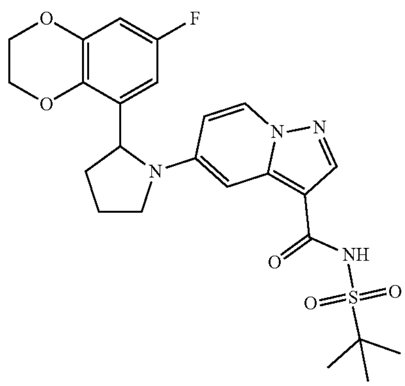 [SMILES: CC(C)(C)S(=O)(=O)NC(=O)c1cnn2ccc(N3CCCC3c3cc(F)cc4c3OCCO4)cc12] | N-(tert-butylsulfonyl)-5-(2-(7-fluoro-2,3-dihydrobenzo[b][1,4]-dioxin-5-yl)pyrrolidin-1-yl)pyrazolo[1,5-a]pyridine-3-carboxamide | |
| 52 (Isomer-I) | 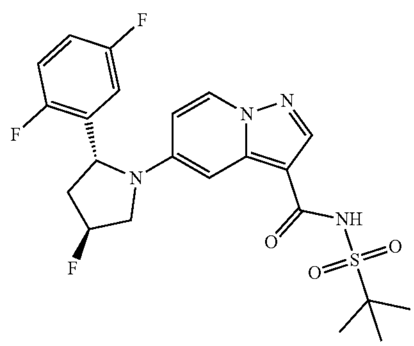 [SMILES: CC(C)(C)S(=O)(=O)NC(=O)c1cnn2ccc(N3C[C@@H](F)C[C@@H]3c3cc(F)ccc3F)cc12] | N-(tert-butylsulfonyl)-5-((2R,4S)-2-(2,5-difluorophenyl)-4-fluoropyrrolidin-1-yl)pyrazolo[1,5-a]pyridine-3-carboxamide | m/z 481.2 |
| 53 (Isomer-II) | 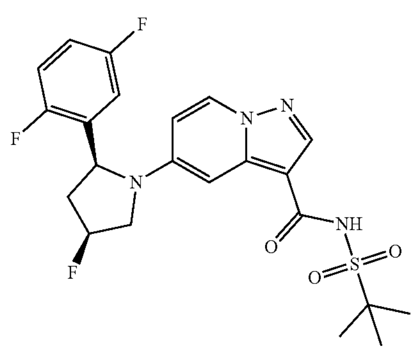 [SMILES: CC(C)(C)S(=O)(=O)NC(=O)c1cnn2ccc(N3C[C@@H](F)C[C@H]3c3cc(F)ccc3F)cc12] | N-(tert-butylsulfonyl)-5-((2R,4S)-2-(2,5-difluorophenyl)-4-fluoropyrrolidin-1-yl)pyrazolo[1,5-a]pyridine-3-carboxamide | m/z 481.3 |
| 54 | 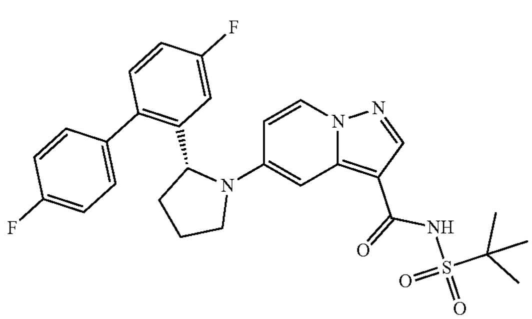 [SMILES: CC(C)(C)S(=O)(=O)NC(=O)c1cnn2ccc(N3CCC[C@@H]3c3cc(F)ccc3-c3ccc(F)cc3)cc12] | (R)-N-(tert-butylsulfonyl)-5-(2-(4,4'-difluoro-[1,1'-biphenyl]-2-yl)pyrrolidin-1-yl)pyrazolo[1,5-a]pyridine-3-carboxamide | m/z 539.1 |

-continued

| Example No. | Structure | IUPAC name | MS(ESI) M + H |
|---|---|---|---|
| 55 (Isomer-I) | 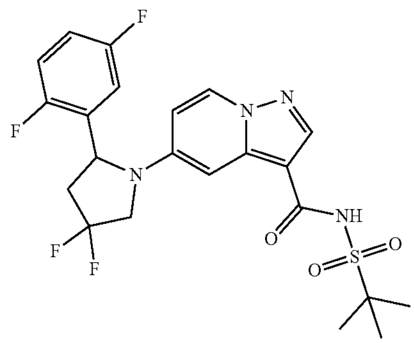 [SMILES: CC(C)(C)S(=O)(=O)NC(=O)c1cnn2ccc(N3CC(F)(F)CC3c3cc(F)ccc3F)cc12] | (S)-N-(tert-butylsulfonyl)-5-(2-(2,5-difluorophenyl)-4,4-difluoropyrrolidin-1-yl)-pyrazolo[1,5-a]pyridine-3-carboxamide | m/z 499.25 |
| 56 (Isomer-II): | 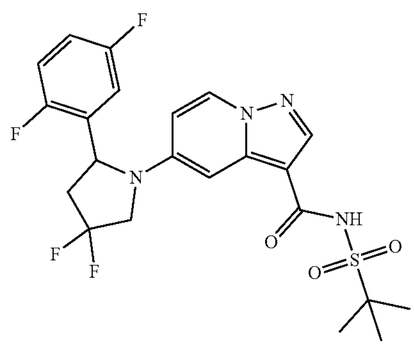 [SMILES: CC(C)(C)S(=O)(=O)NC(=O)c1cnn2ccc(N3CC(F)(F)CC3c3cc(F)ccc3F)cc12] | (R)-N-(tert-butylsulfonyl)-5-(2-(2,5-difluorophenyl)-4,4-difluoropyrrolidin-1-yl)-pyrazolo[1,5-a]pyridine-3-carboxamide | m/z 499.45 |
| 57 | 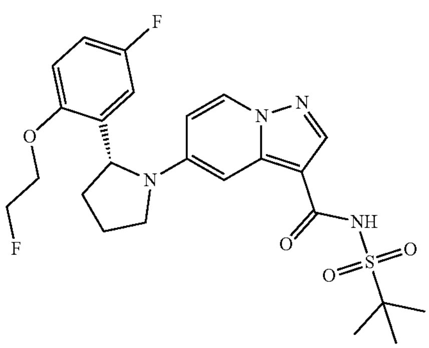 [SMILES: CC(C)(C)S(=O)(=O)NC(=O)c1cnn2ccc(N3CCC[C@@H]3c3cc(F)ccc3OCCF)cc12] | (R)-N-(tert-butylsulfonyl)-5-(2-(5-fluoro-2-(2-fluoroethoxy)phenyl)pyrrolidin-1-yl)pyrazolo[1,5-a]pyridine-3-carboxamide | m/z 507.1 |
| 58 | 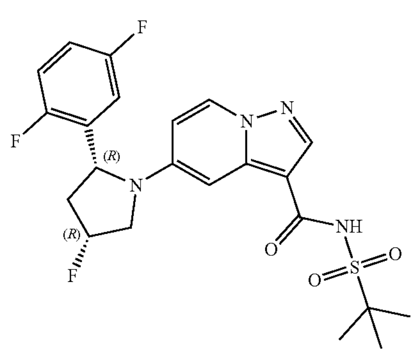 | N-(tert-butylsulfonyl)-5-((2R,4R)-2-(2,5-difluorophenyl)-4-fluoropyrrolidin-1-yl)pyrazolo[1,5-a]pyridine-3-carboxamide | m/z 481.1 |

-continued

| Example No. | Structure | IUPAC name | MS(ESI) M + H |
|---|---|---|---|
| 59 | 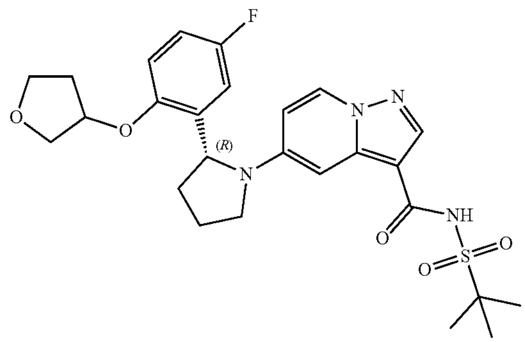 | N-(tert-butylsulfonyl)-5-((2R)-2-(5-fluoro-2-((tetrahydrofuran-3-yl)oxy)phenyl)pyrrolidin-1-yl)pyrazolo[1,5-a]pyridine-3-carboxamide | m/z 531.6 |
| 60: | 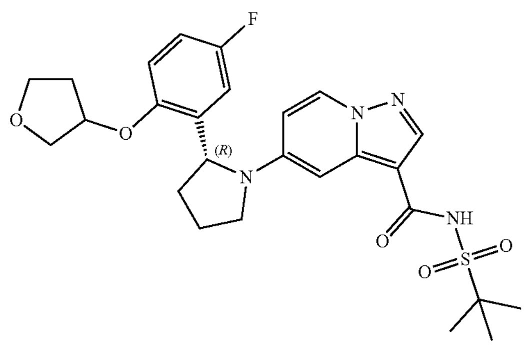 | N-(tert-butylsulfonyl)-5-((2R)-2-(5-fluoro-2-((tetrahydrofuran-3-yl)oxy)phenyl)pyrrolidin-1-yl)pyrazolo[1,5-a]pyridine-3-carboxamide | m/z 531.6 |
| 61 | 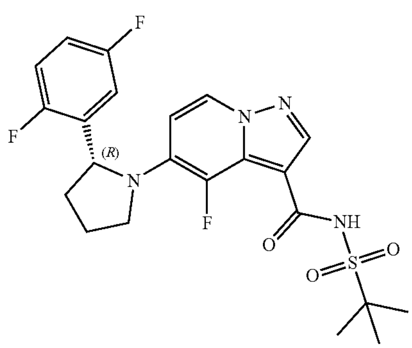 | (R)-N-(tert-butylsulfonyl)-5-(2-(2,5-difluorophenyl)pyrrolidin-1-yl)-4-fluoropyrazolo[1,5-a]pyridine-3-carboxamide | m/z 481.1 |
| 62 | 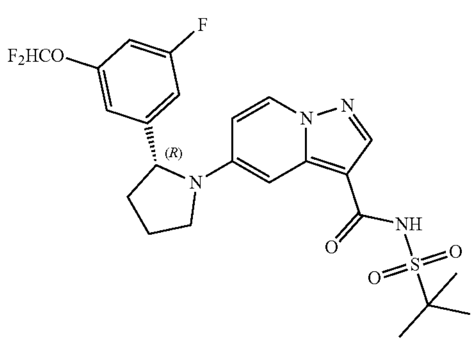 | (R)-N-(tert-butylsulfonyl)-5-(2-(2-(difluoromethoxy)-5-fluorophenyl)pyrrolidin-1-yl)-4-fluoropyrazolo[1,5-a]pyridine-3-carboxamide | m/z 529.1 |

-continued

| Example No. | Structure | IUPAC name | MS(ESI) M + H |
|---|---|---|---|
| 63 | 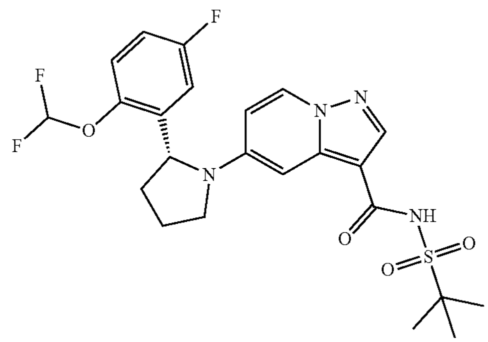 [SMILES: CC(C)(C)S(=O)(=O)NC(=O)c1cnn2ccc(N3CCC[C@@H]3c3cc(F)ccc3OC(F)F)cc12] | (R)-N-(tert-butylsulfonyl)-5-(2-(2-(difluoromethoxy)-5-fluorophenyl)pyrrolidin-1-yl)pyrazolo[1,5-a]pyridine-3-carboxamide | m/z 511.1 |
| 64 | 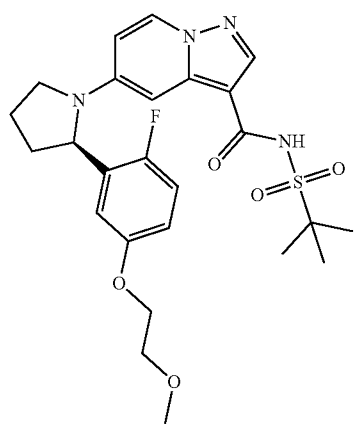 [SMILES: COCCOc1ccc(F)c([C@H]2CCCN2c2ccn3ncc(C(=O)NS(=O)(=O)C(C)(C)C)c3c2)c1] | (R)-N-(tert-butylsulfonyl)-5-(2-(2-fluoro-5-(2-methoxyethoxy)phenyl)pyrrolidin-1-yl)-pyrazolo[1,5-a]pyridine-3-carboxamide | m/z 519.2 |
| 65 | 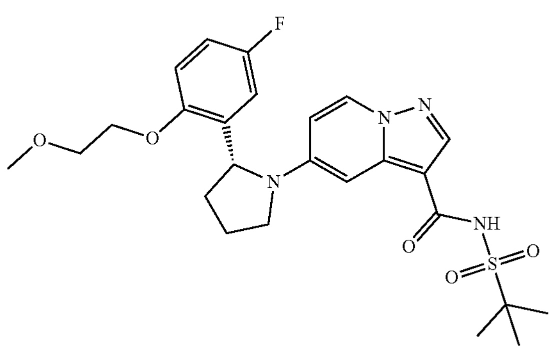 [SMILES: COCCOc1ccc(F)cc1[C@H]1CCCN1c1ccn2ncc(C(=O)NS(=O)(=O)C(C)(C)C)c2c1] | (R)-N-(tert-butylsulfonyl)-5-(2-(5-fluoro-2-(2-methoxyethoxy)phenyl)pyrrolidin-1-yl)pyrazolo[1,5-a]pyridine-3-carboxamide | m/z 519.1 |
| 66 | 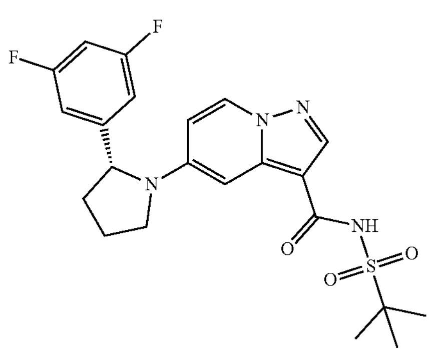 [SMILES: CC(C)(C)S(=O)(=O)NC(=O)c1cnn2ccc(N3CCC[C@@H]3c3cc(F)cc(F)c3)cc12] | (R)-N-(tert-butylsulfonyl)-5-(2-(3,5-difluorophenyl)pyrrolidin-1-yl)pyrazolo[1,5-a]pyridine-3-carboxamide | m/z 463.1 |

-continued

| Example No. | Structure | IUPAC name | MS(ESI) M + H |
|---|---|---|---|
| 67 | 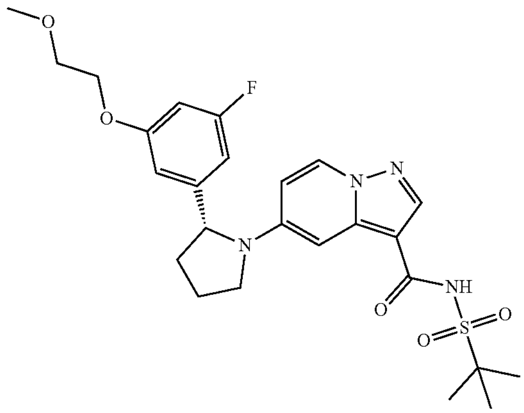 [SMILES: COCCOc1cc(F)cc([C@H]2CCCN2c2ccn3ncc(C(=O)NS(=O)(=O)C(C)(C)C)c3c2)c1] | (R)-N-(tert-butylsulfonyl)-5-(2-(3-fluoro-5-(2-methoxyethoxy)phenyl)pyrrolidin-1-yl)pyrazolo[1,5-a]pyridine-3-carboxamide | m/z 519.2 |
| 68 | 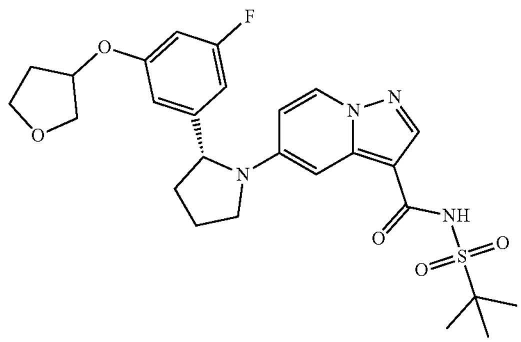 [SMILES: CC(C)(C)S(=O)(=O)NC(=O)c1cnn2ccc(N3CCC[C@@H]3c3cc(F)cc(OC4CCOC4)c3)cc12] | N-(tert-butylsulfonyl)-5-((2R)-2-(3-fluoro-5-((tetrahydrofuran-3-yl)oxy)phenyl)pyrrolidin-1-yl)pyrazolo[1,5-a]pyridine-3-carboxamide | m/z 531.2 |
| 69 | 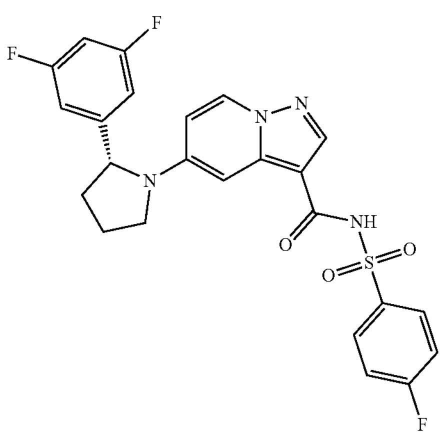 [SMILES: O=C(NS(=O)(=O)c1ccc(F)cc1)c1cnn2ccc(N3CCC[C@@H]3c3cc(F)cc(F)c3)cc12] | (R)-5-(2-(3,5-difluorophenyl)pyrrolidin-1-yl)-N-((4-fluorophenyl)sulfonyl)pyrazolo[1,5-a]pyridine-3-carboxamide | m/z 501 |

-continued

| Example No. | Structure | IUPAC name | MS(ESI) M + H |
|---|---|---|---|
| 70 | 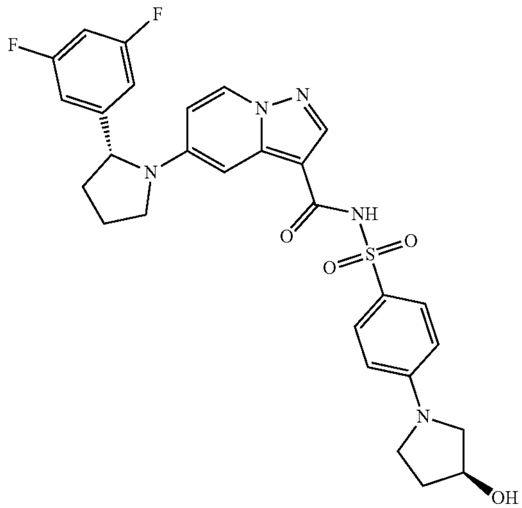 [SMILES: O=C(NS(=O)(=O)c1ccc(N2CC[C@H](O)C2)cc1)c1cnn2ccc(N3CCC[C@@H]3c3cc(F)cc(F)c3)cc12] | 5-((R)-2-(3,5-difluorophenyl) pyrrolidin-1-yl)-N-((4-((S)-3-hydroxypyrrolidin-1-yl)phenyl) sulfonyl)pyrazolo[1,5-a]pyridine-3-carboxamide | m/z 568.1 |
| 71 | 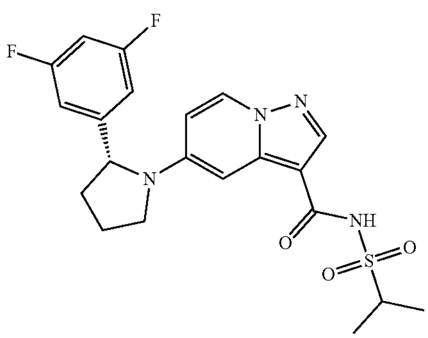 [SMILES: CC(C)S(=O)(=O)NC(=O)c1cnn2ccc(N3CCC[C@@H]3c3cc(F)cc(F)c3)cc12] | (R)-5-(2-(3,5-difluorophenyl) pyrrolidin-1-yl)-N-(isopropyl-sulfonyl)pyrazolo[1,5-a]pyridine-3-carboxamide | m/z 449.1 |
| 72 | 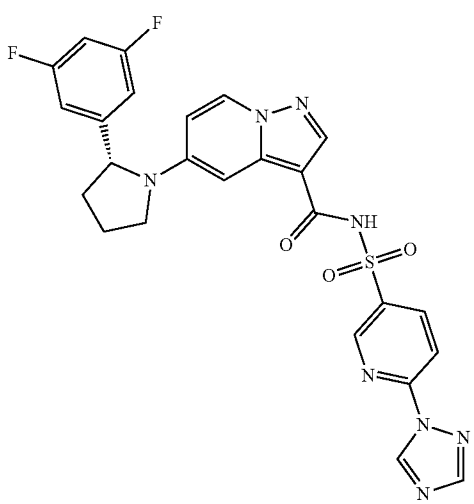 [SMILES: O=C(NS(=O)(=O)c1ccc(-n2cncn2)nc1)c1cnn2ccc(N3CCC[C@@H]3c3cc(F)cc(F)c3)cc12] | (R)-N-((6-(1H-1,2,4-triazol-1-yl)pyridin-3-yl)sulfonyl)-5-(2-(3,5-difluorophenyl)pyrrolidin-1-yl)pyrazolo[1,5-a]pyridine-3-carboxamide | m/z 551.1 |

-continued

| Example No. | Structure | IUPAC name | MS(ESI) M + H |
|---|---|---|---|
| 73 | 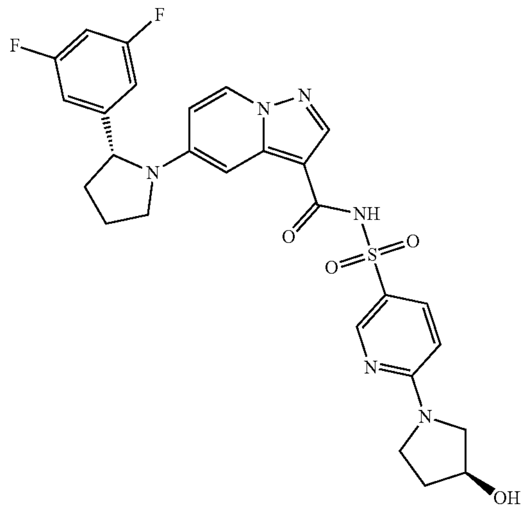 [SMILES: O=C(NS(=O)(=O)c1ccc(N2CC[C@H](O)C2)nc1)c1cnn2ccc(N3CCC[C@@H]3c3cc(F)cc(F)c3)cc12] | 5-((R)-2-(3,5-difluorophenyl)pyrrolidin-1-yl)-N-((6-((S)-3-hydroxypyrrolidin-1-yl)pyridin-3-yl)sulfonyl)pyrazolo[1,5-a]pyridine-3-carboxamide | m/z 568.9 |
| 74 | 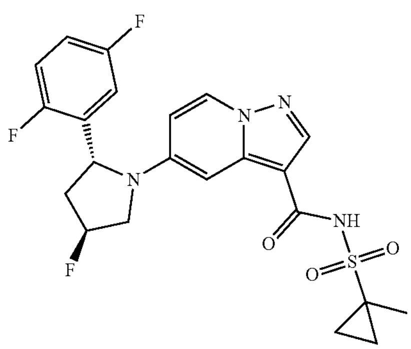 [SMILES: CC1(S(=O)(=O)NC(=O)c2cnn3ccc(N4C[C@@H](F)C[C@@H]4c4cc(F)ccc4F)cc23)CC1] | 5-((2R,4S)-2-(2,5-difluorophenyl)-4-fluoropyrrolidin-1-yl)-N-((1-methylcyclopropyl)sulfonyl)pyrazolo[1,5-a]pyridine-3-carboxamide | m/z 479.1 |
| 75 | 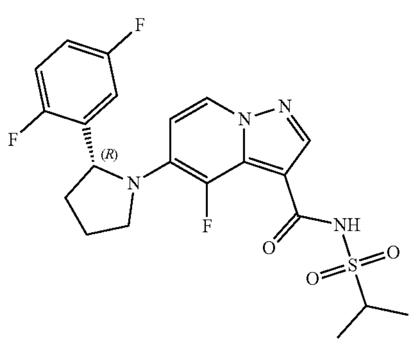 | (R)-5-(2-(2,5-difluorophenyl)pyrrolidin-1-yl)-4-fluoro-N-(isopropylsulfonyl)pyrazolo[1,5-a]pyridine-3-carboxamide | m/z 467.2 |

Example-76: (R)-5-(2-(2, 5-difluorophenyl) pyrrolidin-1-yl)-N—(N,N-dimethylsulfamoyl) pyrazolo [1, 5-a] pyridine-3-carboxamide

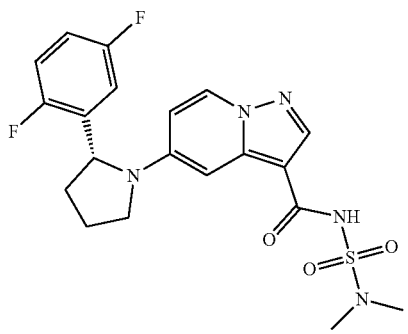 [SMILES: CN(C)S(=O)(=O)NC(=O)c1cnn2ccc(N3CCC[C@@H]3c3cc(F)ccc3F)cc12]

To a stirred solution of (R)-5-(2-(2, 5-difluorophenyl) pyrrolidin-1-yl)pyrazolo[1,5-a]pyridine-3-carboxylic acid (0.1 g, 0.29 mmol) in DCM (20 mL), added EDCI (0.084 g, 0.43 mmol) followed by DMAP (0.18 g, 1.4 mmol) and stirring was continued at 28° C. for 16 hr. To the above reaction added 1,1,-dimethyl sulfamide (0.09 g, 0.69 mmol), stirring was continued at 28° C. for 48 hr. Reaction mixture was diluted with DCM, washed it with saturated KHSO$_4$ solution followed by brine, dried over anhydrous sodium sulphate and concentrated under reduced pressure to afford the crude. The crude obtained was purified by preparative HPLC (AG/AD/PP/C18-25/033, Flow rate: 20 mL/min., Mobile phase: 0.1% TFA in water (A): ACN (B), Gradient—Time: % B=0: 20, 2: 30, 10: 70) to afford (R)-5-(2-(2, 5-difluorophenyl) pyrrolidin-1-yl)-N—(N,N-dimethylsulfamoyl) pyrazolo [1, 5-a] pyridine-3-carboxamide as pale pink solid. MS (ESI): m/z 450.3 (M+H).

$^1$HNMR (300 MHz, DMSO-d6): δ ppm 11.2 (1H, s), 8.6-8.4 (2H, m), 7.2-7.1 (1H, m), 7.1-7.05 (1H, m,), 7.0-6.8 (2H, m), 6.5-6.3 (1H, d), 5.25-5.08 (1H, d), 3.95-3.75 (1H, m), 3.55-3.4 (1H, m), 2.84 (6H, s), 2.15-2.85 (3H, m).

Following acylsulfamides Example-77 to Example-116 were synthesized by a similar procedure as that of Example-76.

| Example | | | |
|---|---|---|---|
| 77 | 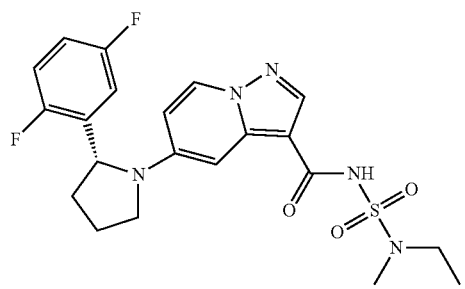 [SMILES: CCN(C)S(=O)(=O)NC(=O)c1cnn2ccc(N3CCC[C@@H]3c3cc(F)ccc3F)cc12] | (R)-5-(2-(2,5-difluorophenyl) pyrrolidin-1-yl)-N-(N-ethyl-N-methylsulfamoyl) pyrazolo[1,5-a]pyridine-3-carboxamide | m/z 463.8 |
| 78 | 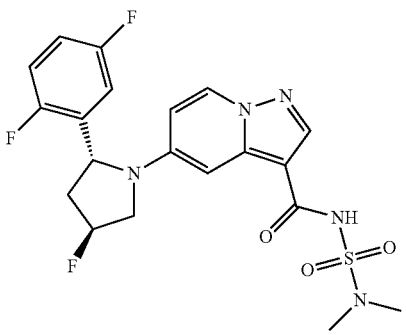 [SMILES: CN(C)S(=O)(=O)NC(=O)c1cnn2ccc(N3C[C@@H](F)C[C@@H]3c3cc(F)ccc3F)cc12] | 5-((2R,4S)-2-(2,5-difluorophenyl)-4-fluoropyrrolidin-1-yl)-N-(N,N-dimethylsulfamoyl)pyrazolo[1,5-a]pyridine-3-carboxamide | m/z 468.1 |
| 79 | 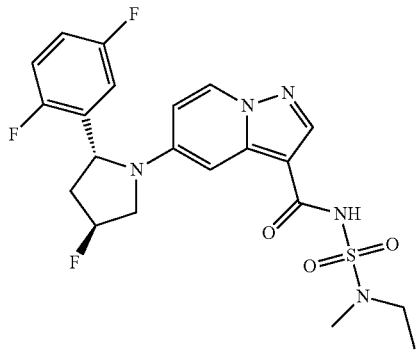 [SMILES: CCN(C)S(=O)(=O)NC(=O)c1cnn2ccc(N3C[C@@H](F)C[C@@H]3c3cc(F)ccc3F)cc12] | 5-((2R,4S)-2-(2,5-difluorophenyl)-4-fluoropyrrolidin-1-yl)-N-(N-ethyl-N-methylsulfamoyl)pyrazolo[1,5-a]pyridine-3-carboxamide | m/z 482.1 |

-continued

| Example | | | |
|---|---|---|---|
| 80 | 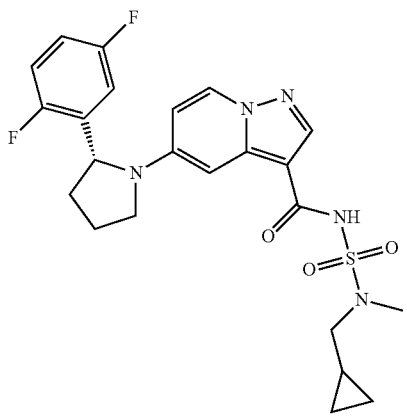 [SMILES: CN(CC1CC1)S(=O)(=O)NC(=O)c1cnn2ccc(N3CCC[C@@H]3c3cc(F)ccc3F)cc12] | (R)-N-(N-(cyclopropylmethyl)-N-methylsulfamoyl)-5-(2-(2,5-difluorophenyl)pyrrolidin-1-yl)pyrazolo[1,5-a]pyridine-3-carboxamide | m/z 490.6 |
| 81 | 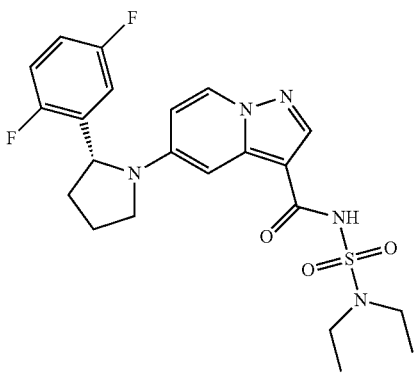 [SMILES: CCN(CC)S(=O)(=O)NC(=O)c1cnn2ccc(N3CCC[C@@H]3c3cc(F)ccc3F)cc12] | (R)-N-(N,N-diethylsulfamoyl)-5-(2-(2,5-difluorophenyl)pyrrolidin-1-yl)pyrazolo[1,5-a]pyridine-3-carboxamide | m/z 478.1 |
| 82 | 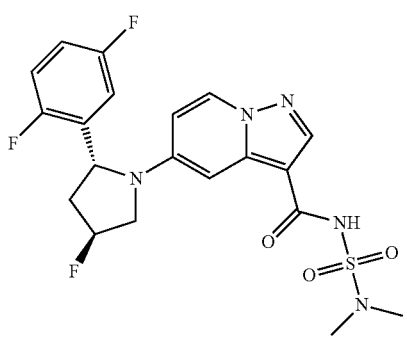 | 5-((2R,4S)-2-(2,5-difluorophenyl)-4-fluoropyrrolidin-1-yl)-N-(N,N-dimethylsulfamoyl)pyrazolo[1,5-a]pyridine-3-carboxamide | m/z 468.1 |
| 83 | 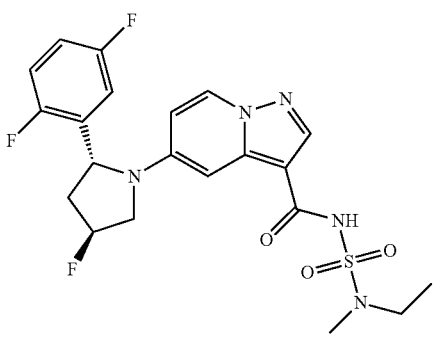 [SMILES: CCN(C)S(=O)(=O)NC(=O)c1cnn2ccc(N3C[C@@H](F)C[C@@H]3c3cc(F)ccc3F)cc12] | 5-((2R,4S)-2-(2,5-difluorophenyl)-4-fluoropyrrolidin-1-yl)-N-(N-ethyl-N-methylsulfamoyl)pyrazolo[1,5-a]pyridine-3-carboxamide | m/z 482.1 |

| Example | | | |
|---|---|---|---|
| 84 | 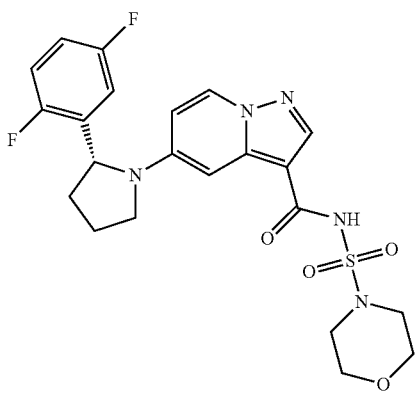 [SMILES: O=C(NS(=O)(=O)N1CCOCC1)c1cnn2ccc(N3CCC[C@@H]3c3cc(F)ccc3F)cc12] | (R)-5-(2-(2,5-difluorophenyl)pyrrolidin-1-yl)-N-(morpholinosulfonyl)pyrazolo[1,5-a]pyridine-3-carboxamide | m/z 492.1 |
| 85 | 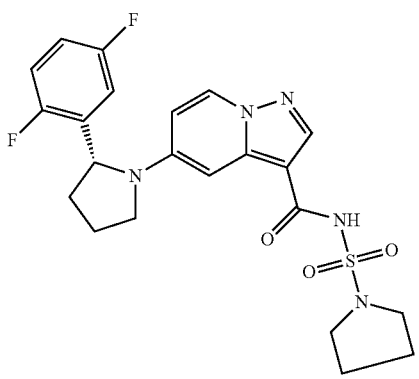 [SMILES: O=C(NS(=O)(=O)N1CCCC1)c1cnn2ccc(N3CCC[C@@H]3c3cc(F)ccc3F)cc12] | (R)-5-(2-(2,5-difluorophenyl)pyrrolidin-1-yl)-N-(pyrrolidin-1-ylsulfonyl)pyrazolo[1,5-a]pyridine-3-carboxamide | m/z 476.3 |
| 86 | 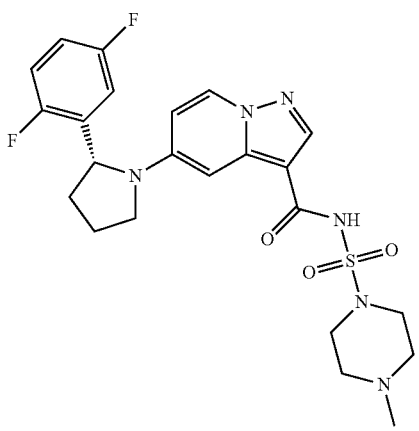 [SMILES: CN1CCN(S(=O)(=O)NC(=O)c2cnn3ccc(N4CCC[C@@H]4c4cc(F)ccc4F)cc23)CC1] | (R)-5-(2-(2,5-difluorophenyl)pyrrolidin-1-yl)-N-((4-methylpiperazin-1-yl)sulfonyl)pyrazolo[1,5-a]pyridine-3-carboxamide | m/z 505.2 |
| 87 | 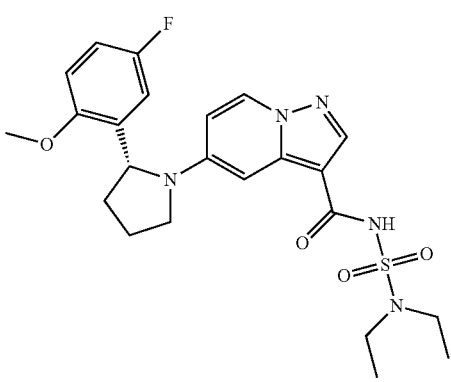 [SMILES: CCN(CC)S(=O)(=O)NC(=O)c1cnn2ccc(N3CCC[C@@H]3c3cc(F)ccc3OC)cc12] | (R)-N-(N,N-diethylsulfamoyl)-5-(2-(5-fluoro-2-methoxy-phenyl)pyrrolidin-1-yl)pyrazolo[1,5-a]pyridine-3-carboxamide | m/z 490.1 |

-continued

| Example | | | |
|---|---|---|---|
| 88 | 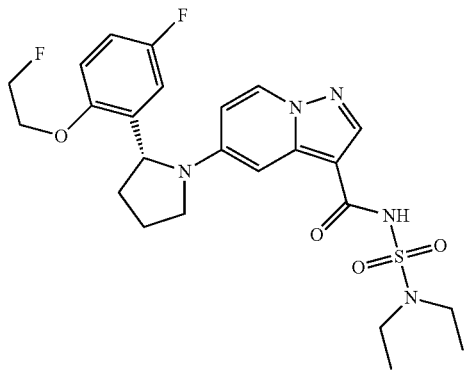 [SMILES: CCN(CC)S(=O)(=O)NC(=O)c1cnn2ccc(N3CCC[C@@H]3c3cc(F)ccc3OCCF)cc12] | (R)-N-(N,N-diethylsulfamoyl)-5-(2-(5-fluoro-2-(2-fluoro-ethoxy)phenyl)pyrrolidin-1-yl)pyrazolo[1,5-a]pyridine-3-carboxamide | m/z 522.55 |
| 89 | 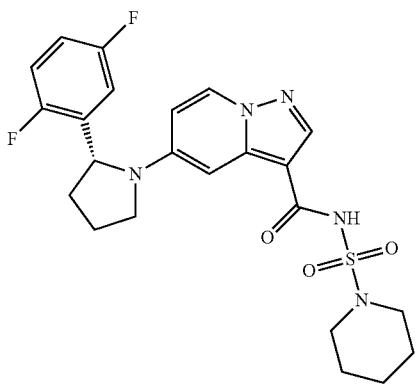 [SMILES: O=C(NS(=O)(=O)N1CCCCC1)c1cnn2ccc(N3CCC[C@@H]3c3cc(F)ccc3F)cc12] | (R)-5-(2-(2,5-difluorophenyl)pyrrolidin-1-yl)-N-(piperidin-1-ylsulfonyl)pyrazolo[1,5-a]pyridine-3-carboxamide | m/z 490.5 |
| 90 | 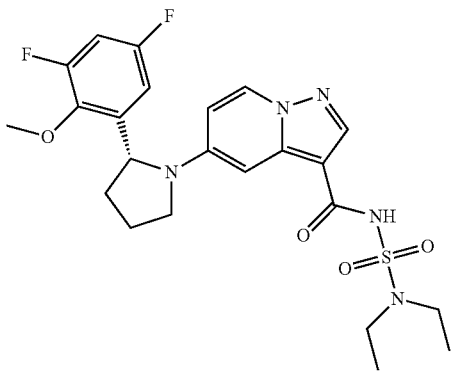 | (R)-5-(2-(3,5-difluoro-2-methoxyphenyl)pyrrolidin-1-yl)-N-(N-ethyl-N-methylsulfamoyl)pyrazolo[1,5-a]pyridine-3-carboxamide | m/z 494.5 |
| 91 | 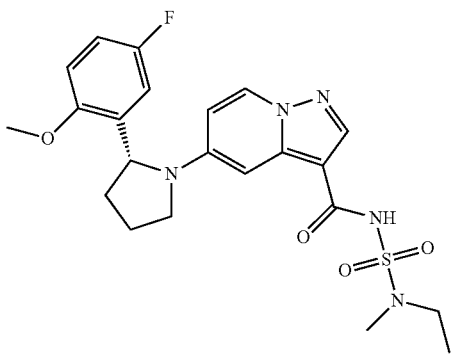 [SMILES: CCN(C)S(=O)(=O)NC(=O)c1cnn2ccc(N3CCC[C@@H]3c3cc(F)ccc3OC)cc12] | (R)-N-(N-ethyl-N-methylsulfamoyl)-5-(2-(5-fluoro-2-methoxyphenyl)pyrrolidin-1-yl)pyrazolo[1,5-a]pyridine-3-carboxamide | m/z 476.55 |

| Example | | | |
|---|---|---|---|
| 92 | 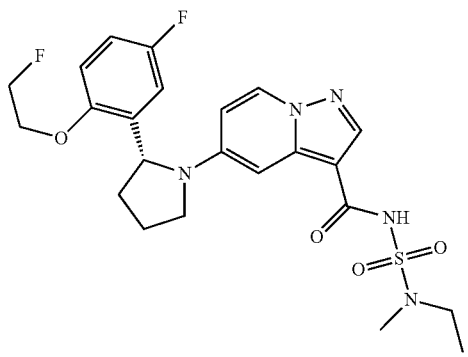 [SMILES: CCN(C)S(=O)(=O)NC(=O)c1cnn2ccc(N3CCC[C@@H]3c3cc(F)ccc3OCCF)cc12] | (R)-N-(N-ethyl-N-methyl-sulfamoyl)-5-(2-(5-fluoro-2-(2-fluoroethoxy)phenyl)pyrrolidin-1-yl)pyrazolo[1,5-a]pyridine-3-carboxamide | m/z 508.6 |
| 93 | 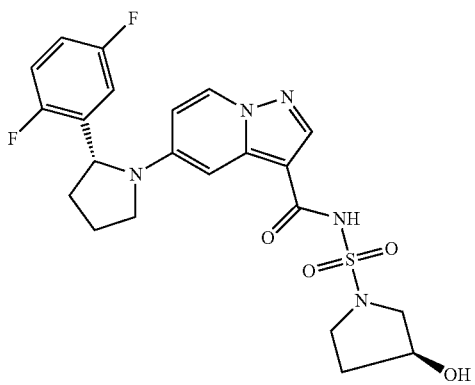 [SMILES: O=C(NS(=O)(=O)N1CC[C@H](O)C1)c1cnn2ccc(N3CCC[C@@H]3c3cc(F)ccc3F)cc12] | 5-((R)-2-(2,5-difluorophenyl)pyrrolidin-1-yl)-N-(((S)-3-hydroxypyrrolidin-1-yl)sulfonyl)pyrazolo[1,5-a]pyridine-3-carboxamide | m/z 492.3 |
| 94 | 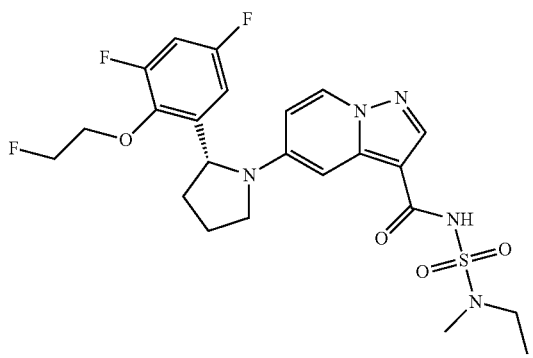 [SMILES: CCN(C)S(=O)(=O)NC(=O)c1cnn2ccc(N3CCC[C@@H]3c3cc(F)cc(F)c3OCCF)cc12] | (R)-5-(2-(3,5-difluoro-2-(2-fluoroethoxy)phenyl)pyrrolidin-1-yl)-N-(N-ethyl-N-methylsulfamoyl)pyrazolo[1,5-a]pyridine-3-carboxamide | m/z 525.8 |
| 95 | 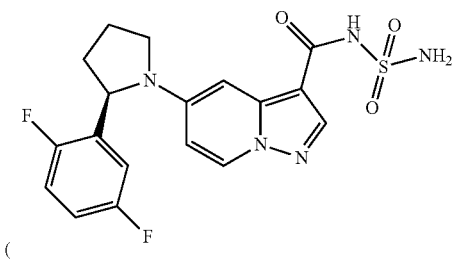 [SMILES: NS(=O)(=O)NC(=O)c1cnn2ccc(N3CCC[C@@H]3c3cc(F)ccc3F)cc12] | (R)-5-(2-(2,5-difluorophenyl)pyrrolidin-1-yl)-N-sulfamoyl-pyrazolo[1,5-a]pyridine-3-carboxamide | m/z 422.3 |

| Example | | | |
|---|---|---|---|
| 96 | 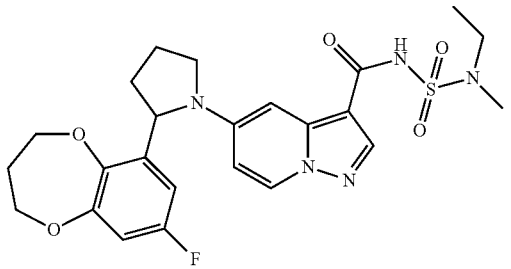 [SMILES: CCN(C)S(=O)(=O)NC(=O)c1cnn2ccc(N3CCCC3c3cc(F)cc4c3OCCCO4)cc12] | N-(N-ethyl-N-methylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I) | m/z 518.2 |
| 97 | 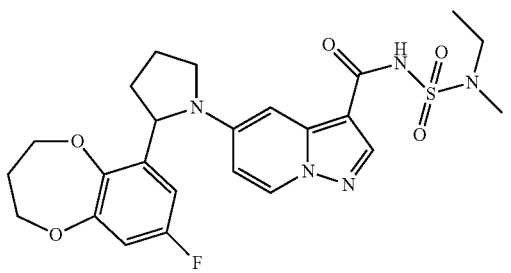 [SMILES: CCN(C)S(=O)(=O)NC(=O)c1cnn2ccc(N3CCCC3c3cc(F)cc4c3OCCCO4)cc12] | N-(N-ethyl-N-methylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diasteromer-II) | m/z 518.2 |
| 98 | 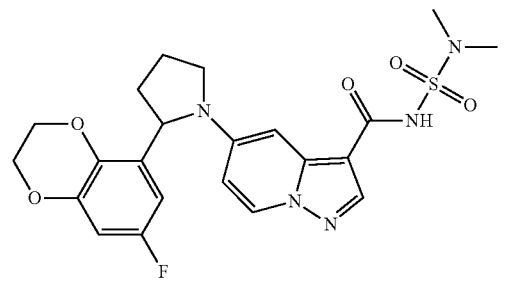 [SMILES: CN(C)S(=O)(=O)NC(=O)c1cnn2ccc(N3CCCC3c3cc(F)cc4c3OCCO4)cc12] | N-(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I) | m/z 490.2 |
| 99 | 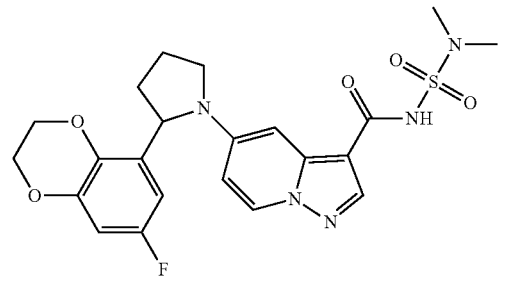 [SMILES: CN(C)S(=O)(=O)NC(=O)c1cnn2ccc(N3CCCC3c3cc(F)cc4c3OCCO4)cc12] | N-(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II) | m/z 489.8 |
| 100 | 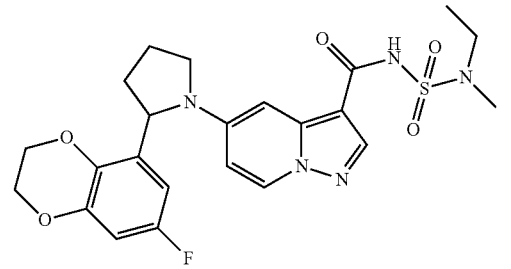 [SMILES: CCN(C)S(=O)(=O)NC(=O)c1cnn2ccc(N3CCCC3c3cc(F)cc4c3OCCO4)cc12] | N-(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I) | m/z 504.1 |

| Example | | | |
|---|---|---|---|
| 101 | 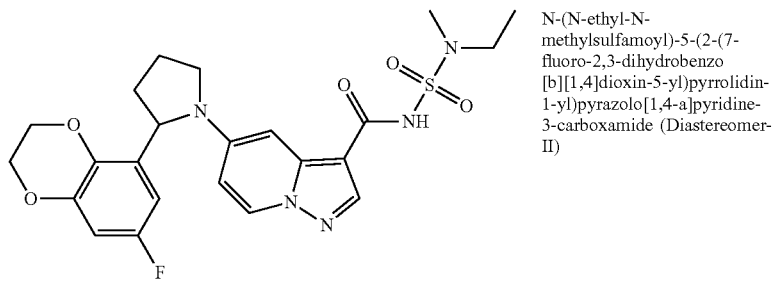 | N-(N-ethyl-N-methylsulfamoyl)-5-(2-(7-fluoro-2,3-dihydrobenzo[b][1,4]dioxin-5-yl)pyrrolidin-1-yl)pyrazolo[1,4-a]pyridine-3-carboxamide (Diastereomer-II) | m/z 504.1 |
| 102 | 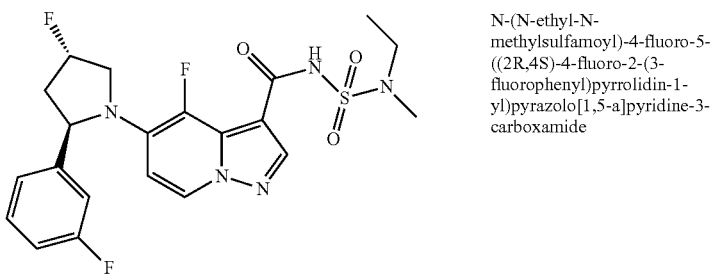 | N-(N-ethyl-N-methylsulfamoyl)-4-fluoro-5-((2R,4S)-4-fluoro-2-(3-fluorophenyl)pyrrolidin-1-yl)pyrazolo[1,5-a]pyridine-3-carboxamide | m/z 481.8 |
| 103 | 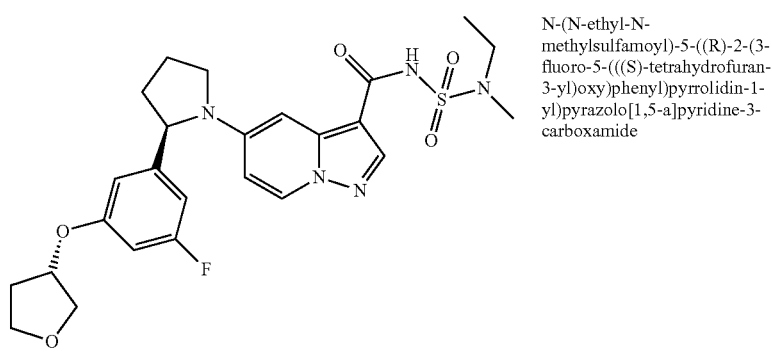 | N-(N-ethyl-N-methylsulfamoyl)-5-((R)-2-(3-fluoro-5-(((S)-tetrahydrofuran-3-yl)oxy)phenyl)pyrrolidin-1-yl)pyrazolo[1,5-a]pyridine-3-carboxamide | m/z 532.4 |
| 104 | 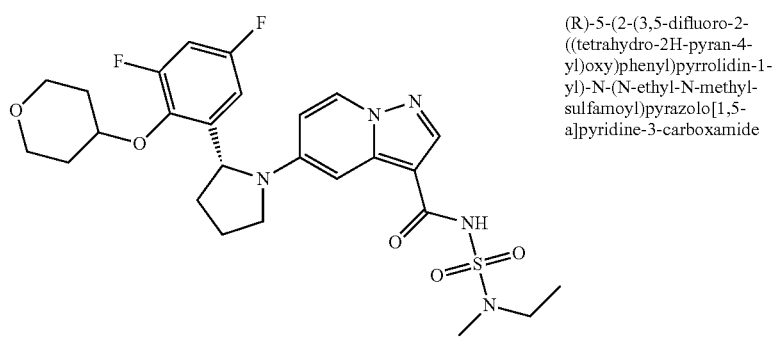 | (R)-5-(2-(3,5-difluoro-2-((tetrahydro-2H-pyran-4-yl)oxy)phenyl)pyrrolidin-1-yl)-N-(N-ethyl-N-methylsulfamoyl)pyrazolo[1,5-a]pyridine-3-carboxamide | m/z 564.2 |
| 105 | 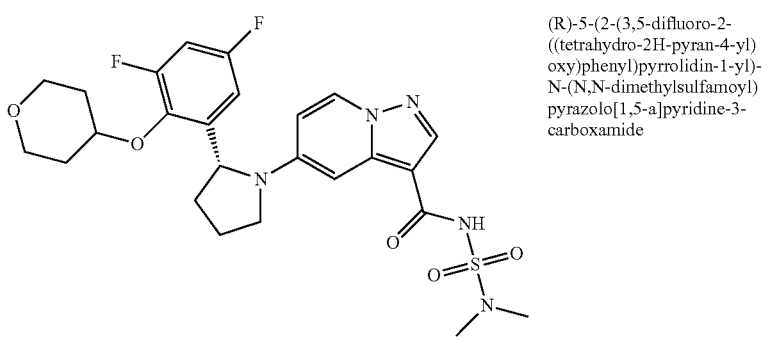 | (R)-5-(2-(3,5-difluoro-2-((tetrahydro-2H-pyran-4-yl)oxy)phenyl)pyrrolidin-1-yl)-N-(N,N-dimethylsulfamoyl)pyrazolo[1,5-a]pyridine-3-carboxamide | m/z 549.8 |

-continued

| Example | | | |
|---|---|---|---|
| 106 | 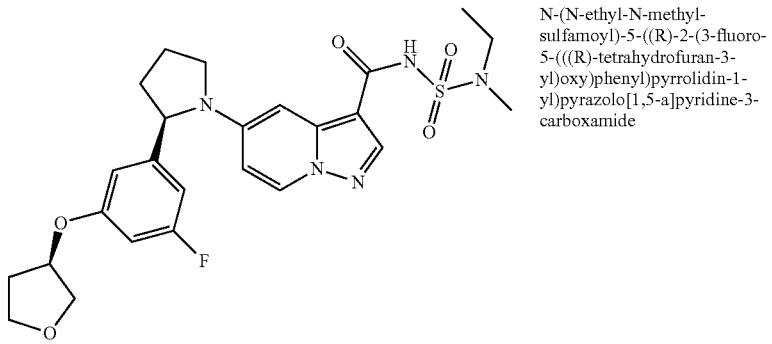 | N-(N-ethyl-N-methyl-sulfamoyl)-5-((R)-2-(3-fluoro-5-(((R)-tetrahydrofuran-3-yl)oxy)phenyl)pyrrolidin-1-yl)pyrazolo[1,5-a]pyridine-3-carboxamide | m/z 532.4 |
| 107 | 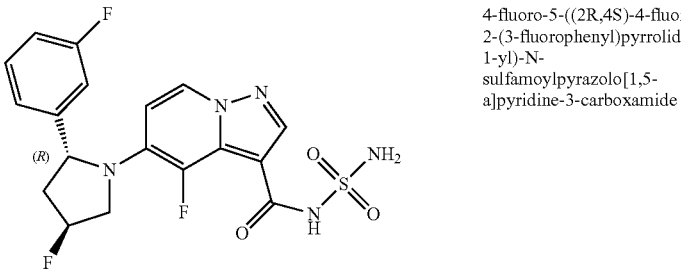 | 4-fluoro-5-((2R,4S)-4-fluoro-2-(3-fluorophenyl)pyrrolidin-1-yl)-N-sulfamoylpyrazolo[1,5-a]pyridine-3-carboxamide | m/z 539.7 |
| 108 | 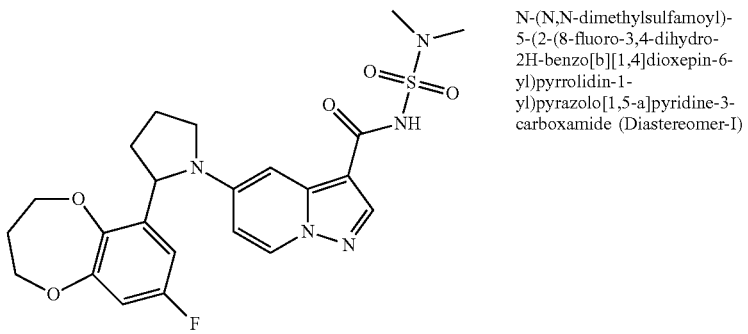 | N-(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-1) | m/z 503.8 |
| 109 | 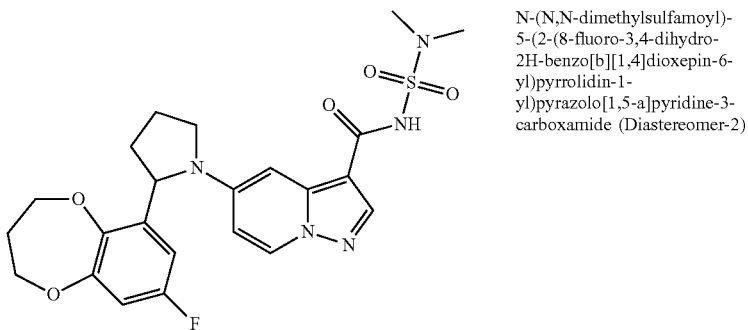 | N-(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2) | m/z 504.1 |

-continued

| Example | | | |
|---|---|---|---|
| 110 | 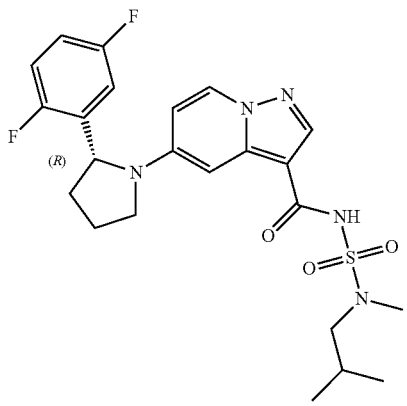 | (R)-5-(2-(2,5-difluorophenyl)pyrrolidin-1-yl)-N-(N-isobutyl-N-methylsulfamoyl)pyrazolo[1,5-a]pyridine-3-carboxamide | m/z 491.8 |
| 111 | 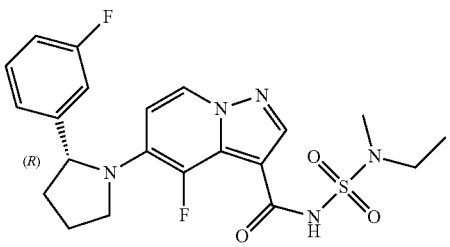 | (R)-N-(N-ethyl-N-methyl-sulfamoyl)-4-fluoro-5-(2-(3-fluorophenyl)pyrrolidin-1-yl)pyrazolo[1,5-a]pyridine-3-carboxamide | m/z 464.2 |
| 112 | 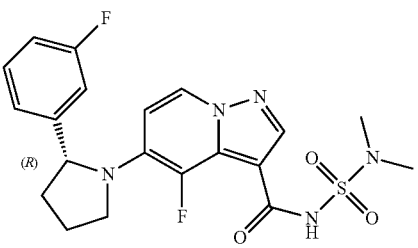 | (R)-N-(N,N-dimethylsulfamoyl)-4-fluoro-5-(2-(3-fluoro-phenyl)pyrrolidin-1-yl)pyrazolo[1,5-a]pyridine-3-carboxamide | m/z 450.1 |
| 113 | 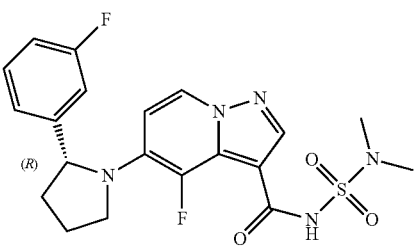 | (R)-N-(N,N-dimethylsulfamoyl)-4-fluoro-5-(2-(3-fluoro-phenyl)pyrrolidin-1-yl)pyrazolo[1,5-a]pyridine-3-carboxamide | m/z 450.1 |
| 114 | 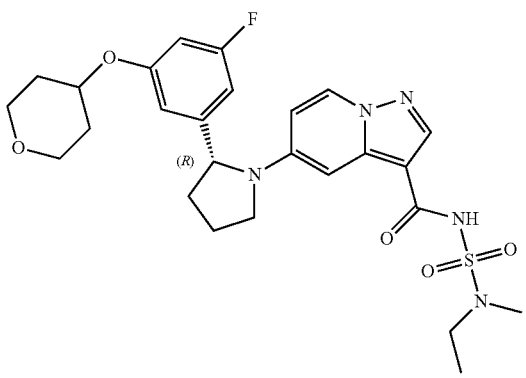 | (R)-N-(N-ethyl-N-methyl-sulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide | m/z 546.2 |

| Example | | | |
|---|---|---|---|
| 115 | 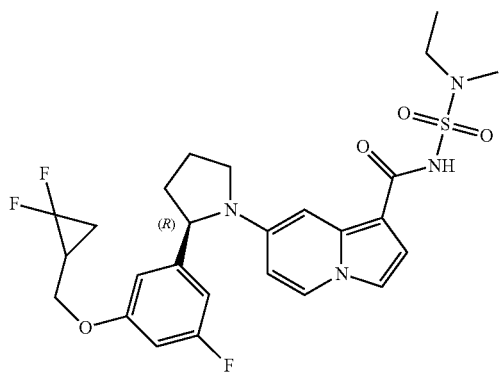 | 5-((2R)-2-(3-((2,2-difluoro-cyclopropyl)methoxy)-5-fluorophenyl)pyrrolidin-1-yl)-N-(N-ethyl-N-methyl-sulfamoyl)pyrazolo[1,5-a]pyridine-3-carboxamide | m/z 552.40 |

Examples 116 to Example-127 were synthesized following a procedure similar to Example-2, except that an appropriate acid counter part was used in place (R)-5-(2-(2,5-difluorophenyl) pyrrolidin-1-yl)pyrazolo[1,5-a]pyridine-3-carboxylic acid and approprite sulfonamides were used in place t-butylsulfonamide to afford the desired product.

| Example | | | |
|---|---|---|---|
| 116 | 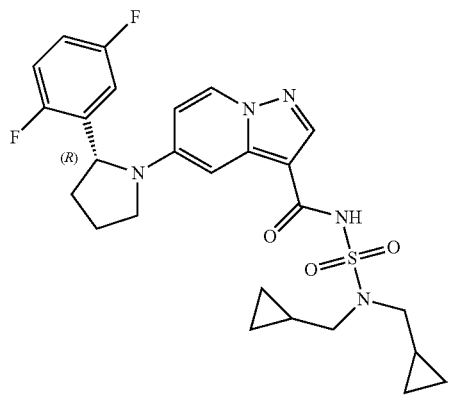 | (R)-N-(N,N-bis(cyclopropylmethyl)sulfamoyl)-5-(2-(2,5-difluorophenyl)pyrrolidin-1-yl)pyrazolo[1,5-a]pyridine-3-carboxamide | m/z 529.8 |
| 117 (Diastereomer-I) | 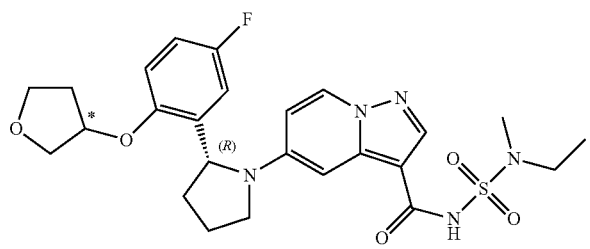 | N-(N-ethyl-N-methyl-sulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide | m/z 532.1 |
| 118 (Diastereomer-II) | 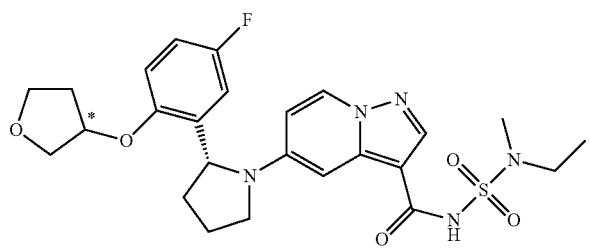 [SMILES: CCN(C)S(=O)(=O)NC(=O)c1cnn2ccc(N3CCC[C@@H]3c3cc(F)ccc3OC3CCOC3)cc12] | N-(N-ethyl-N-methyl-sulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide | m/z 532.2 |

| Example | | | |
|---|---|---|---|
| 119 | 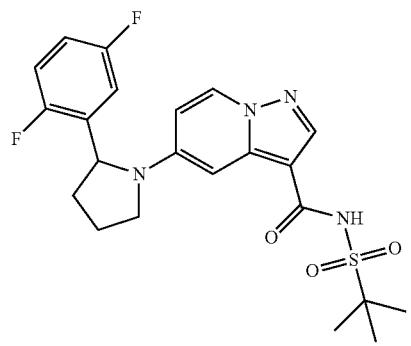 [SMILES: CC(C)(C)S(=O)(=O)NC(=O)c1cnn2ccc(N3CCCC3c3cc(F)ccc3F)cc12] | N-(tert-butylsulfonyl)-5-(2-(2,5-difluorophenyl)pyrrolidin-1-yl)pyrazolo[1,5-a]pyridine-3-carboxamide (Racemic mixture) | |
| 120 | 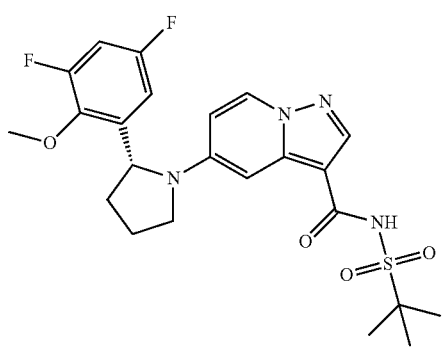 [SMILES: COc1c(F)cc(F)cc1[C@H]1CCCN1c1ccn2ncc(C(=O)NS(=O)(=O)C(C)(C)C)c2c1] | (R)-N-(tert-butylsulfonyl)-5-(2-(3,5-difluoro-2-methoxy-phenyl)pyrrolidin-1-yl)pyrazolo[1,5-a]pyridine-3-carboxamide | m/z 493.3 |
| 121 | 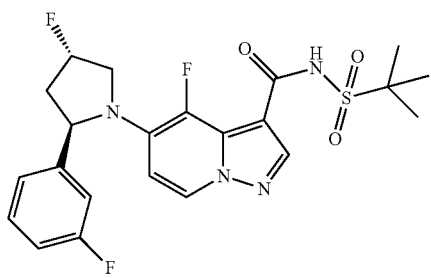 [SMILES: CC(C)(C)S(=O)(=O)NC(=O)c1cnn2ccc(N3C[C@@H](F)C[C@@H]3c3cccc(F)c3)c(F)c12] | N-(tert-butylsulfonyl)-4-fluoro-5-((2R,4S)-4-fluoro-2-(3-fluorophenyl)pyrrolidin-1-yl)pyrazolo[1,5-a]pyridine-3-carboxamide | m/z 481.05 |
| 122 | 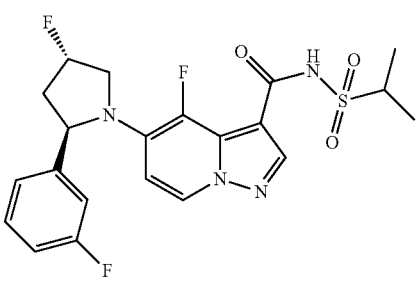 [SMILES: CC(C)S(=O)(=O)NC(=O)c1cnn2ccc(N3C[C@@H](F)C[C@@H]3c3cccc(F)c3)c(F)c12] | 4-fluoro-5-((2R,4S)-4-fluoro-2-(3-fluorophenyl)pyrrolidin-1-yl)-N-(isopropylsulfonyl)pyrazolo[1,5-a]pyridine-3-carboxamide | m/z 467.2 |
| 123 | 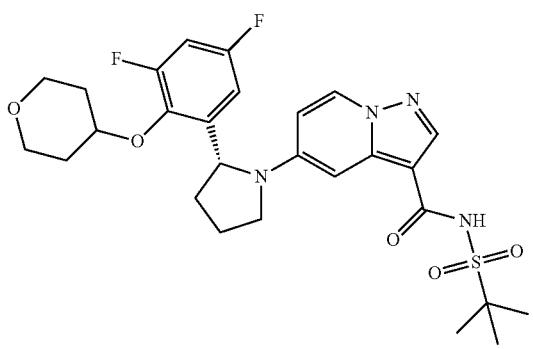 [SMILES: CC(C)(C)S(=O)(=O)NC(=O)c1cnn2ccc(N3CCC[C@@H]3c3cc(F)cc(F)c3OC3CCOCC3)cc12] | (R)-N-(tert-butylsulfonyl)-5-(2-(3,5-difluoro-2-((tetrahydro-2H-pyran-4-yl)oxy)phenyl)pyrrolidin-1-yl)pyrazolo[1,5-a]pyridine-3-carboxamide | m/z 563.50 |

-continued

| Example | | | |
|---|---|---|---|
| 124 | 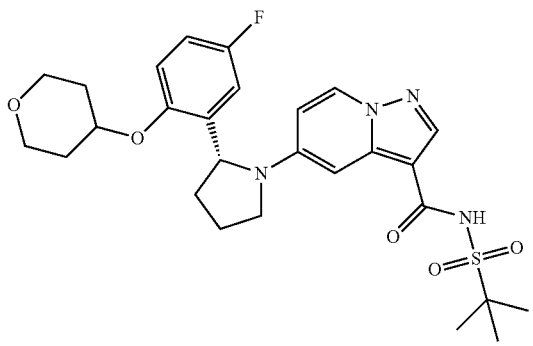 [SMILES: CC(C)(C)S(=O)(=O)NC(=O)c1cnn2ccc(N3CCC[C@@H]3c3cc(F)ccc3OC3CCOCC3)cc12] | (R)-N-(tert-butylsulfonyl)-5-(2-(5-fluoro-2-((tetrahydro-2H-pyran-4-yl)oxy)phenyl)pyrrolidin-1-yl)pyrazolo[1,5-a]pyridine-3-carboxamide | m/z 545.50 |
| 125 | 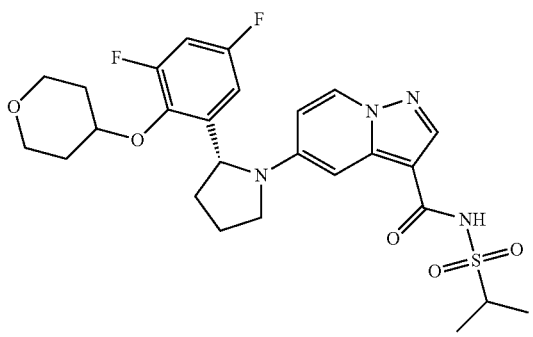 | (R)-5-(2-(3,5-difluoro-2-((tetrahydro-2H-pyran-4-yl)oxy)phenyl)pyrrolidin-1-yl)-N-(isopropylsulfonyl)pyrazolo[1,5-a]pyridine-3-carboxamide | m/z 549.2 |
| 126 | 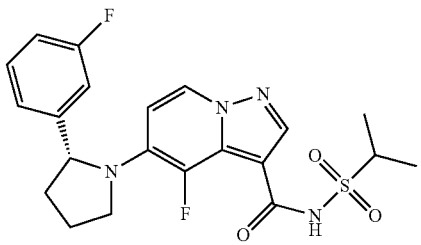 [SMILES: CC(C)S(=O)(=O)NC(=O)c1cnn2ccc(N3CCC[C@@H]3c3cccc(F)c3)c(F)c12] | (R)-4-fluoro-5-(2-(3-fluorophenyl)pyrrolidin-1-yl)-N-(isopropylsulfonyl)pyrazolo[1,5-a]pyridine-3-carboxamide | m/z 449.2 |
| 127 | 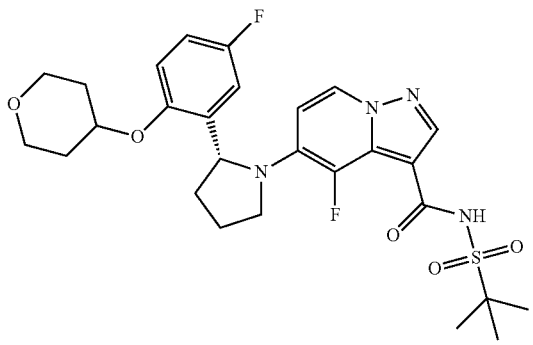 | (R)-N-(tert-butylsulfonyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide | m/z 532.2 |

General Procedure for Salt Synthesis:

Above examples 1-127 can be converted to a pharmaceutically acceptable salt by reacting with a suitable salt, by reacting a solution of the compound (1-127) with suitalble salt. For example a solution of the compound of (1-127)(1 eq) in water sodium hydroxide or potassium hydroxide or calcium hydroxide (1M, 1 eq.) can be added drop wise and to be stirred for 1 h at 25° C.–100° C. Reaction mixture shall be cooled and filtered and the filtrate to be concentrated to get required salt as white powder compound.

Illustrative examples of the salts prepared are as given below:

| Example | | |
|---|---|---|
| 128 | 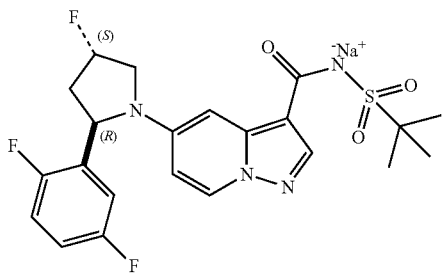<br>Sodium (tert-butylsulfonyl)(5-((2R,4S)-2-(2,5-difluorophenyl)-4-fluoropyrrolidin-1-yl)pyrazolo[1,5-a]pyridine-3-carbonyl)amide | HNMR (400 MHz, DMSO-D6) δ 8.4-8.3 (d, 1H), 7.95 (s, 1H), 7.3-7.2 (m, 1H), 7.2-7.09 (m, 3H), 6.6 (dd, 1H), 5.55-4.9 (d, 1H), 5.3-5.2 (m, 1H), 4.15-4.0 (m, 1H), 3.8-3.65 (m, 1H), 2.95-2.8 (m, 1H), 2.3-2.1 (m, 1H), 1.25 (s, 9H);<br>LCMS (ESI) m/z 481.1 |
| 129 | 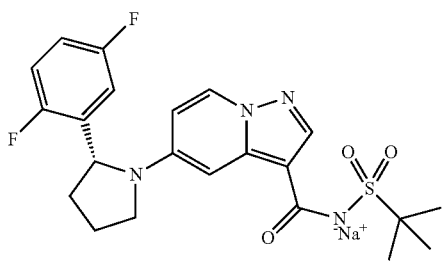<br>Sodium(R)-(tert-butylsulfonyl)(5-(2-(2,5-difluorophenyl)pyrrolidin-1-yl)pyrazolo[1,5-a]pyridine-3-carbonyl)amide | $^1$HNMR (400 MHz, DMSO-D6) δ 8.35-8.333 (d, 1H), 7.93 (s, 1H), 7.32-7.27 (m, 1H), 7.15-7.10 (m, 1H), 7.04 (s, 1H), 6.84-6.79 (m, 1H), 6.28-6.26 (dd, 1H), 5.07-5.05 (dd, 1H), 3.80-3.76 (m, 1H), 3.40-3.38 (m, 1H), 2.46-2.42 (m, 1H), 2.04-2.02 (m, 1H), 1.93-1.85 (m, 2H), 1.25 (s, 9 H);<br>LC-MS (API) 463.1 |
| 130 | 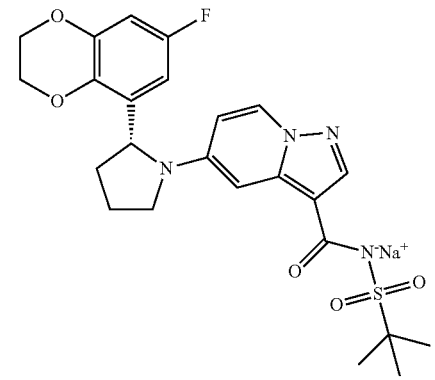<br>Sodium (R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide | $^1$H NMR (400 MHz, DMSO-d$_6$) δ ppm 8.31-8.29 (1H, d), 7.91 (1H, s), 7.10 (1H, s), 6.66-6.62 (1H, dd), 6.25-6.22 (1H, dd), 6.13-6.12 (1H, m), 5.01-4.99 (1H, d), 4.38-4.28 (4H, m), 3.72-3.68 (1H, t), 2.36-2.31 (1H, m), 2.02-1.99 (1H, m), 1.93-1.87 (2H, m), 1.28 (9H, s);<br>MS (ESI): m/z 502.8 |

| Example | | |
|---|---|---|
| 131 | 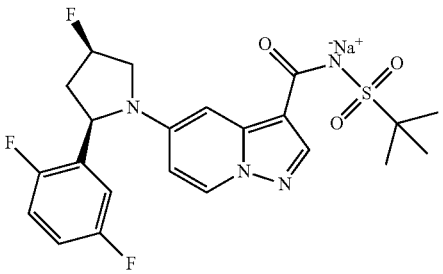<br><br>Sodium (tert-butylsulfonyl)(5-((2R,4R)-2-(2,5-difluorophenyl)-4-fluoropyrrolidin-1-yl)pyrazolo[1,5-a]pyridine-3-carbonyl)amide | $^1$H NMR (400 MHz, DMSO-d$_6$) δ ppm 8.42-8.40 (1H, d), 8.00-7.90 (1H, s), 7.30-7.29 (1H, dt), 7.17-7.09 (1H, m) 7.04 (1H, s), 6.82-6.80 (1H, m), 6.40-6.30 (1H, d), 5.59-5.46 (1H, m), 5.19-5.16 (1H, d), 4.03-4.96 (1H, m), 3.85-3.73 (1H, m), 2.88-2.66 (1H, m), 2.32-2.24 (1H, m), 1.22 (9H, s); MS (ESI): m/z 481.5 |
| 132 | 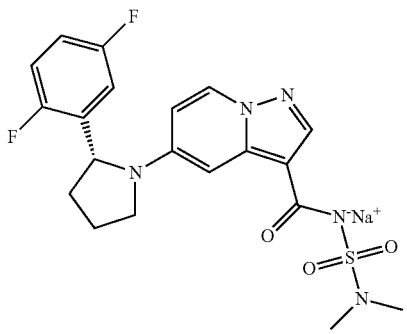<br><br>Sodium (R)-(5-(2-(2,5-difluorophenyl)pyrrolidin-1-yl)pyrazolo[1,5-a]pyridine-3-carbonyl)(N,N-dimethylsulfamoyl)amide | $^1$H NMR (400 MHz, DMSO-d$_6$) δ ppm 8.35-8.33 (1H, d), 7.91 (1H, s), 7.33-7.27 (1H, m), 7.15-7.10 (1H, m), 7.06 (1H, s), 6.85-6.81 (1H, m), 6.31-6.29 (1H, d), 5.06-5.04 (1H, d), 3.83-3.79 (1H, t), 3.44-3.38 (1H, q), 2.06-2.02 (1H, m), 1.93-1.85 (2H, m); MS (ESI): m/z 449.8 |
| 133 | 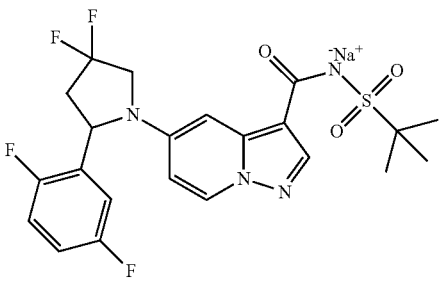<br><br>Sodium (tert-butylsulfonyl)(5-(2-(2,5-difluorophenyl)-4,4-difluoropyrrolidin-1-yl)pyrazolo[1,5-a]pyridine-3-carbonyl)amide | $^1$H NMR (400 MHz, DMSO-d$_6$) δ ppm 8.44-8.42 (1H, d), 7.95 (1H, s), 7.36-7.30 (1H, m), 7.19-7.15 (1H, m), 7.05-7.04 (1H, d), 7.00-6.95 (1H, m), 6.37-6.35 (1H, dd), 5.35-5.32 (1H, d), 4.25-4.23 (1H, m), 3.98-3.93 (1H, m), 1.21 (9H, s); MS (ESI): m/z 499.1 |
| 134 | 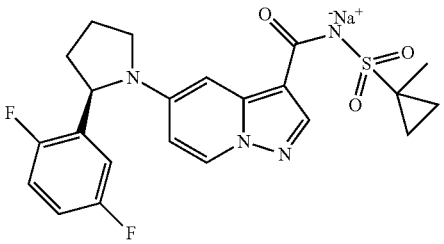<br><br>Sodium (R)-(5-(2-(2,5-difluorophenyl)pyrrolidin-1-yl)pyrazolo[1,5-a]pyridine-3-carbonyl)((1-methylcyclopropyl)sulfonyl)amide | $^1$H NMR (400 MHz, DMSO-d$_6$) δ ppm 8.32-8.30 (1H, d), 7.93 (1H, s), 7.32-7.26 (1H, m), 7.15-7.10 (2H, m), 6.90-6.80 (1H, m), 6.22-6.21 (1H, d), 5.11-5.09 (1H, d), 3.79-3.78 (1H, m), 2.04-1.88 (3H, m), 1.14 (2H, m), 0.50 (2H, m); MS (ESI): m/z 461.8 |

| Example | | |
|---|---|---|
| 135 | 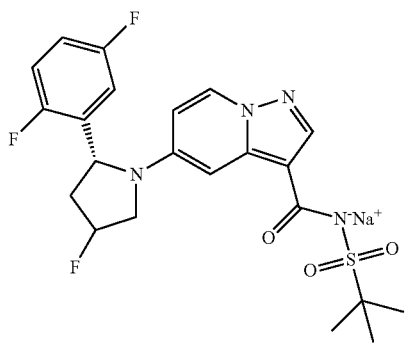<br>Sodium (tert-butylsulfonyl)(5-((2R)-2-(2,5-difluorophenyl)-4-fluoropyrrolidin-1-yl)pyrazolo[1,5-a]pyridine-3-carbonyl)amide | $^1$H NMR (400 MHz, DMSO-d$_6$) δ ppm 8.42-8.40 (1H, d), 7.95 (1H, s), 7.33-7.27 (1H, m), 7.15-7.10 (1H, m), 7.05 (1H, s), 6.84-6.81 (1H, m), 6.36-6.35 (1H, d), 5.59-5.46 (1H, m), 5.18-5.16 (1H, d), 4.06-3.96 (1H, m), 3.85-3.73 (1H, dd), 2.91-2.76 (1H, m), 2.32-2.25 (1H, m), 1.22 (9H, s); MS (ESI): m/z 480.8 |
| 136 | 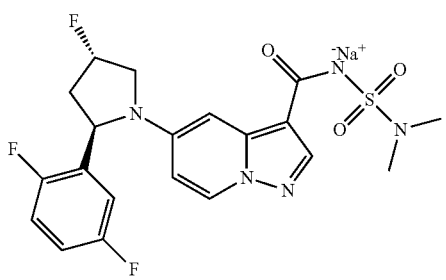<br>Sodium (5-((2R,4S)-2-(2,5-difluorophenyl)-4-fluoropyrrolidin-1-yl)pyrazolo[1,5-a]pyridine-3-carbonyl)(N,N-dimethylsulfamoyl)amide | $^1$H NMR (400 MHz, DMSO-d$_6$) δ ppm 8.35-8.34 (1H, d), 7.93 (1H, s), 7.31-7.25 (1H, m), 7.16-7.13 (2H, m), 7.10-7.04 (1H, m), 6.34-6.32 (1H, dd), 5.56-5.43 (1H, m), 5.23-5.18 (1H, t), 4.16-4.03 (1H, m), 3.81-3.72 (1H, m), 2.92-2.81 (1H, m), 2.52-2.44 (6H, s), 2.17-2.11 (1H, m);<br>MS (ESI): m/z 468.8 |
| 137 | 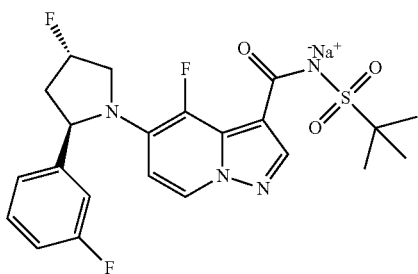<br>Sodium (tert-butylsulfonyl)(4-fluoro-5-((2R,4S)-4-fluoro-2-(3-fluorophenyl)pyrrolidin-1-yl)pyrazolo[1,5-a]pyridine-3-carbonyl)amide | $^1$H NMR (400 MHz, DMSO-d$_6$) δ ppm 8.77-8.75 (1H, d), 7.92 (1H, s), 7.34-7.28 (2H, m), 7.17-7.12 (2H, m), 7.03-6.98 (1H, m), 5.51-5.38 (1H, m), 5.11-5.07 (1H, m), 4.31-4.18 (1H, m), 3.70-3.62 (1H, m), 2.85-2.76 (1H, m), 2.48-1.99 (1H, m), 1.25 (9H, s);<br>MS (ESI): m/z 481.8 |

| Example | | |
|---|---|---|
| 138 | 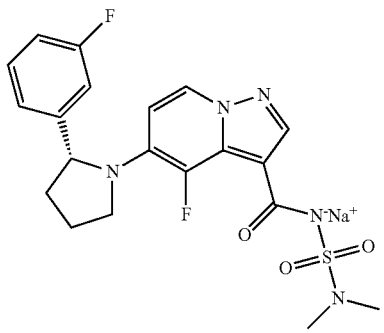<br>Sodium (R)-(N,N-dimethylsulfamoyl)(4-fluoro-5-(2-(3-fluorophenyl)pyrrolidin-1-yl)pyrazolo[1,5-a]pyridine-3-carbonyl)amide | $^1$H NMR (400 MHz, DMSO-d$_6$) δ ppm 8.68-8.66 (1H, d), 7.92 (1H, s), 7.35-7.29 (2H, m), 7.07-6.98 (3H, m), 5.09-5.08 (1H, m), 3.88-3.86 (1H, m), 3.55-3.52 (1H, m), 2.56 (6H, s), 2.00-1.89 (2H, m), 1.86-1.84 (1H, m); MS (ESI): m/z 449.8 |
| 139 | 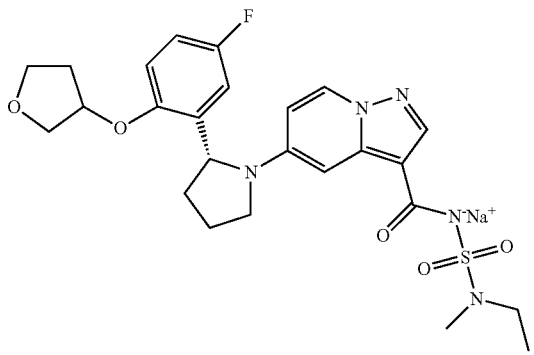<br>Sodium (N-ethyl-N-methylsulfamoyl)(5-((2R)-2-(5-fluoro-2-((tetrahydrofuran-3-yl)oxy)phenyl)pyrrolidin-1-yl)pyrazolo[1,5-a]pyridine-3-carbonyl)amide | $^1$H NMR (400 MHz, DMSO-d$_6$) δ ppm 8.30-8.29 (1H, d), 7.90 (1H, s), 7.08-7.03 (3H, m), 6.70-6.67 (1H, m), 6.10 (1H, bs), 5.16 (1H, m), 4.99-4.97 (1H, m), 3.94-3.88 (2H, m), 3.85-3.73 (3H, m), 3.39-3.37 (2H, m), 2.98-2.92 (2H, m), 2.54 (3H, s), 2.40-2.32 (2H, m), 2.28-2.23 (1H, m), 2.14-2.00 (1H, m), 1.86-1.84 (2H, m), 1.05-1.01 (3H, t); MS (ESI): m/z 531.8 |
| 140 | 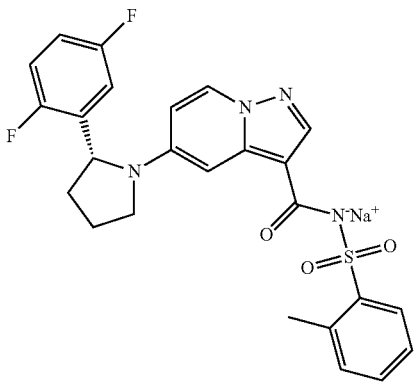<br>Sodium (R)-(5-(2-(2,5-difluorophenyl)pyrrolidin-1-yl)pyrazolo[1,5-a]pyridine-3-carbonyl)(o-tolylsulfonyl)amide | $^1$H NMR (400 MHz, DMSO-d$_6$) δ ppm 8.30-8.29 (1H, d), 7.90 (1H, s), 7.90-7.80 (1H, d), 7.40-7.03 (7H, m), 6.90-81 (1H, m), 6.18 (1H, bs), 5.10-5.05 (1H, m), 3.74-3.70 (2H, m), 2.01-1.89 (4H, m); MS (ESI): m/z 497.1 |

| Example | | |
|---|---|---|
| 141 | 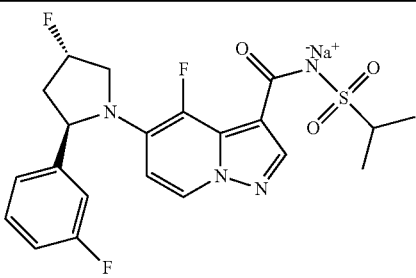<br>Sodium (4-fluoro-5-((2R,4S)-4-fluoro-2-(3-fluorophenyl)pyrrolidin-1-yl)pyrazolo[1,5-a]pyridine-3-carbonyl)(isopropylsulfonyl)amide | $^1$H NMR (400 MHz, DMSO-$d_6$) δ ppm 8.76-8.74 (1H, d), 7.91 (1H, s), 7.51-7.49 (1H, d), 7.32 (2H, bs), 7.24-7.22 (1H, d), 7.03-7.00 (1H, m), 5.52-5.39 (1H, m), 5.02-4.98 (1H, m), 4.38-4.24 (1H, m), 3.71-3.63 (1H, m), 3.50-3.42 (1H, m), 2.80-2.73 (1H, m), 2.17-2.06 (1H, m), 1.15-1.11 (6H, d); MS (ESI): m/z 467.35 |
| 142 | 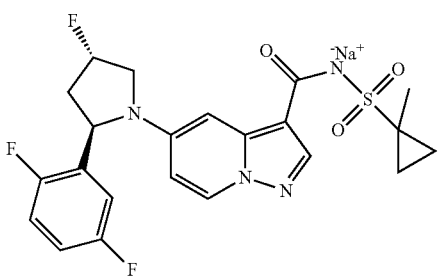<br>Sodium (5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide | $^1$H NMR (400 MHz, DMSO-$d_6$) δ ppm 8.33-8.31 (1H, d), 7.93 (1H, s), 7.30-7.25 (1H, m), 7.16-7.11 (3H, m), 6.28-6.27 (1H, d), 5.58-5.44 (1H, m), 5.25-5.21 (1H, t), 4.15-4.04 (1H, m), 3.79-3.71 (1H, m), 2.88-2.80 (1H, m), 2.92-2.12 (1H, m), 1.38 (3H, s) 1.16 (2H, m), 0.51 (2H, m); MS (ESI): m/z 479.40 |
| 143 | 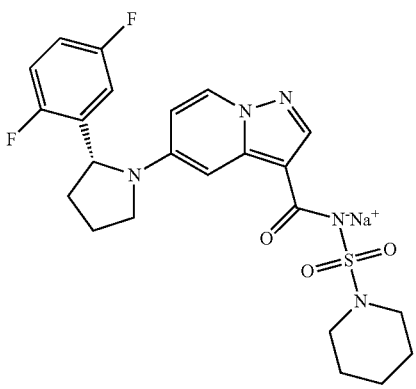<br>Sodium (R)-(5-(2-(2,5-difluorophenyl)pyrrolidin-1-yl)pyrazolo[1,5-a]pyridine-3-carbonyl)(piperidin-1-ylsulfonyl)amide | $^1$H NMR (400 MHz, DMSO-$d_6$) δ ppm 8.30-8.28 (1H, d), 7.93 (1H, s), 7.33-7.27 (1H, m), 7.21 (1H, bs), 7.16-7.10 (1H, m), 6.89-6.85 (1H, m), 6.15-6.14 (1H, d), 5.13-5.11 (1H, d), 3.82-3.79 (1H, t), 3.44-3.38 (1H, q), 3.02 (4H, t), 2.04-1.89 (3H, m), 1.53-1.51 (4H, m), 1.43-1.42 (2H, m); MS (ESI): m/z 489.8 |

Example-144

Determination of In Vitro TrkA Inhibitory Activity Using TR-FRET Assay

Compounds were screened in the TR-FRET assay with TrkA kinase. 5 ng of TrkA [Upstate, USA] kinase was used for assay. The compound was incubated with the kinase for 30 minutes at 20-35° C. After the incubation, substrate mix [40 nM Ultra light poly GT (Perkin Elmer, USA) and 500 µM ATP] was added. The above reaction was stopped by the addition of 40 mM EDTA after 30 minutes. The Eu-labelled antiphospho-tyrosine antibody [Perkin Elmer, USA] was added at 0.5 nM and the fluorescence emission at 615 nm/665 nm [excitation at 340 nm] was measured. The compounds were initially screened at 100 nM, 1 µM and 10 µM concentrations. The potent compounds with >25% inhibition at 1 µM of TrkA were taken for the full dose response studies. The final DMSO concentration in the assay was 1%. For $IC_{50}$ determination, $\frac{1}{3}^{rd}$ serial dilution was made from the 20 mM DMSO stock solution. 2 µl of these were transferred to the test wells containing 20 µl reaction mixture [Total reaction volume 22 µl]. The fluorescence was measured in Perkin Elmer Wallac 1420 Multilabel Counter Victor 3. The $IC_{50}$ was determined by fitting the dose response data to a sigmoidal curve fitting equation using GraphPad Prism software version 5.

Using this protocol, various compounds as described herein and further as exemplified above, were found to exhibit inhibitory effect on TrkA (Table 2).

Examples 2, 7, 8, 9, 10, 25, 31, 39, 40, 41, 52, 57, 59, 65, 70, 73, 74, 76, 77, 78, 79, 80, 81, 82, 83, 84, 85, 87, 88, 89, 90, 91, 94, 128, 132, 136, 137, 138, 139, 140, 141, 142 and 143, as described herein, exhibited a TrkA inhibition in-vitro $IC_{50}$ values less than or equal to about 50 nM;

Examples 4, 26, 34, 35, 38, 44, 45, 46, 47, 60, 63 and 134, as described herein, exhibited a TrkA inhibitory activity in-vitro $IC_{50}$ values between about 50 nm and about 100 nM;

Examples 1, 3, 5, 6, 11, 12, 13, 14, 19, 20, 22, 23, 24, 27, 28, 29, 32, 33, 36, 37, 43, 49, 50, 54, 56, 61, 62, 66, 71, 72, 75, 86, 93, 130 and 133, as described herein, exhibited a TrkA inhibitory activity in-vitro $IC_{50}$ values between about 100 nm to about 500 nm;

Examples 15, 21, 30, 48, 58, 67, 68, 69 and 131, as described herein, exhibited a TrkA inhibitory activity in-vitro $IC_{50}$ values between about 500 nm to about 1 µM;

Examples 16, 17, 18, 51, 53, 55 and 135, as described herein, exhibited a TrkA inhibitory activity in-vitro $IC_{50}$ values between about 1 µM to about 10 µM.

Example-145

Stability Protocol: Metabolic Stability Using Rat Liver Microsomes (RLM) and Human Liver Microsomes (HLM).

This assay was performed using pooled male rat liver microsomes (In-house prepared as per SOP), Pooled Human liver microsomes (XENOTECH; Batch No-H0630-1110189)). The 100 µl reaction contains the compounds at 1 µM, 0.3 mg/ml microsomal protein and both the co-factors (1 mM NADPH) in buffer and the mixture was incubated at different time points (0, 15, 30, 45, 60, & 90 minutes). The reaction was stopped by the addition of equal volume of acetonitrile containing internal standard (Telmesartin). The precipitated protein was removed by centrifugation and the supernatant were analyzed LC/MS-MS method. The percent parent compound remaining was quantified by analysis using following formula (% parent compound remaining= (peak area at Time x/peak area at T0)×100. The intrinsic clearance was calculated using the following formula.

$CL_{int,app}$: (0.693/in vitro t1/2) (incubation volume/ mg of microsomal protein) (45 mg microsomal protein/gram of liver) ($20^a$ g of liver/kg body weight)

a: 20 and 45 g of liver/kg of body weight were used for human and rat, respectively (Lu C et al., DMD, 2006).
Bio-analysis: It was performed in Multiple Reaction Monitoring mode (negative mode) using Applied Biosystems API 4000 coupled to Agilent Technologies 1100 series HPLC on a reverse phase column (Zorbax Eclipse XDB C18, 50×4.6 mm, 5 am). Celecoxib was used as internal standard both in in-vitro and in-vivo experiments. Mobile phase used 0.05% monofluoro acidic water and acetonitrile (10:90) with a flow rate of 0.6 ml/minute. The injection volume was kept as 10 µl.
Examples 1, 2, 3, 4, 10, 24, 25, 26, 35, 38, 39, 40, 42, 43, 45, 46, 50, 52, 57, 59, 65, 74, 75, 76, 77, 78, 79, 91, 96, 102, 106, 107, 121, 122 and 124 as described herein, exhibited metabolic stablility half life (in minutes) of >80, by using Human Liver Microsomes, Example-146: Apparent Aqueous Solubility Assay The 10 mM DMSO solution of test compounds or reference standards were added to Dulbeco's phosphate buffer saline pH 7.4 (DPBS) and DMSO in a 96 deep-well plate to generate theoretical concentration of 200 µM. The solutions were equilibrated by shaking (200 rpm, Ika plate shaker) for 16 hours at 25° C. Undissolved compound was removed by centrifugation, and the supernatant was analyzed by HPLC-UV. The assays were performed in duplicates. Aqueous solubility was calculated using the equation:

Aqueous solubility=200 µM×$PA_{PBS}$/$PA_{DMSO}$

Whereas $PA_{PBS}$ and $PA_{DMSO}$ are the peak areas from the analyses of test compound in PBS with 2% DMSO and of test compound in 100% DMSO, respectively.

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof. For example, the following compounds, their pharmaceutically acceptable salts, pharmaceutically acceptable solvates or stereoisomers thereof are also included in the scope of the present application.

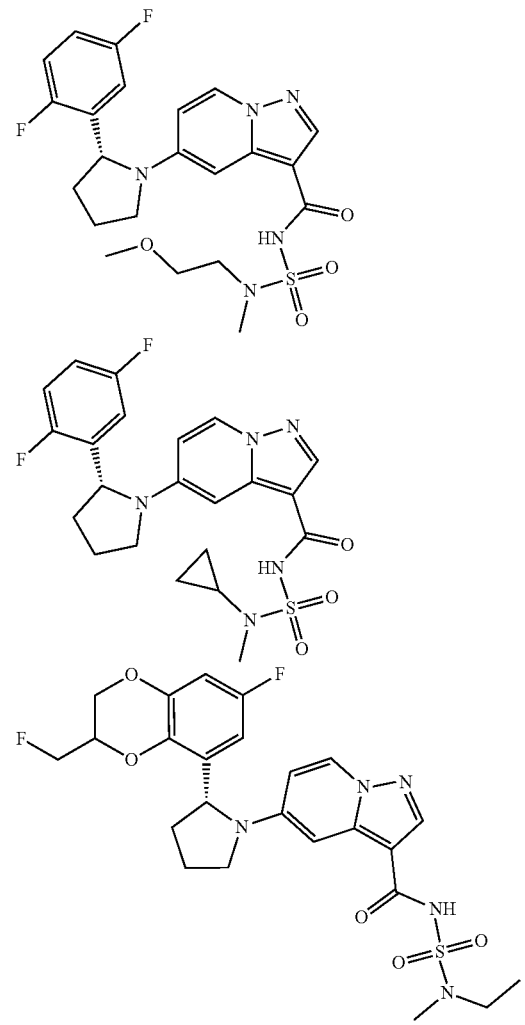

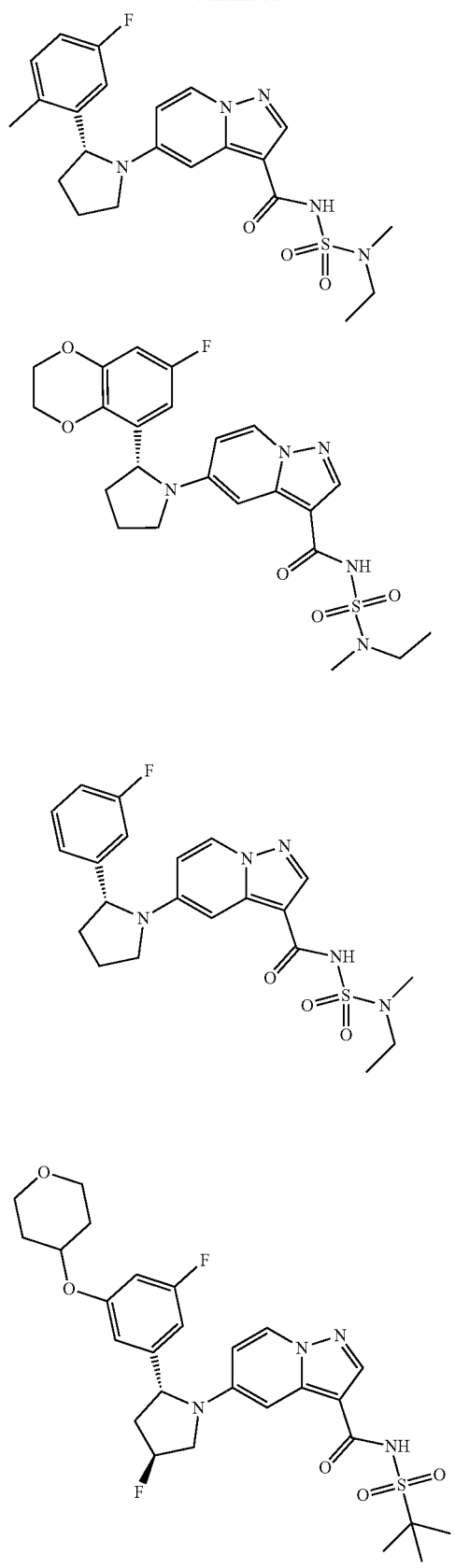
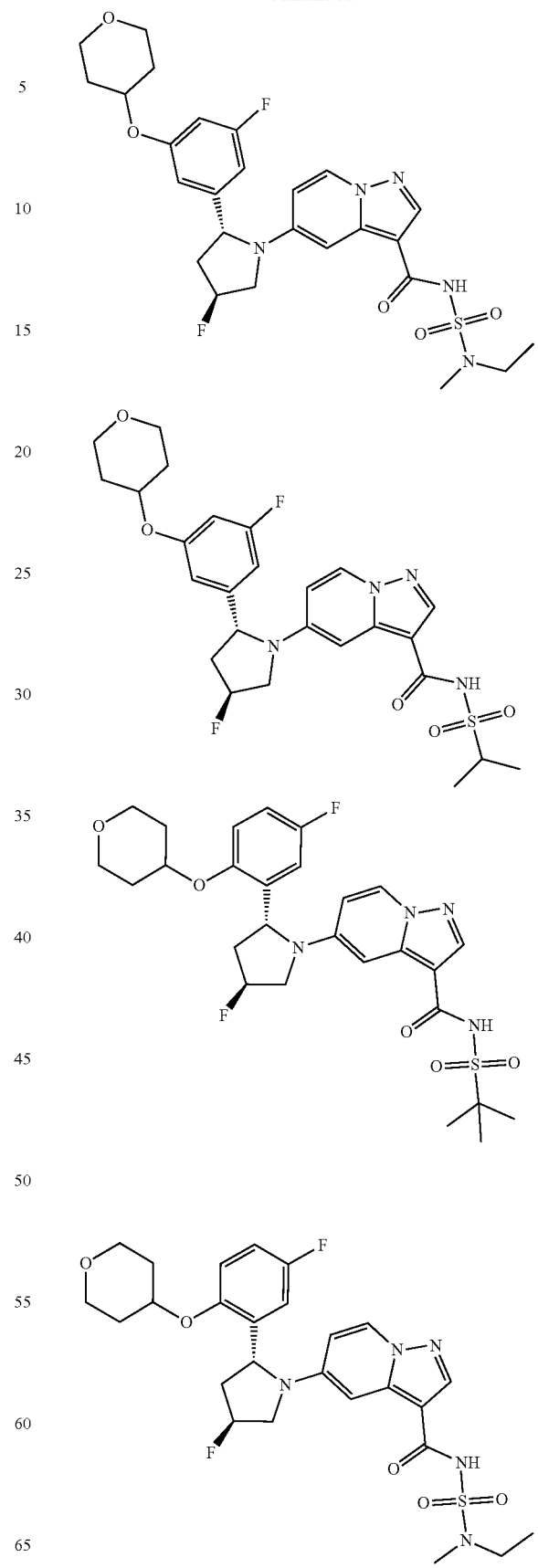

159
-continued
160
-continued
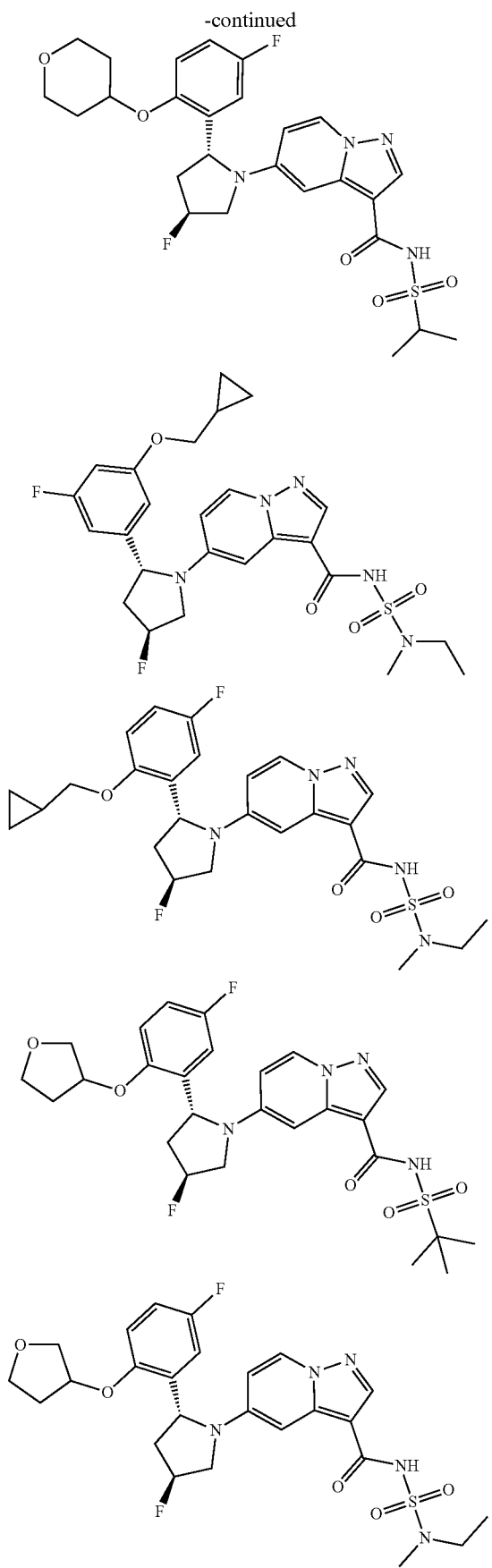
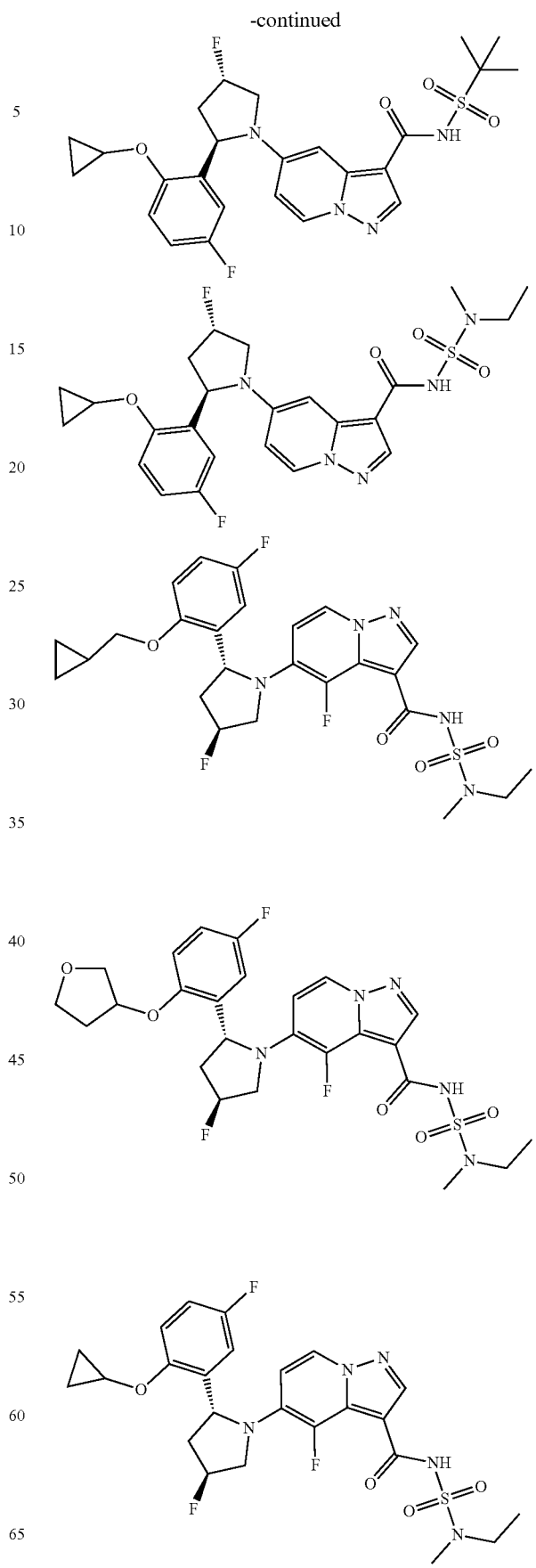

-continued
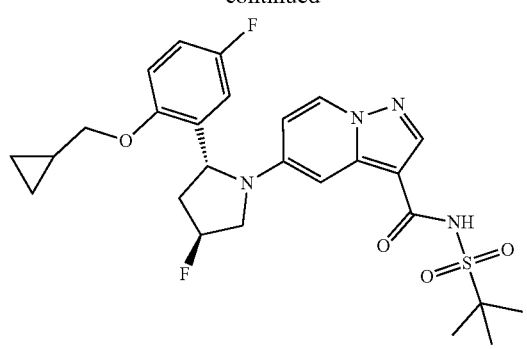
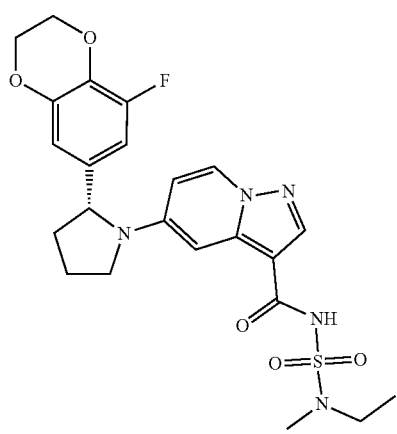
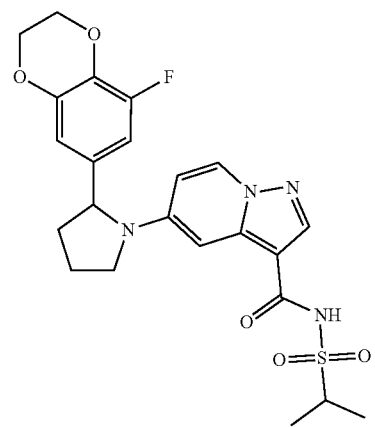
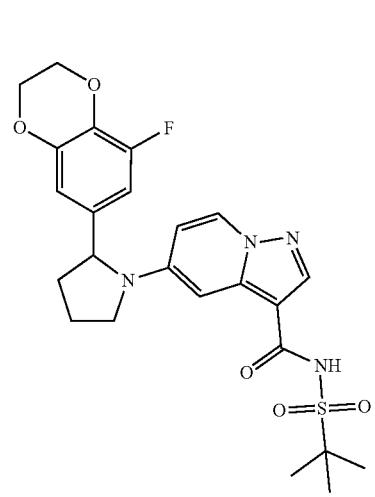
-continued
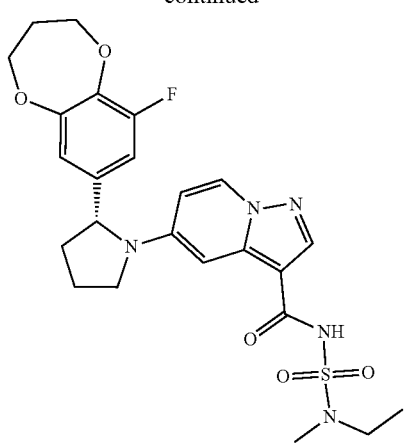
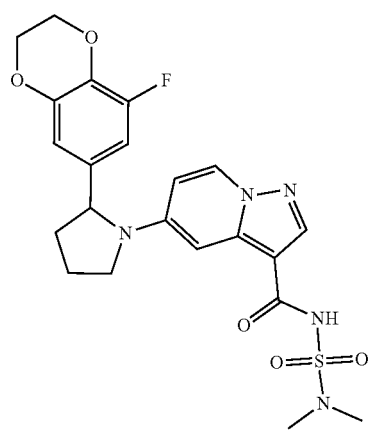
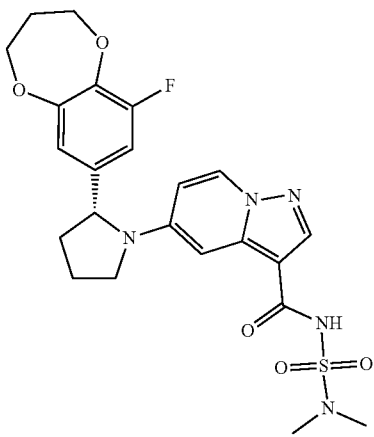
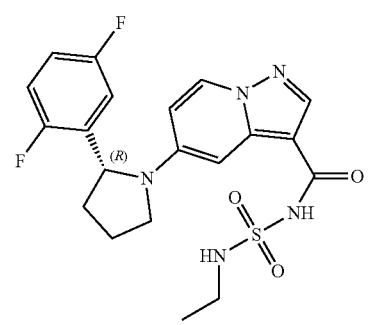

163
-continued
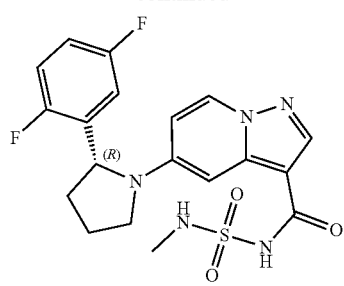
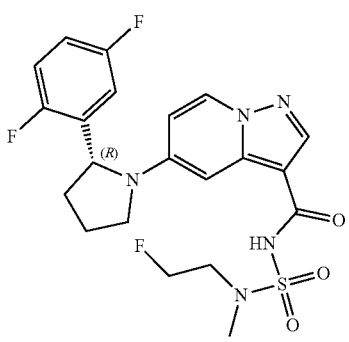
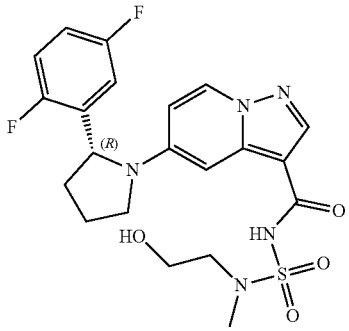
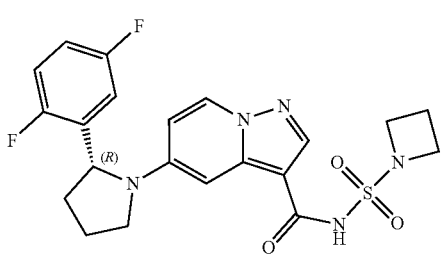
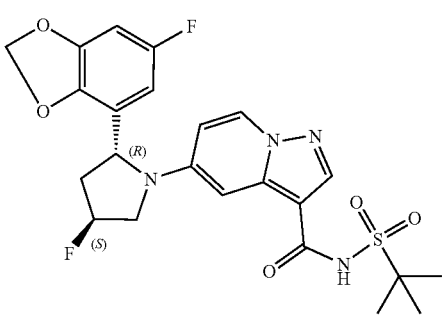
164
-continued
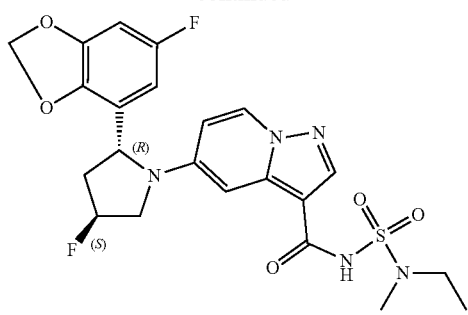
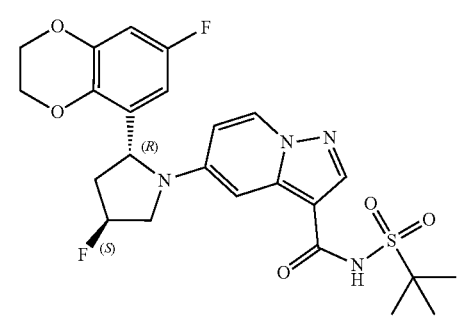
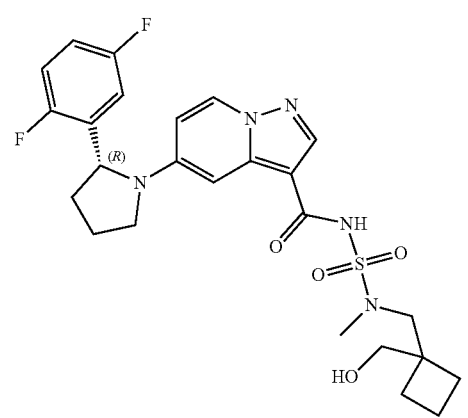
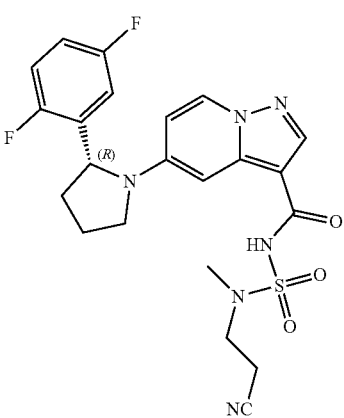

165
-continued
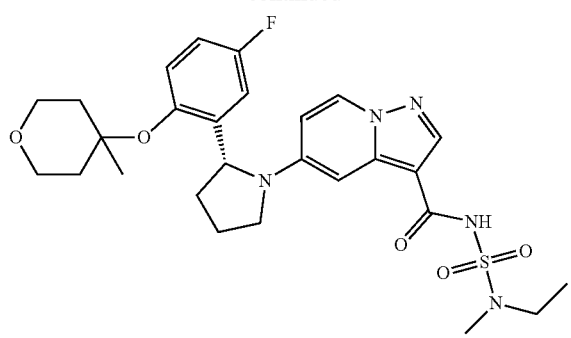
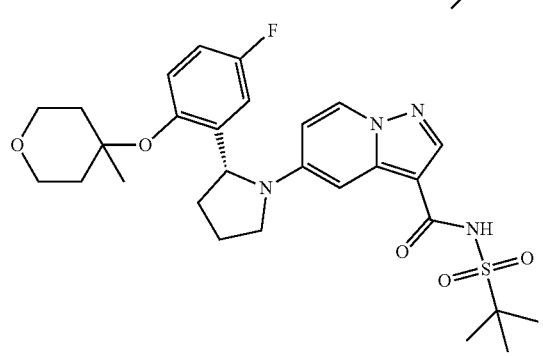
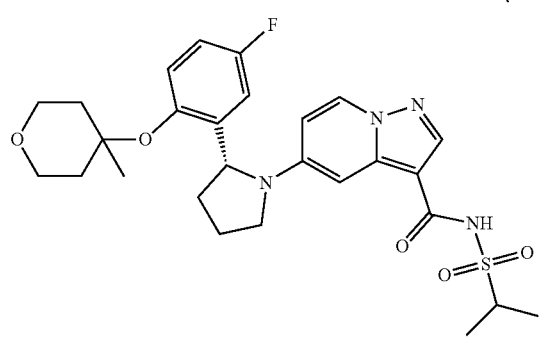
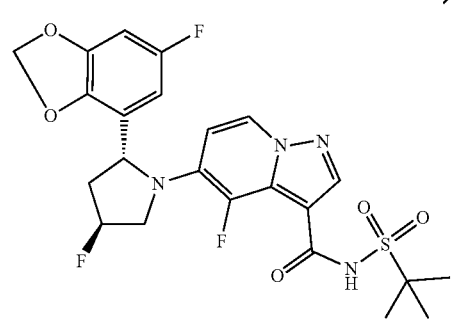
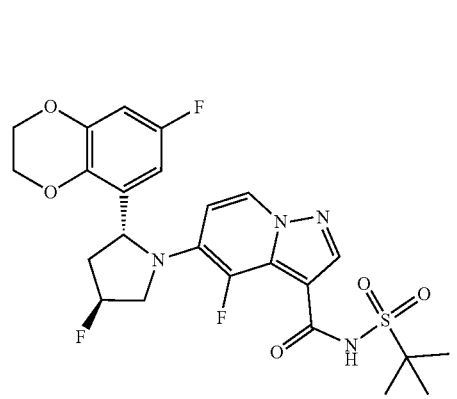
166
-continued
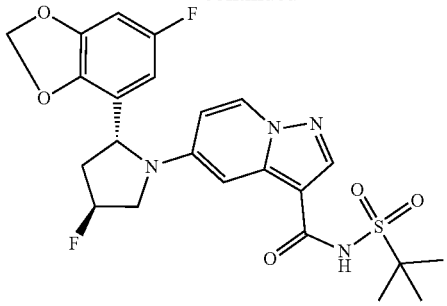
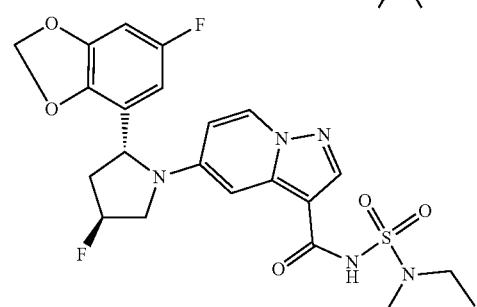
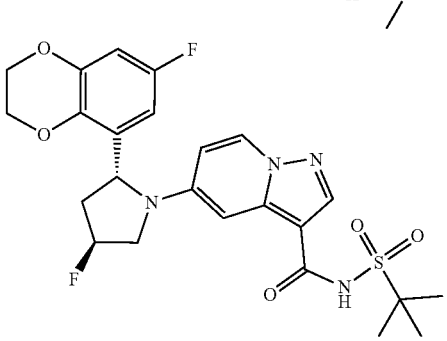
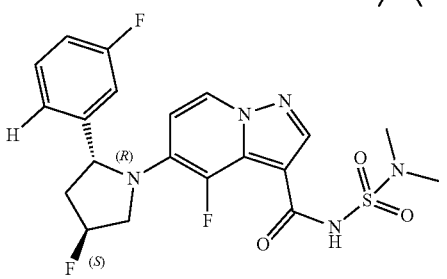
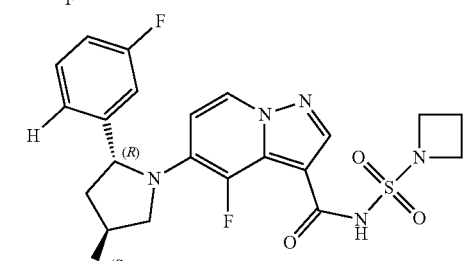
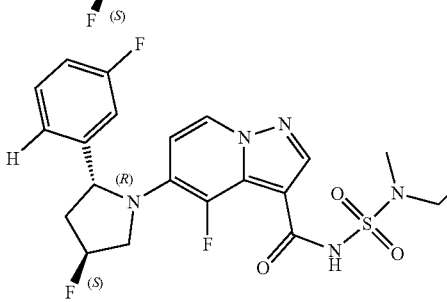

167
-continued

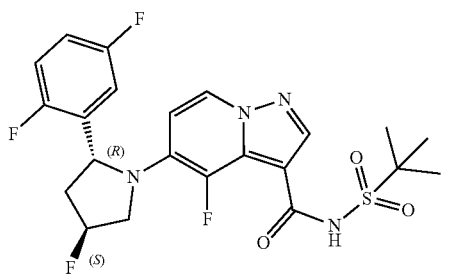

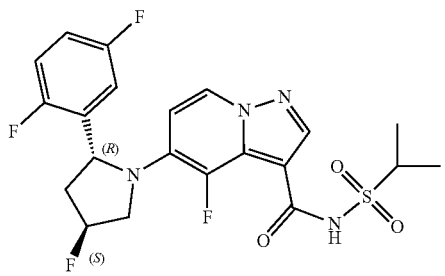

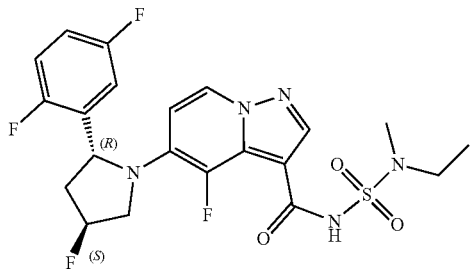

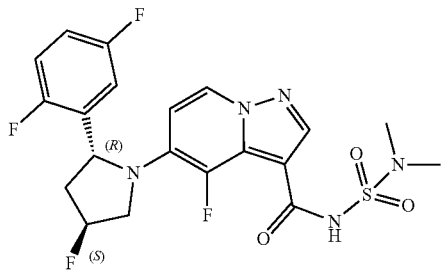

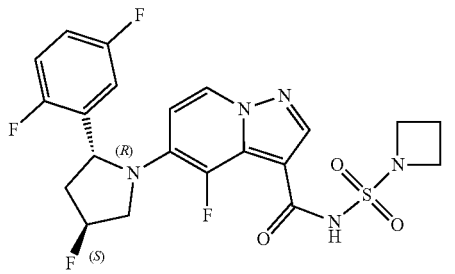

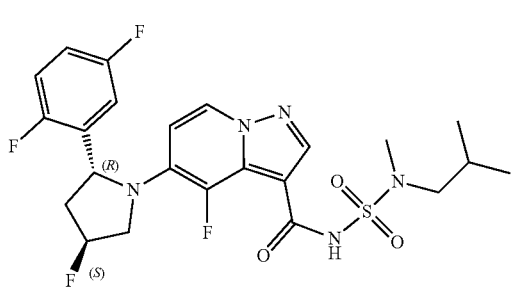

168
-continued

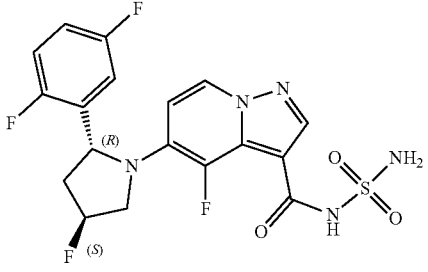

The invention claimed is:

1. A method for treating a cancer associated with a Trk kinase activity in a mammal in need thereof, the method comprising administering to the mammal a therapeutically effective amount of a compound of Formula (I),

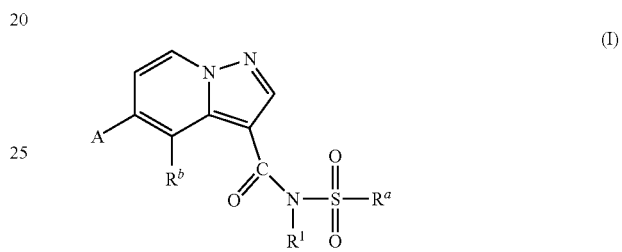

(I)

or their pharmaceutically acceptable salts, pharmaceutically acceptable solvates or stereoisomers thereof, wherein
A is

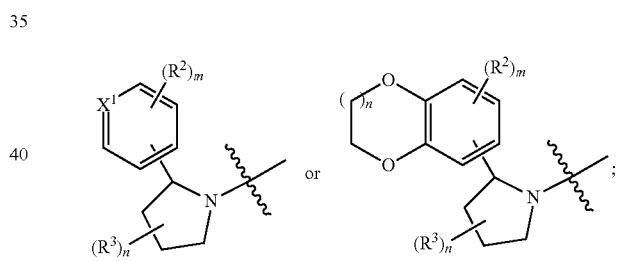

$X^1$ is CH or N;
$R^1$ represents hydrogen or —($C_1$-$C_6$)alkyl;
$R^2$ is independently selected from hydrogen, halogen, cyano, —($C_1$-$C_6$)alkyl, -halo($C_1$-$C_6$)alkyl, -halo($C_1$-$C_6$)alkoxy, phenyl optionally substituted with 1 to 3 halogens; and an optionally substituted —O-heterocyclic wherein the optional substituent is alkyl, —$OR^i$ or —$C(O)N(R^i)_2$;
when $X^1$ is CH, optionally two $R^2$s present on any two adjacent carbon atoms combine to form a 5 to 7 membered heterocyclic ring;
$R^3$ is independently halogen, cyano, —$OR^i$, or —C(O)N($R^i$)$_2$ or two $R^3$s together with the carbon atom they are attached form a ($C_3$-$C_7$)cycloalkyl group spiro attached to pyrrolidine; or two $R^3$ when they are attached to adjacent carbon atoms form a ($C_3$-$C_7$)cycloalkyl ring fused to the pyrrolidine;
$R^a$ is selected from
(i) a group selected from optionally substituted —($C_1$-$C_6$)alkyl, -hydroxy($C_1$-$C_6$)alkyl and —($C_1$-$C_6$)alkyl-($C_1$-$C_6$)alkoxy, wherein the optional substituent is cyano, halogen or —($C_6$-$C_{12}$)aryl, (ii) an optionally substituted —(C₃-C₁₀)cycloalkyl wherein the optional substituent is cyano, —(C₁-C₆)alkyl, hydroxyl, halogen or —R$^s$, (iii) an optionally substituted —(C₆-C₁₂)aryl wherein the optional substituent is cyano, hydroxyl, halogen, —(C₁-C₆)alkyl or —R$^r$ (iv) an optionally substituted 5 to 10 membered heterocyclyl, wherein the optional substituent is cyano, hydroxyl, halogen or —(C₁-C₆)alkyl, (v) an optionally substituted 5 to 10 membered heteroaryl, wherein the optional substituent is cyano, oxo (=O), hydroxyl, halogen, —(C₁-C₆)alkyl, —(C₁-C₆)alkoxy, —NR$^c$R$^d$ or —R$^r$ (vi) —NR⁴R⁵, and (vii) —(C₁-C₆)alkyl-(C₆-C₁₂)aryl;

R$^b$ represents hydrogen or halogen;

R⁴ is selected from hydrogen, —(C₁-C₆)alkyl, —(C₃-C₁₀)cycloalkyl, -hydroxy(C₁-C₆)alkyl, -alkoxy(C₁-C₆)alkyl, -halogen(C₁-C₆)alkyl and —(C₁-C₆)alkyl-(C₃-C₁₀)cycloalkyl;

R⁵ is hydrogen or —(C₁-C₆)alkyl or —(C₁-C₆)alkyl-(C₃-C₁₀)cycloalkyl;

Alternatively R⁴ and R⁵ together with the nitrogen atom to which they are attached may form an optionally substituted 5 to 10 membered heterocyclic ring, optionally containing 1-2 additional heteroatoms or groups selected from —O—, —S—, —N—, —C(=O)—, —S(=O)— or —S(=O)₂—, wherein the optional substituent is hydroxyl, —(C₁-C₆)alkyl, —C(=O)—(C₁-C₆)alkyl, mesyl or COOR$^e$;

R$^c$ and R$^d$ are independently selected from hydrogen and —(C₁-C₆)alkyl;

R$^e$ is selected from hydrogen and alkyl;

R$^i$ is hydrogen, —(C₁-C₆)alkyl, -halo(C₁-C₆)alkyl, —(C₁-C₆)alkyl-(C₁-C₆)alkoxy, —(C₃-C₁₀)cycloalkyl, optionally substituted —(C₁-C₆)alkyl-(C₃-C₁₀)cycloalkyl, wherein the optional substituent is halogen or —(C₁-C₆)alkyl substituted with 1 to 3 hydroxy groups;

R$^r$ is independently selected from a 5 to 10 membered heterocyclyl or a 5 to 10 membered heteroaryl, wherein optional substituent is hydroxyl, halogen, —(C₁-C₆)alkyl or —(C₁-C₆)alkoxy;

R$^s$ is an optionally substituted —(C₁-C₆)alkyl-(C₆-C₁₀)aryl, wherein the optional substituent is halogen;

m is independently represents 0, 1, 2, 3 or 4; and n is independently represents 0, 1, 2, or 3.

2. The method of claim 1, wherein the Trk kinase is TrkA.

3. The method of claim 1, wherein the compound of Formula (I) is

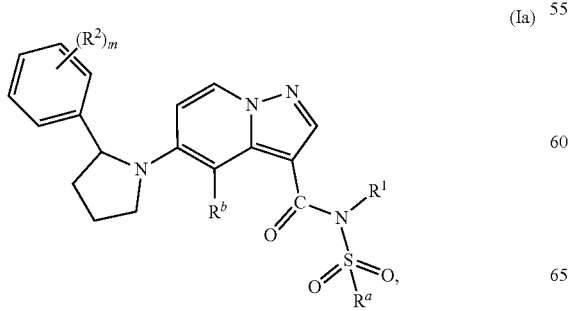
(Ia)

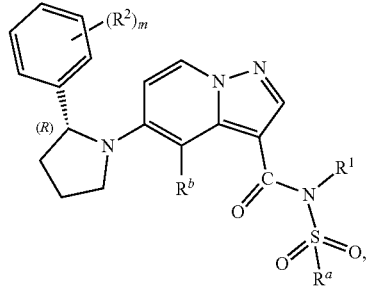
(Ib)

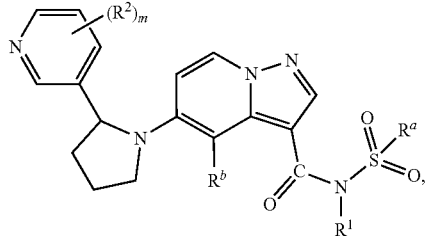
(Ic)

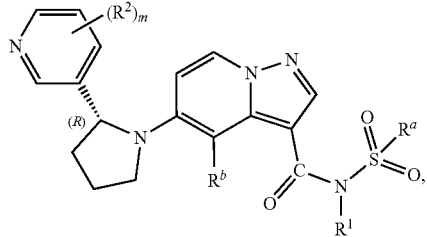
(Id)

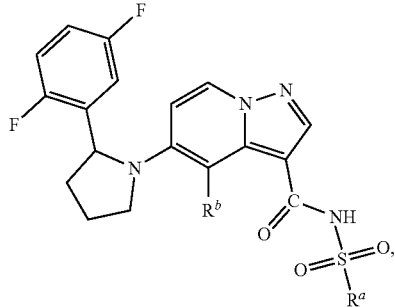
(Ie)

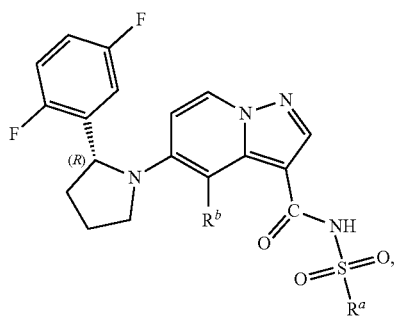
(If)

-continued

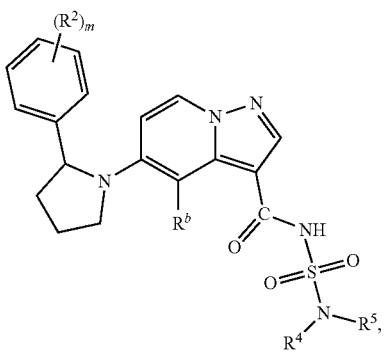
(Ig)

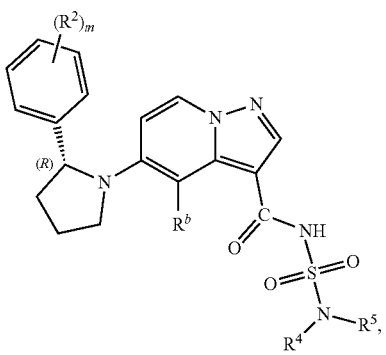
(Ih)

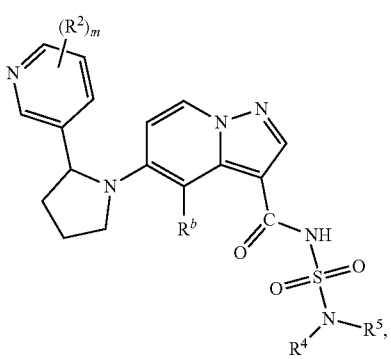
(Ii)

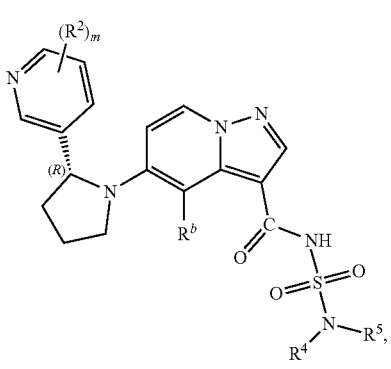
(Ij)

-continued

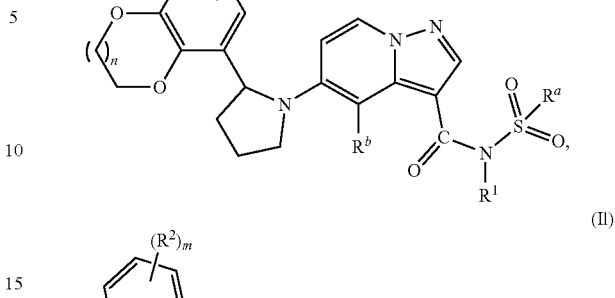
(Ik)

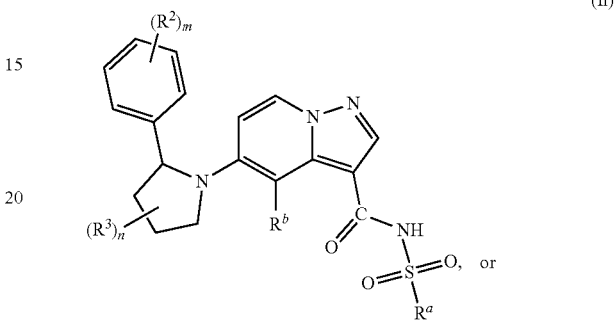
(Il)

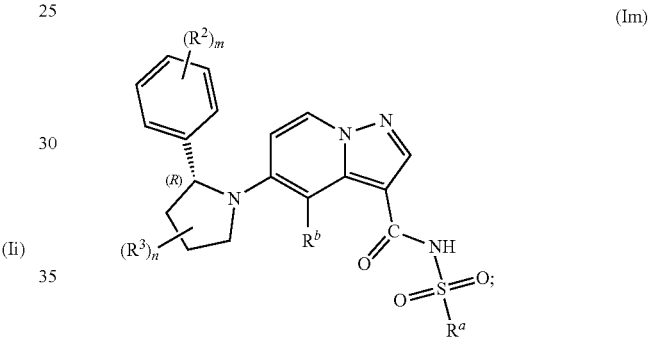
(Im)

or their pharmaceutically acceptable salts, pharmaceutically acceptable solvates or stereoisomers thereof, wherein the values of all the variables are as described in claim 1.

4. The method of claim 1, wherein $R^b$ is hydrogen, fluorine; $R^3$ is fluorine; or $R^2$ is independently represents halogen, cyano or haloalkyl; $R^4$ and $R^5$ are methyl, ethyl or propyl; m is 1 or 2; or $R^a$ methyl, ethyl, propyl, isopropyl, butyl or tert-butyl.

5. The method of claim 1, wherein the compound of formula (I) is (R)-5-(2-(2,5-difluorophenyl)pyrrolidin-1-yl)-N-((4-fluorophenyl)sulfonyl)pyrazolo [1,5-a]pyridine-3-carboxamide, (R)—N-(tert-butylsulfonyl)-5-(2-(2,5-difluorophenyl)pyrrolidin-1-yl)pyrazolo[1,5-a] pyridine-3-carboxamide, (R)-5-(2-(2,5-difluorophenyl)pyrrolidin-1-yl)-N-(ethylsulfonyl)pyrazolo[1,5-a] pyridine-3-carboxamide, (R)—N-((3-cyanophenyl)sulfonyl)-5-(2-(2,5-difluorophenyl)pyrrolidin-1-yl)pyrazolo [1,5-a] pyridine-3-carboxamide, (R)—N-(cyclopropylsulfonyl)-5-(2-(2,5-difluorophenyl)pyrrolidin-1-yl) pyrazolo[1,5-a]pyridine-3-carboxamide, (R)-5-(2-(2,5-difluorophenyl)pyrrolidin-1-yl)-N-(methylsulfonyl)pyrazolo[1,5-a] pyridine-3-carboxamide, (R)-5-(2-(2,5-difluorophenyl)pyrrolidin-1-yl)-N-(isopropylsulfonyl)pyrazolo[1,5-a] pyridine-3-carboxamide, 5-((R)-2-(2,5-difluorophenyl)pyrrolidin-1-yl)-N-((4-((S)-3-hydroxypyrrolidin-1-yl) phenyl) sulfonyl)pyrazolo [1, 5-a]pyridine-3-carboxamide, (R)—N-((3-cyanophenyl)sulfonyl)-5-(2-(2,5-difluorophenyl)pyrrolidin-1-yl)-N-methyl pyrazolo[1,5-a]pyridine-3-carboxamide, (R)-5-(2-(2,5-difluorophenyl)pyrrolidin-1-yl)-N-(propylsulfonyl)pyrazolo[1, 5-a] pyridine-3-carboxamide, (R)-5-(2-(2,5-difluorophenyl)pyrrolidin-1-yl)-N-((3,5-dimethyl isoxazol-4-yl) sulfonyl) pyrazolo [1, 5-a] pyridine-3-carboxamide, (R)—N-(cyclohexylsulfonyl)-5-(2-(2,5-difluorophenyl) pyrrolidin-1-yl)pyrazolo[1,5-a] pyridine-3-carboxamide, (R)—N-(cyclopentylsulfonyl)-5-(2-(2, 5-difluorophenyl) pyrrolidin-1-yl)pyrazolo[1,5-a] pyridine-3-carboxamide, (R)-5-(2-(2,5-difluorophenyl)pyrrolidin-1-yl)-N-(isobutylsulfonyl) pyrazolo[1, 5-a] pyridine-3-carboxamide, (R)-5-(2-(2,5-difluorophenyl) pyrrolidin-1-yl)-N-((1, 2-dimethyl-1H-imidazol-4-yl) sulfonyl) pyrazolo [1, 5-a] pyridine-3-carboxamide, (R)-5-(2-(2, 5-difluorophenyl) pyrrolidin-1-yl)-N-((1, 2-dimethyl-1H-imidazol-5-yl) sulfonyl) pyrazolo [1, 5-a] pyridine-3-carboxamide, (R)-5-(2-(2, 5-difluorophenyl) pyrrolidin-1-yl)-N-(piperidin-4-ylsulfonyl) pyrazolo [1, 5-a] pyridine-3-carboxamide, (R)-5-(2-(2, 5-difluorophenyl) pyrrolidin-1-yl)-N-((1-methyl-1H-imidazol-4-yl) sulfonyl) pyrazolo [1, 5-a] pyridine-3-carboxamide, (R)-5-(2-(2, 5-difluorophenyl) pyrrolidin-1-yl)-N-((1-methyl-1H-pyrazol-5-yl) sulfonyl) pyrazolo [1, 5-a] pyridine-3-carboxamide, (R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide, (R)-5-(2-(2, 5-difluorophenyl) pyrrolidin-1-yl)-N-((1-methyl-2-oxoindolin-5-yl) sulfonyl) pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, (R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, (R)-5-(2-(2, 5-difluorophenyl) pyrrolidin-1-yl)-N-((6-methoxypyridin-3-yl) sulfonyl) pyrazolo [1, 5-a] pyridine-3-carboxamide, (R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide, (R)-5-(2-(2, 5-difluorophenyl) pyrrolidin-1-yl)-N-((1-methyl-1H-pyrazol-4-yl) sulfonyl) pyrazolo [1, 5-a] pyridine-3-carboxamide, (R)-5-(2-(2, 5-difluorophenyl) pyrrolidin-1-yl)-N-((4-morpholinophenyl) sulfonyl)pyrazolo [1, 5-a] pyridine-3-carboxamide, (R)-5-(2-(2,5-difluorophenyl)pyrrolidin-1-yl)-N-(pyridin-3-ylsulfonyl)pyrazolo[1,5-a]pyridine-3-carboxamide, (R)—N-((5-chlorothiophen-2-yl) sulfonyl)-5-(2-(2, 5-difluorophenyl) pyrrolidin-1-yl) pyrazolo [1, 5-a] pyridine-3-carboxamide, (R)—N-((2, 5-dichlorothiophen-3-yl) sulfonyl)-5-(2-(2, 5-difluorophenyl) pyrrolidin-1-yl) pyrazolo [1, 5-a] pyridine-3-carboxamide, (R)—N-(cyclobutylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide, (R)—N-(benzo[d][1,3]dioxol-5-ylsulfonyl)-5-(2-(2,5-difluorophenyl)pyrrolidin-1-yl) pyrazolo[1,5-a]pyridine-3-carboxamide, (R)-5-(2-(2,5-difluorophenyl)pyrrolidin-1-yl)-N-((1-ethylcyclopropyl)sulfonyl)pyrazolo[1,5-a]pyridine-3-carboxamide, (R)-5-(2-(2,5-difluorophenyl)pyrrolidin-1-yl)-N-(neopentylsulfonyl)pyrazolo[1,5-a]pyridine-3-carboxamide, (R)-5-(2-(2,5-difluorophenyl)pyrrolidin-1-yl)-N-((1-methylcyclopropyl)sulfonyl) pyrazolo[1,5-a]pyridine-3-carboxamide, (R)-5-(2-(2,5-difluorophenyl)pyrrolidin-1-yl)-N-(o-tolylsulfonyl)pyrazolo[1,5-a] pyridine-3-carboxamide, (R)—N-(benzylsulfonyl)-5-(2-(2,5-difluorophenyl)pyrrolidin-1-yl)pyrazolo[1,5-a] pyridine-3-carboxamide, (R)-5-(2-(2,5-difluorophenyl)pyrrolidin-1-yl)-N-((1-(4-fluorobenzyl)cyclopropyl) sulfonyl)pyrazolo[1,5-a] pyridine-3-carboxamide, (R)—N-(tert-butylsulfonyl)-5-(2-(5-fluoro-2-methoxyphenyl) pyrrolidin-1-yl) pyrazolo [1, 5-a] pyridine-3-carboxamide, (R)—N-(tert-butylsulfonyl)-5-(2-(3-(difluoromethoxy)-5-fluorophenyl) pyrrolidin-1-yl) pyrazolo [1, 5-a] pyridine-3-carboxamide, (R)—N-(tert-butylsulfonyl)-5-(2-(5-fluoropyridin-3-yl) pyrrolidin-1-yl) pyrazolo [1, 5-a] pyridine-3-carboxamide, (R)—N-(tert-butylsulfonyl)-5-(2-(2-ethoxy-5-fluorophenyl)pyrrolidin-1-yl)pyrazolo [1,5-a]pyridine-3-carboxamide, (R)—N-(tert-butylsulfonyl)-5-(2-(2-(cyclopropylmethoxy)-5-fluorophenyl) pyrrolidin-1-yl)pyrazolo[1, 5-a] pyridine-3-carboxamide, (R)—N-(tert-butylsulfonyl)-5-(2-(2-chloro-5-fluorophenyl)pyrrolidin-1-yl) pyrazolo[1,5-a]pyridine-3-carboxamide, N-(tert-butylsulfonyl)-5-((2R,4R)-2-(2,5-difluorophenyl)-4-hydroxypyrrolidin-1-yl) pyrazolo[1,5-a]pyridine-3-carboxamide, (R)—N-(tert-butylsulfonyl)-5-(2-(5-fluoro-2-(2,2,2-trifluoroethoxy)phenyl) pyrrolidin-1-yl)pyrazolo[1,5-a] pyridine-3-carboxamide, N-(tert-butylsulfonyl)-5-(2-(7-fluoro-2,3-dihydrobenzo [b][1,4]dioxin-5-yl)pyrrolidin-1-yl)pyrazolo[1,5-a] pyridine-3-carboxamide (Isomer-I), N-(tert-butylsulfonyl)-5-(2-(7-fluoro-2,3-dihydrobenzo [b][1,4]dioxin-5-yl)pyrrolidin-1-yl)pyrazolo[1,5-a] pyridine-3-carboxamide (Isomer-II), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-I), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-II), (R)—N-(tert-butylsulfonyl)-5-(2-(4,4'-difluoro-[1,1'-biphenyl]-2-yl)pyrrolidin-1-yl)pyrazolo[1,5-a] pyridine-3-carboxamide, (S)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(5-fluoro-2-(2-fluoroethoxy)phenyl) pyrrolidin-1-yl)pyrazolo[1,5-a] pyridine-3-carboxamide, N-(tert-butylsulfonyl)-5-((2R,4R)-2-(2,5-difluorophenyl)-4-fluoropyrrolidin-1-yl)pyrazolo[1,5-a] pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a] pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a] pyridine-3-carboxamide, (R)—N-(tert-butylsulfonyl)-5-(2-(2, 5-difluorophenyl) pyrrolidin-1-yl)-4-fluoro pyrazolo[1,5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1,5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide, (R)—N-(tert-butylsulfonyl)-5-(2-(3, 5-difluorophenyl) pyrrolidin-1-yl) pyrazolo [1, 5-a] pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a] pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a] pyridine-3-carboxamide, (R)-5-(2-(3, 5-difluorophenyl) pyrrolidin-1-yl)-N-((4-fluorophenyl) sulfonyl) pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, (R)-5-(2-(3, 5-difluorophenyl) pyrrolidin-1-yl)-N-(isopropylsulfonyl) pyrazolo [1, 5-a] pyridine-3-carboxamide, (R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide, 5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, 5-((2R,4S)-2-(2,5-difluorophenyl)-4-fluoropyrrolidin-1-yl)-N-((1-methyl cyclopropyl)sulfonyl)pyrazolo[1,5-a] pyridine-3-carboxamide, (R)-5-(2-(2, 5-difluorophenyl) pyrrolidin-1-yl)-4-fluoro-N-(isopropylsulfonyl) pyrazolo [1, 5-a] pyridine-3-carboxamide, (R)-5-(2-(2, 5-difluorophenyl) pyrrolidin-1-yl)-N—(N,N-dimethylsulfamoyl) pyrazolo [1, 5-a] pyridine-3-carboxamide, (R)-5-(2-(2,5-difluorophenyl)pyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl)pyrazolo[1,5-a]pyridine-3-carboxamide, 5-((2R,4S)-2-(2,5-difluorophenyl)-4-fluoropyrrolidin-1-yl)-N—(N-ethyl-N-methyl sulfamoyl)pyrazolo[1,5-a] pyridine-3-carboxamide, (R)—N—(N-(cyclopropylmethyl)-N-methylsulfamoyl)-5-(2-(2,5-difluorophenyl) pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl) pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a] pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl) pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo[1,5-a]pyridine-3-carboxamide, (R)—N—(N,N-diethylsulfamoyl)-5-(2-(5-fluoro-2-methoxyphenyl)pyrrolidin-1-yl) pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl)pyrazolo[1,5-a] pyridine-3-carboxamide, (R)-5-(2-(2,5-difluorophenyl)pyrrolidin-1-yl)-N-(piperidin-1-ylsulfonyl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a] pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy) phenyl)pyrrolidin-1-yl)pyrazolo[1,5-a]pyridine-3-carboxamide, 5-((R)-2-(2,5-difluorophenyl)pyrrolidin-1-yl)-N—(((S)-3-hydroxypyrrolidin-1-yl) sulfonyl)pyrazolo[1,5-a] pyridine-3-carboxamide, (R)-5-(2-(2,5-difluorophenyl)pyrrolidin-1-yl)-N-sulfamoylpyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo [1,5-a]pyridine-3-carboxamide, N—(N-ethyl-N-methylsulfamoyl)-5-(2-(8-fluoro-3,4-dihydro-2H-benzo[b][1,4] dioxepin-6-yl)pyrrolidin-1-yl) pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4] dioxepin-6-yl)pyrrolidin-1-yl) pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I),
N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II),
N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I),
N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II),
N—(N-ethyl-N-methylsulfamoyl)-4-fluoro-5-((2R,4S)-4-fluoro-2-(3-fluorophenyl) pyrrolidin-1-yl)pyrazolo[1,5-a]pyridine-3-carboxamide,
N—(N-ethyl-N-methylsulfamoyl)-5-((R)-2-(3-fluoro-5-(((S)-tetrahydrofuran-3-yl)oxy)phenyl)pyrrolidin-1-yl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide,
N—(N-ethyl-N-methylsulfamoyl)-5-((R)-2-(3-fluoro-5-(((R)-tetrahydrofuran-3-yl)oxy)phenyl)pyrrolidin-1-yl)pyrazolo[1,5-a]pyridine-3-carboxamide,
4-fluoro-5-((2R,4S)-4-fluoro-2-(3-fluorophenyl)pyrrolidin-1-yl)-N-sulfamoyl pyrazolo[1,5-a]pyridine-3-carboxamide,
N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-1),
N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2);
(R)-5-(2-(2,5-difluorophenyl)pyrrolidin-1-yl)-N—(N-isobutyl-N-methyl sulfamoyl)pyrazolo[1,5-a]pyridine-3-carboxamide,
(R)—N—(N-ethyl-N-methylsulfamoyl)-4-fluoro-5-(2-(3-fluorophenyl)pyrrolidin-1-yl)pyrazolo[1,5-a]pyridine-3-carboxamide,
(R)—N—(N,N-dimethylsulfamoyl)-4-fluoro-5-(2-(3-fluorophenyl)pyrrolidin-1-yl) pyrazolo[1,5-a]pyridine-3-carboxamide,
(R)—N—(N,N-dimethylsulfamoyl)-4-fluoro-5-(2-(3-fluorophenyl)pyrrolidin-1-yl) pyrazolo[1,5-a]pyridine-3-carboxamide,
(R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide,
(R)—N—(N,N-bis(cyclopropylmethyl)sulfamoyl)-5-(2-(2,5-difluorophenyl)pyrrolidin-1-yl)pyrazolo[1,5-a]pyridine-3-carboxamide,
N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide,
N—(N-ethyl-N-methylsulfamoyl)-5-((2R)-2-(5-fluoro-2-((tetrahydrofuran-3-yl)oxy) phenyl)pyrrolidin-1-yl) pyrazolo[1,5-a]pyridine-3-carboxamide (Diastereomer-II),
N-(tert-butylsulfonyl)-5-(2-(2,5-difluorophenyl)pyrrolidin-1-yl)pyrazolo[1,5-a] pyridine-3-carboxamide (Racemic mixture);
(R)—N-(tert-butylsulfonyl)-5-(2-(3,5-difluoro-2-methoxyphenyl)pyrrolidin-1-yl) pyrazolo[1,5-a]pyridine-3-carboxamide,
N-(tert-butylsulfonyl)-4-fluoro-5-((2R,4S)-4-fluoro-2-(3-fluorophenyl)pyrrolidin-1-yl)pyrazolo[1,5-a]pyridine-3-carboxamide,
4-fluoro-5-((2R,4S)-4-fluoro-2-(3-fluorophenyl)pyrrolidin-1-yl)-N-(isopropyl sulfonyl)pyrazolo[1,5-a]pyridine-3-carboxamide,
(R)—N-(tert-butylsulfonyl)-5-(2-(3,5-difluoro-2-((tetrahydro-2H-pyran-4-yl)oxy) phenyl)pyrrolidin-1-yl) pyrazolo[1,5-a]pyridine-3-carboxamide,
(R)—N-(tert-butylsulfonyl)-5-(2-(5-fluoro-2-((tetrahydro-2H-pyran-4-yl)oxy) phenyl)pyrrolidin-1-yl) pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide,
(R)-4-fluoro-5-(2-(3-fluorophenyl)pyrrolidin-1-yl)-N-(isopropylsulfonyl)pyrazolo [1,5-a]pyridine-3-carboxamide,
(R)—N-(tert-butylsulfonyl)-4-fluoro-5-(2-(5-fluoro-2-((tetrahydro-2H-pyran-4-yl) oxy)phenyl)pyrrolidin-1-yl)pyrazolo[1,5-a]pyridine-3-carboxamide,
Sodium (tert-butylsulfonyl)(5-((2R,4S)-2-(2,5-difluorophenyl)-4-fluoropyrrolidin-1-yl) pyrazolo[1,5-a]pyridine-3-carbonyl)amide,
Sodium(R)-(tert-butylsulfonyl)(5-(2-(2,5-difluorophenyl)pyrrolidin-1-yl) pyrazolo [1,5-a] pyridine-3-carbonyl)amide,
Sodium (R)-(tert-butylsulfonyl)(5-(2-(7-fluoro-2,3-dihydrobenzo[b][1,4]dioxin-5-yl)pyrrolidin-1-yl)pyrazolo [1,5-a]pyridine-3-carbonyl)amide,
Sodium (tert-butylsulfonyl)(5-((2R,4R)-2-(2,5-difluorophenyl)-4-fluoropyrrolidin-1-yl) pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl) (N,N-dimethylsulfamoyl)amide,
Sodium (tert-butylsulfonyl)(5-(2-(2,5-difluorophenyl)-4,4-difluoropyrrolidin-1-yl)pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl)((1-methylcyclopropyl) sulfonyl)amide,
Sodium (tert-butylsulfonyl)(5-((2R)-2-(2,5-difluorophenyl)-4-fluoropyrrolidin-1-yl)pyrazolo [1,5-a]pyridine-3-carbonyl)amide,
Sodium (5-((2R,4S)-2-(2,5-difluorophenyl)-4-fluoropyrrolidin-1-yl)pyrazolo[1,5-a]pyridine-3-carbonyl)(N,N-dimethylsulfamoyl)amide,
Sodium (tert-butylsulfonyl)(4-fluoro-5-((2R,4S)-4-fluoro-2-(3-fluorophenyl) pyrrolidin-1-yl)pyrazolo[1,5-a] pyridine-3-carbonyl)amide,
Sodium (R)—(N,N-dimethylsulfamoyl)(4-fluoro-5-(2-(3-fluorophenyl)pyrrolidin-1-yl)pyrazolo [1,5-a] pyridine-3-carbonyl)amide,
Sodium (N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl)(o-tolylsulfonyl)amide, Sodium (4-fluoro-5-((2R,4S)-4-fluoro-2-(3-fluorophenyl)pyrrolidin-1-yl) pyrazolo[1,5-a]pyridine-3-carbonyl)(isopropylsulfonyl)amide, Sodium (5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, or Sodium (R)-(5-(2-(2,5-difluorophenyl) pyrrolidin-1-yl) pyrazolo[1,5-a]pyridine-3-carbonyl)(piperidin-1-ylsulfonyl)amide;

or a pharmaceutically acceptable salt thereof, a pharmaceutically acceptable solvate thereof or a stereoisomer thereof.

6. The method of claim 1, wherein the compound of formula (I) is (R)-5-(2-(2,5-difluorophenyl)pyrrolidin-1-yl)-N-((4-fluorophenyl)sulfonyl)pyrazolo[1,5-a] pyridine-3-carboxamide, (R)—N-((3-cyanophenyl)sulfonyl)-5-(2-(2,5-difluorophenyl)pyrrolidin-1-yl)pyrazolo[1,5-a] pyridine-3-carboxamide, 5-((R)-2-(2,5-difluorophenyl)pyrrolidin-1-yl)-N-((4-((S)-3-hydroxypyrrolidin-1-yl) phenyl) sulfonyl) pyrazolo [1, 5-a] pyridine-3-carboxamide, (R)—N-((3-cyanophenyl) sulfonyl)-5-(2-(2, 5-difluorophenyl) pyrrolidin-1-yl)-N-methylpyrazolo [1, 5-a] pyridine-3-carboxamide, (R)-5-(2-(2, 5-difluorophenyl) pyrrolidin-1-yl)-N-((4-morpholinophenyl) sulfonyl)pyrazolo [1, 5-a] pyridine-3-carboxamide, (R)-5-(2-(2,5-difluorophenyl)pyrrolidin-1-yl)-N-(o-tolylsulfonyl)pyrazolo[1,5-a]pyridine-3-carboxamide, (R)-5-(2-(3, 5-difluorophenyl) pyrrolidin-1-yl)-N-((4-fluorophenyl) sulfonyl) pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, Sodium(R)-(5-(2-(2,5-difluorophenyl)pyrrolidin-1-yl) pyrazolo[1,5-a]pyridine-3-carbonyl) (piperidin-1-ylsulfonyl)amide, Sodium(R)-(5-(2-(2,5-difluorophenyl)pyrrolidin-1-yl) pyrazolo[1,5-a]pyridine-3-carbonyl) (o-tolylsulfonyl)amide;

(R)—N-(tert-butylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-(ethylsulfonyl)pyrazolo[1,5-a]pyridine-3-carboxamide, (R)-5-(2-(2,5-difluorophenyl)pyrrolidin-1-yl)-N-(methylsulfonyl)pyrazolo[1,5-a] pyridine-3-carboxamide, (R)-5-(2-(2, 5-difluorophenyl) pyrrolidin-1-yl)-N-(isopropylsulfonyl)pyrazolo[1, 5-a] pyridine-3-carboxamide, (R)-5-(2-(2, 5-difluorophenyl) pyrrolidin-1-yl)-N-(propylsulfonyl)pyrazolo[1, 5-a] pyridine-3-carboxamide, (R)-5-(2-(2, 5-difluorophenyl) pyrrolidin-1-yl)-N-(isobutylsulfonyl)pyrazolo[1, 5-a] pyridine-3-carboxamide, (R)-5-(2-(2,5-difluorophenyl)pyrrolidin-1-yl)-N-(neopentylsulfonyl)pyrazolo[1,5-a] pyridine-3-carboxamide, (R)—N-(benzylsulfonyl)-5-(2-(2,5-difluorophenyl)pyrrolidin-1-yl)pyrazolo[1,5-a]pyridine-3-carboxamide, (R)—N-(tert-butylsulfonyl)-5-(2-(5-fluoro-2-methoxyphenyl) pyrrolidin-1-yl)pyrazolo [1, 5-a] pyridine-3-carboxamide, (R)—N-(tert-butylsulfonyl)-5-(2-(3-(difluoromethoxy)-5-fluorophenyl) pyrrolidin-1-yl) pyrazolo [1, 5-a] pyridine-3-carboxamide, (R)—N-(tert-butylsulfonyl)-5-(2-(5-fluoropyridin-3-yl)pyrrolidin-1-yl)pyrazolo [1, 5-a] pyridine-3-carboxamide, (R)—N-(tert-butylsulfonyl)-5-(2-(2-ethoxy-5-fluorophenyl)pyrrolidin-1-yl)pyrazolo[1,5-a] pyridine-3-carboxamide, (R)—N-(tert-butylsulfonyl)-5-(2-(2-(cyclopropylmethoxy)-5-fluorophenyl)pyrrolidin-1-yl) pyrazolo[1,5-a]pyridine-3-carboxamide, (R)—N-(tert-butylsulfonyl)-5-(2-(2-chloro-5-fluorophenyl)pyrrolidin-1-yl)pyrazolo[1,5-a]pyridine-3-carboxamide, N-(tert-butylsulfonyl)-5-((2R,4R)-2-(2,5-difluorophenyl)-4-hydroxypyrrolidin-1-yl)pyrazolo[1,5-a]pyridine-3-carboxamide, N-(tert-butylsulfonyl)-5-((2R,4S)-2-(2,5-difluorophenyl)-4-fluoro pyrrolidin-1-yl)pyrazolo [1,5-a]pyridine-3-carboxamide, (R)—N-(tert-butylsulfonyl)-5-(2-(4,4'-difluoro-[1,1'-biphenyl]-2-yl)pyrrolidin-1-yl) pyrazolo[1,5-a]pyridine-3-carboxamide, (R)—N-(tert-butylsulfonyl)-5-(2-(5-fluoro-2-(2-fluoroethoxy)phenyl)pyrrolidin-1-yl) pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, (R)—N-(tert-butylsulfonyl)-5-(2-(2, 5-difluorophenyl) pyrrolidin-1-yl)-4-fluoro pyrazolo[1, 5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide, (R)—N-(tert-butylsulfonyl)-5-(2-(3, 5-difluorophenyl) pyrrolidin-1-yl) pyrazolo [1, 5-a] pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a]pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide, (R)-5-(2-(3, 5-difluorophenyl) pyrrolidin-1-yl)-N-(isopropylsulfonyl) pyrazolo [1, 5-a] pyridine-3-carboxamide, N-(tert-butylsulfonyl)-5-(2-(2,5-difluorophenyl)pyrrolidin-1-yl)pyrazolo[1,5-a] pyridine-3-carboxamide (Racemic mixture), (R)—N-(tert-butylsulfonyl)-5-(2-(3,5-difluoro-2-methoxyphenyl)pyrrolidin-1-yl)pyrazolo[1,5-a]pyridine-3-carboxamide, (R)—N-(tert-butylsulfonyl)-5-(2-(3,5-difluoro-2-((tetrahydro-2H-pyran-4-yl)oxy)phenyl)pyrrolidin-1-yl) pyrazolo[1,5-a]pyridine-3-carboxamide, (R)—N-(tert-butylsulfonyl)-5-(2-(5-fluoro-2-((tetra-hydro-2H-pyran-4-yl)oxy)phenyl)pyrrolidin-1-yl) pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide, (R)-4-fluoro-5-(2-(3-fluorophenyl)pyrrolidin-1-yl)-N-(isopropylsulfonyl)pyrazolo[1,5-a]pyridine-3-carboxamide, (R)—N-(tert-butylsulfonyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, Sodium(tert-butylsulfonyl)(5-((2R,4R)-2-(2,5-difluorophenyl)-4-fluoropyrrolidin-1-yl)pyrazolo[1,5-a]pyridine-3-carbonyl)amide, Sodium(tert-butylsulfonyl)(5-((2R,4S)-2-(2,5-difluorophenyl)-4-fluoropyrrolidin-1-yl)pyrazolo[1,5-a]pyridine-3-carbonyl)amide, Sodium(R)-(tert-butylsulfonyl)(5-(2-(2,5-difluorophenenyl)pyrrolidin-1-yl)pyrazolo[1,5-a] pyridine-3-carbonyl)amide, Sodium(R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide;

(R)—N-(cyclopropylsulfonyl)-5-(2-(2,5-difluorophenyl) pyrrolidin-1-yl)pyrazolo[1,5-a]pyridine-3-carboxamide, (R)—N-(cyclohexyl sulfonyl)-5-(2-(2, 5-difluorophenyl) pyrrolidin-1-yl) pyrazolo [1, 5-a] pyridine-3-carboxamide, (R)—N-(cyclopentyl sulfonyl)-5-(2-(2, 5-difluorophenyl) pyrrolidin-1-yl) pyrazolo [1, 5-a] pyridine-3-carboxamide, (R)—N-(cyclobutylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-((1-ethylcyclopropyl)sulfonyl) pyrazolo[1,5-a]pyridine-3-carboxamide, (R)-5-(2-(2,5-difluorophenyl)pyrrolidin-1-yl)-N-((1-methylcyclopropyl)sulfonyl)pyrazolo [1,5-a]pyridine-3-carboxamide, (R)-5-(2-(2,5-difluorophenyl)pyrrolidin-1-yl)-N-((1-(4-fluorobenzyl)cyclopropyl)sulfonyl) pyrazolo[1,5-a] pyridine-3-carboxamide, (R)-5-(2-(2, 5-difluorophenyl) pyrrolidin-1-yl)-4-fluoro-N-(isopropylsulfonyl)pyrazolo [1, 5-a] pyridine-3-carboxamide, Sodium(R)-(5-(2-(2,5-difluorophenyl)pyrrolidin-1-yl) pyrazolo[1,5-a]pyridine-3-carbonyl)((1-methylcyclopropyl) sulfonyl)amide;

(R)-5-(2-(2,5-difluorophenyl) pyrrolidin-1-yl)-N-((3,5-dimethylisoxazol-4-yl)sulfonyl) pyrazolo [1, 5-a] pyridine-3-carboxamide, (R)-5-(2-(2,5-difluorophenyl) pyrrolidin-1-yl)-N-((1, 2-dimethyl-1H-imidazol-4-yl) sulfonyl) pyrazolo [1, 5-a] pyridine-3-carboxamide, (R)-5-(2-(2,5-difluorophenyl) pyrrolidin-1-yl)-N-((1, 2-dimethyl-1H-imidazol-5-yl) sulfonyl) pyrazolo [1, 5-a] pyridine-3-carboxamide, (R)-5-(2-(2,5-difluorophenyl) pyrrolidin-1-yl)-N-((1-methyl-1H-imidazol-4-yl) sulfonyl) pyrazolo [1, 5-a] pyridine-3-carboxamide, (R)-5-(2-(2,5-difluorophenyl) pyrrolidin-1-yl)-N-((1-methyl-1H-pyrazol-5-yl) sulfonyl) pyrazolo [1, 5-a] pyridine-3-carboxamide, (R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide, (R)-5-(2-(2,5-difluorophenyl)pyrrolidin-1-yl)-N-((1-methyl-2-oxoindolin-5-yl)sulfonyl) pyrazolo [1, 5-a] pyridine-3-carboxamide, (R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide, 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, (R)-5-(2-(2, 5-difluorophenyl) pyrrolidin-1-yl)-N-((6-methoxypyridin-3-yl) sulfonyl) pyrazolo [1, 5-a] pyridine-3-carboxamide, (R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide, (R)-5-(2-(2,5-difluorophenyl) pyrrolidin-1-yl)-N-((1-methyl-1H-pyrazol-4-yl) sulfonyl) pyrazolo [1, 5-a] pyridine-3-carboxamide, (R)-5-(2-(2,5-difluorophenyl)pyrrolidin-1-yl)-N-(pyridin-3-ylsulfonyl)pyrazolo[1,5-a]pyridine-3-carboxamide, (R)—N-((5-chlorothiophen-2-yl) sulfonyl)-5-(2-(2, 5-difluorophenyl) pyrrolidin-1-yl) pyrazolo [1, 5-a] pyridine-3-carboxamide, (R)—N-((2,5-dichlorothiophen-3-yl) sulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide, (R)—N-(benzo[d][1,3]dioxol-5-ylsulfonyl)-5-(2-(2,5-difluorophenyl)pyrrolidin-1-yl)pyrazolo[1,5-a]pyridine-3-carboxamide, (R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide, 5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide;

(R)-5-(2-(2, 5-difluorophenyl) pyrrolidin-1-yl)-N-(piperidin-4-ylsulfonyl) pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl)pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo [1,5-a]pyridine-3-carboxamide, (R)-5-(2-(2,5-difluorophenyl)pyrrolidin-1-yl)-N-(piperidin-1-ylsulfonyl)pyrazolo[1,5-a] pyridine-3-carboxamide, 5-((R)-2-(2,5-difluorophenyl)pyrrolidin-1-yl)-N—(((S)-3-hydroxypyrrolidin-1-yl) sulfonyl) pyrazolo[1,5-a] pyridine-3-carboxamide;

(R)—N-(tert-butylsulfonyl)-5-(2-(5-fluoro-2-(2,2,2-trifluoroethoxy)phenyl)pyrrolidin-1-yl) pyrazolo[1,5-a]pyridine-3-carboxamide,
N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide,
N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide,
N-(tert-butylsulfonyl)-5-((2R,4S)-2-(2,5-difluorophenyl)-4-fluoropyrrolidin-1-yl)pyrazolo[1,5-a]pyridine-3-carboxamide,
N-(tert-butylsulfonyl)-5-((2R,4R)-2-(2,5-difluorophenyl)-4-fluoropyrrolidin-1-yl)pyrazolo[1,5-a]pyridine-3-carboxamide,
5-((2R,4S)-2-(2,5-difluorophenyl)-4-fluoropyrrolidin-1-yl)-N-((1-methyl cyclopropyl) sulfonyl)pyrazolo[1,5-a]pyridine-3-carboxamide,
5-((2R,4S)-2-(2,5-difluorophenyl)-4-fluoropyrrolidin-1-yl)-N—(N,N-dimethylsulfamoyl) pyrazolo[1,5-a]pyridine-3-carboxamide,
5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide,
5-((2R,4S)-2-(2,5-difluorophenyl)-4-fluoropyrrolidin-1-yl)-N—(N,N-dimethylsulfamoyl) pyrazolo[1,5-a]pyridine-3-carboxamide,
5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide,
N—(N-ethyl-N-methylsulfamoyl)-4-fluoro-5-((2R,4S)-4-fluoro-2-(3-fluorophenyl)pyrrolidin-1-yl)pyrazolo[1,5-a] pyridine-3-carboxamide,
N-(tert-butylsulfonyl)-4-fluoro-5-((2R,4S)-4-fluoro-2-(3-fluorophenyl)pyrrolidin-1-yl)pyrazolo [1,5-a]pyridine-3-carboxamide,
4-fluoro-5-((2R,4S)-4-fluoro-2-(3-fluorophenyl)pyrrolidin-1-yl)-N-(isopropylsulfonyl) pyrazolo[1,5-a]pyridine-3-carboxamide,
Sodium(4-fluoro-5-((2R,4S)-4-fluoro-2-(3-fluorophenyl)pyrrolidin-1-yl)pyrazolo[1,5-a]pyridine-3-carbonyl)(isopropylsulfonyl)amide,
Sodium(5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide,
Sodium(tert-butylsulfonyl)(5-((2R)-2-(2,5-difluorophenyl)-4-fluoropyrrolidin-1-yl)pyrazolo[1,5-a]pyridine-3-carbonyl)amide,
Sodium(5-((2R,4S)-2-(2,5-difluorophenyl)-4-fluoropyrrolidin-1-yl)pyrazolo[1,5-a]pyridine-3-carbonyl)(N,N-dimethylsulfamoyl)amide,
Sodium(tert-butylsulfonyl)(4-fluoro-5-((2R,4S)-4-fluoro-2-(3-fluorophenyl)pyrrolidin-1-yl)pyrazolo[1,5-a]pyridine-3-carbonyl)amide,
Sodium (tert-butylsulfonyl)(5-(2-(2,5-difluorophenyl)-4,4-difluoropyrrolidin-1-yl) pyrazolo[1,5-a]pyridine-3-carbonyl)amide;
(R)-5-(2-(2,5-difluorophenyl) pyrrolidin-1-yl)-N—(N,N-dimethylsulfamoyl)pyrazolo[1,5-a] pyridine-3-carboxamide,
(R)-5-(2-(2,5-difluorophenyl)pyrrolidin-1-yl)-N—(N-ethyl-N-methylsulfamoyl)pyrazolo [1,5-a]pyridine-3-carboxamide,
(R)—N—(N-(cyclopropylmethyl)-N-methylsulfamoyl)-5-(2-(2,5-difluorophenyl)pyrrolidin-1-yl)pyrazolo[1,5-a]pyridine-3-carboxamide,
(R)—N—(N,N-diethylsulfamoyl)-5-(2-(2,5-difluorophenyl)pyrrolidin-1-yl)pyrazolo[1,5-a]pyridine-3-carboxamide,
(R)—N—(N,N-diethylsulfamoyl)-5-(2-(5-fluoro-2-methoxyphenyl)pyrrolidin-1-yl)pyrazolo[1,5-a]pyridine-3-carboxamide,
(R)—N—(N,N-diethylsulfamoyl)-5-(2-(5-fluoro-2-(2-fluoroethoxy)phenyl)pyrrolidin-1-yl) pyrazolo[1,5-a]pyridine-3-carboxamide,
(R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide,
(R)—N—(N-ethyl-N-methylsulfamoyl)-5-(2-(5-fluoro-2-methoxyphenyl)pyrrolidin-1-yl)pyrazolo[1,5-a]pyridine-3-carboxamide,
(R)—N—(N-ethyl-N-methylsulfamoyl)-5-(2-(5-fluoro-2-(2-fluoroethoxy)phenyl)pyrrolidin-1-yl)pyrazolo[1,5-a]pyridine-3-carboxamide,
(R)-5-(2-(3,5-difluoro-2-(2-fluoroethoxy)phenyl)pyrrolidin-1-yl)-N—(N-ethyl-N-methylsulfamoyl)pyrazolo[1,5-a]pyridine-3-carboxamide,
(R)-5-(2-(2,5-difluorophenyl)pyrrolidin-1-yl)-N-sulfamoylpyrazolo[1,5-a]pyridine-3-carboxamide,
N—(N-ethyl-N-methylsulfamoyl)-5-((R)-2-(3-fluoro-5-(((S)-tetrahydrofuran-3-yl)oxy) phenyl)pyrrolidin-1-yl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide,
N—(N-ethyl-N-methylsulfamoyl)-5-((R)-2-(3-fluoro-5-(((R)-tetrahydrofuran-3-yl)oxy)phenyl)pyrrolidin-1-yl) pyrazolo[1,5-a]pyridine-3-carboxamide,
4-fluoro-5-((2R,4S)-4-fluoro-2-(3-fluorophenyl)pyrrolidin-1-yl)-N-sulfamoylpyrazolo[1,5-a]pyridine-3-carboxamide,
N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I),
(R)-5-(2-(2,5-difluorophenyl)pyrrolidin-1-yl)-N—(N-isobutyl-N-methylsulfamoyl)pyrazolo[1,5-a] pyridine-3-carboxamide,
(R)—N—(N-ethyl-N-methylsulfamoyl)-4-fluoro-5-(2-(3-fluorophenyl) pyrrolidin-1-yl) pyrazolo[1,5-a]pyridine-3-carboxamide,
(R)—N—(N,N-dimethylsulfamoyl)-4-fluoro-5-(2-(3-fluorophenyl)pyrrolidin-1-yl)pyrazolo[1,5-a] pyridine-3-carboxamide,
(R)—N—(N,N-dimethylsulfamoyl)-4-fluoro-5-(2-(3-fluorophenyl)pyrrolidin-1-yl)pyrazolo[1,5-a] pyridine-3-carboxamide,
(R)—N—(N-ethyl-N-methylsulfamoyl)-4-fluoro-5-(2-(5-fluoro-2-((tetrahydro-2H-pyran-4-yl)oxy)phenyl) pyrrolidin-1-yl)pyrazolo[1,5-a]pyridine-3-carboxamide,
5-((2R)-2-(3-((2, 2-difluorocyclopropyl)methoxy)-5-fluorophenyl)pyrrolidin-1-yl)-N—(N-ethyl-N-methylsulfamoyl)pyrazolo[1,5-a] pyridine-3-carboxamide,
(R)—N—(N,N-bis(cyclopropylmethyl)sulfamoyl)-5-(2-(2,5-difluorophenyl)pyrrolidin-1-yl)pyrazolo[1,5-a] pyridine-3-carboxamide,
N—(N-ethyl-N-methylsulfamoyl)-5-((2R)-2-(5-fluoro-2-((tetrahydrofuran-3-yl)oxy)phenyl)pyrrolidin-1-yl) pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, Sodium(R)-(N,N-dimethylsulfamoyl)(4-fluoro-5-(2-(3-fluorophenyl)pyrrolidin-1-yl)pyrazolo[1,5-a]pyridine-3-carbonyl)amide, Sodium(N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl)(N,N-dimethylsulfamoyl)amide;

N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), or N—(N,N-dimethylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-2);

or a pharmaceutically acceptable salt thereof, a pharmaceutically acceptable solvate thereof or a stereoisomer thereof.

7. The method of claim 1, wherein the compound of formula (I) is (R)-5-(2-(2,5-difluorophenyl)pyrrolidin-1-yl)-N—(N-(2-methoxyethyl)-N-methylsulfamoyl)pyrazolo[1,5-a]pyridine-3-carboxamide (R)—N—(N-cyclopropyl-N-methylsulfamoyl)-5-(2-(2,5-difluorophenyl)pyrrolidin-1-yl)pyrazolo[1,5-a]pyridine-3-carboxamide

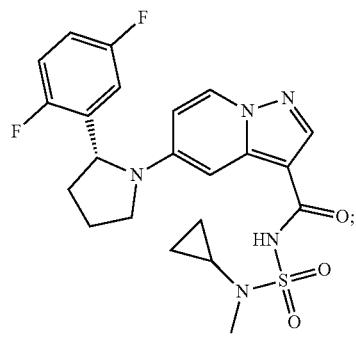 [SMILES: CN(C1CC1)S(=O)(=O)NC(=O)c1cnn2ccc(N3CCC[C@@H]3c3cc(F)ccc3F)cc12]

(R)—N—(N-ethyl-N-methylsulfamoyl)-5-(2-(5-fluoro-2-methylphenyl)pyrrolidin-1-yl)pyrazolo[1,5-a]pyridine-3-carboxamide

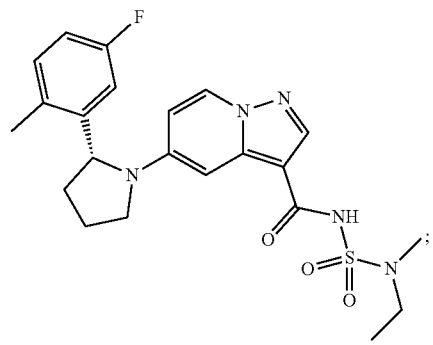

(R)—N—(N-ethyl-N-methylsulfamoyl)-5-(2-(7-fluoro-2,3-dihydrobenzo[b][1,4]dioxin-5-yl)pyrrolidin-1-yl) pyrazolo[1,5-a]pyridine-3-carboxamide

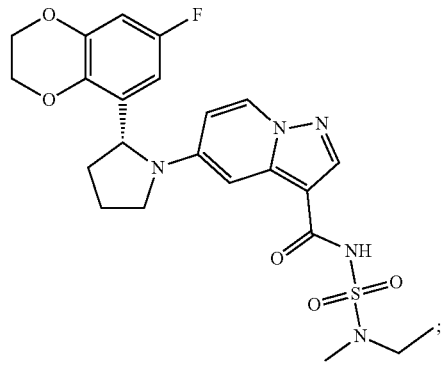 [SMILES: CCN(C)S(=O)(=O)NC(=O)c1cnn2ccc(N3CCC[C@@H]3c3cc(F)cc4c3OCCO4)cc12]

N-(tert-butylsulfonyl)-5-((2R,4S)-4-fluoro-2-(3-fluoro-5-((tetrahydro-2H-pyran-4-yl) oxy)phenyl)pyrrolidin-1-yl)pyrazolo[1,5-a]pyridine-3-carboxamide

187

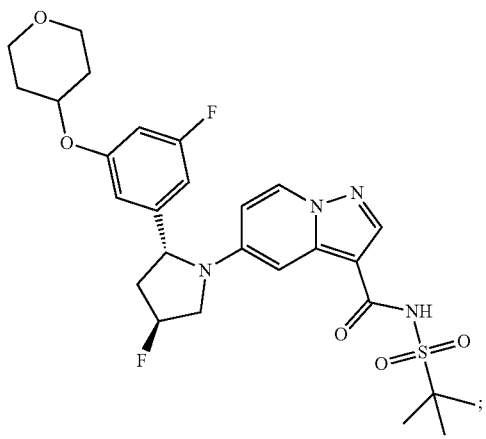 [SMILES: CC(C)(C)S(=O)(=O)NC(=O)c1cnn2ccc(N3C[C@@H](F)C[C@@H]3c3cc(F)cc(OC4CCOCC4)c3)cc12]

N—(N-ethyl-N-methylsulfamoyl)-5-((2R,4S)-4-fluoro-2-(3-fluoro-5-((tetrahydro-2H-pyran-4-yl)oxy)phenyl)pyrrolidin-1-yl)pyrazolo[1,5-a]pyridine-3-carboxamide

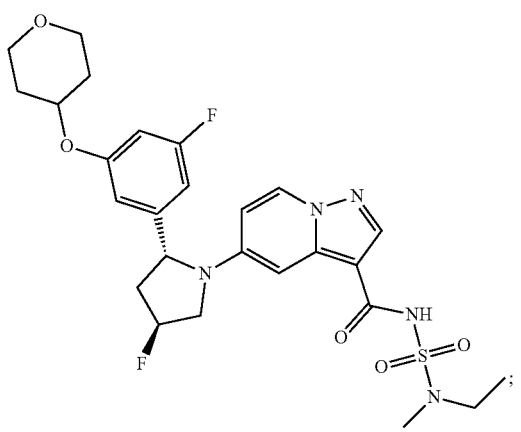 [SMILES: CCN(C)S(=O)(=O)NC(=O)c1cnn2ccc(N3C[C@@H](F)C[C@@H]3c3cc(F)cc(OC4CCOCC4)c3)cc12]

N-(tert-butylsulfonyl)-5-((2R,4S)-4-fluoro-2-(5-fluoro-2-((tetrahydro-2H-pyran-4-yl) oxy)phenyl)pyrrolidin-1-yl)pyrazolo[1,5-a]pyridine-3-carboxamide

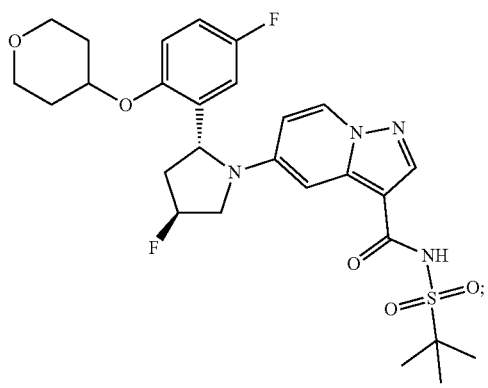 [SMILES: CC(C)(C)S(=O)(=O)NC(=O)c1cnn2ccc(N3C[C@@H](F)C[C@@H]3c3cc(F)ccc3OC3CCOCC3)cc12]

N—(N-ethyl-N-methylsulfamoyl)-5-((2R,4S)-4-fluoro-2-(5-fluoro-2-((tetrahydro-2H-pyran-4-yl)oxy)phenyl)pyrrolidin-1-yl)pyrazolo[1,5-a]pyridine-3-carboxamide

188

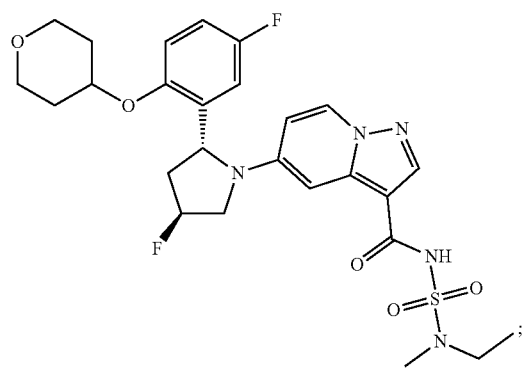 [SMILES: CCN(C)S(=O)(=O)NC(=O)c1cnn2ccc(N3C[C@@H](F)C[C@@H]3c3cc(F)ccc3OC3CCOCC3)cc12]

5-((2R,4S)-4-fluoro-2-(5-fluoro-2-((tetrahydro-2H-pyran-4-yl)oxy)phenyl)pyrrolidin-1-yl)-N-(isopropylsulfonyl)pyrazolo[1,5-a]pyridine-3-carboxamide

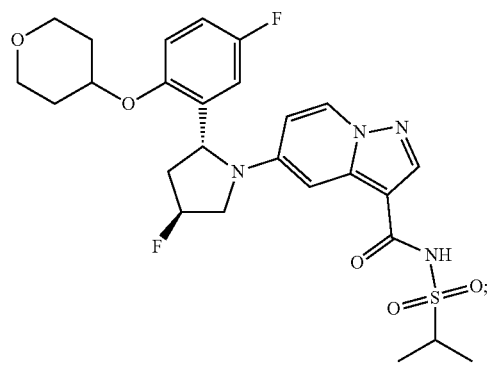 [SMILES: CC(C)S(=O)(=O)NC(=O)c1cnn2ccc(N3C[C@@H](F)C[C@@H]3c3cc(F)ccc3OC3CCOCC3)cc12]

5-((2R,4S)-2-(2-(cyclopropylmethoxy)-5-fluorophenyl)-4-fluoropyrrolidin-1-yl)-N—(N-ethyl-N-methylsulfamoyl)pyrazolo[1,5-a]pyridine-3-carboxamide

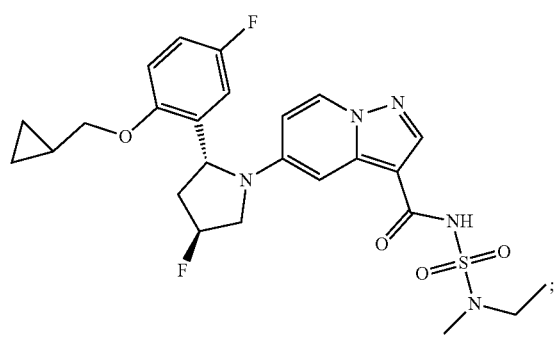 [SMILES: CCN(C)S(=O)(=O)NC(=O)c1cnn2ccc(N3C[C@@H](F)C[C@@H]3c3cc(F)ccc3OCC3CC3)cc12]

N-(tert-butylsulfonyl)-5-((2R,4S)-4-fluoro-2-(5-fluoro-2-((tetrahydrofuran-3-yl)oxy)phenyl)pyrrolidin-1-yl)pyrazolo[1,5-a] pyridine-3-carboxamide

189

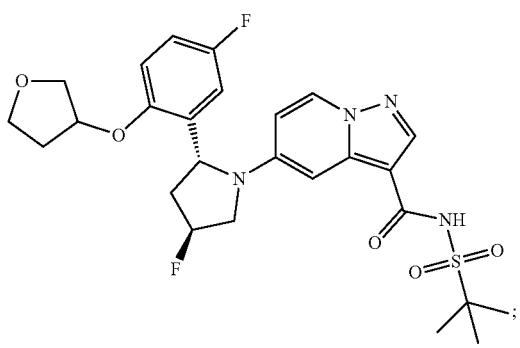 [SMILES: CC(C)(C)S(=O)(=O)NC(=O)c1cnn2ccc(N3C[C@@H](F)C[C@@H]3c3cc(F)ccc3OC3CCOC3)cc12]

N—(N-ethyl-N-methylsulfamoyl)-5-((2R,4S)-4-fluoro-2-(5-fluoro-2-((tetrahydrofuran-3-yl)oxy)phenyl)pyrrolidin-1-yl)pyrazolo[1,5-a] pyridine-3-carboxamide

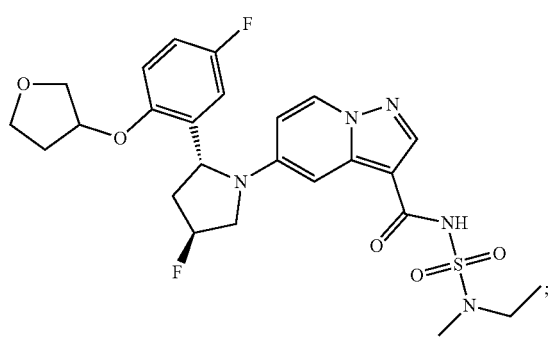 [SMILES: CCN(C)S(=O)(=O)NC(=O)c1cnn2ccc(N3C[C@@H](F)C[C@@H]3c3cc(F)ccc3OC3CCOC3)cc12]

5-((2R,4S)-2-(2-(cyclopropylmethoxy)-5-fluorophenyl)-4-fluoropyrrolidin-1-yl)-N—(N-ethyl-N-methylsulfamoyl)-4-fluoropyrazolo[1,5-a]pyridine-3-carboxamide

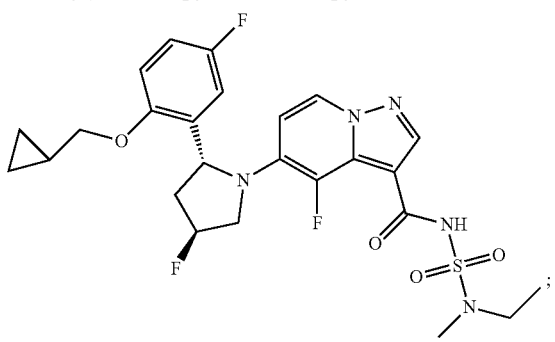 [SMILES: CCN(C)S(=O)(=O)NC(=O)c1cnn2ccc(N3C[C@@H](F)C[C@@H]3c3cc(F)ccc3OCC3CC3)c(F)c12]

N-(tert-butylsulfonyl)-5-((2R,4S)-2-(2-(cyclopropylmethoxy)-5-fluorophenyl)-4-fluoropyrrolidin-1-yl)pyrazolo[1,5-a]pyridine-3-carboxamide

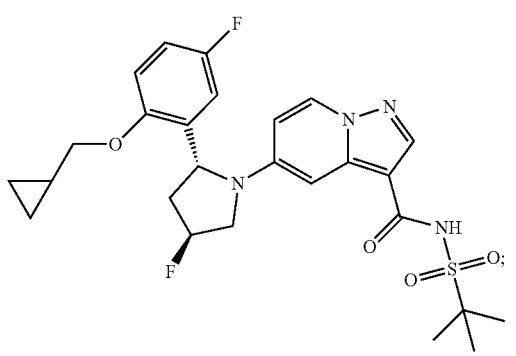 [SMILES: CC(C)(C)S(=O)(=O)NC(=O)c1cnn2ccc(N3C[C@@H](F)C[C@@H]3c3cc(F)ccc3OCC3CC3)cc12]

190

(R)-5-(2-(2,5-difluorophenyl)pyrrolidin-1-yl)-N—(N-ethylsulfamoyl)pyrazolo[1,5-a]pyridine-3-carboxamide

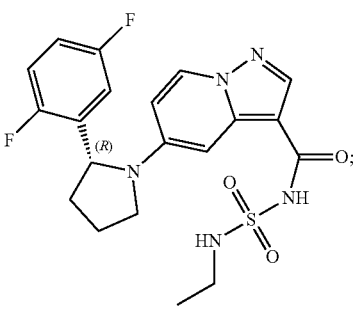

(R)-5-(2-(2,5-difluorophenyl)pyrrolidin-1-yl)-N—(N-methylsulfamoyl)pyrazolo[1,5-a]pyridine-3-carboxamide

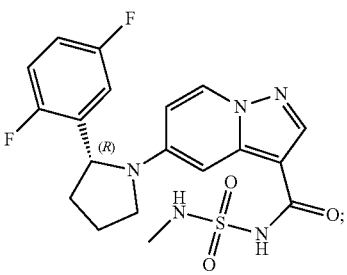

(R)-5-(2-(2,5-difluorophenyl)pyrrolidin-1-yl)-N—(N-(2-fluoroethyl)-N-methylsulfamoyl)pyrazolo[1,5-a]pyridine-3-carboxamide

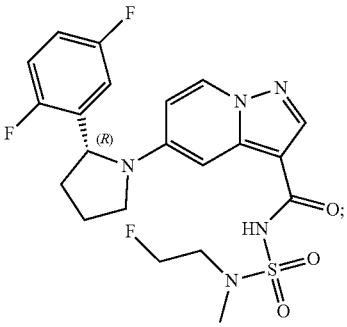

(R)-5-(2-(2,5-difluorophenyl)pyrrolidin-1-yl)-N—(N-(2-hydroxyethyl)-N-methylsulfamoyl)pyrazolo[1,5-a] pyridine-3-carboxamide

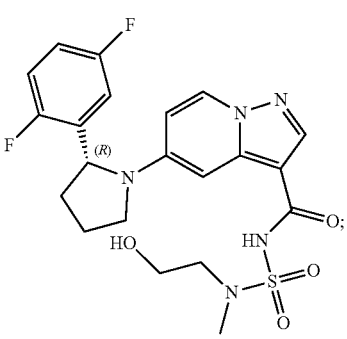

191

(R)—N-(azetidin-1-ylsulfonyl)-5-(2-(2,5-difluorophenyl)pyrrolidin-1-yl)pyrazolo[1,5-a]pyridine-3-carboxamide

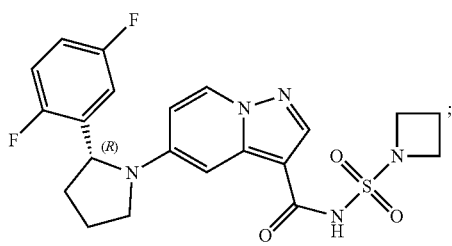

N-(tert-butylsulfonyl)-5-((2R,4S)-4-fluoro-2-(7-fluoro-2,3-dihydrobenzo[b][1,4]dioxin-5-yl)pyrrolidin-1-yl)pyrazolo[1,5-a]pyridine-3-carboxamide

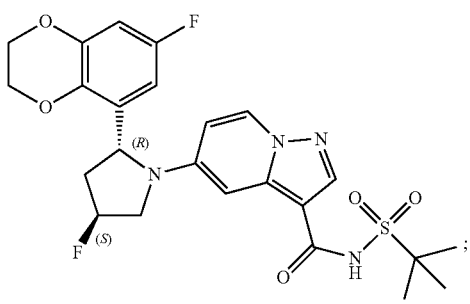

(R)—N—(N-(2-cyanoethyl)-N-methylsulfamoyl)-5-(2-(2,5-difluorophenyl)pyrrolidin-1-yl)pyrazolo[1,5-a]pyridine-3-carboxamide

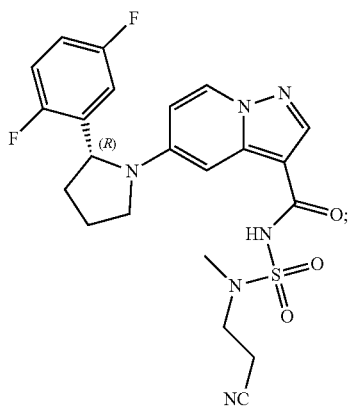

N-(tert-butylsulfonyl)-4-fluoro-5-((2R,4S)-4-fluoro-2-(7-fluoro-2,3-dihydrobenzo[b][1,4]dioxin-5-yl)pyrrolidin-1-yl)pyrazolo[1,5-a]pyridine-3-carboxamide

192

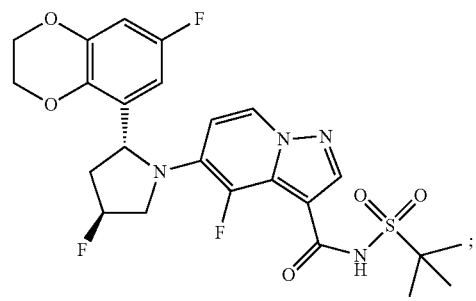 [SMILES: CC(C)(C)S(=O)(=O)NC(=O)c1cnn2ccc(N3C[C@@H](F)C[C@@H]3c3cc(F)cc4c3OCCO4)c(F)c12]

N—(N,N-dimethylsulfamoyl)-4-fluoro-5-((2R,4S)-4-fluoro-2-(3-fluorophenyl)pyrrolidin-1-yl)pyrazolo[1,5-a]pyridine-3-carboxamide

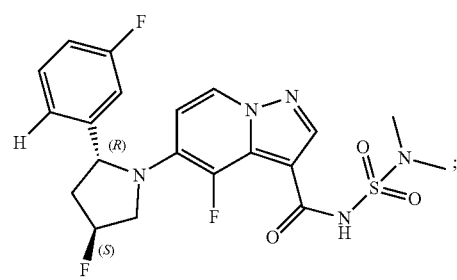

N—(N-ethyl-N-methylsulfamoyl)-5-((2R)-2-(7-fluoro-3-(fluoromethyl)-2,3-dihydrobenzo[b][1,4]dioxin-5-yl)pyrrolidin-1-yl)pyrazolo[1,5-a]pyridine-3-carboxamide

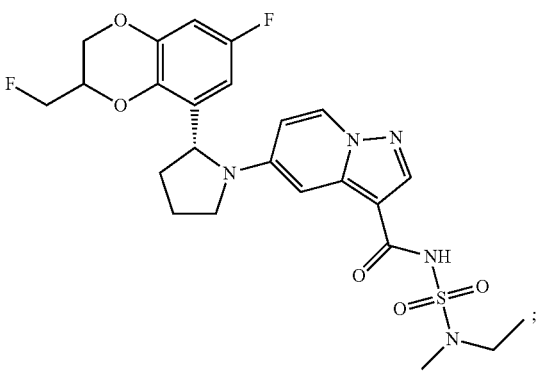 [SMILES: CCN(C)S(=O)(=O)NC(=O)c1cnn2ccc(N3CCC[C@@H]3c3cc(F)cc4c3OC(CF)CO4)cc12]

(R)—N—(N-ethyl-N-methylsulfamoyl)-5-(2-(3-fluorophenyl)pyrrolidin-1-yl)pyrazolo[1,5-a]pyridine-3-carboxamide

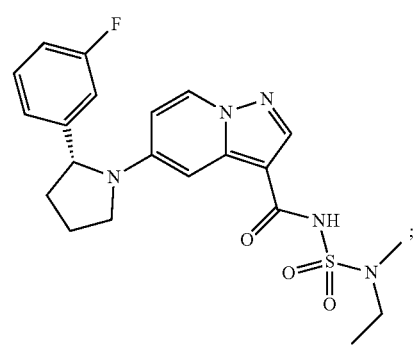 [SMILES: CCN(C)S(=O)(=O)NC(=O)c1cnn2ccc(N3CCC[C@@H]3c3cccc(F)c3)cc12]

5-((2R,4S)-4-fluoro-2-(3-fluoro-5-((tetrahydro-2H-pyran-4-yl)oxy)phenyl) pyrrolidin-yl)-N-(isopropylsulfonyl)pyrazolo[1,5-a]pyridine-3-carboxamide

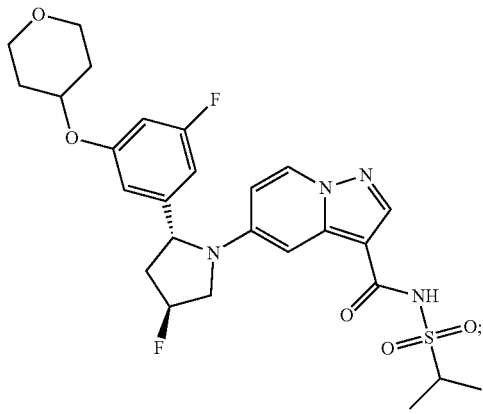 [SMILES: CC(C)S(=O)(=O)NC(=O)c1cnn2ccc(N3C[C@@H](F)C[C@@H]3c3cc(F)cc(OC4CCOCC4)c3)cc12]

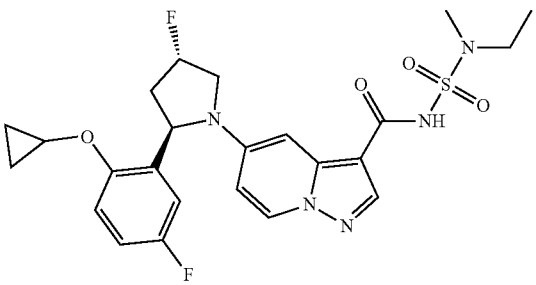

N—(N-ethyl-N-methylsulfamoyl)-4-fluoro-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide 5-((2R,4S)-2-(3-(cyclopropylmethoxy)-5-fluorophenyl)-4-fluoropyrrolidin-1-yl)-N—(N-ethyl-N-methylsulfamoyl)pyrazolo[1,5-a]pyridine-3-carboxamide

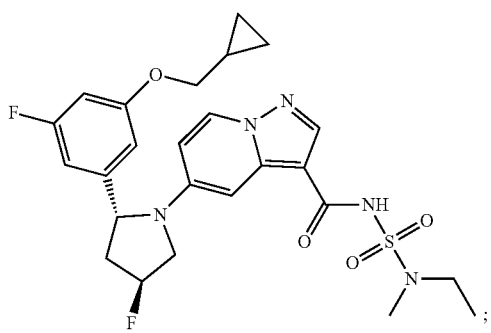 [SMILES: CCN(C)S(=O)(=O)NC(=O)c1cnn2ccc(N3C[C@@H](F)C[C@@H]3c3cc(F)cc(OCC4CC4)c3)cc12]

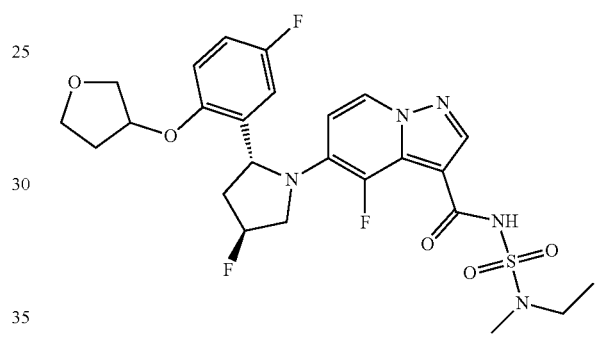

5-((2R,4S)-2-(2-cyclopropoxy-5-fluorophenyl)-4-fluoropyrrolidin-1-yl)-N—(N-ethyl-N-methyl sulfamoyl)-4-fluoropyrazolo[1,5-a]pyridine-3-carboxamide N-(tert-butylsulfonyl)-5-((2R,4S)-2-(2-cyclopropoxy-5-fluorophenyl)-4-fluoropyrrolidin-1-yl) pyrazolo[1,5-a]pyridine-3-carboxamide

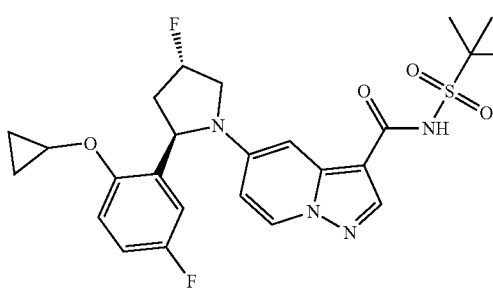

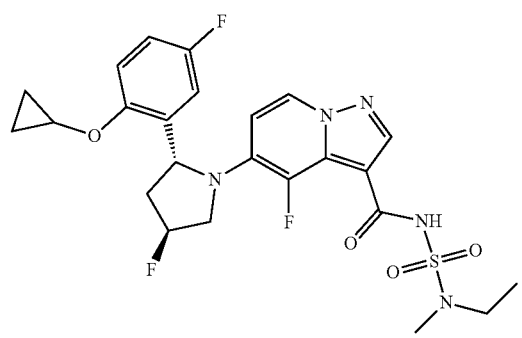

5-((2R,4S)-2-(2-cyclopropoxy-5-fluorophenyl)-4-fluoropyrrolidin-1-yl)-N—(N-ethyl-N-methylsulfamoyl) pyrazolo[1,5-a]pyridine-3-carboxamide (R)—N—(N-ethyl-N-methylsulfamoyl)-5-(2-(8-fluoro-2,3-dihydrobenzo[b][1,4]dioxin-6-yl)pyrrolidin-1-yl) pyrazolo[1,5-a] pyridine-3-carboxamide

195

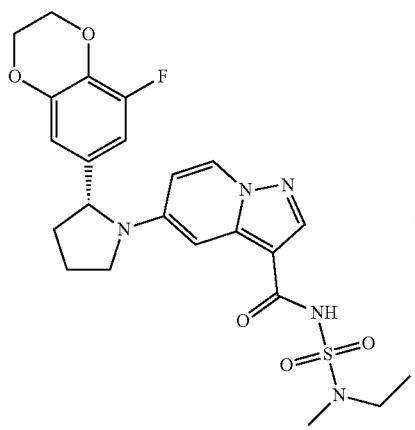

(R)-5-(2-(8-fluoro-2,3-dihydrobenzo[b][1,4]dioxin-6-yl)
pyrrolidin-1-yl)-N-(isopropylsulfonyl)pyrazolo[1,5-a]
pyridine-3-carboxamide

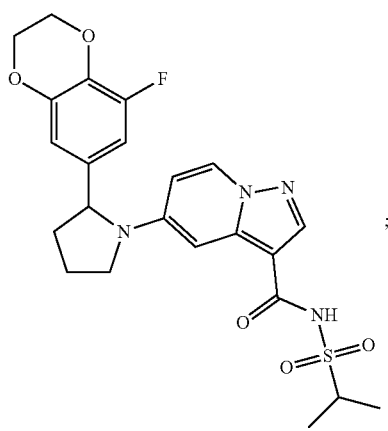 [SMILES: CC(C)S(=O)(=O)NC(=O)c1cnn2ccc(N3CCCC3c3cc(F)c4c(c3)OCCO4)cc12]

N-(tert-butylsulfonyl)-5-(2-(8-fluoro-2,3-dihydrobenzo
[b][1,4]dioxin-6-yl)pyrrolidin-1-yl)pyrazolo[1,5-a]
pyridine-3-carboxamide

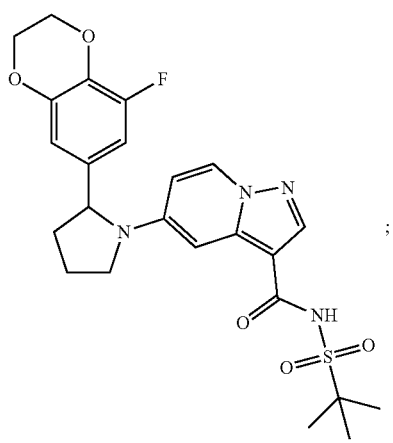 [SMILES: CC(C)(C)S(=O)(=O)NC(=O)c1cnn2ccc(N3CCCC3c3cc(F)c4c(c3)OCCO4)cc12]

N—(N-ethyl-N-methylsulfamoyl)-5-(2-(9-fluoro-3,4-dihydro-2H-benzo[b][1,4]dioxepin-7-yl)pyrrolidin-1-yl)
pyrazolo[1,5-a]pyridine-3-carboxamide

196

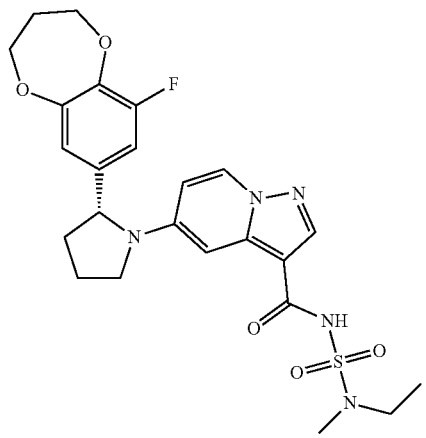

N—(N,N-dimethylsulfamoyl)-5-(2-(8-fluoro-2,3-dihydrobenzo[b][1,4]dioxin-6-yl)pyrrolidin-1-yl)pyrazolo[1,5-a]pyridine-3-carboxamide

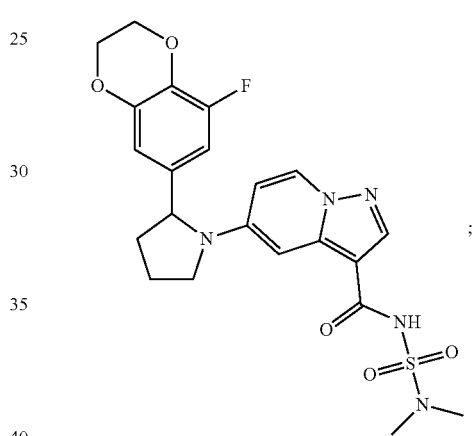

(R)—N—(N,N-dimethylsulfamoyl)-5-(2-(9-fluoro-3,4-dihydro-2H-benzo[b][1,4]dioxepin-7-yl)pyrrolidin-1-yl)pyrazolo[1,5-a]pyridine-3-carboxamide

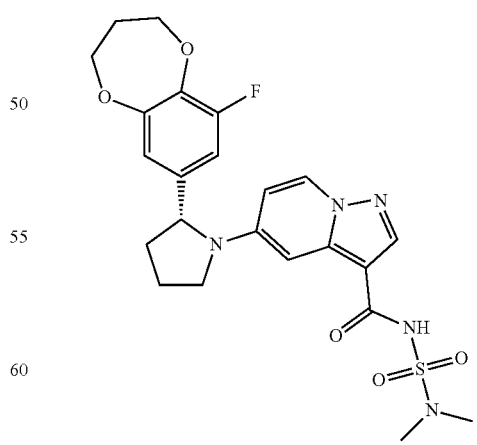

N-(tert-butylsulfonyl)-5-((2R,4S)-4-fluoro-2-(6-fluorobenzo[d][1,3]dioxol-4-yl)pyrrolidin-1-yl)pyrazolo[1,5-a]pyridine-3-carboxamide

197

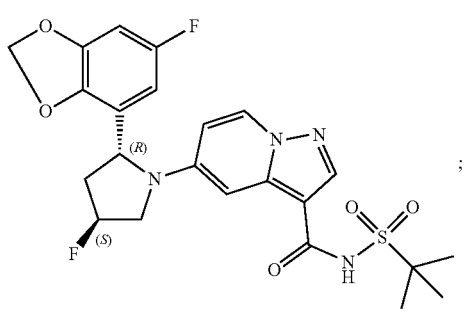

N—(N-ethyl-N-methylsulfamoyl)-5-((2R,4S)-4-fluoro-
2-(6-fluorobenzo[d][1,3]dioxol-4-yl)pyrrolidin-1-yl)
pyrazolo[1,5-a]pyridine-3-carboxamide

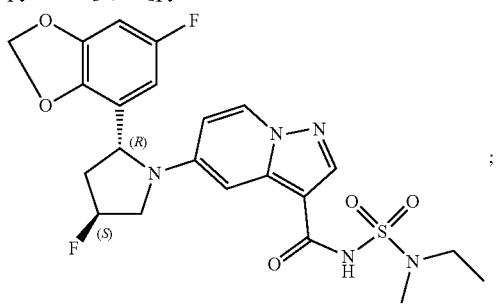

(R)-5-(2-(2,5-difluorophenyl)pyrrolidin-1-yl)-N—(N-
((1-(hydroxymethyl)cyclobutyl)methyl)-N-methylsul-
famoyl)pyrazolo[1,5-a]pyridine-3-carboxamide

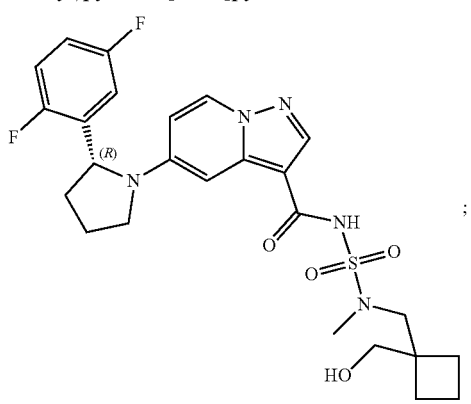

(R)—N—(N-ethyl-N-methylsulfamoyl)-5-(2-(5-fluoro-
2-((4-methyltetrahydro-2H-pyran-4-yl)oxy)phenyl)
pyrrolidin-1-yl)pyrazolo[1,5-a]pyridine-3-carboxam-
ide

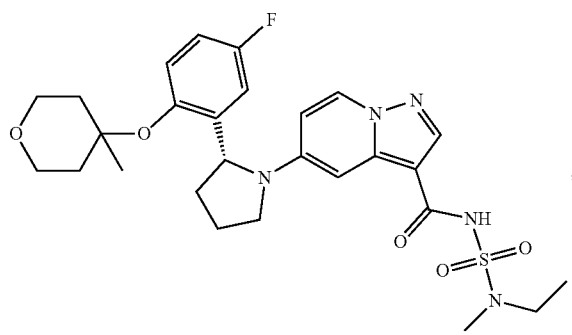

198

(R)—N-(tert-butylsulfonyl)-5-(2-(5-fluoro-2-((4-methyl-
tetrahydro-2H-pyran-4-yl)oxy)phenyl) pyrrolidin-1-yl)
pyrazolo[1,5-a]pyridine-3-carboxamide;

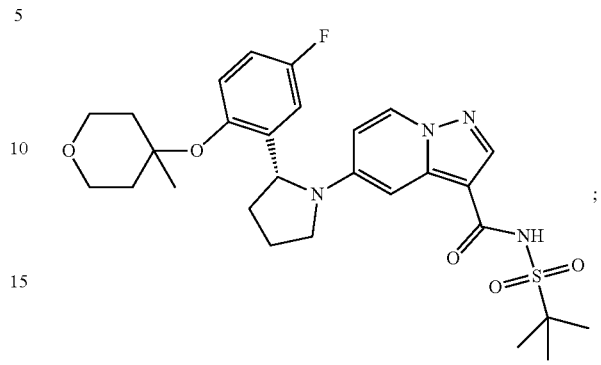

(R)-5-(2-(5-fluoro-2-((4-methyltetrahydro-2H-pyran-4-
yl)oxy)phenyl)pyrrolidin-1-yl)-N-(isopropylsulfonyl)
pyrazolo[1,5-a]pyridine-3-carboxamide

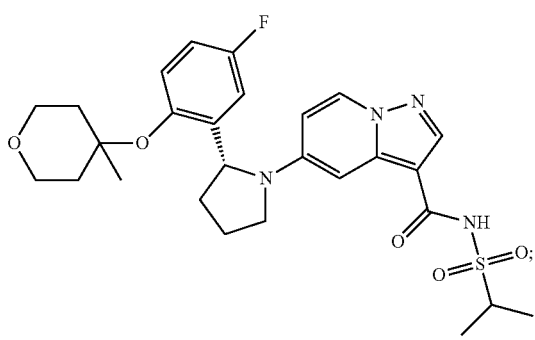 [SMILES: CC(C)S(=O)(=O)NC(=O)c1cnn2ccc(N3CCC[C@@H]3c3cc(F)ccc3OC3(C)CCOCC3)cc12]

N-(tert-butylsulfonyl)-4-fluoro-5-((2R,4S)-(6-fluo-
robenzo[d][1,3]dioxol-4-yl)pyrrolidin-1-yl)pyrazolo[1,
5-a]pyridine-3-carboxamide

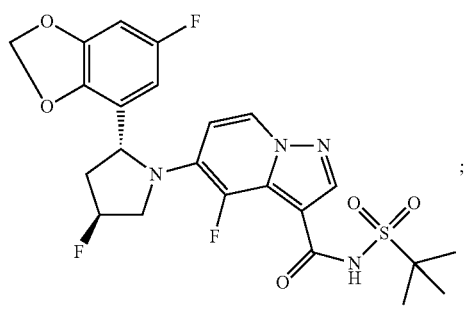 [SMILES: CC(C)(C)S(=O)(=O)NC(=O)c1cnn2ccc(N3C[C@@H](F)C[C@@H]3c3cc(F)cc4c3OCO4)c(F)c12]

N-(tert-butylsulfonyl)-5-((2R,4S)-4-fluoro-2-(6-fluo-
robenzo[d][1,3]dioxol-4-yl)pyrrolidin-1-yl)pyrazolo[1,
5-a]pyridine-3-carboxamide

199

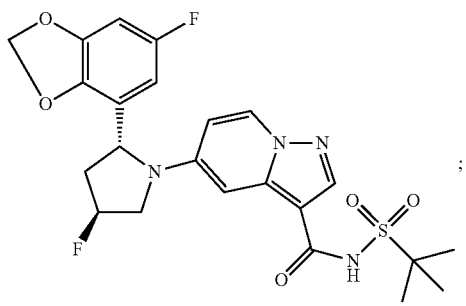 [SMILES: CC(C)(C)S(=O)(=O)NC(=O)c1cnn2ccc(N3C[C@@H](F)C[C@@H]3c3cc(F)cc4c3OCO4)cc12]

N—(N-ethyl-N-methylsulfamoyl)-5-((2R,4S)-4-fluoro-2-(6-fluorobenzo[d][1,3]dioxol-4-yl) pyrrolidin-1-yl)pyrazolo[1,5-a]pyridine-3-carboxamide H

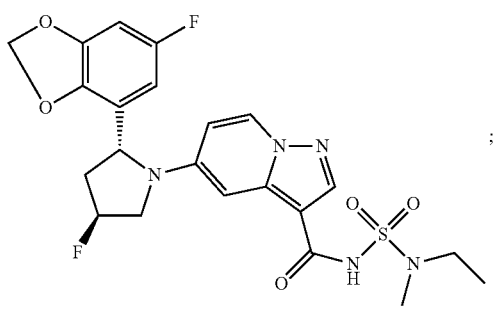 [SMILES: CCN(C)S(=O)(=O)NC(=O)c1cnn2ccc(N3C[C@@H](F)C[C@@H]3c3cc(F)cc4c3OCO4)cc12]

N-(azetidin-1-ylsulfonyl)-4-fluoro-5-((2R,4S)-4-fluoro-2-(3-fluorophenyl)pyrrolidin-1-yl)pyrazolo[1,5-a]pyridine-3-carboxamide

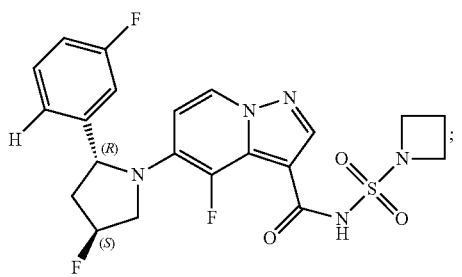

4-fluoro-5-((2R,4S)-4-fluoro-2-(3-fluorophenyl)pyrrolidin-1-yl)-N—(N-isobutyl-N-methylsulfamoyl)pyrazolo[1,5-a] pyridine-3-carboxamide

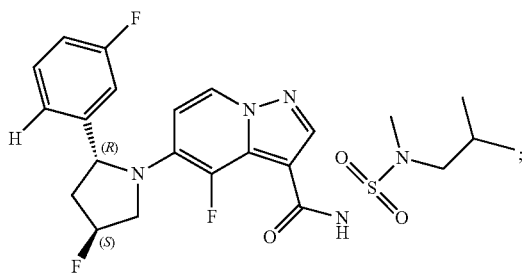

N-(tert-butylsulfonyl)-5-((2R,4S)-2-(2,5-difluorophenyl)-4-fluoropyrrolidin-1-yl)-4-fluoropyrazolo[1,5-a]pyridine-3-carboxamide

200

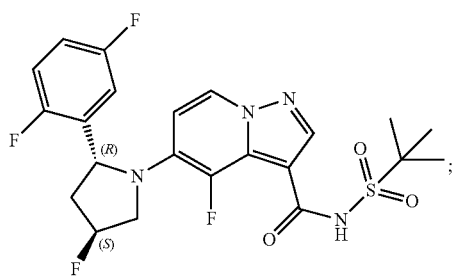

5-((2R,4S)-2-(2,5-difluorophenyl)-4-fluoropyrrolidin-1-yl)-4-fluoro-N-(isopropylsulfonyl) pyrazolo[1,5-a]pyridine-3-carboxamide

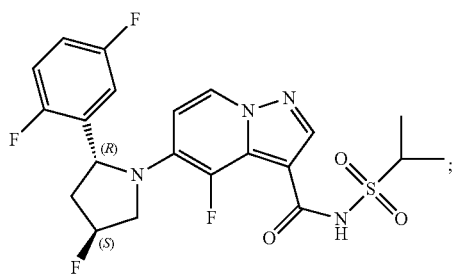

5-((2R,4S)-2-(2,5-difluorophenyl)-4-fluoropyrrolidin-1-yl)-N—(N-ethyl-N-methylsulfamoyl)-4-fluoropyrazolo[1,5-a]pyridine-3-carboxamide

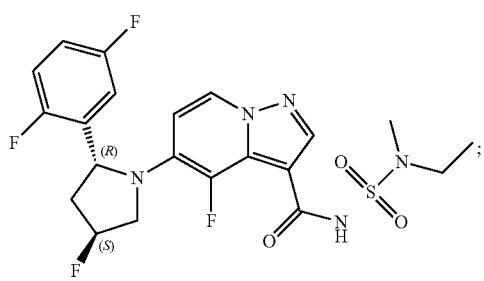

5-((2R,4S)-2-(2,5-difluorophenyl)-4-fluoropyrrolidin-1-yl)-N—(N,N-dimethylsulfamoyl)-4-fluoropyrazolo[1,5-a]pyridine-3-carboxamide

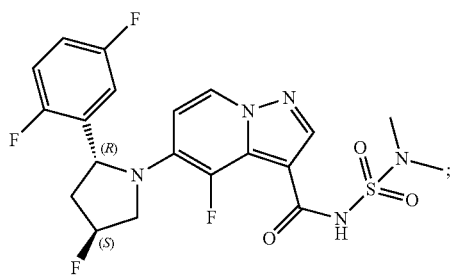

N-(azetidin-1-ylsulfonyl)-5-((2R,4S)-2-(2,5-difluorophenyl)-4-fluoropyrrolidin-1-yl)-4-fluoro pyrazolo[1,5-a]pyridine-3-carboxamide

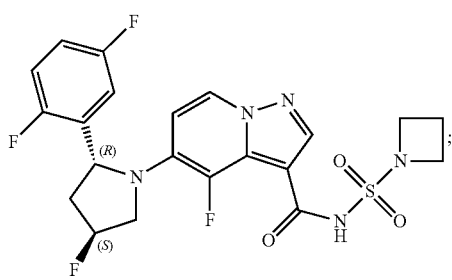

5-((2R,4S)-2-(2,5-difluorophenyl)-4-fluoropyrrolidin-1-yl)-4-fluoro-N—(N-isobutyl-N-methylsulfamoyl)pyrazolo[1,5-a]pyridine-3-carboxamide

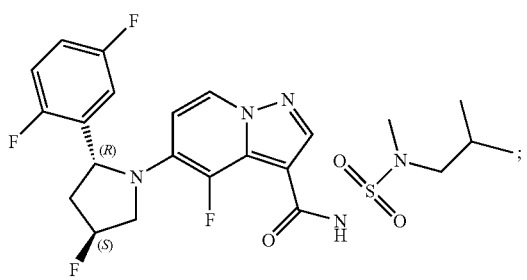

5-((2R,4S)-2-(2,5-difluorophenyl)-4-fluoropyrrolidin-1-yl)-4-fluoro-N-sulfamoyl pyrazolo[1,5-a]pyridine-3-carboxamide

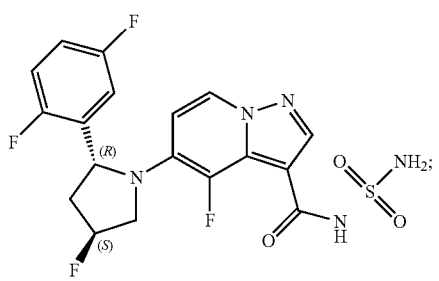

or a pharmaceutically acceptable salt thereof, a pharmaceutically acceptable solvate thereof or a stereoisomer thereof.

8. The method of claim 1, wherein the compound of formula (I) is

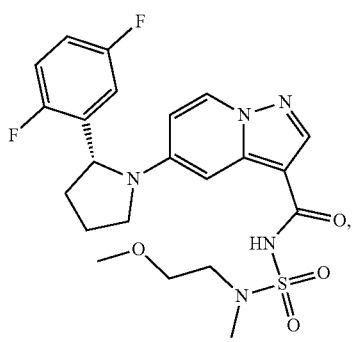

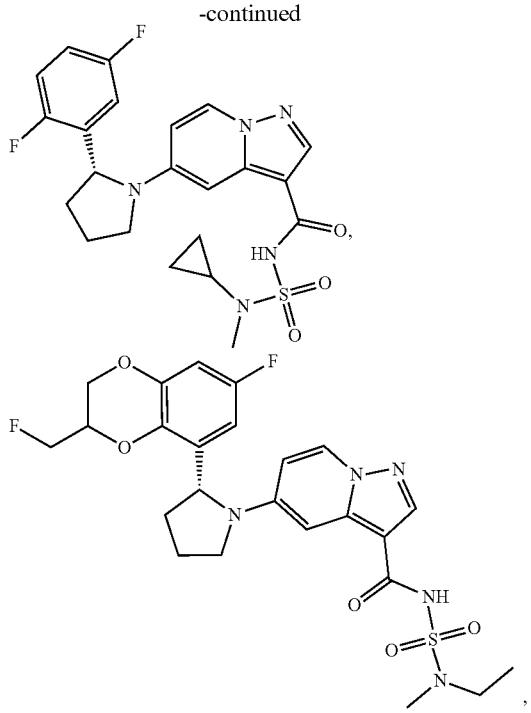

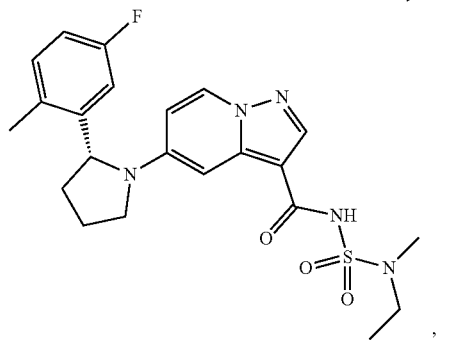

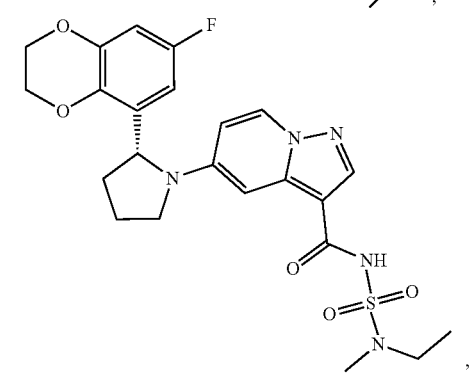

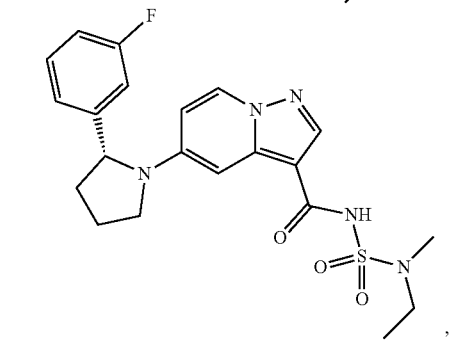

203
-continued
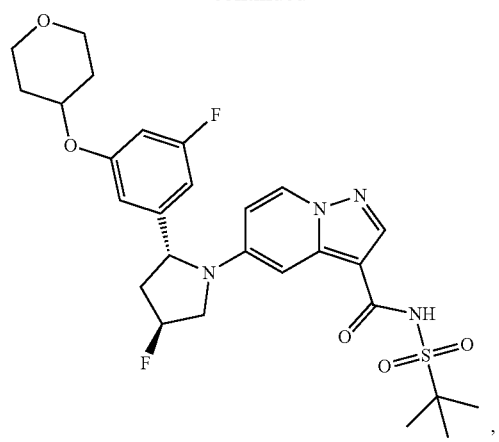
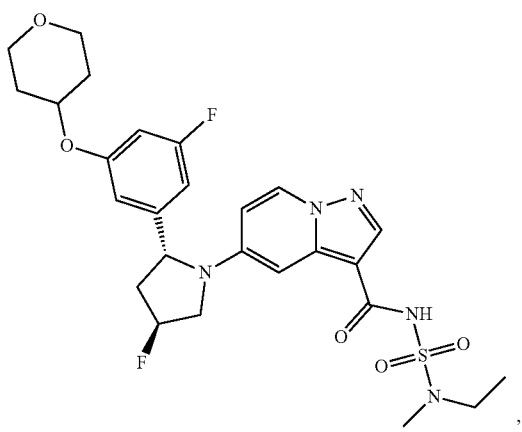
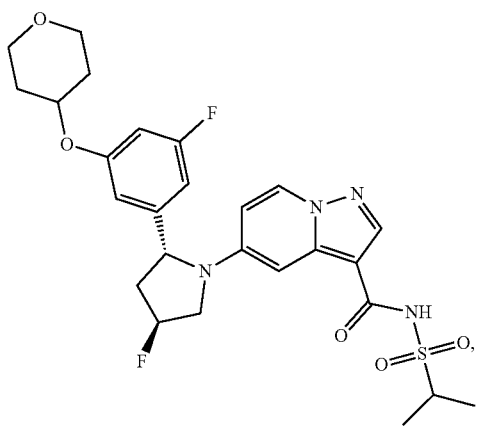
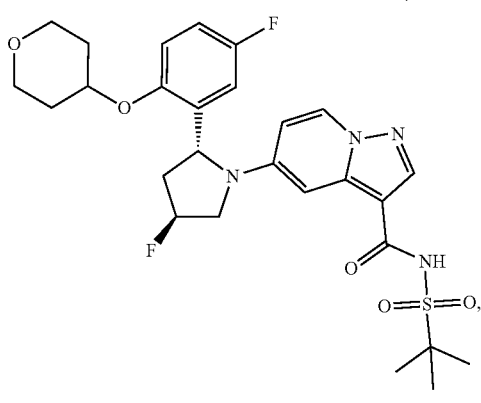
204
-continued
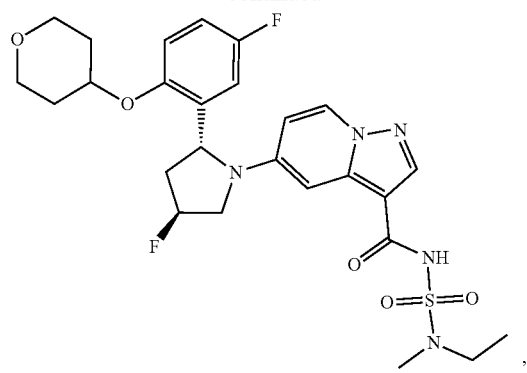
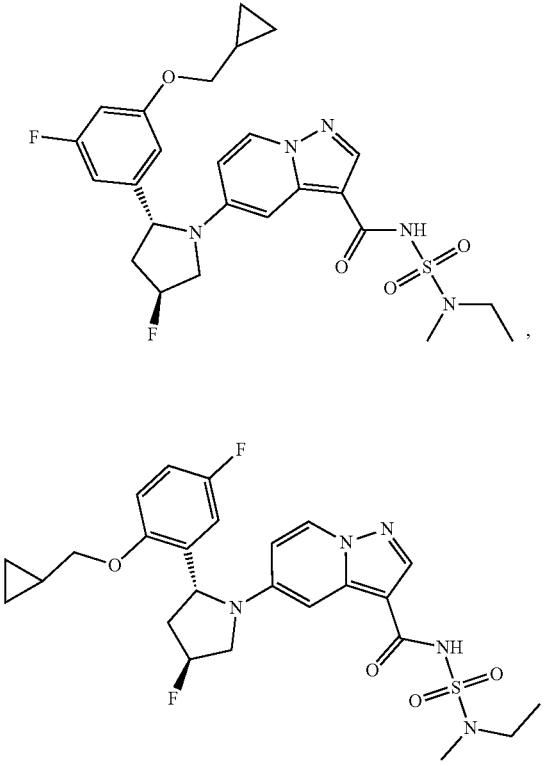

205
-continued
206
-continued
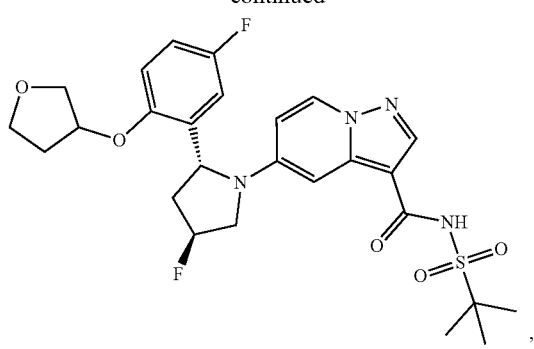
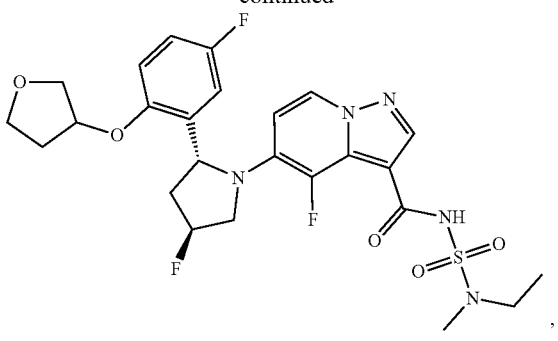
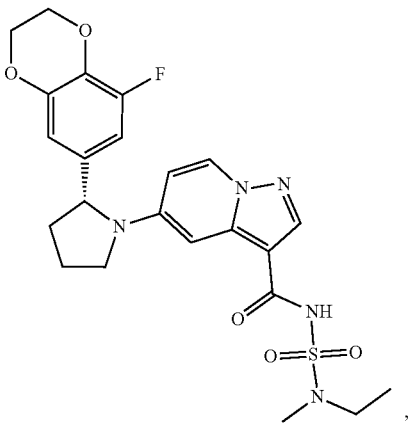

207
-continued
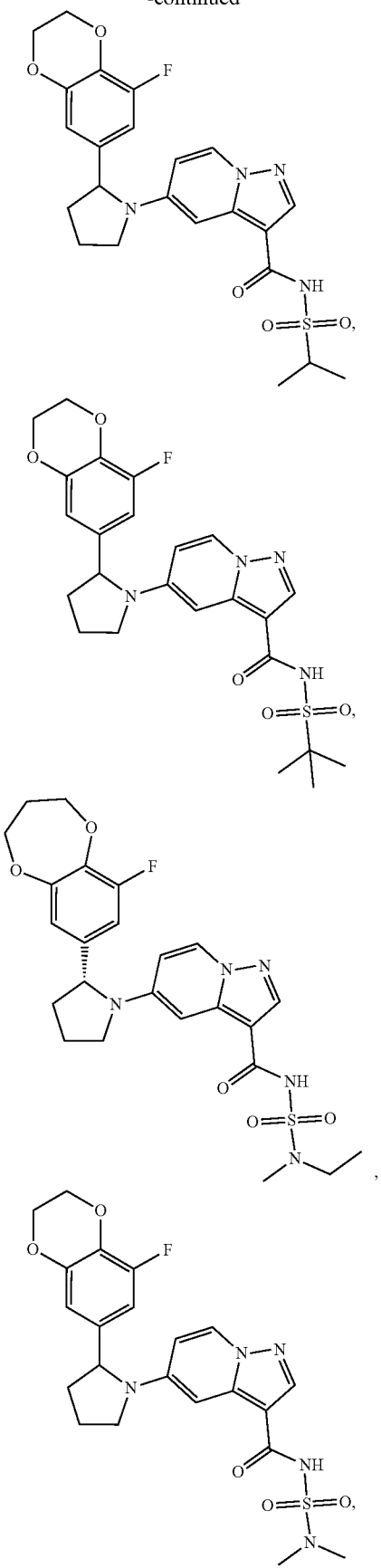
208
-continued
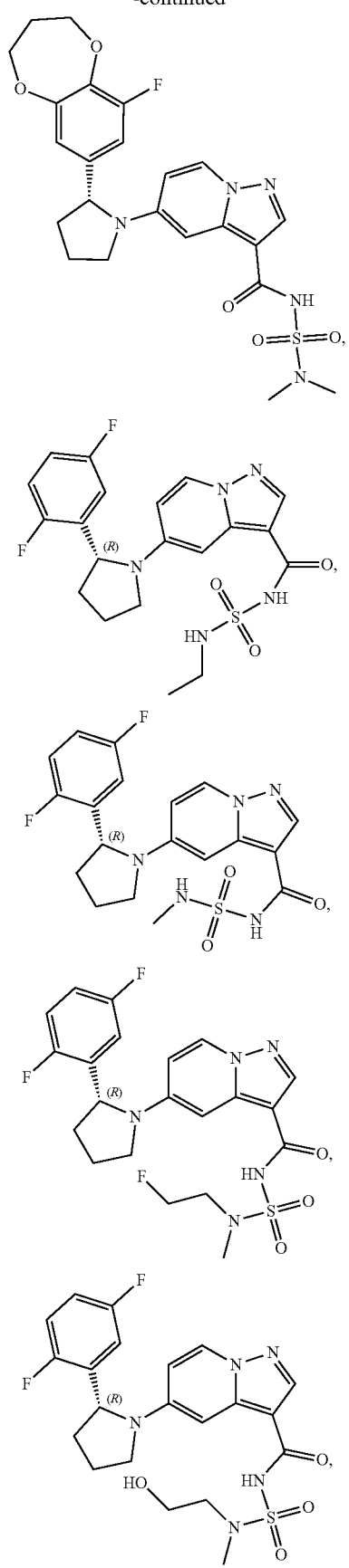

209
-continued
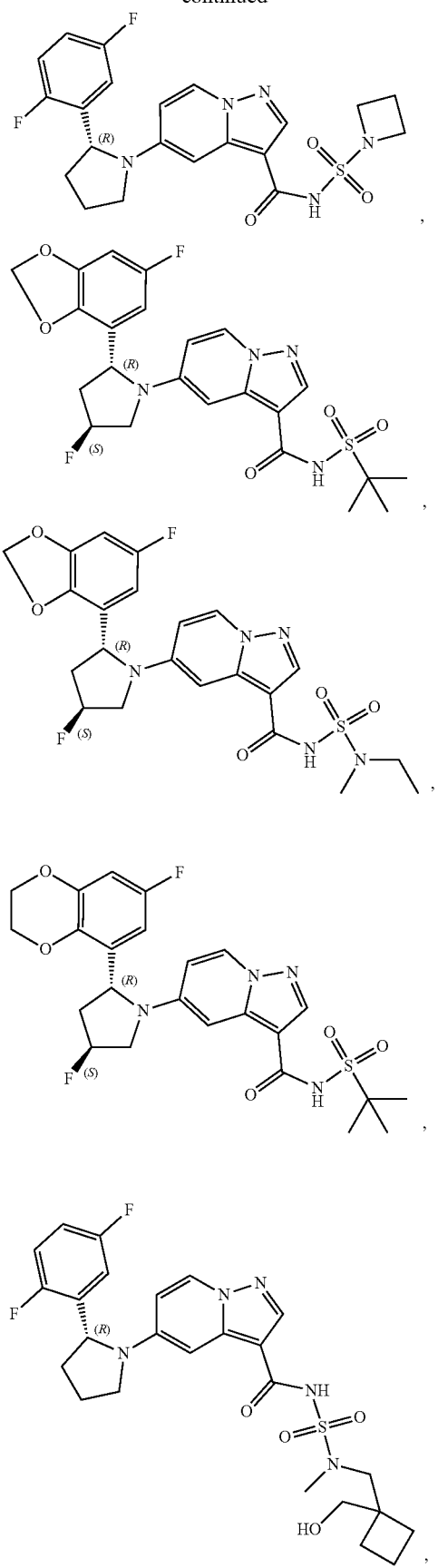
210
-continued
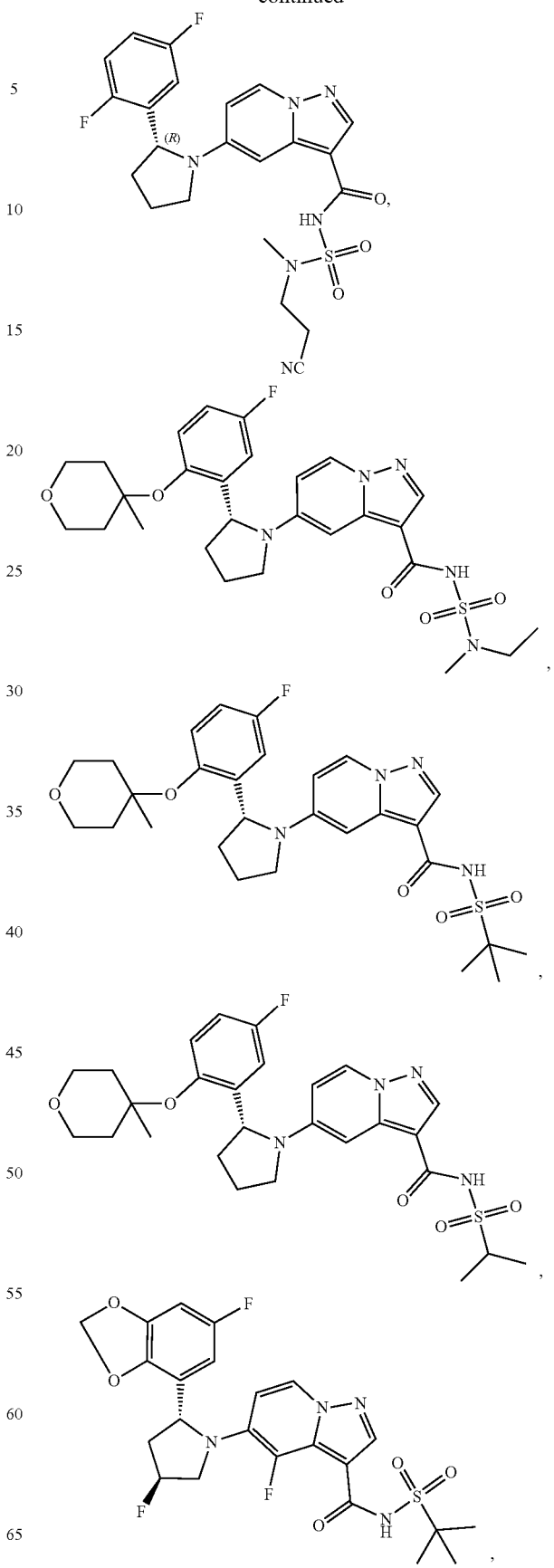

211
-continued
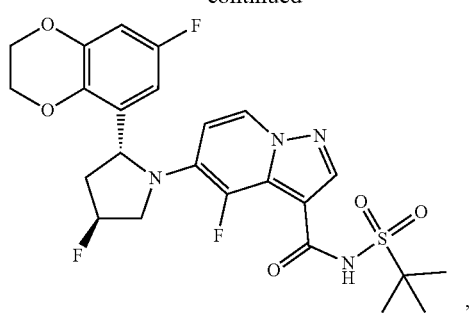
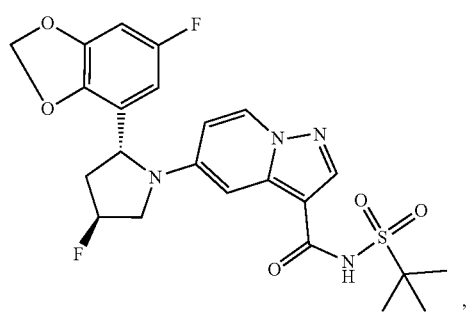
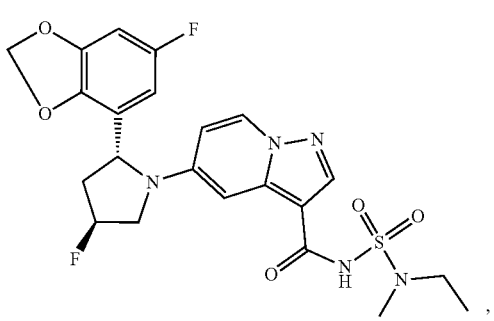
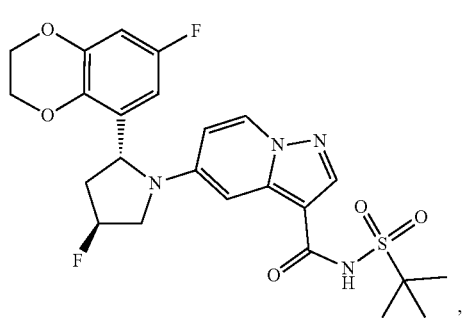
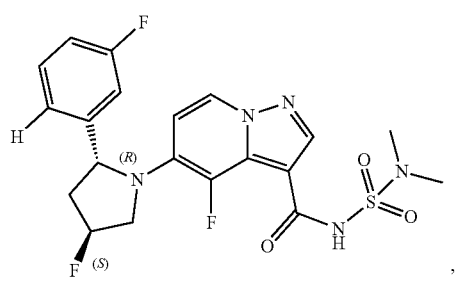
212
-continued
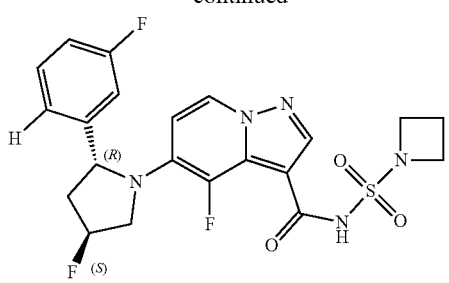
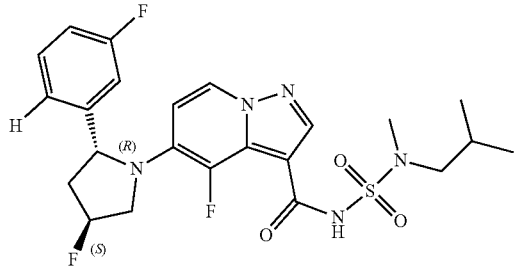
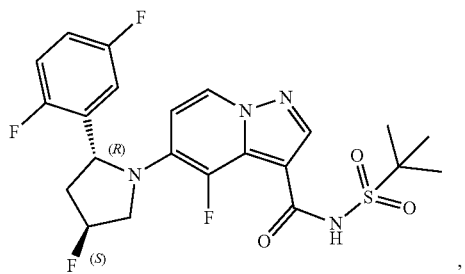
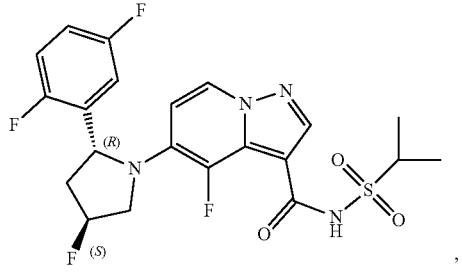
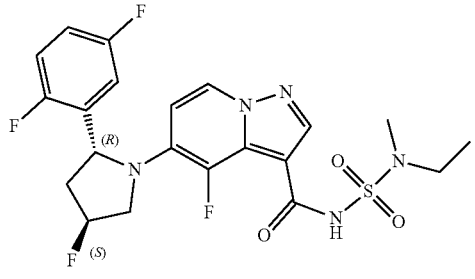
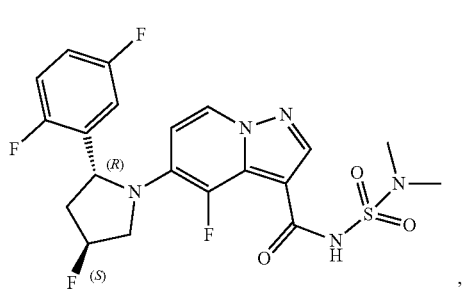

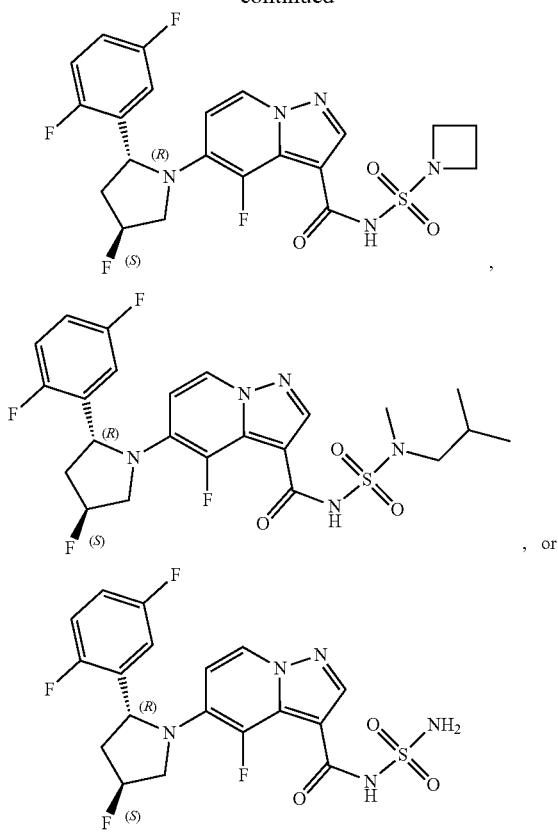

or a pharmaceutically acceptable salt thereof, or a pharmaceutically acceptable solvate thereof or a stereoisomer thereof.

9. The method of claim 1, wherein the compound of formula (I) is a pharmaceutical composition comprising at least one compound of compound of formula (I) and at least one pharmaceutically acceptable excipient.

10. A method of treating a cancer in a subject, the method comprising:
a) determining that the cancer is associated with an abnormal or deregulated Trk kinase; and
b) administering to the subject a therapeutically effective amount of a dosage form comprising a compound of Formula (I)

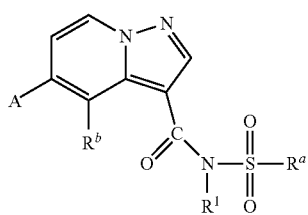
(I)

or their pharmaceutically acceptable salts, pharmaceutically acceptable solvates or stereoisomers thereof, wherein
A is

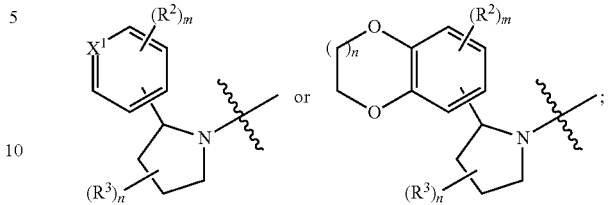

$X^1$ is CH or N;
$R^1$ represents hydrogen or —$(C_1$-$C_6)$alkyl;
$R^2$ is independently selected from hydrogen, halogen, cyano, —$(C_1$-$C_6)$alkyl, -halo$(C_1$-$C_6)$alkyl, -halo$(C_1$-$C_6)$alkoxy, phenyl optionally substituted with 1 to 3 halogens; and an optionally substituted —O-heterocyclyl wherein the optional substituent is alkyl, —$OR^i$ or —$C(O)N(R^i)_2$;
when $X^1$ is CH, optionally two $R^2$s present on any two adjacent carbon atoms combine to form a 5 to 7 membered heterocyclic ring;
$R^3$ is independently halogen, cyano, —$OR^i$, or —C(O)N$(R^i)_2$ or two $R^3$s together with the carbon atom they are attached form a $(C_3$-$C_7)$cycloalkyl group spiro attached to pyrrolidine; or two $R^3$ when they are attached to adjacent carbon atoms form a $(C_3$-$C_7)$cycloalkyl ring fused to the pyrrolidine;
$R^a$ is selected from
(i) a group selected from optionally substituted —$(C_1$-$C_6)$alkyl, -hydroxy$(C_1$-$C_6)$alkyl and —$(C_1$-$C_6)$alkyl-$(C_1$-$C_6)$alkoxy, wherein the optional substituent is cyano, halogen or —$(C_6$-$C_{12})$aryl,
(ii) an optionally substituted —$(C_3$-$C_{10})$cycloalkyl wherein the optional substituent is cyano, —$(C_1$-$C_6)$alkyl, hydroxyl, halogen or —$R^s$,
(iii) an optionally substituted —$(C_6$-$C_{12})$aryl wherein the optional substituent is cyano, hydroxyl, halogen, —$(C_1$-$C_6)$alkyl or —$R^r$
(iv) an optionally substituted 5 to 10 membered heterocyclyl, wherein the optional substituent is cyano, hydroxyl, halogen or —$(C_1$-$C_6)$alkyl,
(v) an optionally substituted 5 to 10 membered heteroaryl, wherein the optional substituent is cyano, oxo (=O), hydroxyl, halogen, —$(C_1$-$C_6)$alkyl, —$(C_1$-$C_6)$alkoxy, —$NR^cR^d$ or —$R^r$,
(vi) —$NR^4R^5$, and
(vii) —$(C_1$-$C_6)$alkyl-$(C_6$-$C_{12})$aryl;
$R^b$ represents hydrogen or halogen;
$R^4$ is selected from hydrogen, —$(C_1$-$C_6)$alkyl, —$(C_3$-$C_{10})$cycloalkyl, -hydroxy$(C_1$-$C_6)$alkyl, -alkoxy$(C_1$-$C_6)$alkyl, -halogen$(C_1$-$C_6)$alkyl and —$(C_1$-$C_6)$alkyl-$(C_3$-$C_{10})$cycloalkyl;
$R^5$ is hydrogen or —$(C_1$-$C_6)$alkyl or —$(C_1$-$C_6)$alkyl-$(C_3$-$C_{10})$cycloalkyl;
Alternatively $R^4$ and $R^5$ together with the nitrogen atom to which they are attached may form an optionally substituted 5 to 10 membered heterocyclic ring, optionally containing 1-2 additional heteroatoms or groups selected from —O—, —S—, —N—, —C(=O)—, —S(=O)— or —S(=O)$_2$—, wherein the optional substituent is hydroxyl, —$(C_1$-$C_6)$alkyl, —C(=O)—$(C_1$-$C_6)$alkyl, mesyl or COO$R^e$;
$R^c$ and $R^d$ are independently selected from hydrogen and —$(C_1$-$C_6)$alkyl;
$R^e$ is selected from hydrogen and alkyl;

R$^i$ is hydrogen, —(C$_1$-C$_6$)alkyl, -halo(C$_1$-C$_6$)alkyl, —(C$_1$-C$_6$)alkyl-(C$_1$-C$_6$)alkoxy, —(C$_3$-C$_{10}$)cycloalkyl, optionally substituted —(C$_1$-C$_6$)alkyl-(C$_3$-C$_{10}$)cycloalkyl, wherein the optional substituent is halogen or —(C$_1$-C$_6$)alkyl substituted with 1 to 3 hydroxy groups;

R$^r$ is independently selected from a 5 to 10 membered heterocyclyl or a 5 to 10 membered heteroaryl, wherein optional substituent is hydroxyl, halogen, —(C$_1$-C$_6$)alkyl or —(C$_1$-C$_6$)alkoxy;

R$^s$ is an optionally substituted —(C$_1$-C$_6$)alkyl-(C$_6$-C$_{10}$)aryl, wherein the optional substituent is halogen;

m is independently represents 0, 1, 2, 3 or 4; and n is independently represents 0, 1, 2, or 3.

11. The method of claim 10, wherein the compound of Formula (I) is

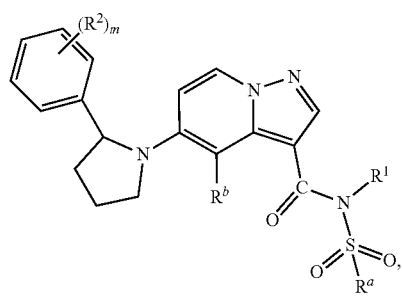
(Ia)

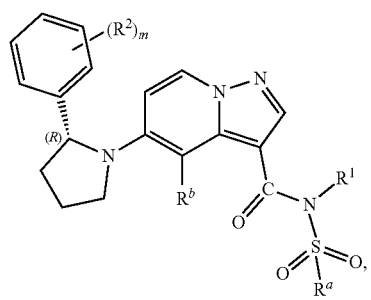
(Ib)

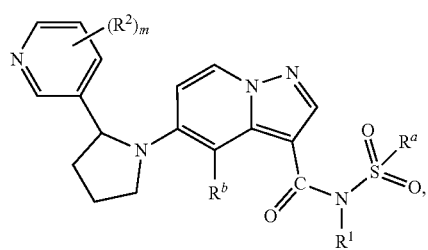
(Ic)

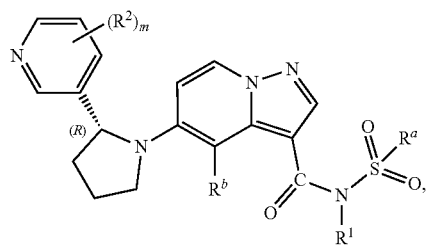
(Id)

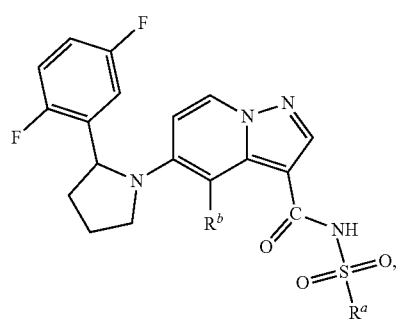
(Ie)

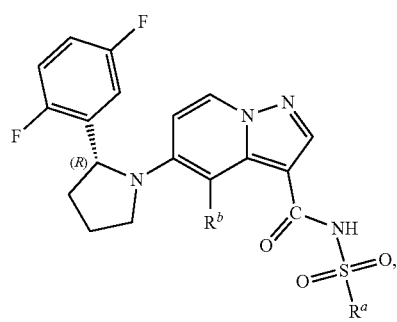
(If)

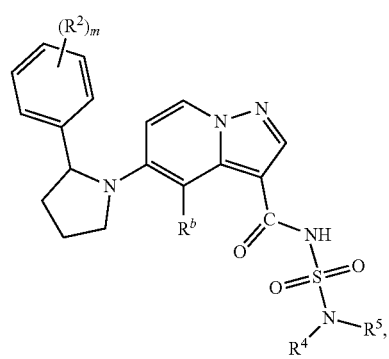
(Ig)

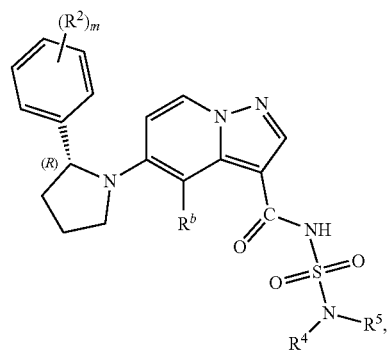
(Ih)

-continued

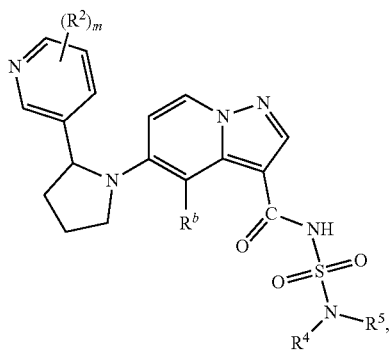

(Ii)

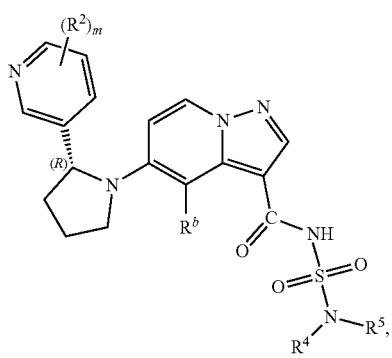

(Ij)

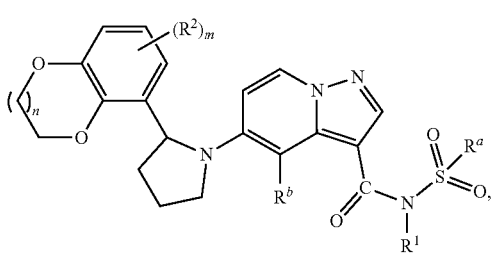

(Ik)

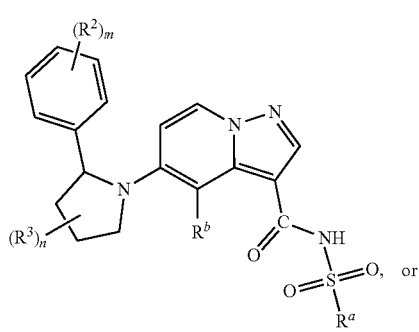

(Il)

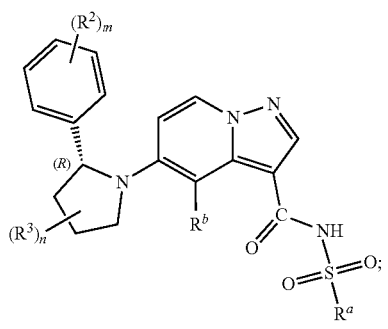

(Im)

or their pharmaceutically acceptable salts, pharmaceutically acceptabl solvates or stereoisomers thereof, wherein the values of all the variables are as described in claim 10.

12. The method of claim 10, wherein $R^b$ is hydrogen, fluorine; $R^3$ is fluorine; or $R^2$ is independently represents halogen, cyano or haloalkyl; $R^4$ and $R^5$ are methyl, ethyl or propyl; m is 1 or 2; or $R^a$ methyl, ethyl, propyl, isopropyl, butyl or tert-butyl.

13. The method of claim 10, wherein the compound of formula (I) is
- (R)-5-(2-(2,5-difluorophenyl)pyrrolidin-1-yl)-N-((4-fluorophenyl)sulfonyl)pyrazolo [1,5-a]pyridine-3-carboxamide,
- (R)—N-(tert-butylsulfonyl)-5-(2-(2,5-difluorophenyl)pyrrolidin-1-yl)pyrazolo[1,5-a] pyridine-3-carboxamide,
- (R)-5-(2-(2,5-difluorophenyl)pyrrolidin-1-yl)-N-(ethylsulfonyl)pyrazolo[1,5-a] pyridine-3-carboxamide,
- (R)—N-((3-cyanophenyl)sulfonyl)-5-(2-(2,5-difluorophenyl)pyrrolidin-1-yl)pyrazolo [1,5-a] pyridine-3-carboxamide,
- (R)—N-(cyclopropylsulfonyl)-5-(2-(2,5-difluorophenyl)pyrrolidin-1-yl) pyrazolo[1,5-a]pyridine-3-carboxamide,
- (R)-5-(2-(2,5-difluorophenyl)pyrrolidin-1-yl)-N-(methylsulfonyl)pyrazolo[1,5-a] pyridine-3-carboxamide,
- (R)-5-(2-(2,5-difluorophenyl)pyrrolidin-1-yl)-N-(isopropylsulfonyl)pyrazolo[1,5-a] pyridine-3-carboxamide,
- 5-((R)-2-(2,5-difluorophenyl)pyrrolidin-1-yl)-N-((4-((S)-3-hydroxypyrrolidin-1-yl) phenyl) sulfonyl)pyrazolo [1, 5-a]pyridine-3-carboxamide,
- (R)—N-((3-cyanophenyl)sulfonyl)-5-(2-(2,5-difluorophenyl)pyrrolidin-1-yl)-N-methyl pyrazolo[1,5-a]pyridine-3-carboxamide,
- (R)-5-(2-(2,5-difluorophenyl)pyrrolidin-1-yl)-N-(propylsulfonyl)pyrazolo[1, 5-a] pyridine-3-carboxamide,
- (R)-5-(2-(2,5-difluorophenyl)pyrrolidin-1-yl)-N-((3,5-dimethyl isoxazol-4-yl) sulfonyl) pyrazolo [1, 5-a] pyridine-3-carboxamide,
- (R)—N-(cyclohexylsulfonyl)-5-(2-(2,5-difluorophenyl)pyrrolidin-1-yl)pyrazolo[1,5-a] pyridine-3-carboxamide,
- (R)—N-(cyclopentylsulfonyl)-5-(2-(2, 5-difluorophenyl)pyrrolidin-1-yl)pyrazolo[1,5-a] pyridine-3-carboxamide,
- (R)-5-(2-(2,5-difluorophenyl)pyrrolidin-1-yl)-N-(isobutylsulfonyl) pyrazolo[1, 5-a] pyridine-3-carboxamide,
- (R)-5-(2-(2,5-difluorophenyl) pyrrolidin-1-yl)-N-((1,2-dimethyl-1H-imidazol-4-yl) sulfonyl) pyrazolo [1, 5-a] pyridine-3-carboxamide,
- (R)-5-(2-(2, 5-difluorophenyl) pyrrolidin-1-yl)-N-((1,2-dimethyl-1H-imidazol-5-yl) sulfonyl) pyrazolo [1, 5-a] pyridine-3-carboxamide,
- (R)-5-(2-(2, 5-difluorophenyl) pyrrolidin-1-yl)-N-(piperidin-4-ylsulfonyl) pyrazolo [1, 5-a] pyridine-3-carboxamide,
- (R)-5-(2-(2, 5-difluorophenyl) pyrrolidin-1-yl)-N-((1-methyl-1H-imidazol-4-yl) sulfonyl) pyrazolo [1, 5-a] pyridine-3-carboxamide,
- (R)-5-(2-(2, 5-difluorophenyl) pyrrolidin-1-yl)-N-((1-methyl-1H-pyrazol-5-yl) sulfonyl) pyrazolo [1, 5-a] pyridine-3-carboxamide,
- (R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide, (R)-5-(2-(2, 5-difluorophenyl) pyrrolidin-1-yl)-N-((1-methyl-2-oxoindolin-5-yl) sulfonyl) pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, (R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, (R)-5-(2-(2, 5-difluorophenyl) pyrrolidin-1-yl)-N-((6-methoxypyridin-3-yl) sulfonyl) pyrazolo [1, 5-a] pyridine-3-carboxamide, (R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide, (R)-5-(2-(2, 5-difluorophenyl) pyrrolidin-1-yl)-N-((1-methyl-1H-pyrazol-4-yl) sulfonyl) pyrazolo [1, 5-a] pyridine-3-carboxamide, (R)-5-(2-(2, 5-difluorophenyl) pyrrolidin-1-yl)-N-((4-morpholinophenyl) sulfonyl) pyrazolo [1, 5-a] pyridine-3-carboxamide, (R)-5-(2-(2,5-difluorophenyl)pyrrolidin-1-yl)-N-(pyridin-3-ylsulfonyl)pyrazolo[1,5-a]pyridine-3-carboxamide, (R)—N-((5-chlorothiophen-2-yl) sulfonyl)-5-(2-(2, 5-difluorophenyl) pyrrolidin-1-yl) pyrazolo [1, 5-a] pyridine-3-carboxamide, (R)—N-((2, 5-dichlorothiophen-3-yl) sulfonyl)-5-(2-(2, 5-difluorophenyl) pyrrolidin-1-yl) pyrazolo [1, 5-a] pyridine-3-carboxamide, (R)—N-(cyclobutylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide, (R)—N-(benzo[d][1,3]dioxol-5-ylsulfonyl)-5-(2-(2,5-difluorophenyl)pyrrolidin-1-yl) pyrazolo[1,5-a]pyridine-3-carboxamide, (R)-5-(2-(2,5-difluorophenyl)pyrrolidin-1-yl)-N-((1-ethylcyclopropyl)sulfonyl)pyrazolo[1,5-a]pyridine-3-carboxamide, (R)-5-(2-(2,5-difluorophenyl)pyrrolidin-1-yl)-N-(neopentylsulfonyl)pyrazolo[1,5-a]pyridine-3-carboxamide, (R)-5-(2-(2,5-difluorophenyl)pyrrolidin-1-yl)-N-((1-methylcyclopropyl)sulfonyl) pyrazolo[1,5-a]pyridine-3-carboxamide, (R)-5-(2-(2,5-difluorophenyl)pyrrolidin-1-yl)-N-(o-tolylsulfonyl)pyrazolo[1,5-a] pyridine-3-carboxamide, (R)—N-(benzylsulfonyl)-5-(2-(2,5-difluorophenyl)pyrrolidin-1-yl) pyrazolo[1,5-a] pyridine-3-carboxamide, (R)-5-(2-(2,5-difluorophenyl)pyrrolidin-1-yl)-N-((1-(4-fluorobenzyl)cyclopropyl) sulfonyl)pyrazolo[1,5-a] pyridine-3-carboxamide, (R)—N-(tert-butylsulfonyl)-5-(2-(5-fluoro-2-methoxyphenyl) pyrrolidin-1-yl) pyrazolo [1, 5-a] pyridine-3-carboxamide, (R)—N-(tert-butylsulfonyl)-5-(2-(3-(difluoromethoxy)-5-fluorophenyl) pyrrolidin-1-yl) pyrazolo [1, 5-a] pyridine-3-carboxamide, (R)—N-(tert-butylsulfonyl)-5-(2-(5-fluoropyridin-3-yl) pyrrolidin-1-yl) pyrazolo [1, 5-a] pyridine-3-carboxamide, (R)—N-(tert-butylsulfonyl)-5-(2-(2-ethoxy-5-fluorophenyl)pyrrolidin-1-yl)pyrazolo [1,5-a]pyridine-3-carboxamide, (R)—N-(tert-butylsulfonyl)-5-(2-(2-(cyclopropylmethoxy)-5-fluorophenyl) pyrrolidin-1-yl)pyrazolo[1, 5-a] pyridine-3-carboxamide, (R)—N-(tert-butylsulfonyl)-5-(2-(2-chloro-5-fluorophenyl)pyrrolidin-1-yl) pyrazolo[1,5-a]pyridine-3-carboxamide, N-(tert-butylsulfonyl)-5-((2R,4R)-2-(2,5-difluorophenyl)-4-hydroxypyrrolidin-1-yl) pyrazolo[1,5-a]pyridine-3-carboxamide, (R)—N-(tert-butylsulfonyl)-5-(2-(5-fluoro-2-(2,2,2-trifluoroethoxy)phenyl) pyrrolidin-1-yl)pyrazolo[1,5-a] pyridine-3-carboxamide, N-(tert-butylsulfonyl)-5-(2-(7-fluoro-2,3-dihydrobenzo[b][1,4]dioxin-5-yl)pyrrolidin-1-yl)pyrazolo[1,5-a] pyridine-3-carboxamide (Isomer-I), N-(tert-butylsulfonyl)-5-(2-(7-fluoro-2,3-dihydrobenzo[b][1,4]dioxin-5-yl)pyrrolidin-1-yl)pyrazolo[1,5-a] pyridine-3-carboxamide (Isomer-II), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-I), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-II), (R)—N-(tert-butylsulfonyl)-5-(2-(4,4'-difluoro-[1,1'-biphenyl]-2-yl)pyrrolidin-1-yl)pyrazolo[1,5-a]pyridine-3-carboxamide, (S)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(5-fluoro-2-(2-fluoroethoxy)phenyl) pyrrolidin-1-yl)pyrazolo[1,5-a]pyridine-3-carboxamide, N-(tert-butylsulfonyl)-5-((2R,4R)-2-(2,5-difluorophenyl)-4-fluoropyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1, 5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1, 5-a]pyridine-3-carboxamide, (R)—N-(tert-butylsulfonyl)-5-(2-(2, 5-difluorophenyl) pyrrolidin-1-yl)-4-fluoro pyrazolo[1, 5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide, (R)—N-(tert-butylsulfonyl)-5-(2-(3, 5-difluorophenyl) pyrrolidin-1-yl) pyrazolo [1, 5-a] pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a]pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide, (R)-5-(2-(3, 5-difluorophenyl) pyrrolidin-1-yl)-N-((4-fluorophenyl) sulfonyl)pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, (R)-5-(2-(3, 5-difluorophenyl) pyrrolidin-1-yl)-N-(isopropylsulfonyl) pyrazolo [1, 5-a] pyridine-3-carboxamide, (R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide, 5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, 5-((2R,4S)-2-(2,5-difluorophenyl)-4-fluoropyrrolidin-1-yl)-N-((1-methyl cyclopropyl)sulfonyl)pyrazolo[1,5-a]pyridine-3-carboxamide, (R)-5-(2-(2, 5-difluorophenyl) pyrrolidin-1-yl)-4-fluoro-N-(isopropylsulfonyl) pyrazolo [1, 5-a] pyridine-3-carboxamide, (R)-5-(2-(2, 5-difluorophenyl) pyrrolidin-1-yl)-N—(N,N-dimethylsulfamoyl) pyrazolo [1, 5-a] pyridine-3-carboxamide, (R)-5-(2-(2,5-difluorophenyl)pyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl)pyrazolo[1,5-a]pyridine-3-carboxamide, 5-((2R,4S)-2-(2,5-difluorophenyl)-4-fluoropyrrolidin-1-yl)-N—(N-ethyl-N-methyl sulfamoyl)pyrazolo[1,5-a]pyridine-3-carboxamide, (R)—N—(N-(cyclopropylmethyl)-N-methylsulfamoyl)-5-(2-(2,5-difluorophenyl) pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl)pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl)pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo[1,5-a]pyridine-3-carboxamide, (R)—N—(N,N-diethylsulfamoyl)-5-(2-(5-fluoro-2-methoxyphenyl)pyrrolidin-1-yl) pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl)pyrazolo[1,5-a]pyridine-3-carboxamide, (R)-5-(2-(2,5-difluorophenyl)pyrrolidin-1-yl)-N-(piperidin-1-ylsulfonyl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy) phenyl)pyrrolidin-1-yl)pyrazolo[1,5-a]pyridine-3-carboxamide, 5-((R)-2-(2,5-difluorophenyl)pyrrolidin-1-yl)-N—(((S)-3-hydroxypyrrolidin-1-yl) sulfonyl)pyrazolo[1,5-a]pyridine-3-carboxamide, (R)-5-(2-(2,5-difluorophenyl)pyrrolidin-1-yl)-N-sulfamoylpyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo [1,5-a]pyridine-3-carboxamide, N—(N-ethyl-N-methylsulfamoyl)-5-(2-(8-fluoro-3,4-dihydro-2H-benzo[b][1,4] dioxepin-6-yl)pyrrolidin-1-yl)pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4] dioxepin-6-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-1), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-1), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-4-fluoro-5-((2R,4S)-4-fluoro-2-(3-fluorophenyl)pyrrolidin-1-yl)pyrazolo[1,5-a]pyridine-3-carboxamide, N—(N-ethyl-N-methylsulfamoyl)-5-((R)-2-(3-fluoro-5-(((S)-tetrahydrofuran-3-yl)oxy)phenyl)pyrrolidin-1-yl) pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide, N—(N-ethyl-N-methylsulfamoyl)-5-((R)-2-(3-fluoro-5-(((R)-tetrahydrofuran-3-yl)oxy)phenyl)pyrrolidin-1-yl) pyrazolo[1,5-a]pyridine-3-carboxamide, 4-fluoro-5-((2R,4S)-4-fluoro-2-(3-fluorophenyl)pyrrolidin-1-yl)-N-sulfamoyl pyrazolo[1,5-a]pyridine-3-carboxamide, N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-1), N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2);
(R)-5-(2-(2,5-difluorophenyl)pyrrolidin-1-yl)-N—(N-isobutyl-N-methyl sulfamoyl)pyrazolo[1,5-a]pyridine-3-carboxamide,
(R)—N—(N-ethyl-N-methylsulfamoyl)-4-fluoro-5-(2-(3-fluorophenyl) pyrrolidin-1-yl)pyrazolo[1,5-a]pyridine-3-carboxamide,
(R)—N—(N,N-dimethylsulfamoyl)-4-fluoro-5-(2-(3-fluorophenyl)pyrrolidin-1-yl) pyrazolo[1,5-a]pyridine-3-carboxamide,
(R)—N—(N,N-dimethylsulfamoyl)-4-fluoro-5-(2-(3-fluorophenyl)pyrrolidin-1-yl) pyrazolo[1,5-a]pyridine-3-carboxamide,
(R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide,
(R)—N—(N,N-bis(cyclopropylmethyl)sulfamoyl)-5-(2-(2,5-difluorophenyl)pyrrolidin-1-yl)pyrazolo[1,5-a]pyridine-3-carboxamide,
N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide,
N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide (Diastereomer-II),
N-(tert-butylsulfonyl)-5-(2-(2,5-difluorophenyl)pyrrolidin-1-yl)pyrazolo[1,5-a] pyridine-3-carboxamide (Racemic mixture);
(R)—N-(tert-butylsulfonyl)-5-(2-(3,5-difluoro-2-methoxyphenyl)pyrrolidin-1-yl) pyrazolo[1,5-a]pyridine-3-carboxamide,
N-(tert-butylsulfonyl)-4-fluoro-5-((2R,4S)-4-fluoro-2-(3-fluorophenyl)pyrrolidin-1-yl)pyrazolo[1,5-a]pyridine-3-carboxamide,
4-fluoro-5-((2R,4S)-4-fluoro-2-(3-fluorophenyl)pyrrolidin-1-yl)-N-(isopropyl sulfonyl)pyrazolo[1,5-a]pyridine-3-carboxamide,
(R)—N-(tert-butylsulfonyl)-5-(2-(3,5-difluoro-2-((tetrahydro-2H-pyran-4-yl)oxy) phenyl)pyrrolidin-1-yl)pyrazolo[1,5-a]pyridine-3-carboxamide,
(R)—N-(tert-butylsulfonyl)-5-(2-(5-fluoro-2-((tetrahydro-2H-pyran-4-yl)oxy) phenyl)pyrrolidin-1-yl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N-(isopropylsulfonyl)pyrazolo[1,5-a]pyridine-3-carboxamide,
(R)-4-fluoro-5-(2-(3-fluorophenyl)pyrrolidin-1-yl)-N-(isopropylsulfonyl)pyrazolo [1,5-a]pyridine-3-carboxamide,
(R)—N-(tert-butylsulfonyl)-4-fluoro-5-(2-(5-fluoro-2-((tetrahydro-2H-pyran-4-yl) oxy)phenyl)pyrrolidin-1-yl)pyrazolo[1,5-a]pyridine-3-carboxamide,
Sodium (tert-butylsulfonyl)(5-((2R,4S)-2-(2,5-difluorophenyl)-4-fluoropyrrolidin-1-yl) pyrazolo[1,5-a]pyridine-3-carbonyl)amide,
Sodium(R)-(tert-butylsulfonyl)(5-(2-(2,5-difluorophenyl) pyrrolidin-1-yl) pyrazolo [1,5-a] pyridine-3-carbonyl)amide,
Sodium (R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide,
Sodium (tert-butylsulfonyl)(5-((2R,4R)-2-(2,5-difluorophenyl)-4-fluoropyrrolidin-1-yl) pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl) (N,N-dimethylsulfamoyl)amide,
Sodium (tert-butylsulfonyl)(5-(2-(2,5-difluorophenyl)-4,4-difluoropyrrolidin-1-yl)pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl)((1-methylcyclopropyl) sulfonyl)amide,
Sodium (tert-butylsulfonyl)(5-((2R)-2-(2,5-difluorophenyl)-4-fluoropyrrolidin-1-yl)pyrazolo [1,5-a]pyridine-3-carbonyl)amide,
Sodium (5-((2R,4S)-2-(2,5-difluorophenyl)-4-fluoropyrrolidin-1-yl)pyrazolo[1,5-a]pyridine-3-carbonyl)(N,N-dimethylsulfamoyl)amide,
Sodium (tert-butylsulfonyl)(4-fluoro-5-((2R,4S)-4-fluoro-2-(3-fluorophenyl) pyrrolidin-1-yl)pyrazolo[1,5-a]pyridine-3-carbonyl)amide,
Sodium (R)-(N,N-dimethylsulfamoyl)(4-fluoro-5-(2-(3-fluorophenyl)pyrrolidin-1-yl)pyrazolo [1,5-a]pyridine-3-carbonyl)amide,
Sodium (N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl)(o-tolylsulfonyl)amide,
Sodium (4-fluoro-5-((2R,4S)-4-fluoro-2-(3-fluorophenyl) pyrrolidin-1-yl) pyrazolo[1,5-a]pyridine-3-carbonyl) (isopropylsulfonyl)amide,
Sodium (5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, or
Sodium (R)-(5-(2-(2,5-difluorophenyl) pyrrolidin-1-yl) pyrazolo[1,5-a]pyridine-3-carbonyl)(piperidin-1-ylsulfonyl)amide;

or a pharmaceutically acceptable salt thereof, a pharmaceutically acceptable solvate thereof or a stereoisomer thereof.

14. The method of claim 10, wherein the compound of formula (I) is
(R)-5-(2-(2,5-difluorophenyl)pyrrolidin-1-yl)-N-((4-fluorophenyl)sulfonyl)pyrazolo[1,5-a] pyridine-3-carboxamide,
(R)—N-((3-cyanophenyl)sulfonyl)-5-(2-(2,5-difluorophenyl)pyrrolidin-1-yl)pyrazolo[1,5-a] pyridine-3-carboxamide,
5-((R)-2-(2,5-difluorophenyl)pyrrolidin-1-yl)-N-((4-((S)-3-hydroxypyrrolidin-1-yl) phenyl) sulfonyl) pyrazolo [1, 5-a] pyridine-3-carboxamide,
(R)—N-((3-cyanophenyl) sulfonyl)-5-(2-(2, 5-difluorophenyl) pyrrolidin-1-yl)-N-methylpyrazolo [1, 5-a] pyridine-3-carboxamide,
(R)-5-(2-(2, 5-difluorophenyl) pyrrolidin-1-yl)-N-((4-morpholinophenyl) sulfonyl)pyrazolo [1, 5-a] pyridine-3-carboxamide,
(R)-5-(2-(2,5-difluorophenyl)pyrrolidin-1-yl)-N-(o-tolylsulfonyl)pyrazolo[1,5-a]pyridine-3-carboxamide,
(R)-5-(2-(3, 5-difluorophenyl) pyrrolidin-1-yl)-N-((4-fluorophenyl) sulfonyl)pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, Sodium(R)-(5-(2-(2,5-difluorophenyl)pyrrolidin-1-yl) pyrazolo[1,5-a]pyridine-3-carbonyl) (piperidin-1-yl-sulfonyl)amide, Sodium(R)-(5-(2-(2,5-difluorophenyl)pyrrolidin-1-yl) pyrazolo[1,5-a]pyridine-3-carbonyl) (o-tolylsulfonyl) amide;

(R)—N-(tert-butylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-(ethylsulfonyl)pyrazolo[1,5-a]pyridine-3-carboxamide, (R)-5-(2-(2,5-difluorophenyl)pyrrolidin-1-yl)-N-(methylsulfonyl)pyrazolo[1,5-a] pyridine-3-carboxamide, (R)-5-(2-(2, 5-difluorophenyl) pyrrolidin-1-yl)-N-(isopropylsulfonyl)pyrazolo[1, 5-a] pyridine-3-carboxamide, (R)-5-(2-(2, 5-difluorophenyl) pyrrolidin-1-yl)-N-(propylsulfonyl)pyrazolo[1, 5-a] pyridine-3-carboxamide, (R)-5-(2-(2, 5-difluorophenyl) pyrrolidin-1-yl)-N-(isobutylsulfonyl)pyrazolo[1, 5-a] pyridine-3-carboxamide, (R)-5-(2-(2,5-difluorophenyl)pyrrolidin-1-yl)-N-(neopentylsulfonyl)pyrazolo[1,5-a] pyridine-3-carboxamide, (R)—N-(benzylsulfonyl)-5-(2-(2,5-difluorophenyl)pyrolidin-1-yl) pyrazolo[1,5-a]pyridine-3-carboxamide, (R)—N-(tert-butylsulfonyl)-5-(2-(5-fluoro-2-methoxyphenyl) pyrrolidin-1-yl)pyrazolo [1, 5-a] pyridine-3-carboxamide, (R)—N-(tert-butylsulfonyl)-5-(2-(3-(difluoromethoxy)-5-fluorophenyl)pyrrolidin-1-yl) pyrazolo [1, 5-a] pyridine-3-carboxamide, (R)—N-(tert-butylsulfonyl)-5-(2-(5-fluoropyridin-3-yl) pyrrolidin-1-yl)pyrazolo [1, 5-a] pyridine-3-carboxamide, (R)—N-(tert-butylsulfonyl)-5-(2-(2-ethoxy-5-fluorophenyl)pyrrolidin-1-yl) pyrazolo[1,5-a] pyridine-3-carboxamide, (R)—N-(tert-butylsulfonyl)-5-(2-(2-(cyclopropylmethoxy)-5-fluorophenyl)pyrrolidin-1-yl) pyrazolo[1,5-a]pyridine-3-carboxamide, (R)—N-(tert-butylsulfonyl)-5-(2-(2-chloro-5-fluorophenyl)pyrrolidin-1-yl)pyrazolo[1,5-a]pyridine-3-carboxamide, N-(tert-butylsulfonyl)-5-((2R,4R)-2-(2,5-difluorophenyl)-4-hydroxypyrrolidin-1-yl)pyrazolo [1,5-a]pyridine-3-carboxamide, N-(tert-butylsulfonyl)-5-((2R,4S)-2-(2,5-difluorophenyl)-4-fluoropyrrolidin-1-yl)pyrazolo [1,5-a]pyridine-3-carboxamide, (R)—N-(tert-butylsulfonyl)-5-(2-(4,4'-difluoro-[1,1'-biphenyl]-2-yl)pyrrolidin-1-yl) pyrazolo[1,5-a]pyridine-3-carboxamide, (R)—N-(tert-butylsulfonyl)-5-(2-(5-fluoro-2-(2-fluoroethoxy)phenyl)pyrrolidin-1-yl) pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1, 5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1, 5-a]pyridine-3-carboxamide, (R)—N-(tert-butylsulfonyl)-5-(2-(2, 5-difluorophenyl) pyrrolidin-1-yl)-4-fluoro pyrazolo[1, 5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide, (R)—N-(tert-butylsulfonyl)-5-(2-(3, 5-difluorophenyl) pyrrolidin-1-yl) pyrazolo [1, 5-a] pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a]pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide, (R)-5-(2-(3, 5-difluorophenyl) pyrrolidin-1-yl)-N-(isopropylsulfonyl) pyrazolo [1, 5-a] pyridine-3-carboxamide, N-(tert-butylsulfonyl)-5-(2-(2,5-difluorophenyl)pyrrolidin-1-yl)pyrazolo[1,5-a]pyridine-3-carboxamide (Racemic mixture), (R)—N-(tert-butylsulfonyl)-5-(2-(3,5-difluoro-2-methoxyphenyl)pyrrolidin-1-yl)pyrazolo[1,5-a]pyridine-3-carboxamide, (R)—N-(tert-butylsulfonyl)-5-(2-(3,5-difluoro-2-((tetrahydro-2H-pyran-4-yl)oxy)phenyl)pyrrolidin-1-yl) pyrazolo[1,5-a]pyridine-3-carboxamide, (R)—N-(tert-butylsulfonyl)-5-(2-(5-fluoro-2-((tetrahydro-2H-pyran-4-yl)oxy)phenyl)pyrrolidin-1-yl) pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide, (R)-4-fluoro-5-(2-(3-fluorophenyl)pyrrolidin-1-yl)-N-(isopropylsulfonyl)pyrazolo[1,5-a]pyridine-3-carboxamide, (R)—N-(tert-butylsulfonyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, Sodium(tert-butylsulfonyl)(5-((2R,4R)-2-(2,5-difluorophenyl)-4-fluoropyrrolidin-1-yl)pyrazolo[1,5-a]pyridine-3-carbonyl)amide, Sodium(tert-butylsulfonyl)(5-((2R,4S)-2-(2,5-difluorophenyl)-4-fluoropyrrolidin-1-yl)pyrazolo[1,5-a]pyridine-3-carbonyl)amide, Sodium(R)-(tert-butylsulfonyl)(5-(2-(2,5-difluorophenyl)pyrrolidin-1-yl)pyrazolo[1,5-a] pyridine-3-carbonyl)amide, Sodium(R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide;

(R)—N-(cyclopropylsulfonyl)-5-(2-(2,5-difluorophenyl) pyrrolidin-1-yl) pyrazolo[1,5-a]pyridine-3-carboxamide, (R)—N-(cyclohexyl sulfonyl)-5-(2-(2, 5-difluorophenyl) pyrrolidin-1-yl) pyrazolo [1, 5-a] pyridine-3-carboxamide, (R)—N-(cyclopentyl sulfonyl)-5-(2-(2, 5-difluorophenyl) pyrrolidin-1-yl) pyrazolo [1, 5-a] pyridine-3-carboxamide, (R)—N-(cyclobutylsulfonyl)-5-(2-(2, 5-difluorophenyl) pyrrolidin-1-yl) pyrazolo [1, 5-a] pyridine-3-carboxamide,
(R)-5-(2-(2,5-difluorophenyl)pyrrolidin-1-yl)-N-((1-ethylcyclopropyl)sulfonyl) pyrazolo[1,5-a]pyridine-3-carboxamide,
(R)-5-(2-(2,5-difluorophenyl)pyrrolidin-1-yl)-N-((1-methylcyclopropyl)sulfonyl)pyrazolo [1,5-a]pyridine-3-carboxamide,
(R)-5-(2-(2,5-difluorophenyl)pyrrolidin-1-yl)-N-((1-(4-fluorobenzyl)cyclopropyl)sulfonyl) pyrazolo[1,5-a]pyridine-3-carboxamide,
(R)-5-(2-(2, 5-difluorophenyl) pyrrolidin-1-yl)-4-fluoro-N-(isopropylsulfonyl)pyrazolo [1, 5-a] pyridine-3-carboxamide,
Sodium(R)-(5-(2-(2,5-difluorophenyl)pyrrolidin-1-yl) pyrazolo[1,5-a]pyridine-3-carbonyl)((1-methylcyclopropyl) sulfonyl)amide;
(R)-5-(2-(2,5-difluorophenyl) pyrrolidin-1-yl)-N-((3,5-dimethylisoxazol-4-yl)sulfonyl) pyrazolo [1, 5-a] pyridine-3-carboxamide,
(R)-5-(2-(2,5-difluorophenyl) pyrrolidin-1-yl)-N-((1, 2-dimethyl-1H-imidazol-4-yl) sulfonyl) pyrazolo [1, 5-a] pyridine-3-carboxamide,
(R)-5-(2-(2,5-difluorophenyl) pyrrolidin-1-yl)-N-((1, 2-dimethyl-1H-imidazol-5-yl) sulfonyl) pyrazolo [1, 5-a] pyridine-3-carboxamide,
(R)-5-(2-(2,5-difluorophenyl) pyrrolidin-1-yl)-N-((1-methyl-1H-imidazol-4-yl) sulfonyl) pyrazolo [1, 5-a] pyridine-3-carboxamide,
(R)-5-(2-(2,5-difluorophenyl) pyrrolidin-1-yl)-N-((1-methyl-1H-pyrazol-5-yl) sulfonyl) pyrazolo [1, 5-a] pyridine-3-carboxamide,
(R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide,
(R)-5-(2-(2,5-difluorophenyl)pyrrolidin-1-yl)-N-((1-methyl-2-oxoindolin-5-yl)sulfonyl) pyrazolo [1, 5-a] pyridine-3-carboxamide,
(R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide,
5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide,
(R)-5-(2-(2, 5-difluorophenyl) pyrrolidin-1-yl)-N-((6-methoxypyridin-3-yl) sulfonyl) pyrazolo [1, 5-a] pyridine-3-carboxamide,
(R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide,
(R)-5-(2-(2,5-difluorophenyl) pyrrolidin-1-yl)-N-((1-methyl-1H-pyrazol-4-yl) sulfonyl) pyrazolo [1, 5-a] pyridine-3-carboxamide,
(R)-5-(2-(2,5-difluorophenyl)pyrrolidin-1-yl)-N-(pyridin-3-ylsulfonyl)pyrazolo[1,5-a]pyridine-3-carboxamide,
(R)—N-((5-chlorothiophen-2-yl) sulfonyl)-5-(2-(2, 5-difluorophenyl) pyrrolidin-1-yl) pyrazolo [1, 5-a] pyridine-3-carboxamide,
(R)—N-((2,5-dichlorothiophen-3-yl) sulfonyl)-5-(2-(2, 5-difluorophenyl) pyrrolidin-1-yl) pyrazolo [1, 5-a] pyridine-3-carboxamide,
(R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide,
(R)—N-(benzo[d][1,3]dioxol-5-ylsulfonyl)-5-(2-(2,5-difluorophenyl)pyrrolidin-1-yl)pyrazolo[1,5-a]pyridine-3-carboxamide,
(R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide,
5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide;
(R)-5-(2-(2, 5-difluorophenyl) pyrrolidin-1-yl)-N-(piperidin-4-ylsulfonyl) pyrazolo [1, 5-a] pyridine-3-carboxamide,
(R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide,
5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide,
(R)-5-(2-(2,5-difluorophenyl)pyrrolidin-1-yl)-N-(morpholinosulfonyl) pyrazolo[1,5-a]pyridine-3-carboxamide,
(R)-5-(2-(2,5-difluorophenyl)pyrrolidin-1-yl)-N-(pyrrolidin-1-ylsulfonyl)pyrazolo[1,5-a]pyridine-3-carboxamide,
(R)-5-(2-(2,5-difluorophenyl)pyrrolidin-1-yl)-N-((4-methylpiperazin-1-yl) sulfonyl)pyrazolo [1,5-a]pyridine-3-carboxamide,
(R)-5-(2-(2,5-difluorophenyl)pyrrolidin-1-yl)-N-(piperidin-1-ylsulfonyl)pyrazolo[1,5-a]pyridine-3-carboxamide,
5-((R)-2-(2,5-difluorophenyl)pyrrolidin-1-yl)-N—(((S)-3-hydroxypyrrolidin-1-yl) sulfonyl) pyrazolo[1,5-a] pyridine-3-carboxamide;
(R)—N-(tert-butylsulfonyl)-5-(2-(5-fluoro-2-(2,2, 2-trifluoroethoxy)phenyl)pyrrolidin-1-yl) pyrazolo[1,5-a] pyridine-3-carboxamide,
N-(tert-butylsulfonyl)-5-(2-(7-fluoro-2,3-dihydrobenzo [b][1,4]dioxin-5-yl)pyrrolidin-1-yl)pyrazolo[1,5-a] pyridine-3-carboxamide,
N-(tert-butylsulfonyl)-5-(2-(7-fluoro-2,3-dihydrobenzo [b][1,4]dioxin-5-yl)pyrrolidin-1-yl)pyrazolo[1,5-a] pyridine-3-carboxamide,
N-(tert-butylsulfonyl)-5-((2R,4S)-2-(2,5-difluorophenyl)-4-fluoropyrrolidin-1-yl)pyrazolo[1,5-a]pyridine-3-carboxamide,
N-(tert-butylsulfonyl)-5-((2R,4R)-2-(2,5-difluorophenyl)-4-fluoropyrrolidin-1-yl)pyrazolo[1,5-a]pyridine-3-carboxamide,
5-((2R,4S)-2-(2,5-difluorophenyl)-4-fluoropyrrolidin-1-yl)-N-((1-methyl cyclopropyl) sulfonyl)pyrazolo[1,5-a]pyridine-3-carboxamide,
5-((2R,4S)-2-(2,5-difluorophenyl)-4-fluoropyrrolidin-1-yl)-N—(N,N-dimethylsulfamoyl) pyrazolo[1,5-a]pyridine-3-carboxamide,
5-((2R,4S)-2-(2,5-difluorophenyl)-4-fluoropyrrolidin-1-yl)-N—(N-ethyl-N-methylsulfamoyl) pyrazolo[1,5-a] pyridine-3-carboxamide,
5-((2R,4S)-2-(2,5-difluorophenyl)-4-fluoropyrrolidin-1-yl)-N—(N,N-dimethylsulfamoyl) pyrazolo[1,5-a]pyridine-3-carboxamide,
5-((2R,4S)-2-(2,5-difluorophenyl)-4-fluoropyrrolidin-1-yl)-N—(N-ethyl-N-methylsulfamoyl) pyrazolo[1,5-a] pyridine-3-carboxamide,
N—(N-ethyl-N-methylsulfamoyl)-4-fluoro-5-((2R,4S)-4-fluoro-2-(3-fluorophenyl) pyrrolidin-1-yl)pyrazolo [1,5-a]pyridine-3-carboxamide, N-(tert-butylsulfonyl)-4-fluoro-5-((2R,4S)-4-fluoro-2-(3-fluorophenyl)pyrrolidin-1-yl)pyrazolo [1,5-a]pyridine-3-carboxamide,
4-fluoro-5-((2R,4S)-4-fluoro-2-(3-fluorophenyl)pyrrolidin-1-yl)-N-(isopropylsulfonyl) pyrazolo[1,5-a]pyridine-3-carboxamide,
Sodium(4-fluoro-5-((2R,4S)-4-fluoro-2-(3-fluorophenyl)pyrrolidin-1-yl)pyrazolo[1,5-a]pyridine-3-carbonyl)(isopropylsulfonyl)amide,
Sodium(5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide,
Sodium(tert-butylsulfonyl)(5-((2R)-2-(2,5-difluorophenyl)-4-fluoropyrrolidin-1-yl)pyrazolo[1,5-a]pyridine-3-carbonyl)amide,
Sodium(5-((2R,4S)-2-(2,5-difluorophenyl)-4-fluoropyrrolidin-1-yl)pyrazolo[1,5-a]pyridine-3-carbonyl)(N,N-dimethylsulfamoyl)amide,
Sodium(tert-butylsulfonyl)(4-fluoro-5-((2R,4S)-4-fluoro-2-(3-fluorophenyl)pyrrolidin-1-yl)pyrazolo[1,5-a]pyridine-3-carbonyl)amide,
Sodium (tert-butylsulfonyl)(5-(2-(2,5-difluorophenyl)-4,4-difluoropyrrolidin-1-yl) pyrazolo[1,5-a]pyridine-3-carbonyl)amide;
(R)-5-(2-(2,5-difluorophenyl) pyrrolidin-1-yl)-N—(N,N-dimethylsulfamoyl)pyrazolo[1,5-a] pyridine-3-carboxamide,
(R)-5-(2-(2,5-difluorophenyl)pyrrolidin-1-yl)-N—(N-ethyl-N-methylsulfamoyl)pyrazolo [1,5-a]pyridine-3-carboxamide,
(R)—N—(N-(cyclopropylmethyl)-N-methylsulfamoyl)-5-(2-(2,5-difluorophenyl)pyrrolidin-1-yl) pyrazolo[1,5-a]pyridine-3-carboxamide,
(R)—N—(N,N-diethylsulfamoyl)-5-(2-(2,5-difluorophenyl)pyrrolidin-1-yl)pyrazolo[1,5-a]pyridine-3-carboxamide,
(R)—N—(N,N-diethylsulfamoyl)-5-(2-(5-fluoro-2-methoxyphenyl)pyrrolidin-1-yl)pyrazolo[1,5-a]pyridine-3-carboxamide,
(R)—N—(N,N-diethylsulfamoyl)-5-(2-(5-fluoro-2-(2-fluoroethoxy)phenyl)pyrrolidin-1-yl) pyrazolo[1,5-a] pyridine-3-carboxamide,
(R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide,
(R)—N—(N-ethyl-N-methylsulfamoyl)-5-(2-(5-fluoro-2-methoxyphenyl)pyrrolidin-1-yl)pyrazolo[1,5-a]pyridine-3-carboxamide,
(R)—N—(N-ethyl-N-methylsulfamoyl)-5-(2-(5-fluoro-2-(2-fluoroethoxy)phenyl)pyrrolidin-1-yl)pyrazolo[1,5-a]pyridine-3-carboxamide,
(R)-5-(2-(3,5-difluoro-2-(2-fluoroethoxy)phenyl)pyrrolidin-1-yl)-N—(N-ethyl-N-methylsulfamoyl)pyrazolo [1,5-a]pyridine-3-carboxamide,
(R)-5-(2-(2,5-difluorophenyl)pyrrolidin-1-yl)-N-sulfamoylpyrazolo[1,5-a]pyridine-3-carboxamide,
N—(N-ethyl-N-methylsulfamoyl)-5-((R)-2-(3-fluoro-5-(((S)-tetrahydrofuran-3-yl)oxy) phenyl)pyrrolidin-1-yl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide,
N—(N-ethyl-N-methylsulfamoyl)-5-((R)-2-(3-fluoro-5-(((R)-tetrahydrofuran-3-yl)oxy)phenyl)pyrrolidin-1-yl)pyrazolo[1,5-a] pyridine-3-carboxamide,
4-fluoro-5-((2R,4S)-4-fluoro-2-(3-fluorophenyl)pyrrolidin-1-yl)-N-sulfamoylpyrazolo[1,5-a]pyridine-3-carboxamide,
N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I),
(R)-5-(2-(2,5-difluorophenyl)pyrrolidin-1-yl)-N—(N-isobutyl-N-methylsulfamoyl)pyrazolo[1,5-a] pyridine-3-carboxamide,
(R)—N—(N-ethyl-N-methylsulfamoyl)-4-fluoro-5-(2-(3-fluorophenyl) pyrrolidin-1-yl)pyrazolo[1,5-a]pyridine-3-carboxamide,
(R)—N—(N,N-dimethylsulfamoyl)-4-fluoro-5-(2-(3-fluorophenyl)pyrrolidin-1-yl)pyrazolo[1,5-a]pyridine-3-carboxamide,
(R)—N—(N,N-dimethylsulfamoyl)-4-fluoro-5-(2-(3-fluorophenyl)pyrrolidin-1-yl)pyrazolo[1,5-a]pyridine-3-carboxamide,
(R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
5-((2R)-2-(3-((2, 2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide,
(R)—N—(N,N-bis(cyclopropylmethyl)sulfamoyl)-5-(2-(2,5-difluorophenyl)pyrrolidin-1-yl)pyrazolo[1,5-a] pyridine-3-carboxamide,
N—(N-ethyl-N-methylsulfamoyl)-5-((2R)-2-(5-fluoro-2-((tetrahydrofuran-3-yl)oxy)phenyl)pyrrolidin-1-yl) pyrazolo[1,5-a]pyridine-3-carboxamide,
N—(N-ethyl-N-methylsulfamoyl)-5-((2R)-2-(5-fluoro-2-((tetrahydrofuran-3-yl)oxy)phenyl)pyrrolidin-1-yl) pyrazolo[1,5-a]pyridine-3-carboxamide,
Sodium(R)—(N,N-dimethylsulfamoyl)(4-fluoro-5-(2-(3-fluorophenyl)pyrrolidin-1-yl)pyrazolo[1,5-a]pyridine-3-carbonyl)amide,
Sodium(N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide,
Sodium (R)-(5-(2-(2,5-difluorophenyl) pyrrolidin-1-yl) pyrazolo[1,5-a]pyridine-3-carbonyl)(N,N-dimethylsulfamoyl)amide;
N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-I),
N—(N-ethyl-N-methylsulfamoyl)-5-(2-(8-fluoro-3,4-dihydro-2H-benzo[b][1,4]dioxepin-6-yl)pyrrolidin-1-yl) pyrazolo[1,5-a]pyridine-3-carboxamide (Diastereomer-II),
N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I),
N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II),
N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-di-hydrobenzo[b][1,4]dioxin-5-yl)pyrrolidin-1-yl)pyrazolo[1,5-a]pyridine-3-carboxamide (Diastereomer-II), or N—(N,N-dimethylsulfamoyl)-5-(2-(8-fluoro-3,4-di-hydro-2H-benzo[b][1,4]dioxepin-6-yl)pyrrolidin-1-yl)pyrazolo[1,5-a]pyridine-3-carboxamide (Diastereomer-2);

or a pharmaceutically acceptable salt thereof, a pharmaceutically acceptable solvate thereof or a stereoisomer thereof.

15. The method of claim 10, wherein the compound of formula (I) is

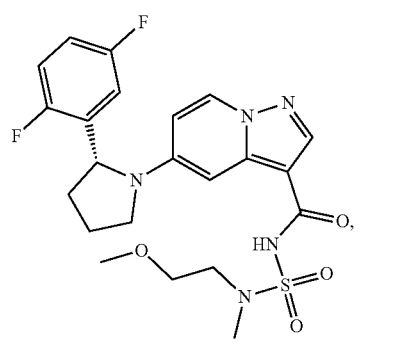

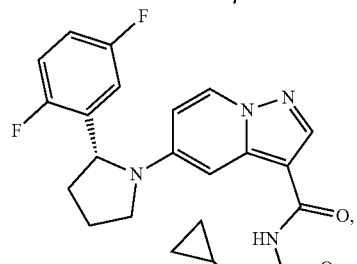

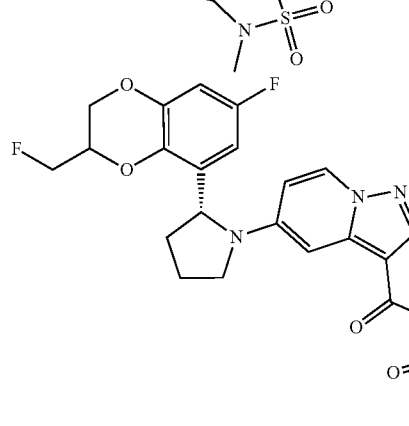

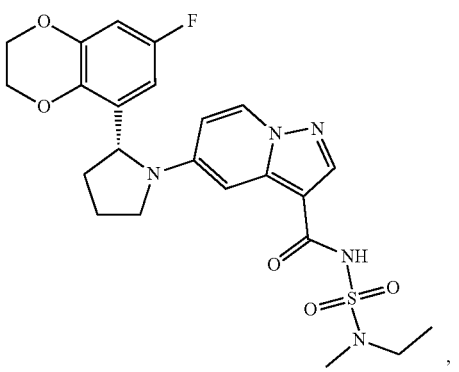

-continued

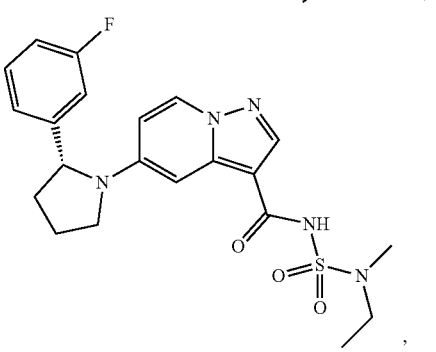

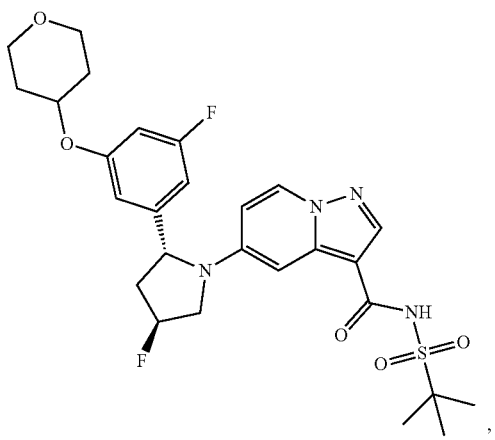

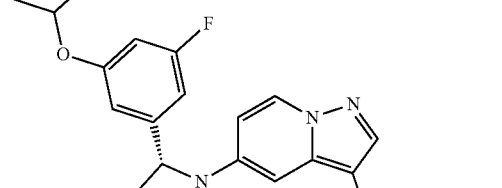

233
-continued
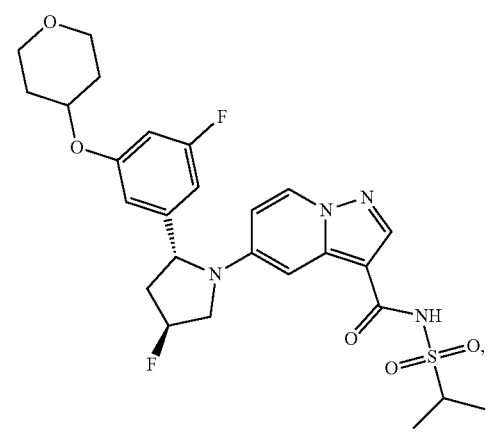
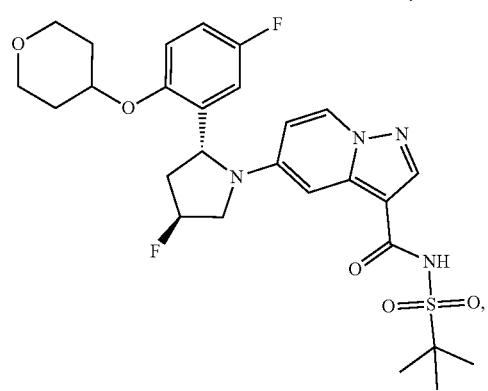
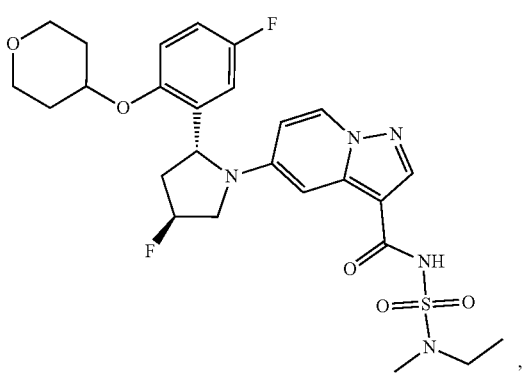
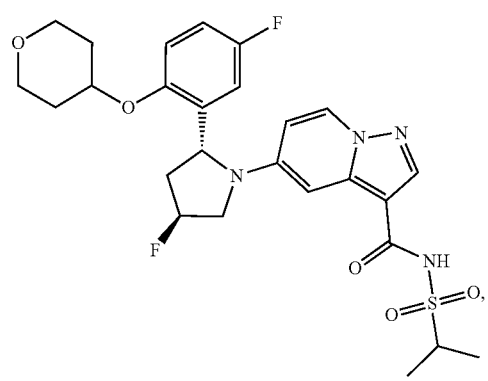
234
-continued
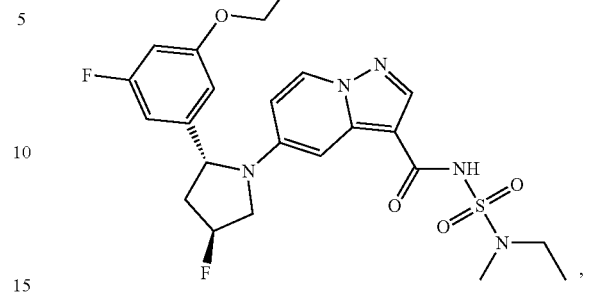
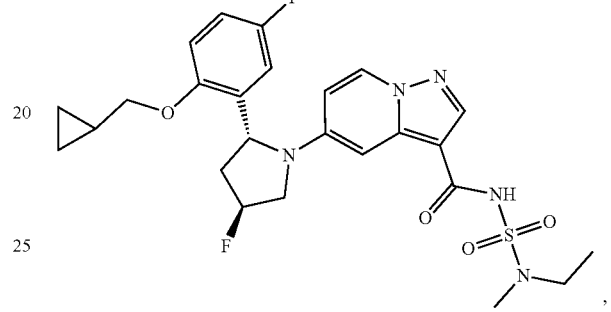
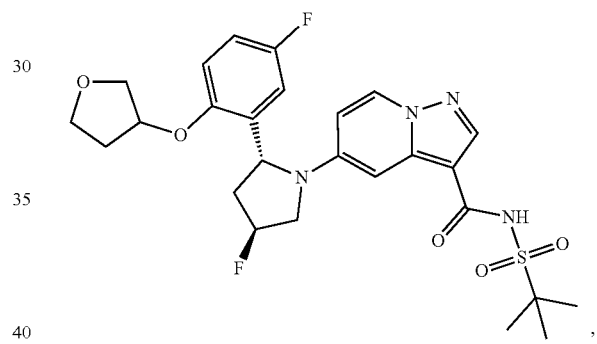
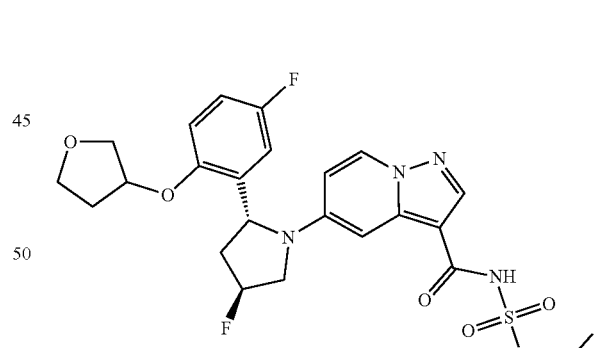
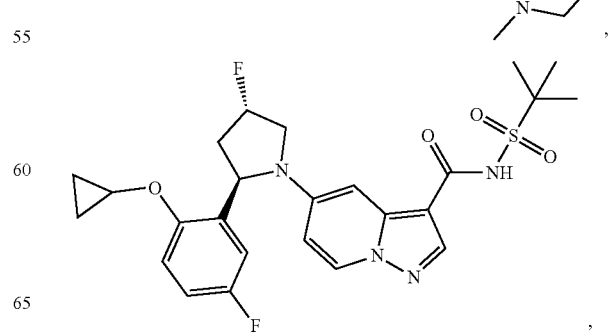

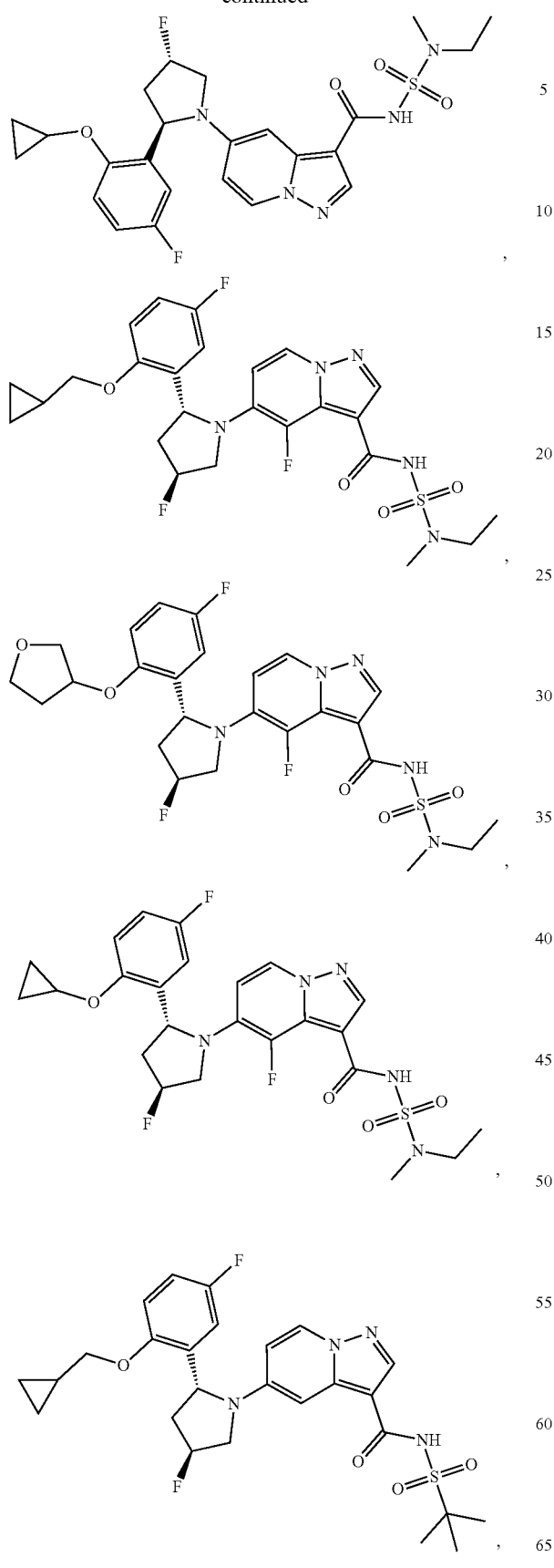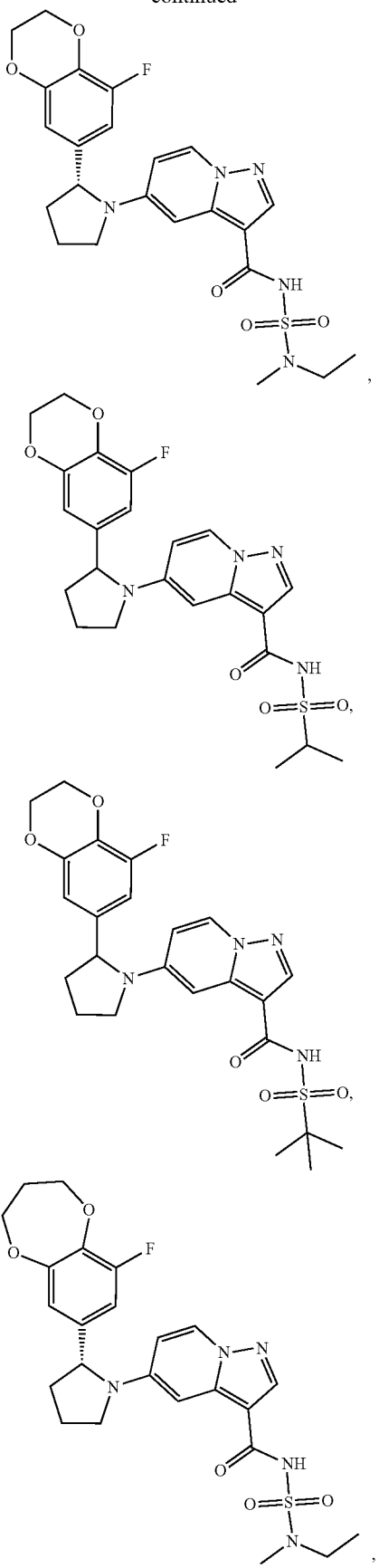

237
-continued
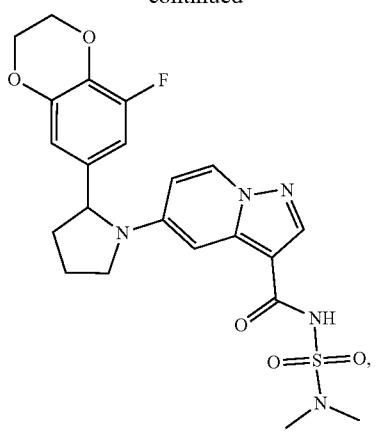
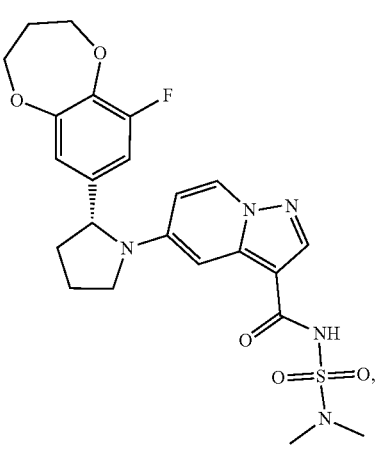
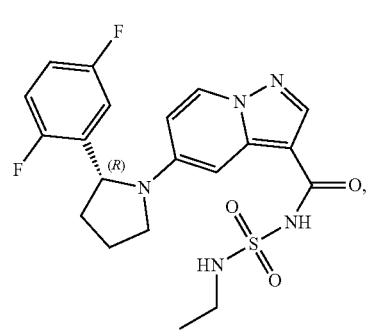
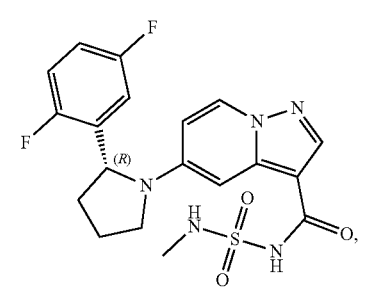
238
-continued
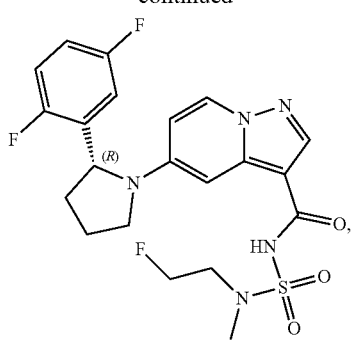
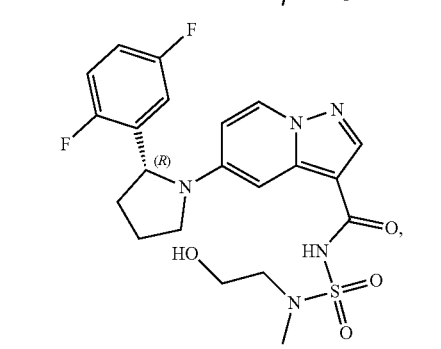
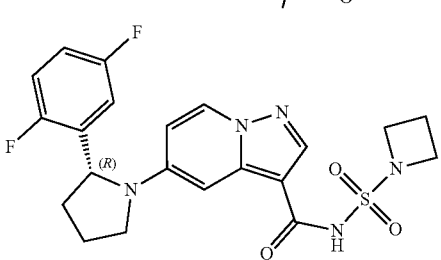
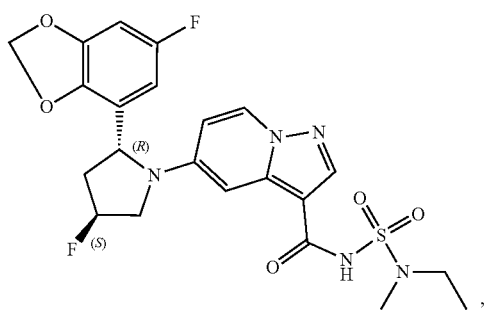

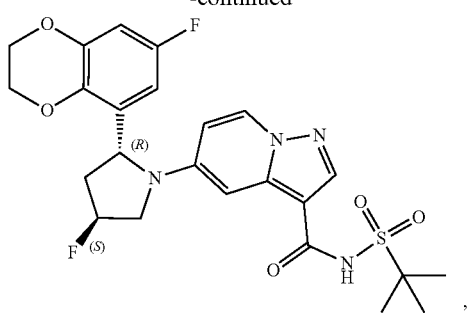
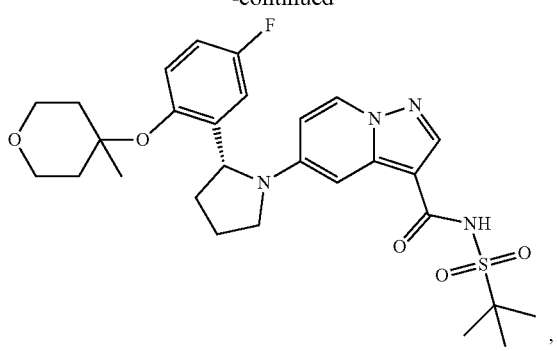
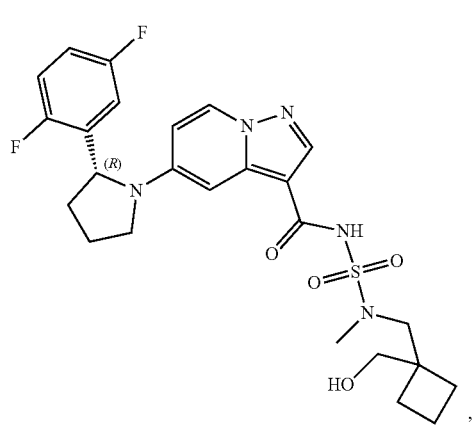
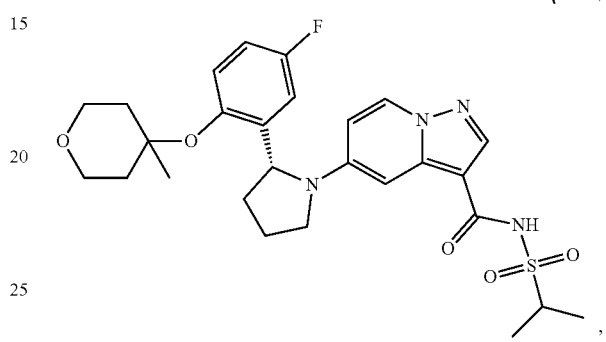
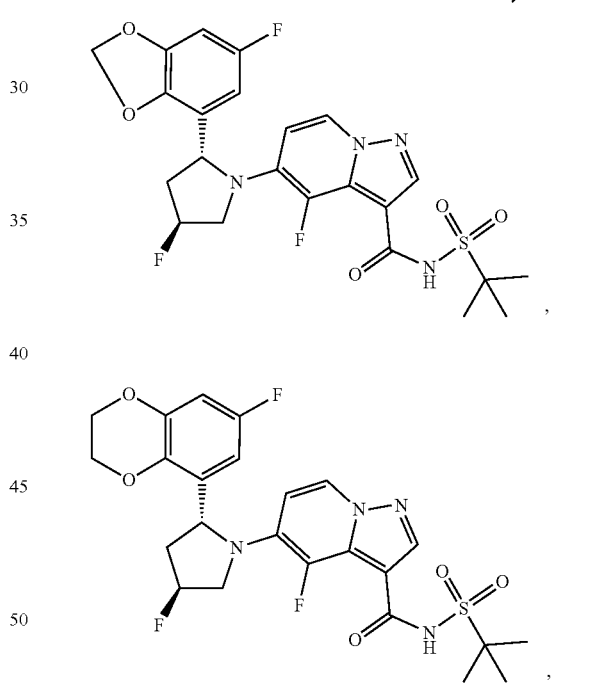
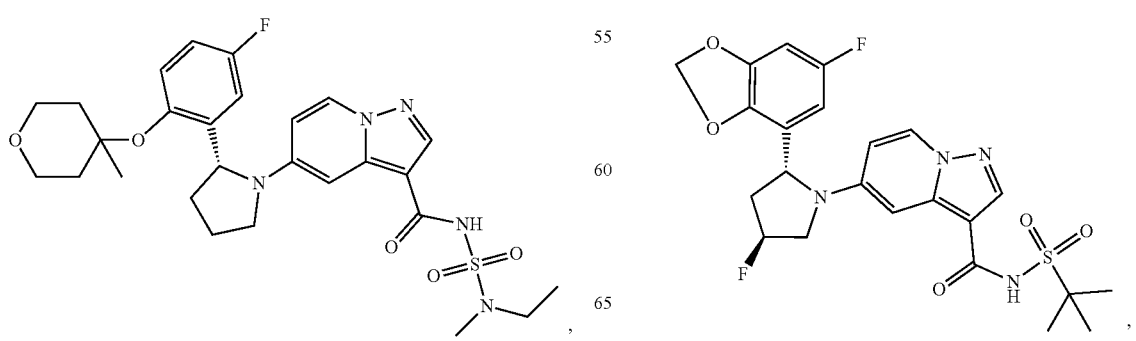

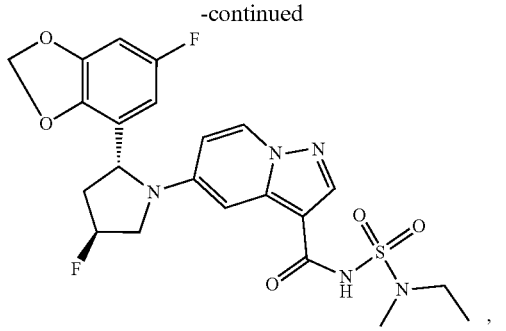
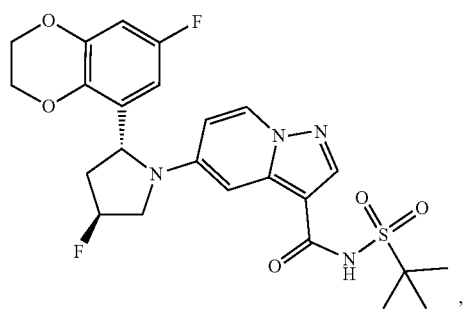
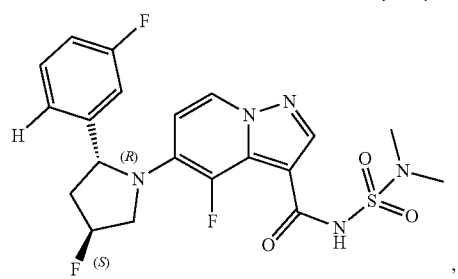
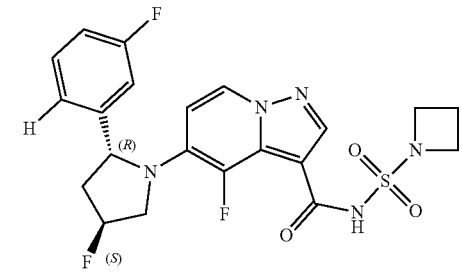
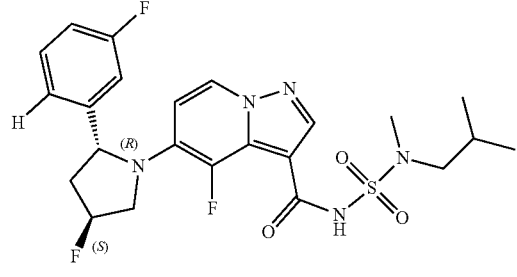
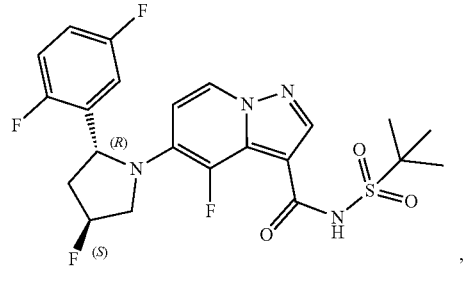
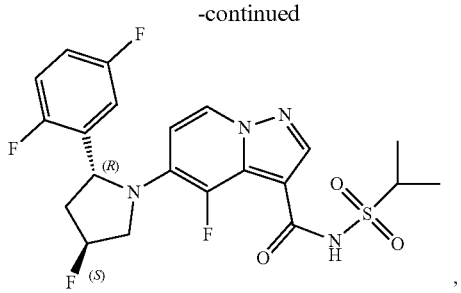
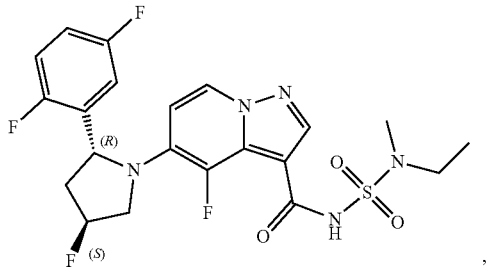
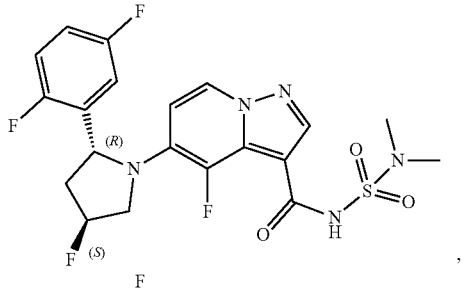
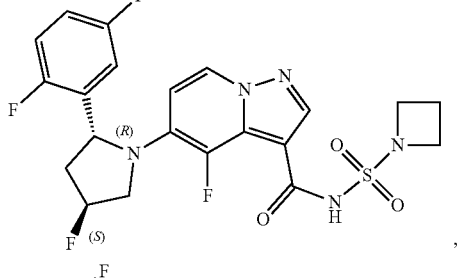
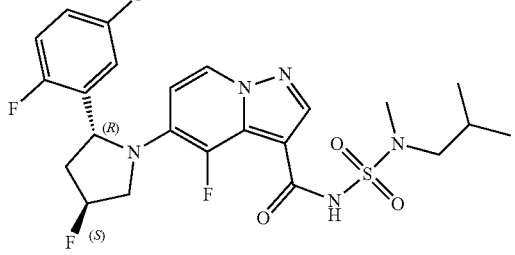
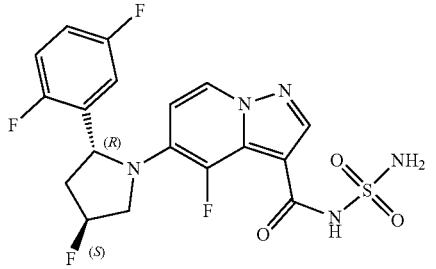
or a pharmaceutically acceptable salt thereof, or a pharmaceutically acceptable solvate thereof or a stereoisomer thereof.

16. A method for treating a cancer associated with a Trk kinase activity in a mammal in need thereof, the method comprising administering to the mammal a therapeutically effective amount of a compound

- (R)-5-(2-(2,5-difluorophenyl)pyrrolidin-1-yl)-N-((4-fluorophenyl)sulfonyl)pyrazolo [1,5-a]pyridine-3-carboxamide,
- (R)—N-(tert-butylsulfonyl)-5-(2-(2,5-difluorophenyl)pyrrolidin-1-yl)pyrazolo[1,5-a] pyridine-3-carboxamide,
- (R)-5-(2-(2,5-difluorophenyl)pyrrolidin-1-yl)-N-(ethylsulfonyl)pyrazolo[1,5-a] pyridine-3-carboxamide,
- (R)—N-((3-cyanophenyl)sulfonyl)-5-(2-(2,5-difluorophenyl)pyrrolidin-1-yl)pyrazolo [1,5-a] pyridine-3-carboxamide,
- (R)—N-(cyclopropylsulfonyl)-5-(2-(2,5-difluorophenyl)pyrrolidin-1-yl) pyrazolo[1,5-a]pyridine-3-carboxamide,
- (R)-5-(2-(2,5-difluorophenyl)pyrrolidin-1-yl)-N-(methylsulfonyl)pyrazolo[1,5-a] pyridine-3-carboxamide,
- (R)-5-(2-(2,5-difluorophenyl)pyrrolidin-1-yl)-N-(isopropylsulfonyl)pyrazolo[1,5-a] pyridine-3-carboxamide,
- 5-((R)-2-(2,5-difluorophenyl)pyrrolidin-1-yl)-N-((4-((S)-3-hydroxypyrrolidin-1-yl) phenyl) sulfonyl)pyrazolo [1, 5-a]pyridine-3-carboxamide,
- (R)—N-((3-cyanophenyl)sulfonyl)-5-(2-(2,5-difluorophenyl)pyrrolidin-1-yl)-N-methyl pyrazolo[1,5-a]pyridine-3-carboxamide,
- (R)-5-(2-(2,5-difluorophenyl)pyrrolidin-1-yl)-N-(propylsulfonyl)pyrazolo[1, 5-a] pyridine-3-carboxamide,
- (R)-5-(2-(2,5-difluorophenyl)pyrrolidin-1-yl)-N-((3,5-dimethyl isoxazol-4-yl) sulfonyl) pyrazolo [1, 5-a] pyridine-3-carboxamide,
- (R)—N-(cyclohexylsulfonyl)-5-(2-(2,5-difluorophenyl)pyrrolidin-1-yl)pyrazolo[1,5-a] pyridine-3-carboxamide,
- (R)—N-(cyclopentylsulfonyl)-5-(2-(2, 5-difluorophenyl)pyrrolidin-1-yl)pyrazolo[1,5-a] pyridine-3-carboxamide,
- (R)-5-(2-(2,5-difluorophenyl)pyrrolidin-1-yl)-N-(isobutylsulfonyl) pyrazolo[1, 5-a] pyridine-3-carboxamide,
- (R)-5-(2-(2,5-difluorophenyl) pyrrolidin-1-yl)-N-((1, 2-dimethyl-1H-imidazol-4-yl) sulfonyl) pyrazolo [1, 5-a] pyridine-3-carboxamide,
- (R)-5-(2-(2, 5-difluorophenyl) pyrrolidin-1-yl)-N-((1, 2-dimethyl-1H-imidazol-5-yl) sulfonyl) pyrazolo [1, 5-a] pyridine-3-carboxamide,
- (R)-5-(2-(2, 5-difluorophenyl) pyrrolidin-1-yl)-N-(piperidin-4-ylsulfonyl)pyrazolo [1, 5-a] pyridine-3-carboxamide,
- (R)-5-(2-(2, 5-difluorophenyl) pyrrolidin-1-yl)-N-((1-methyl-1H-imidazol-4-yl) sulfonyl) pyrazolo [1, 5-a] pyridine-3-carboxamide,
- (R)-5-(2-(2, 5-difluorophenyl) pyrrolidin-1-yl)-N-((1-methyl-1H-pyrazol-5-yl) sulfonyl) pyrazolo [1, 5-a] pyridine-3-carboxamide,
- (R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide,
- (R)-5-(2-(2, 5-difluorophenyl) pyrrolidin-1-yl)-N-((1-methyl-2-oxoindolin-5-yl) sulfonyl) pyrazolo [1, 5-a] pyridine-3-carboxamide,
- (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide,
- (R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide,
- 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide,
- 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide,
- (R)-5-(2-(2, 5-difluorophenyl) pyrrolidin-1-yl)-N-((6-methoxypyridin-3-yl) sulfonyl) pyrazolo [1, 5-a] pyridine-3-carboxamide,
- (R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide,
- (R)-5-(2-(2, 5-difluorophenyl) pyrrolidin-1-yl)-N-((1-methyl-1H-pyrazol-4-yl) sulfonyl) pyrazolo [1, 5-a] pyridine-3-carboxamide,
- (R)-5-(2-(2, 5-difluorophenyl) pyrrolidin-1-yl)-N-((4-morpholinophenyl) sulfonyl) pyrazolo [1, 5-a] pyridine-3-carboxamide,
- (R)-5-(2-(2,5-difluorophenyl)pyrrolidin-1-yl)-N-(pyridin-3-ylsulfonyl)pyrazolo[1,5-a]pyridine-3-carboxamide,
- (R)—N-((5-chlorothiophen-2-yl) sulfonyl)-5-(2-(2, 5-difluorophenyl) pyrrolidin-1-yl) pyrazolo [1, 5-a] pyridine-3-carboxamide,
- (R)—N-((2, 5-dichlorothiophen-3-yl) sulfonyl)-5-(2-(2, 5-difluorophenyl) pyrrolidin-1-yl) pyrazolo [1, 5-a] pyridine-3-carboxamide,
- (R)—N-(cyclobutylsulfonyl)-5-(2-(2, 5-difluorophenyl) pyrrolidin-1-yl) pyrazolo [1, 5-a] pyridine-3-carboxamide,
- (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide,
- (R)—N-(benzo[d][1,3]dioxol-5-ylsulfonyl)-5-(2-(2,5-difluorophenyl)pyrrolidin-1-yl) pyrazolo[1,5-a]pyridine-3-carboxamide,
- (R)-5-(2-(2,5-difluorophenyl)pyrrolidin-1-yl)-N-((1-ethylcyclopropyl)sulfonyl) pyrazolo[1,5-a]pyridine-3-carboxamide,
- (R)-5-(2-(2,5-difluorophenyl)pyrrolidin-1-yl)-N-(neopentylsulfonyl)pyrazolo[1,5-a]pyridine-3-carboxamide,
- (R)-5-(2-(2,5-difluorophenyl)pyrrolidin-1-yl)-N-((1-methylcyclopropyl)sulfonyl) pyrazolo[1,5-a]pyridine-3-carboxamide,
- (R)-5-(2-(2,5-difluorophenyl)pyrrolidin-1-yl)-N-(o-tolylsulfonyl)pyrazolo[1,5-a] pyridine-3-carboxamide,
- (R)—N-(benzylsulfonyl)-5-(2-(2,5-difluorophenyl)pyrrolidin-1-yl)pyrazolo[1,5-a] pyridine-3-carboxamide,
- (R)-5-(2-(2,5-difluorophenyl)pyrrolidin-1-yl)-N-((1-(4-fluorobenzyl)cyclopropyl) sulfonyl)pyrazolo[1,5-a]pyridine-3-carboxamide,
- (R)—N-(tert-butylsulfonyl)-5-(2-(5-fluoro-2-methoxyphenyl) pyrrolidin-1-yl) pyrazolo [1, 5-a] pyridine-3-carboxamide,
- (R)—N-(tert-butylsulfonyl)-5-(2-(3-(difluoromethoxy)-5-fluorophenyl) pyrrolidin-1-yl) pyrazolo [1, 5-a] pyridine-3-carboxamide,
- (R)—N-(tert-butylsulfonyl)-5-(2-(5-fluoropyridin-3-yl) pyrrolidin-1-yl) pyrazolo [1, 5-a]pyridine-3-carboxamide,
- (R)—N-(tert-butylsulfonyl)-5-(2-(2-ethoxy-5-fluorophenyl)pyrrolidin-1-yl) pyrazolo[1,5-a]pyridine-3-carboxamide, (R)—N-(tert-butylsulfonyl)-5-(2-(2-(cyclopropyl-methoxy)-5-fluorophenyl) pyrrolidin-1-yl)pyrazolo[1,5-a]pyridine-3-carboxamide,
(R)—N-(tert-butylsulfonyl)-5-(2-(2-chloro-5-fluorophenyl)pyrrolidin-1-yl) pyrazolo[1,5-a]pyridine-3-carboxamide,
N-(tert-butylsulfonyl)-5-((2R,4R)-2-(2,5-difluorophenyl)-4-hydroxypyrrolidin-1-yl) pyrazolo[1,5-a]pyridine-3-carboxamide,
(R)—N-(tert-butylsulfonyl)-5-(2-(5-fluoro-2-(2,2,2-trifluoroethoxy)phenyl) pyrrolidin-1-yl)pyrazolo[1,5-a]pyridine-3-carboxamide,
N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide (Isomer-I),
N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide (Isomer-II),
N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-I),
N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-II),
(R)—N-(tert-butylsulfonyl)-5-(2-(4,4'-difluoro-[1,1'-biphenyl]-2-yl)pyrrolidin-1-yl)pyrazolo[1,5-a] pyridine-3-carboxamide,
(S)—N-(tert-butylsulfonyl)-5-(2-(2, 5-difluorophenyl)-4,4-difluoropyrrolidin-1-yl) pyrazolo [1, 5-a] pyridine-3-carboxamide,
(R)—N-(tert-butylsulfonyl)-5-(2-(2, 5-difluorophenyl)-4,4-difluoropyrrolidin-1-yl) pyrazolo [1, 5-a] pyridine-3-carboxamide,
(R)—N-(tert-butylsulfonyl)-5-(2-(5-fluoro-2-(2-fluoroethoxy)phenyl)pyrrolidin-1-yl)pyrazolo[1,5-a]pyridine-3-carboxamide,
N-(tert-butylsulfonyl)-5-((2R,4R)-2-(2,5-difluorophenyl)-4-fluoropyrrolidin-1-yl)pyrazolo[1,5-a]pyridine-3-carboxamide,
N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide,
N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide,
(R)—N-(tert-butylsulfonyl)-5-(2-(2, 5-difluorophenyl) pyrrolidin-1-yl)-4-fluoro pyrazolo[1, 5-a] pyridine-3-carboxamide,
(R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide,
(R)—N-(tert-butylsulfonyl)-5-(2-(2-(difluoromethoxy)-5-fluorophenyl) pyrrolidin-1-yl) pyrazolo [1, 5-a] pyridine-3-carboxamide,
(R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide,
(R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide,
(R)—N-(tert-butylsulfonyl)-5-(2-(3, 5-difluorophenyl) pyrrolidin-1-yl) pyrazolo [1, 5-a] pyridine-3-carboxamide,
(R)—N-(tert-butylsulfonyl)-5-(2-(3-fluoro-5-(2-methoxyethoxy)phenyl)pyrrolidin-1-yl)pyrazolo[1,5-a]pyridine-3-carboxamide,
N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide,
(R)-5-(2-(3, 5-difluorophenyl) pyrrolidin-1-yl)-N-((4-fluorophenyl) sulfonyl) pyrazolo [1, 5-a] pyridine-3-carboxamide,
5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide,
(R)-5-(2-(3, 5-difluorophenyl) pyrrolidin-1-yl)-N-(isopropylsulfonyl) pyrazolo [1, 5-a] pyridine-3-carboxamide,
(R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide,
5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide,
5-((2R,4S)-2-(2,5-difluorophenyl)-4-fluoropyrrolidin-1-yl)-N-((1-methyl cyclopropyl)sulfonyl)pyrazolo[1,5-a] pyridine-3-carboxamide,
(R)-5-(2-(2, 5-difluorophenyl) pyrrolidin-1-yl)-4-fluoro-N-(isopropylsulfonyl) pyrazolo [1, 5-a] pyridine-3-carboxamide,
(R)-5-(2-(2, 5-difluorophenyl) pyrrolidin-1-yl)-N—(N,N-dimethylsulfamoyl) pyrazolo [1, 5-a] pyridine-3-carboxamide,
(R)-5-(2-(2,5-difluorophenyl)pyrrolidin-1-yl)-N—(N-ethyl-N-methylsulfamoyl) pyrazolo[1,5-a]pyridine-3-carboxamide,
5-((2R,4S)-2-(2,5-difluorophenyl)-4-fluoropyrrolidin-1-yl)-N—(N,N-dimethyl sulfamoyl)pyrazolo[1,5-a]pyridine-3-carboxamide,
5-((2R,4S)-2-(2,5-difluorophenyl)-4-fluoropyrrolidin-1-yl)-N—(N-ethyl-N-methyl sulfamoyl)pyrazolo[1,5-a]pyridine-3-carboxamide,
(R)—N—(N-(cyclopropylmethyl)-N-methylsulfamoyl)-5-(2-(2,5-difluorophenyl) pyrrolidin-1-yl)pyrazolo[1,5-a] pyridine-3-carboxamide,
(R)—N—(N,N-diethylsulfamoyl)-5-(2-(2,5-difluorophenyl)pyrrolidin-1-yl)pyrazolo[1,5-a]pyridine-3-carboxamide,
5-((2R,4S)-2-(2,5-difluorophenyl)-4-fluoropyrrolidin-1-yl)-N—(N,N-dimethyl sulfamoyl) pyrazolo[1,5-a]pyridine-3-carboxamide,
5-((2R,4S)-2-(2,5-difluorophenyl)-4-fluoropyrrolidin-1-yl)-N—(N-ethyl-N-methylsulfamoyl) pyrazolo[1,5-a] pyridine-3-carboxamide,
(R)-5-(2-(2,5-difluorophenyl)pyrrolidin-1-yl)-N-(morpholinosulfonyl) pyrazolo[1,5-a]pyridine-3-carboxamide,
(R)-5-(2-(2,5-difluorophenyl)pyrrolidin-1-yl)-N-(pyrrolidin-1-ylsulfonyl) pyrazolo[1,5-a]pyridine-3-carboxamide,
(R)-5-(2-(2,5-difluorophenyl)pyrrolidin-1-yl)-N-((4-methylpiperazin-1-yl) sulfonyl)pyrazolo[1,5-a]pyridine-3-carboxamide,
(R)—N—(N,N-diethylsulfamoyl)-5-(2-(5-fluoro-2-methoxyphenyl)pyrrolidin-1-yl) pyrazolo[1,5-a]pyridine-3-carboxamide,
(R)—N—(N,N-diethylsulfamoyl)-5-(2-(5-fluoro-2-(2-fluoroethoxy)phenyl) pyrrolidin-1-yl)pyrazolo[1,5-a]pyridine-3-carboxamide,
(R)-5-(2-(2,5-difluorophenyl)pyrrolidin-1-yl)-N-(piperidin-1-ylsulfonyl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy) phenyl)pyrrolidin-1-yl)pyrazolo[1,5-a]pyridine-3-carboxamide, 5-((R)-2-(2,5-difluorophenyl)pyrrolidin-1-yl)-N—(((S)-3-hydroxypyrrolidin-1-yl) sulfonyl)pyrazolo[1,5-a]pyridine-3-carboxamide, (R)-5-(2-(2,5-difluorophenyl)pyrrolidin-1-yl)-N-sulfamoylpyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo[1,5-a]pyridine-3-carboxamide, N—(N-ethyl-N-methylsulfamoyl)-5-(2-(8-fluoro-3,4-dihydro-2H-benzo[b][1,4] dioxepin-6-yl)pyrrolidin-1-yl)pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4] dioxepin-6-yl)pyrrolidin-1-yl)pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-4-fluoro-5-((2R,4S)-4-fluoro-2-(3-fluorophenyl)pyrrolidin-1-yl)pyrazolo[1,5-a]pyridine-3-carboxamide, N—(N-ethyl-N-methylsulfamoyl)-5-((R)-2-(3-fluoro-5-(((S)-tetrahydrofuran-3-yl)oxy)phenyl)pyrrolidin-1-yl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide, N—(N-ethyl-N-methylsulfamoyl)-5-((R)-2-(3-fluoro-5-(((R)-tetrahydrofuran-3-yl)oxy)phenyl)pyrrolidin-1-yl)pyrazolo[1,5-a]pyridine-3-carboxamide, 4-fluoro-5-((2R,4S)-4-fluoro-2-(3-fluorophenyl)pyrrolidin-1-yl)-N-sulfamoyl pyrazolo[1,5-a]pyridine-3-carboxamide, N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I), N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2);

(R)-5-(2-(2,5-difluorophenyl)pyrrolidin-1-yl)-N—(N-isobutyl-N-methyl sulfamoyl)pyrazolo[1,5-a]pyridine-3-carboxamide, (R)—N—(N-ethyl-N-methylsulfamoyl)-4-fluoro-5-(2-(3-fluorophenyl) pyrrolidin-1-yl)pyrazolo[1,5-a]pyridine-3-carboxamide, (R)—N—(N,N-dimethylsulfamoyl)-4-fluoro-5-(2-(3-fluorophenyl)pyrrolidin-1-yl) pyrazolo[1,5-a]pyridine-3-carboxamide, (R)—N—(N,N-dimethylsulfamoyl)-4-fluoro-5-(2-(3-fluorophenyl)pyrrolidin-1-yl) pyrazolo[1,5-a]pyridine-3-carboxamide, (R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, 5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide, (R)—N—(N, N-bis(cyclopropylmethyl)sulfamoyl)-5-(2-(2,5-difluorophenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy) phenyl)pyrrolidin-1-yl) pyrazolo[1,5-a]pyridine-3-carboxamide, N—(N-ethyl-N-methylsulfamoyl)-5-((2R)-2-(5-fluoro-2-((tetrahydrofuran-3-yl)oxy) phenyl)pyrrolidin-1-yl) pyrazolo[1,5-a]pyridine-3-carboxamide (Diastereomer-II), N-(tert-butylsulfonyl)-5-(2-(2,5-difluorophenyl)pyrrolidin-1-yl)pyrazolo[1,5-a] pyridine-3-carboxamide (Racemic mixture);

(R)—N-(tert-butylsulfonyl)-5-(2-(3,5-difluoro-2-methoxyphenyl)pyrrolidin-1-yl) pyrazolo[1,5-a]pyridine-3-carboxamide, N-(tert-butylsulfonyl)-4-fluoro-5-((2R,4S)-4-fluoro-2-(3-fluorophenyl)pyrrolidin-1-yl)pyrazolo[1,5-a]pyridine-3-carboxamide, 4-fluoro-5-((2R,4S)-4-fluoro-2-(3-fluorophenyl)pyrrolidin-1-yl)-N-(isopropyl sulfonyl)pyrazolo[1,5-a]pyridine-3-carboxamide, (R)—N-(tert-butylsulfonyl)-5-(2-(3,5-difluoro-2-((tetrahydro-2H-pyran-4-yl)oxy) phenyl)pyrrolidin-1-yl) pyrazolo[1,5-a]pyridine-3-carboxamide, (R)—N-(tert-butylsulfonyl)-5-(2-(5-fluoro-2-((tetrahydro-2H-pyran-4-yl)oxy) phenyl)pyrrolidin-1-yl) pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide, (R)-4-fluoro-5-(2-(3-fluorophenyl)pyrrolidin-1-yl)-N-(isopropylsulfonyl)pyrazolo [1,5-a]pyridine-3-carboxamide, (R)—N-(tert-butylsulfonyl)-4-fluoro-5-(2-(5-fluoro-2-((tetrahydro-2H-pyran-4-yl) oxy)phenyl)pyrrolidin-1-yl)pyrazolo[1,5-a]pyridine-3-carboxamide, Sodium (tert-butylsulfonyl)(5-((2R,4S)-2-(2,5-difluorophenyl)-4-fluoropyrrolidin-1-yl) pyrazolo[1,5-a]pyridine-3-carbonyl)amide, Sodium(R)-(tert-butylsulfonyl)(5-(2-(2,5-difluorophenyl)pyrrolidin-1-yl) pyrazolo [1,5-a] pyridine-3-carbonyl)amide, Sodium (R)-(tert-butylsulfonyl)(5-(2-(7-fluoro-2,3-dihydrobenzo[b][1,4]dioxin-5-yl)pyrrolidin-1-yl)pyrazolo [1,5-a]pyridine-3-carbonyl)amide, Sodium (tert-butylsulfonyl)(5-((2R,4R)-2-(2,5-difluorophenyl)-4-fluoropyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl) (N,N-dimethylsulfamoyl)amide, Sodium (tert-butylsulfonyl)(5-(2-(2,5-difluorophenyl)-4,4-difluoropyrrolidin-1-yl)pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl)((1-methylcyclopropyl) sulfonyl)amide, Sodium (tert-butylsulfonyl)(5-((2R)-2-(2,5-difluorophenyl)-4-fluoropyrrolidin-1-yl)pyrazolo [1,5-a]pyridine-3-carbonyl)amide, Sodium (5-((2R,4S)-2-(2,5-difluorophenyl)-4-fluoropyrrolidin-1-yl)pyrazolo[1,5-a]pyridine-3-carbonyl)(N,N-dimethylsulfamoyl)amide, Sodium (tert-butylsulfonyl)(4-fluoro-5-((2R,4S)-4-fluoro-2-(3-fluorophenyl) pyrrolidin-1-yl)pyrazolo[1,5-a]pyridine-3-carbonyl)amide, Sodium (R)—(N,N-dimethylsulfamoyl)(4-fluoro-5-(2-(3-fluorophenyl)pyrrolidin-1-yl)pyrazolo [1,5-a]pyridine-3-carbonyl)amide, Sodium (N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl)(o-tolylsulfonyl)amide, Sodium (4-fluoro-5-((2R,4S)-4-fluoro-2-(3-fluorophenyl) pyrrolidin-1-yl) pyrazolo[1,5-a]pyridine-3-carbonyl) (isopropylsulfonyl)amide, Sodium (5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, Sodium (R)-(5-(2-(2,5-difluorophenyl) pyrrolidin-1-yl) pyrazolo[1,5-a]pyridine-3-carbonyl)(piperidin-1-ylsulfonyl)amide;

(R)-5-(2-(2,5-difluorophenyl)pyrrolidin-1-yl)-N-((4-fluorophenyl)sulfonyl)pyrazolo[1,5-a] pyridine-3-carboxamide, (R)—N-((3-cyanophenyl)sulfonyl)-5-(2-(2,5-difluorophenyl)pyrrolidin-1-yl)pyrazolo[1,5-a] pyridine-3-carboxamide, 5-((R)-2-(2,5-difluorophenyl)pyrrolidin-1-yl)-N-((4-((S)-3-hydroxypyrrolidin-1-yl) phenyl) sulfonyl) pyrazolo [1, 5-a] pyridine-3-carboxamide, (R)—N-((3-cyanophenyl) sulfonyl)-5-(2-(2, 5-difluorophenyl) pyrrolidin-1-yl)-N-methylpyrazolo [1, 5-a] pyridine-3-carboxamide, (R)-5-(2-(2, 5-difluorophenyl) pyrrolidin-1-yl)-N-((4-morpholinophenyl) sulfonyl) pyrazolo [1, 5-a] pyridine-3-carboxamide, (R)-5-(2-(2,5-difluorophenyl)pyrrolidin-1-yl)-N-(o-tolylsulfonyl)pyrazolo[1,5-a]pyridine-3-carboxamide, (R)-5-(2-(3, 5-difluorophenyl) pyrrolidin-1-yl)-N-((4-fluorophenyl) sulfonyl) pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, Sodium(R)-(5-(2-(2,5-difluorophenyl)pyrrolidin-1-yl) pyrazolo[1,5-a]pyridine-3-carbonyl) (piperidin-1-ylsulfonyl)amide, Sodium(R)-(5-(2-(2,5-difluorophenyl)pyrrolidin-1-yl) pyrazolo[1,5-a]pyridine-3-carbonyl) (o-tolylsulfonyl)amide;

(R)—N-(tert-butylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-(ethylsulfonyl)pyrazolo[1,5-a]pyridine-3-carboxamide, (R)-5-(2-(2,5-difluorophenyl)pyrrolidin-1-yl)-N-(methylsulfonyl)pyrazolo[1,5-a] pyridine-3-carboxamide, (R)-5-(2-(2, 5-difluorophenyl) pyrrolidin-1-yl)-N-(isopropylsulfonyl)pyrazolo[1, 5-a] pyridine-3-carboxamide, (R)-5-(2-(2, 5-difluorophenyl) pyrrolidin-1-yl)-N-(propylsulfonyl)pyrazolo[1, 5-a] pyridine-3-carboxamide, (R)-5-(2-(2, 5-difluorophenyl) pyrrolidin-1-yl)-N-(isobutylsulfonyl)pyrazolo[1, 5-a] pyridine-3-carboxamide, (R)-5-(2-(2,5-difluorophenyl)pyrrolidin-1-yl)-N-(neopentylsulfonyl)pyrazolo[1,5-a] pyridine-3-carboxamide, (R)—N-(benzylsulfonyl)-5-(2-(2,5-difluorophenyl)pyrrolidin-1-yl) pyrazolo[1,5-a]pyridine-3-carboxamide, (R)—N-(tert-butylsulfonyl)-5-(2-(5-fluoro-2-methoxyphenyl) pyrrolidin-1-yl)pyrazolo [1,5-a] pyridine-3-carboxamide, (R)—N-(tert-butylsulfonyl)-5-(2-(3-(difluoromethoxy)-5-fluorophenyl)pyrrolidin-1-yl) pyrazolo [1, 5-a] pyridine-3-carboxamide, (R)—N-(tert-butylsulfonyl)-5-(2-(5-fluoropyridin-3-yl) pyrrolidin-1-yl)pyrazolo [1, 5-a] pyridine-3-carboxamide, (R)—N-(tert-butylsulfonyl)-5-(2-(2-ethoxy-5-fluorophenyl)pyrrolidin-1-yl) pyrazolo[1,5-a] pyridine-3-carboxamide, (R)—N-(tert-butylsulfonyl)-5-(2-(2-(cyclopropylmethoxy)-5-fluorophenyl)pyrrolidin-1-yl) pyrazolo[1, 5-a]pyridine-3-carboxamide, (R)—N-(tert-butylsulfonyl)-5-(2-(2-chloro-5-fluorophenyl)pyrrolidin-1-yl)pyrazolo[1,5-a]pyridine-3-carboxamide, N-(tert-butylsulfonyl)-5-((2R,4R)-2-(2,5-difluorophenyl)-4-hydroxypyrrolidin-1-yl)pyrazolo[1,5-a]pyridine-3-carboxamide, N-(tert-butylsulfonyl)-5-((2R,4S)-2-(2,5-difluorophenyl)-4-fluoropyrrolidin-1-yl)pyrazolo [1,5-a]pyridine-3-carboxamide, (R)—N-(tert-butylsulfonyl)-5-(2-(4,4'-difluoro-[1,1'-biphenyl]-2-yl)pyrrolidin-1-yl) pyrazolo[1,5-a]pyridine-3-carboxamide, (R)—N-(tert-butylsulfonyl)-5-(2-(5-fluoro-2-(2-fluoroethoxy)phenyl)pyrrolidin-1-yl) pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, (R)—N-(tert-butylsulfonyl)-5-(2-(2, 5-difluorophenyl) pyrrolidin-1-yl)-4-fluoro pyrazolo[1, 5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide,

- (R)—N-(tert-butylsulfonyl)-5-(2-(5-fluoro-2-(2-methoxyethoxy) phenyl) pyrrolidin-1-yl) pyrazolo [1,5-a] pyridine-3-carboxamide,
- (R)—N-(tert-butylsulfonyl)-5-(2-(3, 5-difluorophenyl) pyrrolidin-1-yl) pyrazolo [1, 5-a] pyridine-3-carboxamide,
- (R)—N-(tert-butylsulfonyl)-5-(2-(3-fluoro-5-(2-methoxyethoxy)phenyl)pyrrolidin-1-yl)pyrazolo[1,5-a]pyridine-3-carboxamide,
- N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide,
- (R)-5-(2-(3, 5-difluorophenyl) pyrrolidin-1-yl)-N-(isopropylsulfonyl) pyrazolo [1, 5-a] pyridine-3-carboxamide,
- N-(tert-butylsulfonyl)-5-(2-(2,5-difluorophenyl)pyrrolidin-1-yl)pyrazolo[1,5-a]pyridine-3-carboxamide (Racemic mixture),
- (R)—N-(tert-butylsulfonyl)-5-(2-(3,5-difluoro-2-methoxyphenyl)pyrrolidin-1-yl)pyrazolo[1,5-a]pyridine-3-carboxamide,
- (R)—N-(tert-butylsulfonyl)-5-(2-(3,5-difluoro-2-((tetrahydro-2H-pyran-4-yl)oxy)phenyl)pyrrolidin-1-yl)pyrazolo[1,5-a]pyridine-3-carboxamide,
- (R)—N-(tert-butylsulfonyl)-5-(2-(5-fluoro-2-((tetrahydro-2H-pyran-4-yl)oxy)phenyl)pyrrolidin-1-yl)pyrazolo[1,5-a]pyridine-3-carboxamide,
- (R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide,
- (R)-4-fluoro-5-(2-(3-fluorophenyl)pyrrolidin-1-yl)-N-(isopropylsulfonyl)pyrazolo[1,5-a]pyridine-3-carboxamide,
- (R)—N-(tert-butylsulfonyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
- Sodium(tert-butylsulfonyl)(5-((2R,4R)-2-(2,5-difluorophenyl)-4-fluoropyrrolidin-1-yl)pyrazolo[1,5-a]pyridine-3-carbonyl)amide,
- Sodium(tert-butylsulfonyl)(5-((2R,4S)-2-(2,5-difluorophenyl)-4-fluoropyrrolidin-1-yl)pyrazolo[1,5-a]pyridine-3-carbonyl)amide,
- Sodium(R)-(tert-butylsulfonyl)(5-(2-(2,5-difluorophenyl)pyrrolidin-1-yl)pyrazolo[1,5-a] pyridine-3-carbonyl) amide,
- Sodium(R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide;
- (R)—N-(cyclopropylsulfonyl)-5-(2-(2,5-difluorophenyl) pyrrolidin-1-yl) pyrazolo[1,5-a]pyridine-3-carboxamide,
- (R)—N-(cyclohexyl sulfonyl)-5-(2-(2, 5-difluorophenyl) pyrrolidin-1-yl) pyrazolo [1, 5-a] pyridine-3-carboxamide,
- (R)—N-(cyclopentyl sulfonyl)-5-(2-(2, 5-difluorophenyl) pyrrolidin-1-yl) pyrazolo [1, 5-a] pyridine-3-carboxamide,
- (R)—N-(cyclobutylsulfonyl)-5-(2-(2, 5-difluorophenyl) pyrrolidin-1-yl) pyrazolo [1, 5-a] pyridine-3-carboxamide,
- (R)-5-(2-(2,5-difluorophenyl)pyrrolidin-1-yl)-N-((1-ethylcyclopropyl)sulfonyl) pyrazolo[1,5-a]pyridine-3-carboxamide,
- (R)-5-(2-(2,5-difluorophenyl)pyrrolidin-1-yl)-N-((1-methylcyclopropyl)sulfonyl)pyrazolo [1,5-a]pyridine-3-carboxamide,
- (R)-5-(2-(2,5-difluorophenyl)pyrrolidin-1-yl)-N-((1-(4-fluorobenzyl)cyclopropyl)sulfonyl) pyrazolo[1,5-a]pyridine-3-carboxamide,
- (R)-5-(2-(2, 5-difluorophenyl) pyrrolidin-1-yl)-4-fluoro-N-(isopropylsulfonyl)pyrazolo [1, 5-a] pyridine-3-carboxamide,
- Sodium(R)-(5-(2-(2,5-difluorophenyl)pyrrolidin-1-yl)pyrazolo[1,5-a]pyridine-3-carbonyl)((1-methylcyclopropyl) sulfonyl)amide;
- (R)-5-(2-(2,5-difluorophenyl) pyrrolidin-1-yl)-N-((3,5-dimethylisoxazol-4-yl)sulfonyl) pyrazolo [1, 5-a] pyridine-3-carboxamide,
- (R)-5-(2-(2,5-difluorophenyl) pyrrolidin-1-yl)-N-((1,2-dimethyl-1H-imidazol-4-yl) sulfonyl) pyrazolo [1, 5-a] pyridine-3-carboxamide,
- (R)-5-(2-(2,5-difluorophenyl) pyrrolidin-1-yl)-N-((1,2-dimethyl-1H-imidazol-5-yl) sulfonyl) pyrazolo [1, 5-a] pyridine-3-carboxamide,
- (R)-5-(2-(2,5-difluorophenyl) pyrrolidin-1-yl)-N-((1-methyl-1H-imidazol-4-yl) sulfonyl) pyrazolo [1, 5-a] pyridine-3-carboxamide,
- (R)-5-(2-(2,5-difluorophenyl) pyrrolidin-1-yl)-N-((1-methyl-1H-pyrazol-5-yl) sulfonyl) pyrazolo [1, 5-a] pyridine-3-carboxamide,
- (R)-5-(2-(2, 5-difluorophenyl) pyrrolidin-1-yl)-N-((2,4-dimethylthiazol-5-yl) sulfonyl) pyrazolo [1, 5-a] pyridine-3-carboxamide,
- (R)-5-(2-(2,5-difluorophenyl)pyrrolidin-1-yl)-N-((1-methyl-2-oxoindolin-5-yl)sulfonyl)pyrazolo [1, 5-a] pyridine-3-carboxamide,
- (R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide,
- 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide,
- (R)-5-(2-(2, 5-difluorophenyl) pyrrolidin-1-yl)-N-((6-methoxypyridin-3-yl) sulfonyl) pyrazolo [1, 5-a] pyridine-3-carboxamide,
- (R)—N-((6-(1H-1, 2,4-triazol-1-yl)pyridin-3-yl)sulfonyl)-5-(2-(2,5-difluorophenyl) pyrrolidin-1-yl) pyrazolo [1, 5-a] pyridine-3-carboxamide,
- (R)-5-(2-(2,5-difluorophenyl) pyrrolidin-1-yl)-N-((1-methyl-1H-pyrazol-4-yl) sulfonyl) pyrazolo [1, 5-a] pyridine-3-carboxamide,
- (R)-5-(2-(2,5-difluorophenyl)pyrrolidin-1-yl)-N-(pyridin-3-ylsulfonyl)pyrazolo[1,5-a]pyridine-3-carboxamide,
- (R)—N-((5-chlorothiophen-2-yl) sulfonyl)-5-(2-(2, 5-difluorophenyl) pyrrolidin-1-yl) pyrazolo [1, 5-a] pyridine-3-carboxamide,
- (R)—N-((2,5-dichlorothiophen-3-yl) sulfonyl)-5-(2-(2, 5-difluorophenyl) pyrrolidin-1-yl) pyrazolo [1, 5-a] pyridine-3-carboxamide,
- (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide,
- (R)—N-(benzo[d][1,3]dioxol-5-ylsulfonyl)-5-(2-(2,5-difluorophenyl)pyrrolidin-1-yl) pyrazolo[1,5-a]pyridine-3-carboxamide,
- (R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide,
- 5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide;

(R)-5-(2-(2, 5-difluorophenyl) pyrrolidin-1-yl)-N-(piperidin-4-ylsulfonyl) pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl) pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo [1,5-a]pyridine-3-carboxamide, (R)-5-(2-(2,5-difluorophenyl)pyrrolidin-1-yl)-N-(piperidin-1-ylsulfonyl)pyrazolo[1,5-a]pyridine-3-carboxamide, 5-((R)-2-(2,5-difluorophenyl)pyrrolidin-1-yl)-N—(((S)-3-hydroxypyrrolidin-1-yl) sulfonyl) pyrazolo[1,5-a]pyridine-3-carboxamide;

(R)—N-(tert-butylsulfonyl)-5-(2-(5-fluoro-2-(2,2,2-trifluoroethoxy)phenyl)pyrrolidin-1-yl) pyrazolo[1,5-a]pyridine-3-carboxamide, N-(tert-butylsulfonyl)-5-(2-(7-fluoro-2,3-dihydrobenzo[b][1,4]dioxin-5-y)pyrrolidin-1-yl)pyrazolo[1,5-a]pyridine-3-carboxamide, N-(tert-butylsulfonyl)-5-(2-(7-fluoro-2,3-dihydrobenzo[b][1,4]dioxin-5-y)pyrrolidin-1-yl)pyrazolo[1,5-a]pyridine-3-carboxamide, N-(tert-butylsulfonyl)-5-((2R,4S)-2-(2, 5-difluorophenyl)-4-fluoropyrrolidin-1-yl)pyrazolo[1,5-a]pyridine-3-carboxamide, N-(tert-butylsulfonyl)-5-((2R,4R)-2-(2,5-difluorophenyl)-4-fluoropyrrolidin-1-yl)pyrazolo[1,5-a]pyridine-3-carboxamide, 5-((2R,4S)-2-(2,5-difluorophenyl)-4-fluoropyrrolidin-1-yl)-N-((1-methyl cyclopropyl) sulfonyl)pyrazolo[1,5-a]pyridine-3-carboxamide, 5-((2R,4S)-2-(2,5-difluorophenyl)-4-fluoropyrrolidin-1-yl)-N—(N,N-dimethylsulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethylsulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, N—(N-ethyl-N-methylsulfamoyl)-4-fluoro-5-((2R,4S)-4-fluoro-2-(3-fluorophenyl) pyrrolidin-1-yl)pyrazolo[1,5-a]pyridine-3-carboxamide, N-(tert-butylsulfonyl)-4-fluoro-5-((2R,4S)-4-fluoro-2-(3-fluorophenyl)pyrrolidin-1-yl)pyrazolo [1,5-a]pyridine-3-carboxamide, 4-fluoro-5-((2R,4S)-4-fluoro-2-(3-fluorophenyl)pyrrolidin-1-yl)-N-(isopropylsulfonyl) pyrazolo[1,5-a]pyridine-3-carboxamide, Sodium(4-fluoro-5-((2R,4S)-4-fluoro-2-(3-fluorophenyl) pyrrolidin-1-yl)pyrazolo[1,5-a]pyridine-3-carbonyl)(isopropylsulfonyl)amide, Sodium(5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, Sodium(tert-butylsulfonyl)(5-((2R)-2-(2,5-difluorophenyl)-4-fluoropyrrolidin-1-yl)pyrazolo[1,5-a]pyridine-3-carbonyl)amide, Sodium(5-((2R,4S)-2-(2,5-difluorophenyl)-4-fluoropyrrolidin-1-yl)pyrazolo[1,5-a]pyridine-3-carbonyl)(N,N-dimethylsulfamoyl)amide, Sodium(tert-butylsulfonyl)(4-fluoro-5-((2R,4S)-4-fluoro-2-(3-fluorophenyl)pyrrolidin-1-yl)pyrazolo[1,5-a]pyridine-3-carbonyl)amide, Sodium (tert-butylsulfonyl)(5-(2-(2,5-difluorophenyl)-4,4-difluoropyrrolidin-1-yl) pyrazolo[1,5-a]pyridine-3-carbonyl)amide;

(R)-5-(2-(2,5-difluorophenyl) pyrrolidin-1-yl)-N—(N,N-dimethylsulfamoyl)pyrazolo[1,5-a] pyridine-3-carboxamide, (R)-5-(2-(2,5-difluorophenyl)pyrrolidin-1-yl)-N—(N-ethyl-N-methylsulfamoyl)pyrazolo [1,5-a]pyridine-3-carboxamide, (R)—N—(N-(cyclopropylmethyl)-N-methylsulfamoyl)-5-(2-(2,5-difluorophenyl)pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl) pyrazolo[1,5-a]pyridine-3-carboxamide, (R)—N—(N,N-diethylsulfamoyl)-5-(2-(5-fluoro-2-methoxyphenyl)pyrrolidin-1-yl)pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy)phenyl)pyrrolidin-1-yl)pyrazolo[1, 5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo [1,5-a]pyridine-3-carboxamide, (R)-5-(2-(2,5-difluorophenyl)pyrrolidin-1-yl)-N-sulfamoylpyrazolo[1,5-a]pyridine-3-carboxamide, N—(N-ethyl-N-methylsulfamoyl)-5-((R)-2-(3-fluoro-5-(((S)-tetrahydrofuran-3-yl)oxy) phenyl)pyrrolidin-1-yl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide, N—(N-ethyl-N-methylsulfamoyl)-5-((R)-2-(3-fluoro-5-(((R)-tetrahydrofuran-3-yl)oxy)phenyl)pyrrolidin-1-yl) pyrazolo[1,5-a]pyridine-3-carboxamide, 4-fluoro-5-((2R,4S)-4-fluoro-2-(3-fluorophenyl)pyrrolidin-1-yl)-N-sulfamoylpyrazolo[1,5-a]pyridine-3-carboxamide, N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I), (R)-5-(2-(2,5-difluorophenyl)pyrrolidin-1-yl)-N—(N-isobutyl-N-methylsulfamoyl)pyrazolo[1,5-a]pyridine-3-carboxamide, (R)—N—(N-ethyl-N-methylsulfamoyl)-4-fluoro-5-(2-(3-fluorophenyl) pyrrolidin-1-yl) pyrazolo[1,5-a]pyridine-3-carboxamide, (R)—N—(N,N-dimethylsulfamoyl)-4-fluoro-5-(2-(3-fluorophenyl)pyrrolidin-1-yl)pyrazolo[1,5-a]pyridine-3-carboxamide, (R)—N—(N,N-dimethylsulfamoyl)-4-fluoro-5-(2-(3-fluorophenyl)pyrrolidin-1-yl)pyrazolo[1,5-a]pyridine-3-carboxamide, (R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, 5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide, (R)—N—(N, N-bis(cyclopropylmethyl)sulfamoyl)-5-(2-(2,5-difluorophenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, Sodium(R)—(N,N-dimethylsulfamoyl)(4-fluoro-5-(2-(3-fluorophenyl)pyrrolidin-1-yl)pyrazolo[1,5-a]pyridine-3-carbonyl)amide, Sodium(N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl)(N,N-dimethylsulfamoyl)amide, N—(N-ethyl-N-methylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2), (R)-5-(2-(2,5-difluorophenyl)pyrrolidin-1-yl)-N—(N-(2-methoxyethyl)-N-methylsulfamoyl)pyrazolo[1,5-a]pyridine-3-carboxamide, (R)—N—(N-cyclopropyl-N-methylsulfamoyl)-5-(2-(2,5-difluorophenyl)pyrrolidin-1-yl)pyrazolo[1,5-a]pyridine-3-carboxamide, (R)—N—(N-ethyl-N-methylsulfamoyl)-5-(2-(5-fluoro-2-methylphenyl) pyrrolidin-1-yl)pyrazolo[1,5-a]pyridine-3-carboxamide, (R)—N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide, N-(tert-butylsulfonyl)-5-((2R,4S)-4-fluoro-2-(3-fluoro-5-((tetrahydro-2H-pyran-4-yl)oxy)phenyl)pyrrolidin-1-yl)pyrazolo[1,5-a]pyridine-3-carboxamide, N—(N-ethyl-N-methylsulfamoyl)-5-((2R,4S)-4-fluoro-2-(3-fluoro-5-((tetrahydro-2H-pyran-4-yl)oxy)phenyl)pyrrolidin-1-yl)pyrazolo[1,5-a]pyridine-3-carboxamide;

N-(tert-butylsulfonyl)-5-((2R,4S)-4-fluoro-2-(5-fluoro-2-((tetrahydro-2H-pyran-4-yl)oxy)phenyl)pyrrolidin-1-yl)pyrazolo[1,5-a]pyridine-3-carboxamide, N—(N-ethyl-N-methylsulfamoyl)-5-((2R,4S)-4-fluoro-2-(5-fluoro-2-((tetrahydro-2H-pyran-4-yl)oxy)phenyl)pyrrolidin-1-yl)pyrazolo[1,5-a]pyridine-3-carboxamide, 5-((2R,4S)-4-fluoro-2-(5-fluoro-2-((tetrahydro-2H-pyran-4-yl)oxy)phenyl)pyrrolidin-1-yl)-N-(isopropylsulfonyl)pyrazolo[1,5-a]pyridine-3-carboxamide, 5-((2R,4S)-2-(2-(cyclopropylmethoxy)-5-fluorophenyl)-4-fluoropyrrolidin-1-yl)-N—(N-ethyl-N-methylsulfamoyl)pyrazolo[1,5-a]pyridine-3-carboxamide, N-(tert-butylsulfonyl)-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide N—(N-ethyl-N-methylsulfamoyl)-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide, 5-((2R,4S)-2-(2-(cyclopropylmethoxy)-5-fluorophenyl)-4-fluoropyrrolidin-1-yl)-N—(N-ethyl-N-methylsulfamoyl)-4-fluoropyrazolo[1,5-a]pyridine-3-carboxamide, N-(tert-butylsulfonyl)-5-((2R,4S)-2-(2-(cyclopropylmethoxy)-5-fluorophenyl)-4-fluoropyrrolidin-1-yl)pyrazolo[1,5-a]pyridine-3-carboxamide, (R)-5-(2-(2,5-difluorophenyl)pyrrolidin-1-yl)-N—(N-ethyl sulfamoyl)pyrazolo[1,5-a]pyridine-3-carboxamide, (R)-5-(2-(2,5-difluorophenyl)pyrrolidin-1-yl)-N—(N-methyl sulfamoyl)pyrazolo[1,5-a]pyridine-3-carboxamide, (R)-5-(2-(2,5-difluorophenyl)pyrrolidin-1-yl)-N—(N-(2-fluoroethyl)-N-methylsulfamoyl)pyrazolo[1,5-a]pyridine-3-carboxamide, (R)-5-(2-(2,5-difluorophenyl)pyrrolidin-1-yl)-N—(N-(2-hydroxyethyl)-N-methylsulfamoyl)pyrazolo[1,5-a]pyridine-3-carboxamide, (R)—N-(azetidin-1-ylsulfonyl)-5-(2-(2,5-difluorophenyl)pyrrolidin-1-yl)pyrazolo[1,5-a]pyridine-3-carboxamide, N-(tert-butylsulfonyl)-5-((2R,4S)-4-fluoro-2-(7-fluoro-2,3-dihydrobenzo[b][1,4]dioxin-5-yl)pyrrolidin-1-yl)pyrazolo[1,5-a]pyridine-3-carboxamide, (R)—N—(N-(2-cyanoethyl)-N-methylsulfamoyl)-5-(2-(2,5-difluorophenyl) pyrrolidin-1-yl)pyrazolo[1,5-a]pyridine-3-carboxamide, N-(tert-butylsulfonyl)-4-fluoro-5-((2R,4S)-4-fluoro-2-(7-fluoro-2,3-dihydrobenzo[b][1,4]dioxin-5-yl)pyrrolidin-1-yl)pyrazolo[1,5-a]pyridine-3-carboxamide, N—(N,N-dimethylsulfamoyl)-4-fluoro-5-((2R,4S)-4-fluoro-2-(3-fluorophenyl)pyrrolidin-1-yl)pyrazolo[1,5-a]pyridine-3-carboxamide, N—(N-ethyl-N-methylsulfamoyl)-5-((2R)-2-(7-fluoro-3-(fluoromethyl)-2,3-dihydrobenzo[b][1,4]dioxin-5-yl)pyrrolidin-1-yl)pyrazolo[1,5-a]pyridine-3-carboxamide, (R)—N—(N-ethyl-N-methylsulfamoyl)-5-(2-(3-fluorophenyl)pyrrolidin-1-yl)pyrazolo[1,5-a]pyridine-3-carboxamide, 5-((2R,4S)-4-fluoro-2-(3-fluoro-5-((tetrahydro-2H-pyran-4-yl)oxy)phenyl)pyrrolidin-1-yl)-N-(isopropylsulfonyl)pyrazolo[1,5-a]pyridine-3-carboxamide, 5-((2R,4S)-2-(3-(cyclopropylmethoxy)-5-fluorophenyl)-4-fluoropyrrolidin-1-yl)-N—(N-ethyl-N-methylsulfamoyl)pyrazolo[1,5-a]pyridine-3-carboxamide, N-(tert-butylsulfonyl)-5-((2R,4S)-2-(2-cyclopropoxy-5-fluorophenyl)-4-fluoropyrrolidin-1-yl)pyrazolo[1,5-a]pyridine-3-carboxamide, 5-((2R,4S)-2-(2-cyclopropoxy-5-fluorophenyl)-4-fluoropyrrolidin-1-yl)-N—(N-ethyl-N-methylsulfamoyl)pyrazolo[1,5-a]pyridine-3-carboxamide, N—(N-ethyl-N-methylsulfamoyl)-4-fluoro-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide, 5-((2R,4S)-2-(2-cyclopropoxy-5-fluorophenyl)-4-fluoropyrrolidin-1-yl)-N—(N-ethyl-N-methylsulfamoyl)-4-fluoropyrazolo[1,5-a]pyridine-3-carboxamide, (R)—N—(N-ethyl-N-methylsulfamoyl)-5-(2-(8-fluoro-2,3-dihydrobenzo[b][1,4]dioxin-6-yl)pyrrolidin-1-yl)pyrazolo[1,5-a]pyridine-3-carboxamide, (R)-5-(2-(8-fluoro-2,3-dihydrobenzo[b][1,4]dioxin-6-yl)pyrrolidin-1-yl)-N-(isopropylsulfonyl)pyrazolo[1,5-a]pyridine-3-carboxamide, N-(tert-butylsulfonyl)-5-(2-(8-fluoro-2,3-dihydrobenzo[b][1,4]dioxin-6-y)pyrrolidin-1-yl)pyrazolo[1,5-a]pyridine-3-carboxamide, N—(N-ethyl-N-methylsulfamoyl)-5-(2-(9-fluoro-3,4-dihydro-2H-benzo[b][1,4]dioxepin-7-yl)pyrrolidin-1-yl)pyrazolo[1,5-a]pyridine-3-carboxamide, N—(N,N-dimethylsulfamoyl)-5-(2-(8-fluoro-2,3-dihydrobenzo[b][1,4]dioxin-6-yl)pyrrolidin-1-yl)pyrazolo[1,5-a]pyridine-3-carboxamide, (R)—N—(N,N-dimethylsulfamoyl)-5-(2-(9-fluoro-3,4-dihydro-2H-benzo[b][1,4]dioxepin-7-yl)pyrrolidin-1-yl)pyrazolo[1,5-a]pyridine-3-carboxamide, N-(tert-butylsulfonyl)-5-((2R,4S)-4-fluoro-2-(6-fluorobenzo[d][1,3]dioxol-4-yl)pyrrolidin-1-yl)pyrazolo[1,5-a]pyridine-3-carboxamide, N—(N-ethyl-N-methylsulfamoyl)-5-((2R,4S)-4-fluoro-2-(6-fluorobenzo[d][1,3]dioxol-4-yl)pyrrolidin-1-yl)pyrazolo[1,5-a]pyridine-3-carboxamide, (R)-5-(2-(2,5-difluorophenyl)pyrrolidin-1-yl)-N—(N-((1-(hydroxymethyl)cyclo butyl)methyl)-N-methylsulfamoyl)pyrazolo[1,5-a]pyridine-3-carboxamide, (R)—N—(N-ethyl-N-methylsulfamoyl)-5-(2-(5-fluoro-2-((4-methyltetrahydro-2H-pyran-4-yl)oxy)phenyl)pyrrolidin-1-yl)pyrazolo[1,5-a]pyridine-3-carboxamide, (R)—N-(tert-butylsulfonyl)-5-(2-(5-fluoro-2-((4-methyltetrahydro-2H-pyran-4-yl)oxy)phenyl)pyrrolidin-1-yl)pyrazolo[1,5-a]pyridine-3-carboxamide, (R)-5-(2-(5-fluoro-2-((4-methyltetrahydro-2H-pyran-4-yl)oxy)phenyl)pyrrolidin-1-yl)-N-(isopropylsulfonyl)pyrazolo[1,5-a]pyridine-3-carboxamide, N-(tert-butylsulfonyl)-4-fluoro-5-((2R,4S)-4-fluoro-2-(6-fluorobenzo[d][1,3]dioxol-4-yl)pyrrolidin-1-yl)pyrazolo[1,5-a]pyridine-3-carboxamide, N-(tert-butylsulfonyl)-5-((2R,4S)-4-fluoro-2-(6-fluorobenzo[d][1,3]dioxol-4-yl)pyrrolidin-1-yl)pyrazolo[1,5-a]pyridine-3-carboxamide, N—(N-ethyl-N-methylsulfamoyl)-5-((2R,4S)-4-fluoro-2-(6-fluorobenzo[d][1,3]dioxol-4-yl)pyrrolidin-1-yl)pyrazolo[1,5-a]pyridine-3-carboxamide, N-(azetidin-1-ylsulfonyl)-4-fluoro-5-((2R,4S)-4-fluoro-2-(3-fluoro phenyl) pyrrolidin-1-yl)pyrazolo[1,5-a]pyridine-3-carboxamide, 4-fluoro-5-((2R,4S)-4-fluoro-2-(3-fluorophenyl)pyrrolidin-1-yl)-N—(N-isobutyl-N-methylsulfamoyl)pyrazolo[1,5-a]pyridine-3-carboxamide, N-(tert-butylsulfonyl)-5-((2R,4S)-2-(2, 5-difluorophenyl)-4-fluoropyrrolidin-1-yl)-4-fluoropyrazolo[1,5-a]pyridine-3-carboxamide, 5-((2R,4S)-2-(2,5-difluorophenyl)-4-fluoropyrrolidin-1-yl)-4-fluoro-N-(isopropylsulfonyl)pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl)-4-fluoropyrazolo[1,5-a]pyridine-3-carboxamide, 5-((2R,4S)-2-(2,5-difluorophenyl)-4-fluoropyrrolidin-1-yl)-N—(N,N-dimethylsulfamoyl)-4-fluoropyrazolo[1,5-a]pyridine-3-carboxamide, N-(azetidin-1-ylsulfonyl)-5-((2R,4S)-2-(2, 5-difluorophenyl)-4-fluoropyrrolidin-1-yl)-4-fluoropyrazolo[1,5-a]pyridine-3-carboxamide, 5-((2R,4S)-2-(2,5-difluorophenyl)-4-fluoropyrrolidin-1-yl)-4-fluoro-N—(N-isobutyl-N-methylsulfamoyl)pyrazolo[1,5-a]pyridine-3-carboxamide, or 5-((2R,4S)-2-(2,5-difluorophenyl)-4-fluoropyrrolidin-1-yl)-4-fluoro-N-sulfamoylpyrazolo[1,5-a]pyridine-3-carboxamide, or a pharmaceutically acceptable salt thereof, a pharmaceutically acceptable solvate thereof or a stereoisomer thereof.

17. The method of claim 16, wherein the compound having formula

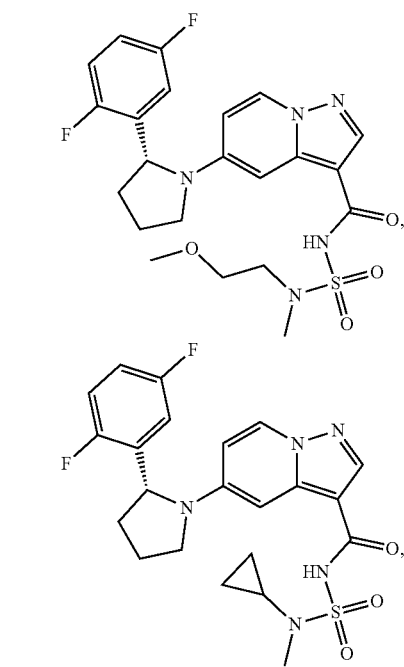

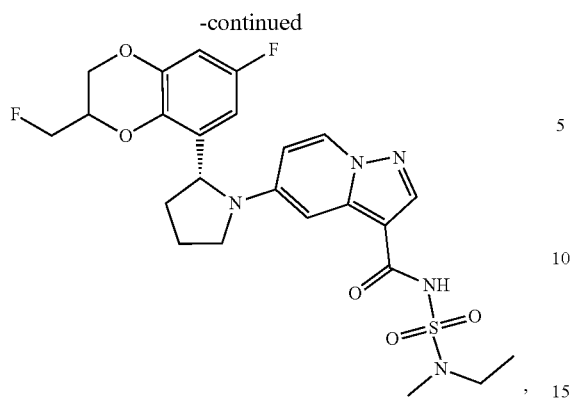
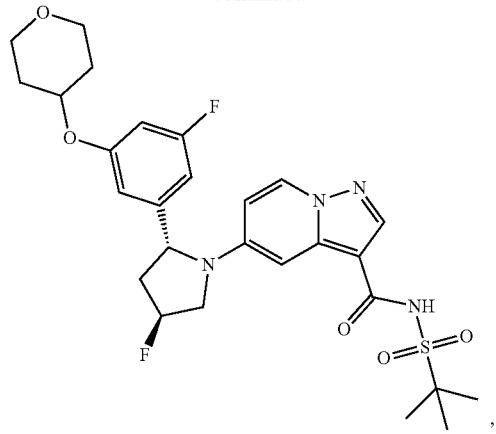
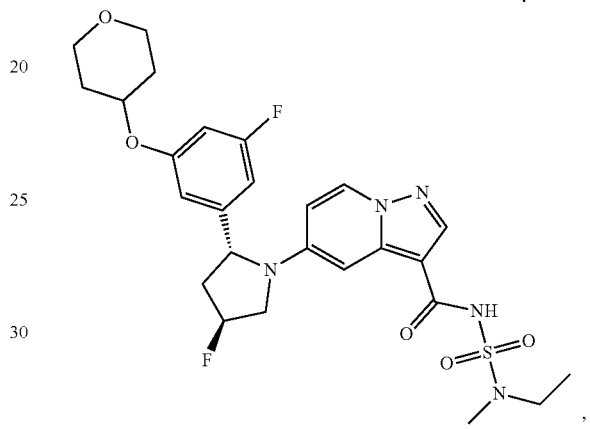
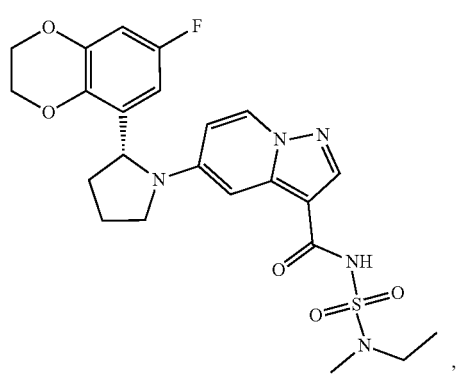
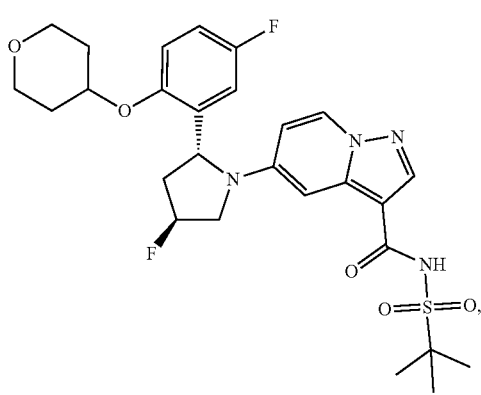

261
-continued
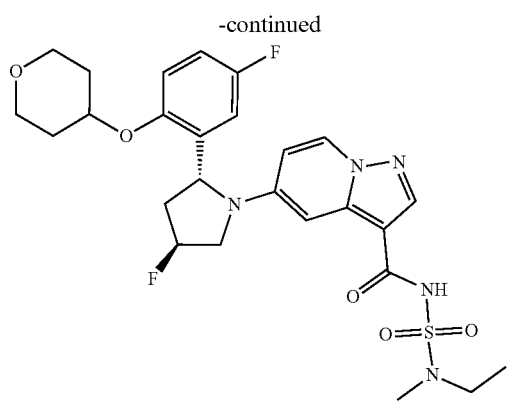
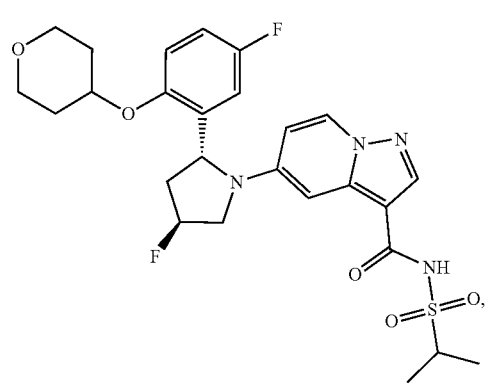
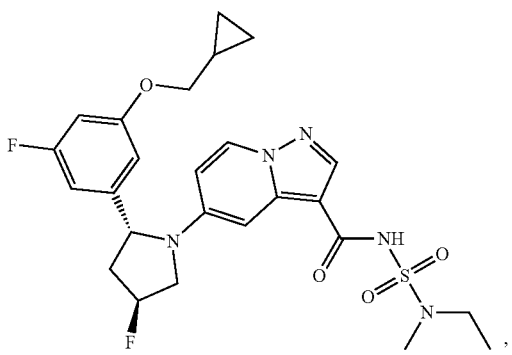
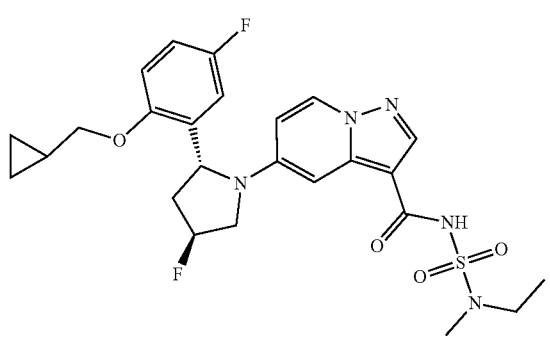
262
-continued
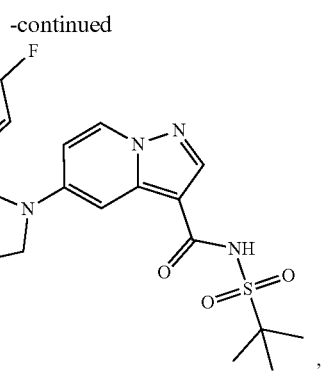
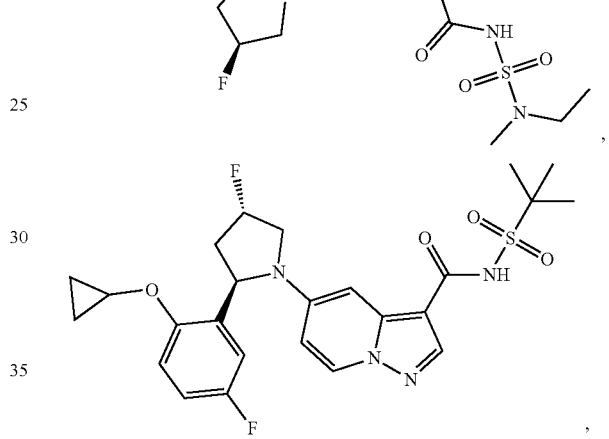
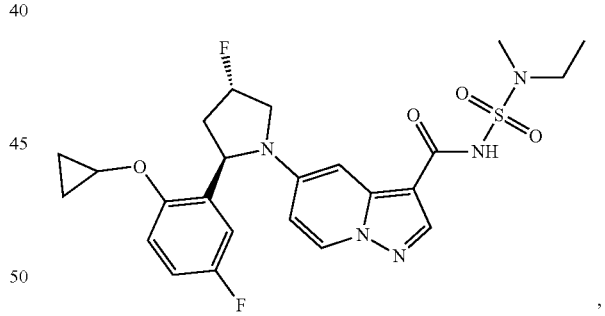
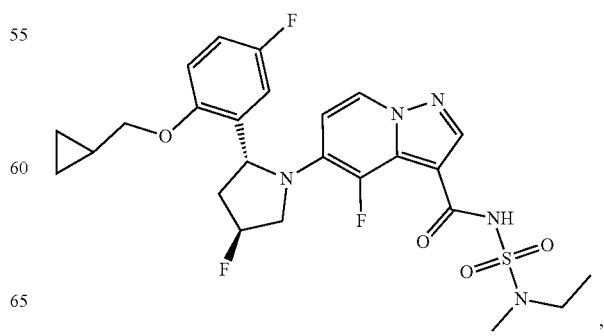

263
-continued
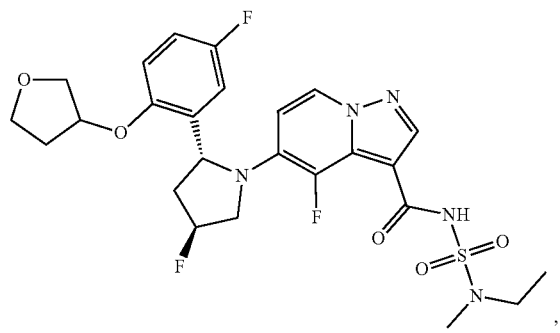
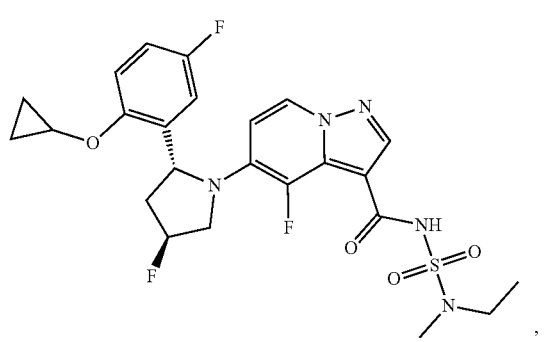
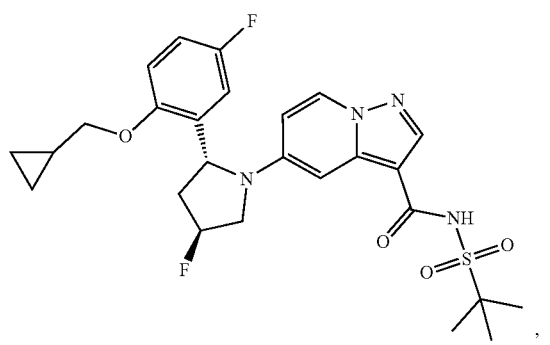
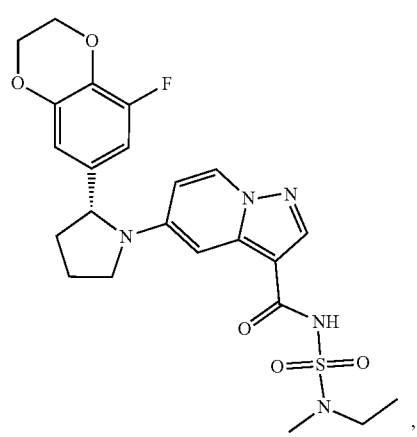
264
-continued
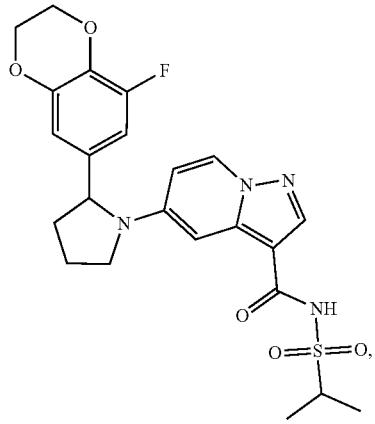
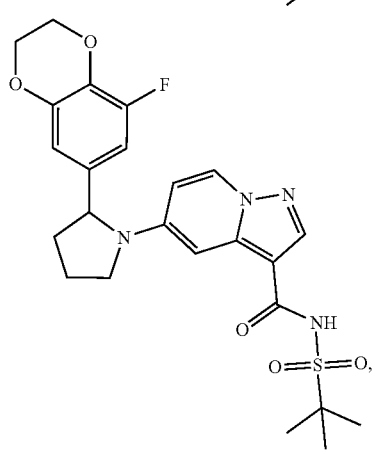
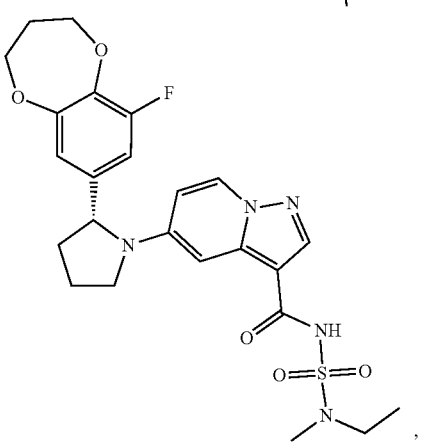
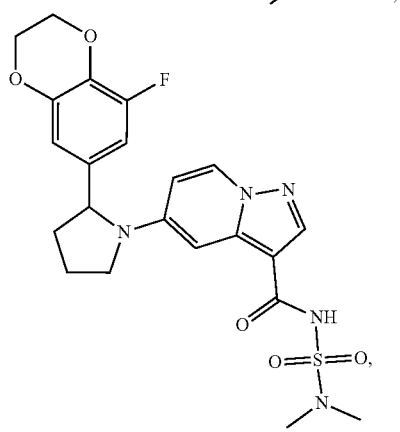

-continued
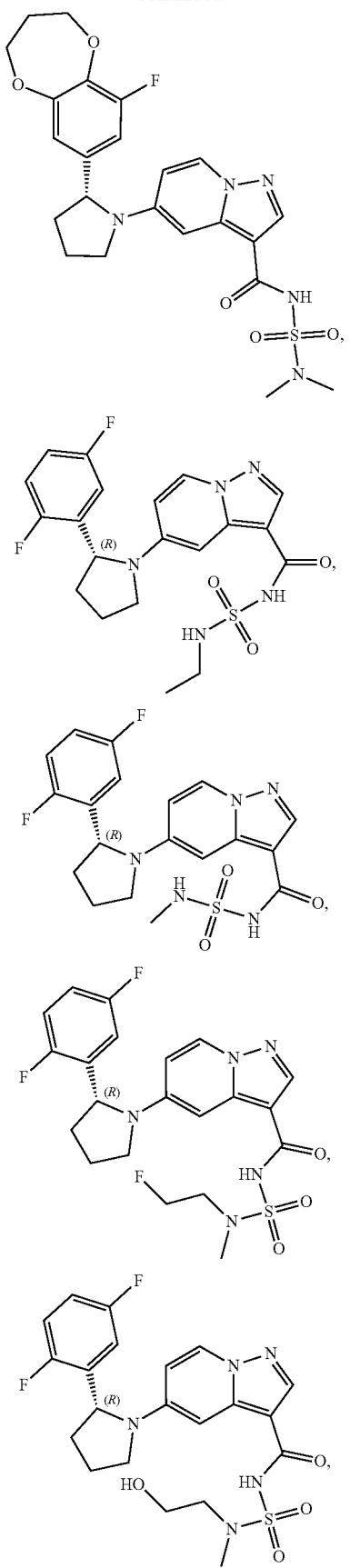
-continued
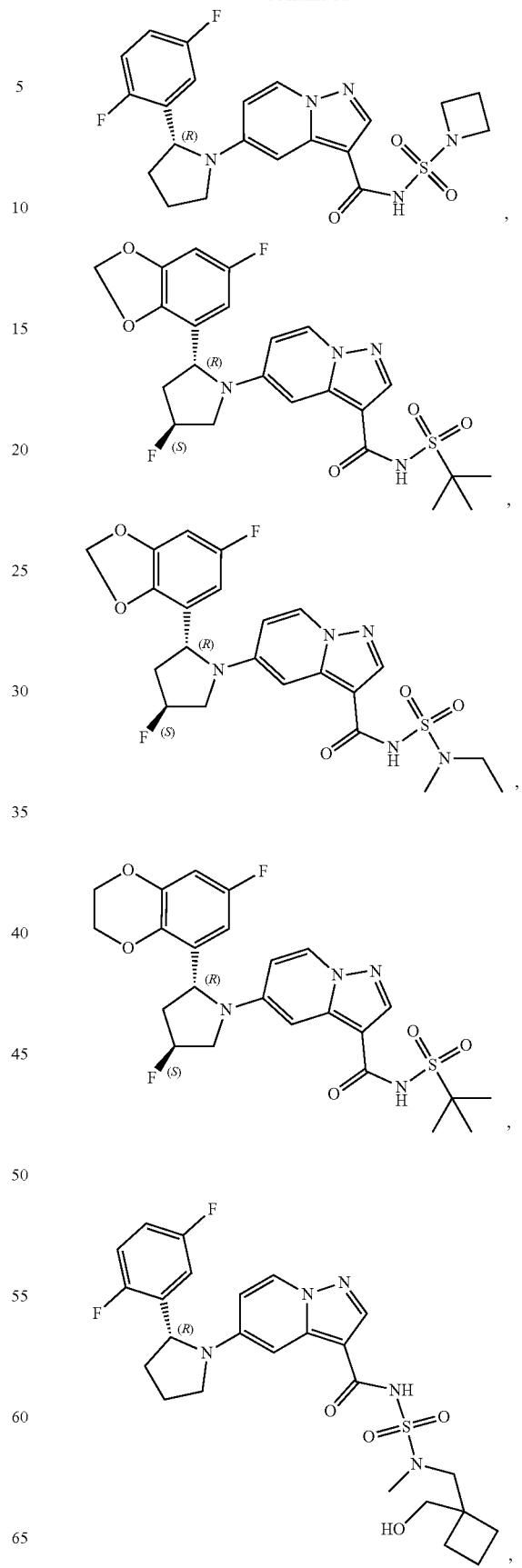

267
-continued
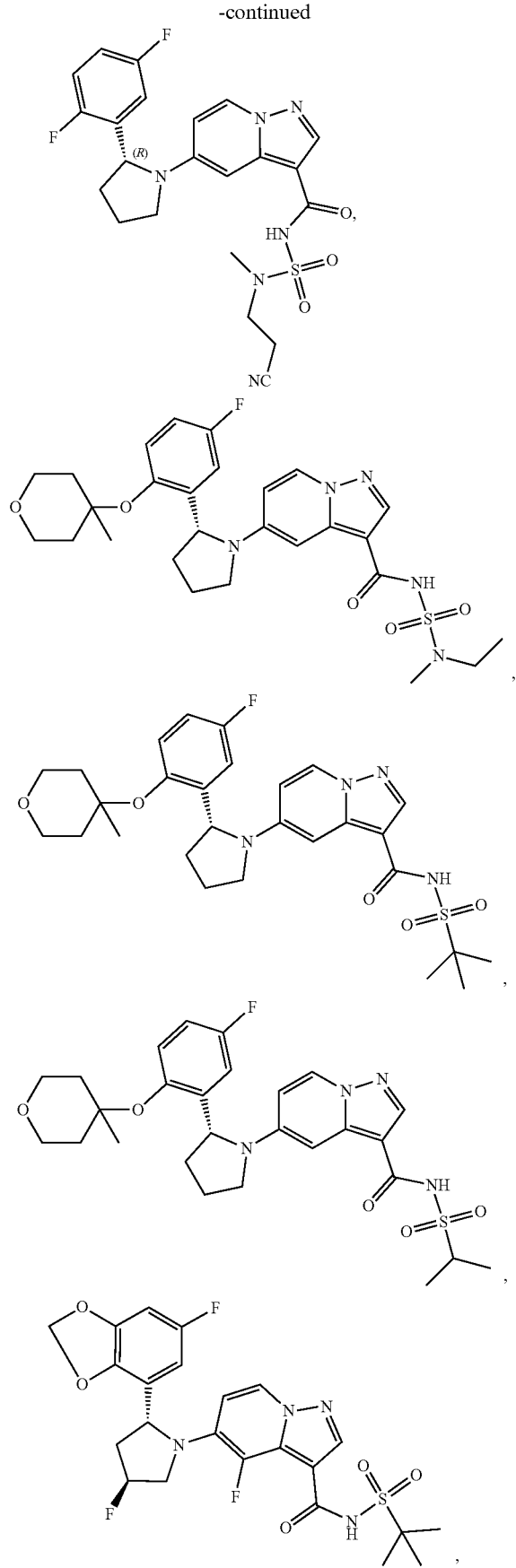
268
-continued
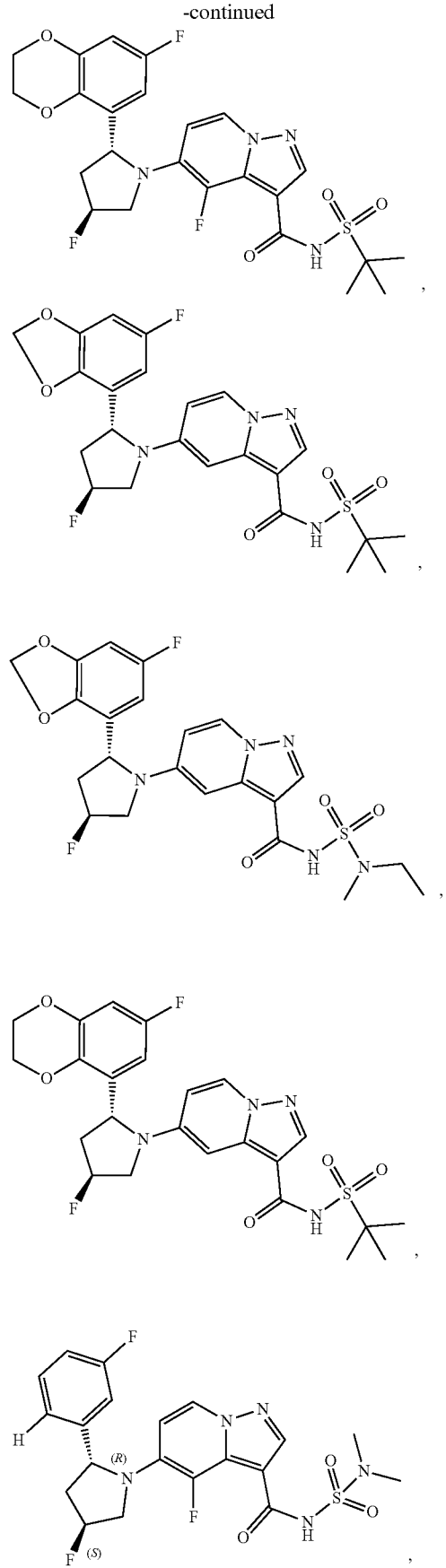

269
-continued

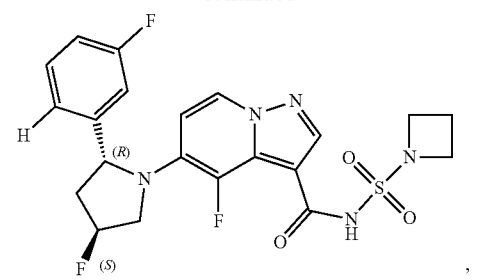

,

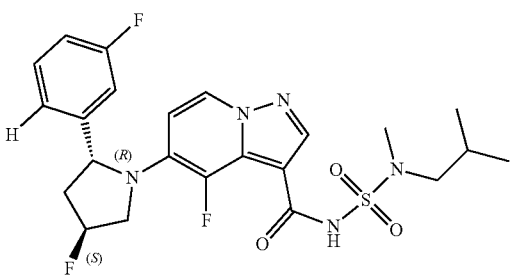

,

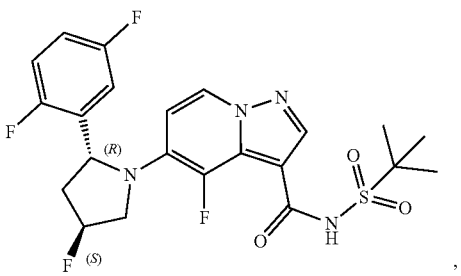

,

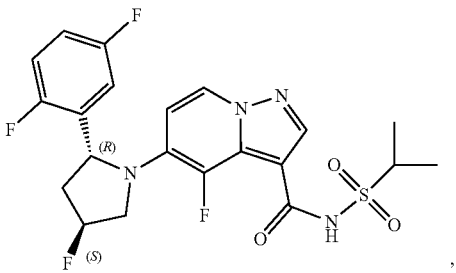

,

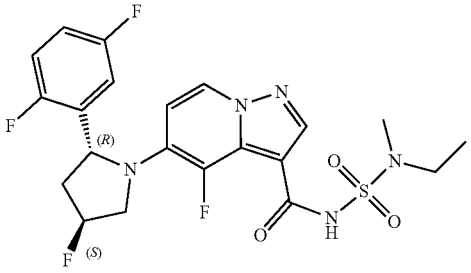

,

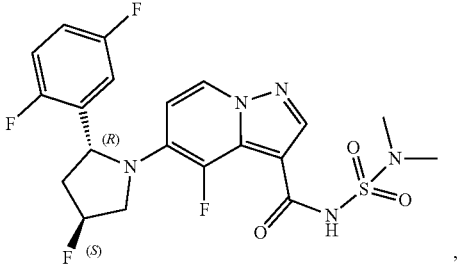

,

270
-continued

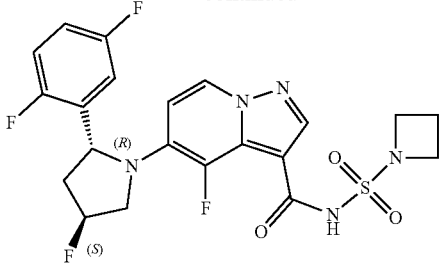

,

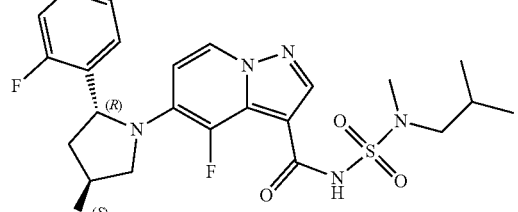

, or

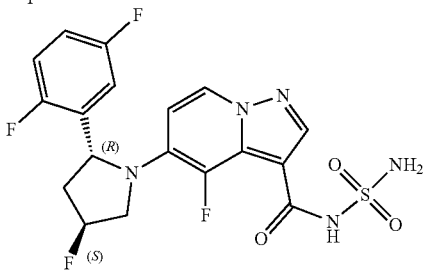

or a pharmaceutically acceptable salt thereof, or a pharmaceutically acceptable solvate thereof or a stereoisomer thereof.

18. A method of treating a cancer in a subject, the method comprising:
   a) determining that the cancer is associated with an abnormal or deregulated Trk kinase; and
   b) administering to the subject a therapeutically effective amount of a dosage form comprising a compound
   (R)-5-(2-(2,5-difluorophenyl)pyrrolidin-1-yl)-N-((4-fluorophenyl)sulfonyl)pyrazolo [1,5-a]pyridine-3-carboxamide,
   (R)—N-(tert-butylsulfonyl)-5-(2-(2,5-difluorophenyl)pyrrolidin-1-yl)pyrazolo[1,5-a] pyridine-3-carboxamide,
   (R)-5-(2-(2,5-difluorophenyl)pyrrolidin-1-yl)-N-(ethylsulfonyl)pyrazolo[1,5-a] pyridine-3-carboxamide,
   (R)—N-((3-cyanophenyl)sulfonyl)-5-(2-(2,5-difluorophenyl)pyrrolidin-1-yl)pyrazolo [1,5-a] pyridine-3-carboxamide,
   (R)—N-(cyclopropylsulfonyl)-5-(2-(2,5-difluorophenyl)pyrrolidin-1-yl) pyrazolo[1,5-a]pyridine-3-carboxamide,
   (R)-5-(2-(2,5-difluorophenyl)pyrrolidin-1-yl)-N-(methylsulfonyl)pyrazolo[1,5-a] pyridine-3-carboxamide,
   (R)-5-(2-(2,5-difluorophenyl)pyrrolidin-1-yl)-N-(isopropylsulfonyl)pyrazolo[1,5-a] pyridine-3-carboxamide,
   5-((R)-2-(2,5-difluorophenyl)pyrrolidin-1-yl)-N-((4-((S)-3-hydroxypyrrolidin-1-yl) phenyl) sulfonyl)pyrazolo [1, 5-a]pyridine-3-carboxamide,
   (R)—N-((3-cyanophenyl)sulfonyl)-5-(2-(2,5-difluorophenyl)pyrrolidin-1-yl)-N-methyl pyrazolo[1,5-a]pyridine-3-carboxamide, (R)-5-(2-(2,5-difluorophenyl)pyrrolidin-1-yl)-N-(propylsulfonyl)pyrazolo[1, 5-a] pyridine-3-carboxamide, (R)-5-(2-(2,5-difluorophenyl)pyrrolidin-1-yl)-N-((3,5-dimethyl isoxazol-4-yl) sulfonyl) pyrazolo [1, 5-a] pyridine-3-carboxamide, (R)—N-(cyclohexylsulfonyl)-5-(2-(2,5-difluorophenyl) pyrrolidin-1-yl)pyrazolo[1,5-a] pyridine-3-carboxamide, (R)—N-(cyclopentylsulfonyl)-5-(2-(2, 5-difluorophenyl) pyrrolidin-1-yl)pyrazolo[1,5-a] pyridine-3-carboxamide, (R)-5-(2-(2,5-difluorophenyl)pyrrolidin-1-yl)-N-(isobutylsulfonyl) pyrazolo[1, 5-a] pyridine-3-carboxamide, (R)-5-(2-(2,5-difluorophenyl) pyrrolidin-1-yl)-N-((1, 2-dimethyl-1H-imidazol-4-yl) sulfonyl) pyrazolo [1, 5-a] pyridine-3-carboxamide, (R)-5-(2-(2, 5-difluorophenyl) pyrrolidin-1-yl)-N-((1, 2-dimethyl-1H-imidazol-5-yl) sulfonyl) pyrazolo [1, 5-a] pyridine-3-carboxamide, (R)-5-(2-(2, 5-difluorophenyl) pyrrolidin-1-yl)-N-(piperidin-4-ylsulfonyl) pyrazolo [1, 5-a] pyridine-3-carboxamide, (R)-5-(2-(2, 5-difluorophenyl) pyrrolidin-1-yl)-N-((1-methyl-1H-imidazol-4-yl) sulfonyl) pyrazolo [1, 5-a] pyridine-3-carboxamide, (R)-5-(2-(2, 5-difluorophenyl) pyrrolidin-1-yl)-N-((1-methyl-1H-pyrazol-5-yl) sulfonyl) pyrazolo [1, 5-a] pyridine-3-carboxamide, (R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide, (R)-5-(2-(2, 5-difluorophenyl) pyrrolidin-1-yl)-N-((1-methyl-2-oxoindolin-5-yl) sulfonyl) pyrazolo [1, 5-a] pyridine-3-carboxamide, (R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide, (R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide, 5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide, 5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, (R)-5-(2-(2, 5-difluorophenyl) pyrrolidin-1-yl)-N-((6-methoxypyridin-3-yl) sulfonyl) pyrazolo [1, 5-a] pyridine-3-carboxamide, (R)—N-((6-(1H-1,2,4-triazol-1-yl)pyridin-3-yl)sulfonyl)-5-(2-(2,5-difluorophenyl) pyrrolidin-1-yl) pyrazolo [1, 5-a] pyridine-3-carboxamide, (R)-5-(2-(2, 5-difluorophenyl) pyrrolidin-1-yl)-N-((1-methyl-1H-pyrazol-4-yl) sulfonyl) pyrazolo [1, 5-a] pyridine-3-carboxamide, (R)-5-(2-(2, 5-difluorophenyl) pyrrolidin-1-yl)-N-((4-morpholinophenyl) sulfonyl) pyrazolo [1, 5-a] pyridine-3-carboxamide, (R)-5-(2-(2,5-difluorophenyl)pyrrolidin-1-yl)-N-(pyridin-3-ylsulfonyl)pyrazolo[1,5-a]pyridine-3-carboxamide, (R)—N-((5-chlorothiophen-2-yl) sulfonyl)-5-(2-(2, 5-difluorophenyl) pyrrolidin-1-yl) pyrazolo [1, 5-a] pyridine-3-carboxamide, (R)—N-((2, 5-dichlorothiophen-3-yl) sulfonyl)-5-(2-(2, 5-difluorophenyl) pyrrolidin-1-yl) pyrazolo [1, 5-a] pyridine-3-carboxamide, (R)—N-(cyclobutylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide, (R)—N-(benzo[d][1,3]dioxol-5-ylsulfonyl)-5-(2-(2,5-difluorophenyl)pyrrolidin-1-yl) pyrazolo[1,5-a]pyridine-3-carboxamide, (R)-5-(2-(2,5-difluorophenyl)pyrrolidin-1-yl)-N-((1-ethylcyclopropyl)sulfonyl) pyrazolo[1,5-a]pyridine-3-carboxamide, (R)-5-(2-(2,5-difluorophenyl)pyrrolidin-1-yl)-N-(neopentylsulfonyl)pyrazolo[1,5-a]pyridine-3-carboxamide, (R)-5-(2-(2,5-difluorophenyl)pyrrolidin-1-yl)-N-((1-methylcyclopropyl)sulfonyl) pyrazolo[1,5-a]pyridine-3-carboxamide, (R)-5-(2-(2,5-difluorophenyl)pyrrolidin-1-yl)-N-(o-tolylsulfonyl)pyrazolo[1,5-a] pyridine-3-carboxamide, (R)—N-(benzylsulfonyl)-5-(2-(2,5-difluorophenyl)pyrrolidin-1-yl)pyrazolo[1,5-a] pyridine-3-carboxamide, (R)-5-(2-(2,5-difluorophenyl)pyrrolidin-1-yl)-N-((1-(4-fluorobenzyl)cyclopropyl) sulfonyl)pyrazolo[1,5-a] pyridine-3-carboxamide, (R)—N-(tert-butylsulfonyl)-5-(2-(5-fluoro-2-methoxyphenyl) pyrrolidin-1-yl) pyrazolo [1, 5-a] pyridine-3-carboxamide, (R)—N-(tert-butylsulfonyl)-5-(2-(3-(difluoromethoxy)-5-fluorophenyl) pyrrolidin-1-yl) pyrazolo [1, 5-a] pyridine-3-carboxamide, (R)—N-(tert-butylsulfonyl)-5-(2-(5-fluoropyridin-3-yl) pyrrolidin-1-yl) pyrazolo [1, 5-a] pyridine-3-carboxamide, (R)—N-(tert-butylsulfonyl)-5-(2-(2-ethoxy-5-fluorophenyl)pyrrolidin-1-yl)pyrazolo [1,5-a]pyridine-3-carboxamide, (R)—N-(tert-butylsulfonyl)-5-(2-(2-(cyclopropylmethoxy)-5-fluorophenyl) pyrrolidin-1-yl)pyrazolo[1, 5-a]pyridine-3-carboxamide, (R)—N-(tert-butylsulfonyl)-5-(2-(2-chloro-5-fluorophenyl)pyrrolidin-1-yl) pyrazolo[1,5-a]pyridine-3-carboxamide, N-(tert-butylsulfonyl)-5-((2R,4R)-2-(2,5-difluorophenyl)-4-hydroxypyrrolidin-1-yl) pyrazolo[1,5-a]pyridine-3-carboxamide, (R)—N-(tert-butylsulfonyl)-5-(2-(5-fluoro-2-(2,2,2-trifluoroethoxy)phenyl) pyrrolidin-1-yl)pyrazolo[1,5-a]pyridine-3-carboxamide, N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide (Isomer-I), N-(tert-butylsulfonyl)-5-(2-(7-fluoro-2,3-dihydrobenzo[b][1,4]dioxin-5-yl)pyrrolidin-1-yl)pyrazolo[1,5-a]pyridine-3-carboxamide (Isomer-II), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-I), N-(tert-butylsulfonyl)-5-((2R,4S)-2-(2,5-difluorophenyl)-4-fluoropyrrolidin-1-yl)pyrazolo[1,5-a]pyridine-3-carboxamide (Isomer-II), (R)—N-(tert-butylsulfonyl)-5-(2-(4,4'-difluoro-[1,1'-biphenyl]-2-yl)pyrrolidin-1-yl)pyrazolo[1,5-a]pyridine-3-carboxamide, (S)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(2, 5-difluorophenyl)-4,4-difluoropyrrolidin-1-yl) pyrazolo [1, 5-a] pyridine-3-carboxamide, (R)—N-(tert-butylsulfonyl)-5-(2-(5-fluoro-2-(2-fluoroethoxy)phenyl) pyrrolidin-1-yl)pyrazolo[1,5-a]pyridine-3-carboxamide, N-(tert-butylsulfonyl)-5-((2R,4R)-2-(2,5-difluorophenyl)-4-fluoropyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, (R)—N-(tert-butylsulfonyl)-5-(2-(2, 5-difluorophenyl) pyrrolidin-1-yl)-4-fluoro pyrazolo[1,5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1,5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide, (R)—N-(tert-butylsulfonyl)-5-(2-(3, 5-difluorophenyl) pyrrolidin-1-yl) pyrazolo [1, 5-a] pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a] pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide, (R)-5-(2-(3, 5-difluorophenyl) pyrrolidin-1-yl)-N-((4-fluorophenyl) sulfonyl) pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, (R)-5-(2-(3, 5-difluorophenyl) pyrrolidin-1-yl)-N-(isopropylsulfonyl) pyrazolo [1, 5-a] pyridine-3-carboxamide, (R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide, 5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide, 5-((2R,4S)-2-(2,5-difluorophenyl)-4-fluoropyrrolidin-1-yl)-N-((1-methyl cyclopropyl)sulfonyl)pyrazolo[1,5-a]pyridine-3-carboxamide, (R)-5-(2-(2, 5-difluorophenyl) pyrrolidin-1-yl)-4-fluoro-N-(isopropylsulfonyl) pyrazolo [1, 5-a] pyridine-3-carboxamide, (R)-5-(2-(2, 5-difluorophenyl) pyrrolidin-1-yl)-N—(N,N-dimethylsulfamoyl) pyrazolo [1, 5-a] pyridine-3-carboxamide, (R)-5-(2-(2,5-difluorophenyl)pyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl)pyrazolo[1,5-a]pyridine-3-carboxamide, 5-((2R,4S)-2-(2,5-difluorophenyl)-4-fluoropyrrolidin-1-yl)-N—(N-ethyl-N-methyl sulfamoyl)pyrazolo[1,5-a]pyridine-3-carboxamide, (R)—N—(N-(cyclopropylmethyl)-N-methylsulfamoyl)-5-(2-(2,5-difluorophenyl) pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl) pyrazolo[1,5-a]pyridine-3-carboxamide, 5-((2R,4S)-2-(2,5-difluorophenyl)-4-fluoropyrrolidin-1-yl)-N—(N,N-dimethyl sulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, (R)-5-(2-(2,5-difluorophenyl)pyrrolidin-1-yl)-N-(morpholinosulfonyl) pyrazolo[1,5-a]pyridine-3-carboxamide, (R)-5-(2-(2,5-difluorophenyl)pyrrolidin-1-yl)-N-(pyrrolidin-1-ylsulfonyl) pyrazolo[1,5-a]pyridine-3-carboxamide, (R)-5-(2-(2,5-difluorophenyl)pyrrolidin-1-yl)-N-((4-methylpiperazin-1-yl) sulfonyl)pyrazolo[1,5-a]pyridine-3-carboxamide, (R)—N—(N,N-diethylsulfamoyl)-5-(2-(5-fluoro-2-methoxyphenyl)pyrrolidin-1-yl) pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl)pyrazolo[1,5-a]pyridine-3-carboxamide, (R)-5-(2-(2,5-difluorophenyl)pyrrolidin-1-yl)-N-(piperidin-1-ylsulfonyl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy) phenyl)pyrrolidin-1-yl)pyrazolo[1,5-a]pyridine-3-carboxamide, 5-((R)-2-(2,5-difluorophenyl)pyrrolidin-1-yl)-N—(((S)-3-hydroxypyrrolidin-1-yl) sulfonyl)pyrazolo[1,5-a]pyridine-3-carboxamide, (R)-5-(2-(2,5-difluorophenyl)pyrrolidin-1-yl)-N-sulfamoylpyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo[1,5-a]pyridine-3-carboxamide, N—(N-ethyl-N-methylsulfamoyl)-5-(2-(8-fluoro-3,4-dihydro-2H-benzo[b][1,4] dioxepin-6-yl)pyrrolidin-1-yl) pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4] dioxepin-6-yl)pyrrolidin-1-yl) pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I),
N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II),
N—(N-ethyl-N-methylsulfamoyl)-4-fluoro-5-((2R,4S)-4-fluoro-2-(3-fluorophenyl)pyrrolidin-1-yl)pyrazolo[1,5-a]pyridine-3-carboxamide,
N—(N-ethyl-N-methylsulfamoyl)-5-((R)-2-(3-fluoro-5-(((S)-tetrahydrofuran-3-yl)oxy)phenyl)pyrrolidin-1-yl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide,
N—(N-ethyl-N-methylsulfamoyl)-5-((R)-2-(3-fluoro-5-(((R)-tetrahydrofuran-3-yl)oxy)phenyl)pyrrolidin-1-yl)pyrazolo[1,5-a]pyridine-3-carboxamide,
4-fluoro-5-((2R,4S)-4-fluoro-2-(3-fluorophenyl)pyrrolidin-1-yl)-N-sulfamoyl pyrazolo[1,5-a]pyridine-3-carboxamide,
N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I),
N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-2);
(R)-5-(2-(2,5-difluorophenyl)pyrrolidin-1-yl)-N—(N-isobutyl-N-methyl sulfamoyl)pyrazolo[1,5-a]pyridine-3-carboxamide,
(R)—N—(N-ethyl-N-methylsulfamoyl)-4-fluoro-5-(2-(3-fluorophenyl) pyrrolidin-1-yl)pyrazolo[1,5-a]pyridine-3-carboxamide,
(R)—N—(N,N-dimethylsulfamoyl)-4-fluoro-5-(2-(3-fluorophenyl)pyrrolidin-1-yl) pyrazolo[1,5-a]pyridine-3-carboxamide,
(R)—N—(N,N-dimethylsulfamoyl)-4-fluoro-5-(2-(3-fluorophenyl)pyrrolidin-1-yl)pyrazolo[1,5-a]pyridine-3-carboxamide,
(R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide,
(R)—N—(N,N-bis(cyclopropylmethyl)sulfamoyl)-5-(2-(2,5-difluorophenyl)pyrrolidin-1-yl)pyrazolo[1,5-a]pyridine-3-carboxamide,
N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide,
N—(N-ethyl-N-methylsulfamoyl)-5-((2R)-2-(5-fluoro-2-((tetrahydrofuran-3-yl)oxy) phenyl)pyrrolidin-1-yl)pyrazolo[1,5-a]pyridine-3-carboxamide (Diastereomer-II),
N-(tert-butylsulfonyl)-2-(2,5-difluorophenyl)pyrrolidin-1-yl)pyrazolo[1,5-a] pyridine-3-carboxamide (Racemic mixture);
(R)—N-(tert-butylsulfonyl)-5-(2-(3,5-difluoro-2-methoxyphenyl)pyrrolidin-1-yl) pyrazolo[1,5-a]pyridine-3-carboxamide,
N-(tert-butylsulfonyl)-4-fluoro-5-((2R,4S)-4-fluoro-2-(3-fluorophenyl)pyrrolidin-1-yl)pyrazolo[1,5-a]pyridine-3-carboxamide,
4-fluoro-5-((2R,4S)-4-fluoro-2-(3-fluorophenyl)pyrrolidin-1-yl)-N-(isopropyl sulfonyl)pyrazolo[1,5-a]pyridine-3-carboxamide,
(R)—N-(tert-butylsulfonyl)-5-(2-(3,5-difluoro-2-((tetrahydro-2H-pyran-4-yl)oxy) phenyl)pyrrolidin-1-yl) pyrazolo[1,5-a]pyridine-3-carboxamide,
(R)—N-(tert-butylsulfonyl)-5-(2-(5-fluoro-2-((tetrahydro-2H-pyran-4-yl)oxy) phenyl)pyrrolidin-1-yl) pyrazolo[1,5-a]pyridine-3-carboxamide,
(R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide,
(R)-4-fluoro-5-(2-(3-fluorophenyl)pyrrolidin-1-yl)-N-(isopropylsulfonyl)pyrazolo [1,5-a]pyridine-3-carboxamide,
(R)—N-(tert-butylsulfonyl)-4-fluoro-5-(2-(5-fluoro-2-((tetrahydro-2H-pyran-4-yl) oxy)phenyl)pyrrolidin-1-yl)pyrazolo[1,5-a]pyridine-3-carboxamide,
Sodium (tert-butylsulfonyl)(5-((2R,4S)-2-(2,5-difluorophenyl)-4-fluoropyrrolidin-1-yl) pyrazolo[1,5-a]pyridine-3-carbonyl)amide,
Sodium(R)-(tert-butylsulfonyl)(5-(2-(2,5-difluorophenyl)pyrrolidin-1-yl) pyrazolo [1,5-a] pyridine-3-carbonyl)amide,
Sodium (R)-(tert-butylsulfonyl)(5-(2-(7-fluoro-2,3-dihydrobenzo[b][1,4]dioxin-5-yl)pyrrolidin-1-yl)pyrazolo [1,5-a]pyridine-3-carbonyl)amide,
Sodium (tert-butylsulfonyl)(5-((2R,4R)-2-(2,5-difluorophenyl)-4-fluoropyrrolidin-1-yl) pyrazolo[1,5-a]pyridine-3-carbonyl)amide,
Sodium (R)-(5-(2-(2,5-difluorophenyl) pyrrolidin-1-yl)pyrazolo[1,5-a]pyridine-3-carbonyl) (N,N-dimethylsulfamoyl)amide,
Sodium (tert-butylsulfonyl)(5-(2-(2,5-difluorophenyl)-4,4-difluoropyrrolidin-1-yl)pyrazolo[1,5-a]pyridine-3-carbonyl)amide,
Sodium (R)-(5-(2-(2,5-difluorophenyl) pyrrolidin-1-yl)pyrazolo[1,5-a]pyridine-3-carbonyl)((1-methylcyclopropyl) sulfonyl)amide,
Sodium (tert-butylsulfonyl)(5-((2R)-2-(2,5-difluorophenyl)-4-fluoropyrrolidin-1-yl)pyrazolo [1,5-a]pyridine-3-carbonyl)amide,
Sodium (5-((2R,4S)-2-(2,5-difluorophenyl)-4-fluoropyrrolidin-1-yl)pyrazolo[1,5-a]pyridine-3-carbonyl)(N,N-dimethylsulfamoyl)amide,
Sodium (tert-butylsulfonyl)(4-fluoro-5-((2R,4S)-4-fluoro-2-(3-fluorophenyl) pyrrolidin-1-yl)pyrazolo[1,5-a]pyridine-3-carbonyl)amide,
Sodium (R)—(N,N-dimethylsulfamoyl)(4-fluoro-5-(2-(3-fluorophenyl)pyrrolidin-1-yl)pyrazolo [1,5-a]pyridine-3-carbonyl)amide,
Sodium (N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide,
Sodium (R)-(5-(2-(2,5-difluorophenyl) pyrrolidin-1-yl)pyrazolo[1,5-a]pyridine-3-carbonyl)(o-tolylsulfonyl) amide,
Sodium (4-fluoro-5-((2R,4S)-4-fluoro-2-(3-fluorophenyl) pyrrolidin-1-yl) pyrazolo[1,5-a]pyridine-3-carbonyl)(isopropylsulfonyl)amide,
Sodium (5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, Sodium (R)-(5-(2-(2,5-difluorophenyl) pyrrolidin-1-yl) pyrazolo[1,5-a]pyridine-3-carbonyl)(piperidin-1-ylsulfonyl)amide;

(R)-5-(2-(2,5-difluorophenyl)pyrrolidin-1-yl)-N-((4-fluorophenyl)sulfonyl)pyrazolo[1,5-a] pyridine-3-carboxamide, (R)—N-((3-cyanophenyl)sulfonyl)-5-(2-(2,5-difluorophenyl)pyrrolidin-1-yl)pyrazolo[1,5-a] pyridine-3-carboxamide, 5-((R)-2-(2,5-difluorophenyl)pyrrolidin-1-yl)-N-((4-((S)-3-hydroxypyrrolidin-1-yl) phenyl) sulfonyl) pyrazolo [1, 5-a] pyridine-3-carboxamide, (R)—N-((3-cyanophenyl) sulfonyl)-5-(2-(2, 5-difluorophenyl) pyrrolidin-1-yl)-N-methylpyrazolo [1, 5-a] pyridine-3-carboxamide, (R)-5-(2-(2, 5-difluorophenyl) pyrrolidin-1-yl)-N-((4-morpholinophenyl) sulfonyl) pyrazolo [1, 5-a] pyridine-3-carboxamide, (R)-5-(2-(2,5-difluorophenyl)pyrrolidin-1-yl)-N-(o-tolylsulfonyl)pyrazolo[1,5-a]pyridine-3-carboxamide, (R)-5-(2-(3, 5-difluorophenyl) pyrrolidin-1-yl)-N-((4-fluorophenyl) sulfonyl) pyrazolo [1, 5-a] pyridine-3-carboxamide, 5-((R)-2-(3, 5-difluorophenyl) pyrrolidin-1-yl)-N-((4-((S)-3-hydroxypyrrolidin-1-yl) phenyl) sulfonyl) pyrazolo [1, 5-a] pyridine-3-carboxamide, Sodium(R)-(5-(2-(2,5-difluorophenyl)pyrrolidin-1-yl) pyrazolo[1,5-a]pyridine-3-carbonyl) (piperidin-1-ylsulfonyl)amide, Sodium(R)-(5-(2-(2,5-difluorophenyl)pyrrolidin-1-yl) pyrazolo[1,5-a]pyridine-3-carbonyl) (o-tolylsulfonyl)amide;

(R)—N-(tert-butylsulfonyl)-5-(2-(2, 5-difluorophenyl) pyrrolidin-1-yl) pyrazolo [1, 5-a] pyridine-3-carboxamide, (R)-5-(2-(2,5-difluorophenyl)pyrrolidin-1-yl)-N-(ethylsulfonyl)pyrazolo[1,5-a]pyridine-3-carboxamide, (R)-5-(2-(2,5-difluorophenyl)pyrrolidin-1-yl)-N-(methylsulfonyl)pyrazolo[1,5-a] pyridine-3-carboxamide, (R)-5-(2-(2, 5-difluorophenyl) pyrrolidin-1-yl)-N-(isopropylsulfonyl)pyrazolo[1, 5-a] pyridine-3-carboxamide, (R)-5-(2-(2, 5-difluorophenyl) pyrrolidin-1-yl)-N-(propylsulfonyl)pyrazolo[1, 5-a] pyridine-3-carboxamide, (R)-5-(2-(2, 5-difluorophenyl) pyrrolidin-1-yl)-N-(isobutylsulfonyl)pyrazolo[1, 5-a] pyridine-3-carboxamide, (R)-5-(2-(2,5-difluorophenyl)pyrrolidin-1-yl)-N-(neopentylsulfonyl)pyrazolo[1,5-a] pyridine-3-carboxamide, (R)—N-(benzylsulfonyl)-5-(2-(2,5-difluorophenyl)pyrrolidin-1-yl) pyrazolo[1,5-a]pyridine-3-carboxamide, (R)—N-(tert-butylsulfonyl)-5-(2-(5-fluoro-2-methoxyphenyl) pyrrolidin-1-yl)pyrazolo [1, 5-a] pyridine-3-carboxamide, (R)—N-(tert-butylsulfonyl)-5-(2-(3-(difluoromethoxy)-5-fluorophenyl)pyrrolidin-1-yl) pyrazolo [1, 5-a] pyridine-3-carboxamide, (R)—N-(tert-butylsulfonyl)-5-(2-(5-fluoropyridin-3-yl) pyrrolidin-1-yl)pyrazolo [1, 5-a] pyridine-3-carboxamide, (R)—N-(tert-butylsulfonyl)-5-(2-(2-ethoxy-5-fluorophenyl)pyrrolidin-1-yl) pyrazolo[1,5-a] pyridine-3-carboxamide, (R)—N-(tert-butylsulfonyl)-5-(2-(2-(cyclopropylmethoxy)-5-fluorophenyl)pyrrolidin-1-yl) pyrazolo[1, 5-a]pyridine-3-carboxamide, (R)—N-(tert-butylsulfonyl)-5-(2-(2-chloro-5-fluorophenyl)pyrrolidin-1-yl)pyrazolo[1,5-a]pyridine-3-carboxamide, N-(tert-butylsulfonyl)-5-((2R,4R)-2-(2,5-difluorophenyl)-4-hydroxypyrrolidin-1-yl)pyrazolo[1,5-a]pyridine-3-carboxamide, N-(tert-butylsulfonyl)-5-((2R,4S)-2-(2,5-difluorophenyl)-4-fluoropyrrolidin-1-yl)pyrazolo [1,5-a]pyridine-3-carboxamide, (R)—N-(tert-butylsulfonyl)-5-(2-(4,4'-difluoro-[1,1'-biphenyl]-2-yl)pyrrolidin-1-yl) pyrazolo[1,5-a]pyridine-3-carboxamide, (R)—N-(tert-butylsulfonyl)-5-(2-(5-fluoro-2-(2-fluoroethoxy)phenyl)pyrrolidin-1-yl) pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, N-(tert-butylsulfonyl)-5-((2R)-2-(5-fluoro-2-((tetrahydrofuran-3-yl)oxy)phenyl) pyrrolidin-1-yl)pyrazolo[1,5-a]pyridine-3-carboxamide, (R)—N-(tert-butylsulfonyl)-5-(2-(2, 5-difluorophenyl) pyrrolidin-1-yl)-4-fluoro pyrazolo[1, 5-a] pyridine-3-carboxamide, (R)—N-(tert-butylsulfonyl)-5-(2-(2-(difluoromethoxy)-5-fluorophenyl) pyrrolidin-1-yl)-4-fluoropyrazolo [1, 5-a] pyridine-3-carboxamide, (R)—N-(tert-butylsulfonyl)-5-(2-(2-(difluoromethoxy)-5-fluorophenyl) pyrrolidin-1-yl) pyrazolo [1, 5-a] pyridine-3-carboxamide, (R)—N-(tert-butylsulfonyl)-5-(2-(2-fluoro-5-(2-methoxyethoxy) phenyl) pyrrolidin-1-yl)pyrazolo [1, 5-a] pyridine-3-carboxamide, (R)—N-(tert-butylsulfonyl)-5-(2-(5-fluoro-2-(2-methoxyethoxy) phenyl) pyrrolidin-1-yl) pyrazolo [1, 5-a] pyridine-3-carboxamide, (R)—N-(tert-butylsulfonyl)-5-(2-(3, 5-difluorophenyl) pyrrolidin-1-yl) pyrazolo [1, 5-a] pyridine-3-carboxamide, (R)—N-(tert-butylsulfonyl)-5-(2-(3-fluoro-5-(2-methoxyethoxy)phenyl)pyrrolidin-1-yl)pyrazolo[1,5-a]pyridine-3-carboxamide, N-(tert-butylsulfonyl)-5-((2R)-2-(3-fluoro-5-((tetrahydrofuran-3-yl)oxy)phenyl) pyrrolidin-1-yl)pyrazolo[1,5-a]pyridine-3-carboxamide, (R)-5-(2-(3, 5-difluorophenyl) pyrrolidin-1-yl)-N-(isopropylsulfonyl) pyrazolo [1, 5-a] pyridine-3-carboxamide, N-(tert-butylsulfonyl)-5-(2-(2,5-difluorophenyl)pyrrolidin-1-yl)pyrazolo[1,5-a]pyridine-3-carboxamide (Racemic mixture), (R)—N-(tert-butylsulfonyl)-5-(2-(3,5-difluoro-2-methoxyphenyl)pyrrolidin-1-yl)pyrazolo[1,5-a]pyridine-3-carboxamide, (R)—N-(tert-butylsulfonyl)-5-(2-(3,5-difluoro-2-((tetrahydro-2H-pyran-4-yl)oxy)phenyl)pyrrolidin-1-yl) pyrazolo[1,5-a]pyridine-3-carboxamide, (R)—N-(tert-butylsulfonyl)-5-(2-(5-fluoro-2-((tetrahydro-2H-pyran-4-yl)oxy)phenyl)pyrrolidin-1-yl) pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N-(isopropylsulfonyl) pyrazolo[1,5-a]pyridine-3-carboxamide, (R)-4-fluoro-5-(2-(3-fluorophenyl)pyrrolidin-1-yl)-N-(isopropylsulfonyl)pyrazolo[1,5-a]pyridine-3-carboxamide, (R)—N-(tert-butylsulfonyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide,
Sodium(tert-butylsulfonyl)(5-((2R,4R)-2-(2,5-difluorophenyl)-4-fluoropyrrolidin-1-yl)pyrazolo[1,5-a]pyridine-3-carbonyl)amide,
Sodium(tert-butylsulfonyl)(5-((2R,4S)-2-(2,5-difluorophenyl)-4-fluoropyrrolidin-1-yl)pyrazolo[1,5-a]pyridine-3-carbonyl)amide,
Sodium(R)-(tert-butylsulfonyl)(5-(2-(2,5-difluorophenyl)pyrrolidin-1-yl)pyrazolo[1,5-a] pyridine-3-carbonyl)amide,
Sodium(R)-(tert-butylsulfonyl)(5-(2-(7-fluoro-2,3-dihydrobenzo[b][1,4]dioxin-5-yl)pyrrolidin-1-yl)pyrazolo[1,5-a]pyridine-3-carbonyl)amide;
(R)—N-(cyclopropylsulfonyl)-5-(2-(2,5-difluorophenyl)pyrrolidin-1-yl)pyrazolo[1,5-a]pyridine-3-carboxamide,
(R)—N-(cyclohexyl sulfonyl)-5-(2-(2, 5-difluorophenyl) pyrrolidin-1-yl) pyrazolo [1, 5-a] pyridine-3-carboxamide,
(R)—N-(cyclopentyl sulfonyl)-5-(2-(2, 5-difluorophenyl) pyrrolidin-1-yl) pyrazolo [1, 5-a] pyridine-3-carboxamide,
(R)—N-(cyclobutylsulfonyl)-5-(2-(2, 5-difluorophenyl) pyrrolidin-1-yl) pyrazolo [1, 5-a] pyridine-3-carboxamide,
(R)-5-(2-(2,5-difluorophenyl)pyrrolidin-1-yl)-N-((1-ethylcyclopropyl)sulfonyl) pyrazolo[1,5-a]pyridine-3-carboxamide,
(R)-5-(2-(2,5-difluorophenyl)pyrrolidin-1-yl)-N-((1-methylcyclopropyl)sulfonyl)pyrazolo [1,5-a]pyridine-3-carboxamide,
(R)-5-(2-(2,5-difluorophenyl)pyrrolidin-1-yl)-N-((1-(4-fluorobenzyl)cyclopropyl)sulfonyl) pyrazolo[1,5-a]pyridine-3-carboxamide,
(R)-5-(2-(2, 5-difluorophenyl) pyrrolidin-1-yl)-4-fluoro-N-(isopropylsulfonyl)pyrazolo [1, 5-a] pyridine-3-carboxamide,
Sodium(R)-(5-(2-(2,5-difluorophenyl)pyrrolidin-1-yl)pyrazolo[1,5-a]pyridine-3-carbonyl)((1-methylcyclopropyl) sulfonyl)amide;
(R)-5-(2-(2,5-difluorophenyl) pyrrolidin-1-yl)-N-((3,5-dimethylisoxazol-4-yl)sulfonyl) pyrazolo [1, 5-a] pyridine-3-carboxamide,
(R)-5-(2-(2,5-difluorophenyl) pyrrolidin-1-yl)-N-((1, 2-dimethyl-1H-imidazol-4-yl) sulfonyl) pyrazolo [1, 5-a] pyridine-3-carboxamide,
(R)-5-(2-(2,5-difluorophenyl) pyrrolidin-1-yl)-N-((1, 2-dimethyl-1H-imidazol-5-yl) sulfonyl) pyrazolo [1, 5-a] pyridine-3-carboxamide,
(R)-5-(2-(2,5-difluorophenyl) pyrrolidin-1-yl)-N-((1-methyl-1H-imidazol-4-yl) sulfonyl) pyrazolo [1, 5-a] pyridine-3-carboxamide,
(R)-5-(2-(2,5-difluorophenyl) pyrrolidin-1-yl)-N-((1-methyl-1H-pyrazol-5-yl) sulfonyl) pyrazolo [1, 5-a] pyridine-3-carboxamide,
(R)-5-(2-(2, 5-difluorophenyl) pyrrolidin-1-yl)-N-((2, 4-dimethylthiazol-5-yl) sulfonyl) pyrazolo [1, 5-a] pyridine-3-carboxamide,
(R)-5-(2-(2,5-difluorophenyl)pyrrolidin-1-yl)-N-((1-methyl-2-oxoindolin-5-yl)sulfonyl) pyrazolo [1, 5-a] pyridine-3-carboxamide,
(R)-5-(2-(2, 5-difluorophenyl) pyrrolidin-1-yl)-N-((6-(dimethylamino) pyridin-3-yl) sulfonyl) pyrazolo [1, 5-a] pyridine-3-carboxamide,
5-((R)-2-(2, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide,
(R)-5-(2-(2, 5-difluorophenyl) pyrrolidin-1-yl)-N-((6-methoxypyridin-3-yl) sulfonyl) pyrazolo [1, 5-a] pyridine-3-carboxamide,
(R)—N-((6-(1H-1, 2,4-triazol-1-yl)pyridin-3-yl)sulfonyl)-5-(2-(2,5-difluorophenyl) pyrrolidin-1-yl) pyrazolo [1, 5-a] pyridine-3-carboxamide,
(R)-5-(2-(2,5-difluorophenyl) pyrrolidin-1-yl)-N-((1-methyl-1H-pyrazol-4-yl) sulfonyl) pyrazolo [1, 5-a] pyridine-3-carboxamide,
(R)-5-(2-(2,5-difluorophenyl)pyrrolidin-1-yl)-N-(pyridin-3-ylsulfonyl)pyrazolo[1,5-a]pyridine-3-carboxamide,
(R)—N-((5-chlorothiophen-2-yl) sulfonyl)-5-(2-(2, 5-difluorophenyl) pyrrolidin-1-yl) pyrazolo [1, 5-a] pyridine-3-carboxamide,
(R)—N-((2,5-dichlorothiophen-3-yl) sulfonyl)-5-(2-(2, 5-difluorophenyl) pyrrolidin-1-yl) pyrazolo [1, 5-a] pyridine-3-carboxamide,
(R)-5-(2-(2,5-difluorophenyl)pyrrolidin-1-yl)-N-((2,3-dihydrobenzo[b][1,4]dioxin-6-yl)sulfonyl)pyrazolo[1,5-a]pyridine-3-carboxamide,
(R)—N-(benzo[d][1,3]dioxol-5-ylsulfonyl)-5-(2-(2,5-difluorophenyl)pyrrolidin-1-yl) pyrazolo[1,5-a]pyridine-3-carboxamide,
(R)—N-((6-(1H-1, 2, 4-triazol-1-yl) pyridin-3-yl) sulfonyl)-5-(2-(3, 5-difluorophenyl) pyrrolidin-1-yl) pyrazolo [1, 5-a] pyridine-3-carboxamide,
5-((R)-2-(3, 5-difluorophenyl) pyrrolidin-1-yl)-N-((6-((S)-3-hydroxypyrrolidin-1-yl) pyridin-3-yl) sulfonyl) pyrazolo [1, 5-a] pyridine-3-carboxamide;
(R)-5-(2-(2, 5-difluorophenyl) pyrrolidin-1-yl)-N-(piperidin-4-ylsulfonyl) pyrazolo [1, 5-a] pyridine-3-carboxamide,
(R)-5-(2-(2, 5-difluorophenyl) pyrrolidin-1-yl)-N-((tetrahydro-2H-pyran-4-yl) sulfonyl) pyrazolo [1, 5-a] pyridine-3-carboxamide,
5-((R)-2-(2, 5-difluorophenyl) pyrrolidin-1-yl)-N-((2-methyltetrahydrofuran-3-yl) sulfonyl) pyrazolo [1, 5-a] pyridine-3-carboxamide,
(R)-5-(2-(2,5-difluorophenyl)pyrrolidin-1-yl)-N-(morpholinosulfonyl) pyrazolo[1,5-a]pyridine-3-carboxamide,
(R)-5-(2-(2,5-difluorophenyl)pyrrolidin-1-yl)-N-(pyrrolidin-1-ylsulfonyl) pyrazolo[1,5-a]pyridine-3-carboxamide,
(R)-5-(2-(2,5-difluorophenyl)pyrrolidin-1-yl)-N-((4-methylpiperazin-1-yl) sulfonyl) pyrazolo [1,5-a]pyridine-3-carboxamide,
(R)-5-(2-(2,5-difluorophenyl)pyrrolidin-1-yl)-N-(piperidin-1-ylsulfonyl)pyrazolo[1,5-a]pyridine-3-carboxamide,
5-((R)-2-(2,5-difluorophenyl)pyrrolidin-1-yl)-N—(((S)-3-hydroxypyrrolidin-1-yl) sulfonyl) pyrazolo[1,5-a]pyridine-3-carboxamide;
(R)—N-(tert-butylsulfonyl)-5-(2-(5-fluoro-2-(2,2,2-trifluoroethoxy)phenyl)pyrrolidin-1-yl) pyrazolo[1,5-a]pyridine-3-carboxamide,
N-(tert-butylsulfonyl)-5-(2-(7-fluoro-2,3-dihydrobenzo[b][1,4]dioxin-5-y)pyrrolidin-1-yl)pyrazolo[1,5-a]pyridine-3-carboxamide,
N-(tert-butylsulfonyl)-5-(2-(7-fluoro-2,3-dihydrobenzo[b][1,4]dioxin-5-y)pyrrolidin-1-yl)pyrazolo[1,5-a]pyridine-3-carboxamide, N-(tert-butylsulfonyl)-5-((2R,4S)-2-(2, 5-difluorophenyl)-4-fluoropyrrolidin-1-yl)pyrazolo[1,5-a]pyridine-3-carboxamide, N-(tert-butylsulfonyl)-5-((2R,4R)-2-(2,5-difluorophenyl)-4-fluoropyrrolidin-1-yl)pyrazolo[1,5-a]pyridine-3-carboxamide, 5-((2R,4S)-2-(2,5-difluorophenyl)-4-fluoropyrrolidin-1-yl)-N-((1-methyl cyclopropyl) sulfonyl)pyrazolo[1,5-a]pyridine-3-carboxamide, 5-((2R,4S)-2-(2,5-difluorophenyl)-4-fluoropyrrolidin-1-yl)-N—(N,N-dimethylsulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, 5-((2R,4S)-2-(2,5-difluorophenyl)-4-fluoropyrrolidin-1-yl)-N—(N,N-dimethylsulfamoyl) pyrazolo[1,5-a]pyridine-3-carboxamide, 5-((2R,4S)-2-(2,5-difluorophenyl)-4-fluoropyrrolidin-1-yl)-N—(N-ethyl-N-methylsulfamoyl) pyrazolo[1,5-a]pyridine-3-carboxamide, N—(N-ethyl-N-methylsulfamoyl)-4-fluoro-5-((2R,4S)-4-fluoro-2-(3-fluorophenyl)pyrrolidin-1-yl)pyrazolo[1,5-a]pyridine-3-carboxamide, N-(tert-butylsulfonyl)-4-fluoro-5-((2R,4S)-4-fluoro-2-(3-fluorophenyl)pyrrolidin-1-yl)pyrazolo [1,5-a]pyridine-3-carboxamide, 4-fluoro-5-((2R,4S)-4-fluoro-2-(3-fluorophenyl)pyrrolidin-1-yl)-N-(isopropylsulfonyl) pyrazolo[1,5-a]pyridine-3-carboxamide, Sodium(4-fluoro-5-((2R,4S)-4-fluoro-2-(3-fluorophenyl)pyrrolidin-1-yl)pyrazolo[1,5-a]pyridine-3-carbonyl)(isopropylsulfonyl)amide, Sodium(5-((2R,4S)-2-(2,5-difluorophenyl)-4-fluoropyrrolidin-1-yl)pyrazolo[1,5-a]pyridine-3-carbonyl)((1-methylcyclopropyl)sulfonyl)amide, Sodium(tert-butylsulfonyl)(5-((2R)-2-(2,5-difluorophenyl)-4-fluoropyrrolidin-1-yl)pyrazolo[1,5-a]pyridine-3-carbonyl)amide, Sodium(5-((2R,4S)-2-(2,5-difluorophenyl)-4-fluoropyrrolidin-1-yl)pyrazolo[1,5-a]pyridine-3-carbonyl)(N,N-dimethylsulfonyl)amide, Sodium(tert-butylsulfonyl)(4-fluoro-5-((2R,4S)-4-fluoro-2-(3-fluorophenyl)pyrrolidin-1-yl)pyrazolo[1,5-a]pyridine-3-carbonyl)amide, Sodium (tert-butylsulfonyl)(5-(2-(2,5-difluorophenyl)-4,4-difluoropyrrolidin-1-yl) pyrazolo[1,5-a]pyridine-3-carbonyl)amide;

(R)-5-(2-(2,5-difluorophenyl) pyrrolidin-1-yl)-N—(N,N-dimethylsulfamoyl)pyrazolo[1,5-a] pyridine-3-carboxamide, (R)-5-(2-(2,5-difluorophenyl)pyrrolidin-1-yl)-N—(N-ethyl-N-methylsulfamoyl)pyrazolo [1,5-a]pyridine-3-carboxamide, (R)—N—(N-(cyclopropylmethyl)-N-methylsulfamoyl)-5-(2-(2,5-difluorophenyl) pyrrolidin-1-yl)pyrazolo[1,5-a]pyridine-3-carboxamide, (R)—N—(N,N-diethylsulfamoyl)-5-(2-(2,5-difluorophenyl)pyrrolidin-1-yl) pyrazolo[1,5-a]pyridine-3-carboxamide, (R)—N—(N,N-diethylsulfamoyl)-5-(2-(5-fluoro-2-methoxyphenyl)pyrrolidin-1-yl)pyrazolo[1,5-a]pyridine-3-carboxamide, (R)—N—(N,N-diethylsulfamoyl)-5-(2-(5-fluoro-2-(2-fluoroethoxy)phenyl)pyrrolidin-1-yl) pyrazolo[1,5-a]pyridine-3-carboxamide, (R)-5-(2-(3,5-difluoro-2-methoxyphenyl)pyrrolidin-1-yl)-N—(N-ethyl-N-methyl sulfamoyl)pyrazolo[1,5-a]pyridine-3-carboxamide, (R)—N—(N-ethyl-N-methylsulfamoyl)-5-(2-(5-fluoro-2-methoxyphenyl)pyrrolidin-1-yl)pyrazolo[1,5-a]pyridine-3-carboxamide, (R)—N—(N-ethyl-N-methylsulfamoyl)-5-(2-(5-fluoro-2-(2-fluoroethoxy)phenyl)pyrrolidin-1-yl)pyrazolo[1,5-a]pyridine-3-carboxamide, (R)-5-(2-(3,5-difluoro-2-(2-fluoroethoxy)phenyl)pyrrolidin-1-yl)-N—(N-ethyl-N-methylsulfamoyl)pyrazolo[1,5-a]pyridine-3-carboxamide, (R)-5-(2-(2,5-difluorophenyl)pyrrolidin-1-yl)-N-sulfamoylpyrazolo[1,5-a]pyridine-3-carboxamide, N—(N-ethyl-N-methylsulfamoyl)-5-((R)-2-(3-fluoro-5-(((S)-tetrahydrofuran-3-yl)oxy) phenyl)pyrrolidin-1-yl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N-ethyl-N-methylsulfamoyl)pyrazolo[1,5-a]pyridine-3-carboxamide, (R)-5-(2-(3,5-difluoro-2-((tetrahydro-2H-pyran-4-yl)oxy)phenyl)pyrrolidin-1-yl)-N—(N,N-dimethylsulfamoyl)pyrazolo[1,5-a]pyridine-3-carboxamide, N—(N-ethyl-N-methylsulfamoyl)-5-((R)-2-(3-fluoro-5-(((R)-tetrahydrofuran-3-yl)oxy)phenyl)pyrrolidin-1-yl)pyrazolo[1,5-a]pyridine-3-carboxamide, 4-fluoro-5-((2R,4S)-4-fluoro-2-(3-fluorophenyl)pyrrolidin-1-yl)-N-sulfamoylpyrazolo[1,5-a]pyridine-3-carboxamide, N—(N,N-dimethylsulfamoyl)-5-(2-(8-fluoro-3,4-dihydro-2H-benzo[b][1,4]dioxepin-6-yl)pyrrolidin-1-yl)pyrazolo[1,5-a]pyridine-3-carboxamide (Diastereomer-I), (R)-5-(2-(2,5-difluorophenyl)pyrrolidin-1-yl)-N—(N-isobutyl-N-methylsulfamoyl)pyrazolo[1,5-a]pyridine-3-carboxamide, (R)—N—(N-ethyl-N-methylsulfamoyl)-4-fluoro-5-(2-(3-fluorophenyl)pyrrolidin-1-yl)pyrazolo[1,5-a]pyridine-3-carboxamide, (R)—N—(N,N-dimethylsulfamoyl)-4-fluoro-5-(2-(3-fluorophenyl)pyrrolidin-1-yl)pyrazolo[1,5-a]pyridine-3-carboxamide, (R)—N—(N,N-dimethylsulfamoyl)-5-(2-(3-fluorophenyl)pyrrolidin-1-yl)pyrazolo[1,5-a]pyridine-3-carboxamide, (R)—N—(N-ethyl-N-methylsulfamoyl)-4-fluoro-5-(2-(5-fluoro-2-((tetrahydro-2H-pyran-4-yl)oxy)phenyl)pyrrolidin-1-yl)pyrazolo[1,5-a]pyridine-3-carboxamide, 5-((2R)-2-(3-((2,2-difluorocyclopropyl)methoxy)-5-fluorophenyl)pyrrolidin-1-yl)-N—(N-ethyl-N-methylsulfamoyl)pyrazolo[1,5-a]pyridine-3-carboxamide, (R)—N—(N,N-bis(cyclopropylmethyl)sulfamoyl)-5-(2-(2,5-difluorophenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, N—(N-ethyl-N-methylsulfamoyl)-5-((2R)-2-(5-fluoro-2-((tetrahydrofuran-3-yl)oxy)phenyl)pyrrolidin-1-yl)pyrazolo[1,5-a]pyridine-3-carboxamide, Sodium(R)—N—(N,N-dimethylsulfamoyl)(4-fluoro-5-(2-(3-fluorophenyl)pyrrolidin-1-yl)pyrazolo[1,5-a]pyridine-3-carbonyl)amide Sodium(N-ethyl-N-methylsulfamoyl)(5-((2R)-2-(5-fluoro-2-((tetrahydrofuran-3-yl)oxy) phenyl)pyrrolidin-1-yl) pyrazolo[1,5-a]pyridine-3-carbonyl)amide, Sodium (R)-(5-(2-(2,5-difluorophenyl) pyrrolidin-1-yl) pyrazolo[1,5-a]pyridine-3-carbonyl)(N,N-dimethylsulfamoyl)amide, N—(N-ethyl-N-methylsulfamoyl)-5-(2-(8-fluoro-3,4-dihydro-2H-benzo[b][1,4]dioxepin-6-yl)pyrrolidin-1-y)pyrazolo[1,5-a]pyridine-3-carboxamide (Diastereomer-I), N—(N-ethyl-N-methylsulfamoyl)-5-(2-(8-fluoro-3,4-dihydro-2H-benzo[b][1,4]dioxepin-6-yl)pyrrolidin-1-y)pyrazolo[1,5-a]pyridine-3-carboxamide (Diastereomer-II), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N,N-dimethylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-II), N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide (Diastereomer-I), N—(N-ethyl-N-methylsulfamoyl)-5-(2-(7-fluoro-2,3-dihydrobenzo[b][1,4]dioxin-5-y)pyrrolidin-1-yl)pyrazolo[1,5-a]pyridine-3-carboxamide (Diastereomer-II), N—(N,N-dimethylsulfamoyl)-5-(2-(8-fluoro-3,4-dihydro-2H-benzo[b][1,4]dioxepin-6-yl)pyrrolidin-1-y)pyrazolo[1,5-a]pyridine-3-carboxamide (Diastereomer-2), (R)-5-(2-(2,5-difluorophenyl)pyrrolidin-1-yl)-N—(N-(2-methoxyethyl)-N-methylsulfamoyl)pyrazolo[1,5-a]pyridine-3-carboxamide, (R)—N—(N-cyclopropyl-N-methylsulfamoyl)-5-(2-(2,5-difluorophenyl)pyrrolidin-1-yl)pyrazolo[1,5-a]pyridine-3-carboxamide, (R)—N—(N-ethyl-N-methylsulfamoyl)-5-(2-(5-fluoro-2-methylphenyl)pyrrolidin-1-yl)pyrazolo[1,5-a]pyridine-3-carboxamide, (R)—N—(N-ethyl-N-methylsulfamoyl)-5-(2-(7-fluoro-2,3-dihydrobenzo[b][1,4]dioxin-5-yl)pyrrolidin-1-yl)pyrazolo[1,5-a]pyridine-3-carboxamide, N-(tert-butylsulfonyl)-5-((2R,4S)-4-fluoro-2-(3-fluoro-5-((tetrahydro-2H-pyran-4-yl)oxy)phenyl)pyrrolidin-1-yl)pyrazolo[1,5-a]pyridine-3-carboxamide, N—(N-ethyl-N-methylsulfamoyl)-5-((2R,4S)-4-fluoro-2-(3-fluoro-5-((tetrahydro-2H-pyran-4-yl)oxy)phenyl)pyrrolidin-1-yl)pyrazolo[1,5-a]pyridine-3-carboxamide;

N-(tert-butylsulfonyl)-5-((2R,4S)-4-fluoro-2-(5-fluoro-2-((tetrahydro-2H-pyran-4-yl)oxy)phenyl)pyrrolidin-1-yl)pyrazolo[1,5-a]pyridine-3-carboxamide, N—(N-ethyl-N-methylsulfamoyl)-5-((2R,4S)-4-fluoro-2-(5-fluoro-2-((tetrahydro-2H-pyran-4-yl)oxy)phenyl)pyrrolidin-1-yl)pyrazolo[1,5-a]pyridine-3-carboxamide, 5-((2R,4S)-4-fluoro-2-(5-fluoro-2-((tetrahydro-2H-pyran-4-yl)oxy)phenyl)pyrrolidin-1-yl)-N-(isopropylsulfonyl)pyrazolo[1,5-a]pyridine-3-carboxamide, 5-((2R,4S)-2-(2-(cyclopropylmethoxy)-5-fluorophenyl)-4-fluoropyrrolidin-1-yl)-N—(N-ethyl-N-methylsulfamoyl)pyrazolo[1,5-a]pyridine-3-carboxamide, N-(tert-butylsulfonyl)-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide N—(N-ethyl-N-methylsulfamoyl)-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide, 5-((2R,4S)-2-(2-(cyclopropylmethoxy)-5-fluorophenyl)-4-fluoropyrrolidin-1-yl)-N—(N-ethyl-N-methylsulfamoyl)-4-fluoropyrazolo[1,5-a]pyridine-3-carboxamide, N-(tert-butylsulfonyl)-5-((2R,4S)-2-(2-(cyclopropylmethoxy)-5-fluorophenyl)-4-fluoropyrrolidin-1-yl)pyrazolo[1,5-a]pyridine-3-carboxamide, (R)-5-(2-(2,5-difluorophenyl)pyrrolidin-1-yl)-N—(N-ethyl sulfamoyl)pyrazolo[1,5-a]pyridine-3-carboxamide, (R)-5-(2-(2,5-difluorophenyl)pyrrolidin-1-yl)-N—(N-methyl sulfamoyl)pyrazolo[1,5-a]pyridine-3-carboxamide, (R)-5-(2-(2,5-difluorophenyl)pyrrolidin-1-yl)-N—(N-(2-fluoroethyl)-N-methylsulfamoyl)pyrazolo[1,5-a]pyridine-3-carboxamide, (R)-5-(2-(2,5-difluorophenyl)pyrrolidin-1-yl)-N—(N-(2-hydroxyethyl)-N-methylsulfamoyl)pyrazolo[1,5-a]pyridine-3-carboxamide, (R)—N-(azetidin-1-ylsulfonyl)-5-(2-(2,5-difluorophenyl)pyrrolidin-1-yl)pyrazolo[1,5-a]pyridine-3-carboxamide, N-(tert-butylsulfonyl)-5-((2R,4S)-4-fluoro-2-(7-fluoro-2,3-dihydrobenzo[b][1,4]dioxin-5-yl)pyrrolidin-1-yl)pyrazolo[1,5-a]pyridine-3-carboxamide, (R)—N—(N-(2-cyanoethyl)-N-methylsulfamoyl)-5-(2-(2,5-difluorophenyl) pyrrolidin-1-yl)pyrazolo[1,5-a]pyridine-3-carboxamide, N-(tert-butylsulfonyl)-4-fluoro-5-((2R,4S)-4-fluoro-2-(7-fluoro-2,3-dihydrobenzo[b][1,4]dioxin-5-yl)pyrrolidin-1-yl)pyrazolo[1,5-a]pyridine-3-carboxamide, N—(N,N-dimethylsulfamoyl)-4-fluoro-5-((2R,4S)-4-fluoro-2-(3-fluorophenyl)pyrrolidin-1-yl)pyrazolo[1,5-a]pyridine-3-carboxamide, N—(N-ethyl-N-methylsulfamoyl)-5-((2R)-2-(7-fluoro-3-(fluoromethyl)-2,3-dihydrobenzo[b][1,4]dioxin-5-yl)pyrrolidin-1-yl)pyrazolo[1,5-a]pyridine-3-carboxamide, (R)—N—(N-ethyl-N-methylsulfamoyl)-5-(2-(3-fluorophenyl)pyrrolidin-1-yl)pyrazolo[1,5-a]pyridine-3-carboxamide, 5-((2R,4S)-4-fluoro-2-(3-fluoro-5-((tetrahydro-2H-pyran-4-yl)oxy)phenyl)pyrrolidin-1-yl)-N-(isopropylsulfonyl)pyrazolo[1,5-a]pyridine-3-carboxamide, 5-((2R,4S)-2-(3-(cyclopropylmethoxy)-5-fluorophenyl)-4-fluoropyrrolidin-1-yl)-N—(N-ethyl-N-methylsulfamoyl)pyrazolo[1,5-a]pyridine-3-carboxamide, N-(tert-butylsulfonyl)-5-((2R,4S)-2-(2-cyclopropoxy-5-fluorophenyl)-4-fluoropyrrolidin-1-yl)pyrazolo[1,5-a]pyridine-3-carboxamide, 5-((2R,4S)-2-(2-cyclopropoxy-5-fluorophenyl)-4-fluoropyrrolidin-1-yl)-N—(N-ethyl-N-methylsulfamoyl)pyrazolo[1,5-a]pyridine-3-carboxamide, N—(N-ethyl-N-methylsulfamoyl)-4-fluoro-5-((2R,4S)-4-fluoro-2-(5-fluoro-2-((tetrahydrofuran-3-yl)oxy)phenyl)pyrrolidin-1-yl)pyrazolo[1,5-a]pyridine-3-carboxamide, 5-((2R,4S)-2-(2-cyclopropoxy-5-fluorophenyl)-4-fluoropyrrolidin-1-yl)-N—(N-ethyl-N-methylsulfamoyl)-4-fluoropyrazolo[1,5-a]pyridine-3-carboxamide, (R)—N—(N-ethyl-N-methylsulfamoyl)-5-(2-(8-fluoro-2,3-dihydrobenzo[b][1,4]dioxin-6-yl)pyrrolidin-1-yl)pyrazolo[1,5-a]pyridine-3-carboxamide, (R)-5-(2-(8-fluoro-2,3-dihydrobenzo[b][1,4]dioxin-6-yl)pyrrolidin-1-yl)-N-(isopropylsulfonyl)pyrazolo[1,5-a]pyridine-3-carboxamide, N-(tert-butylsulfonyl)-5-(2-(8-fluoro-2,3-dihydrobenzo[b][1,4]dioxin-6-yl)pyrrolidin-1-yl)pyrazolo[1,5-a]pyridine-3-carboxamide,
N—(N-ethyl-N-methylsulfamoyl)-5-(2-(9-fluoro-3,4-dihydro-2H-benzo[b][1,4]dioxepin-7-yl)pyrrolidin-1-yl)pyrazolo[1,5-a]pyridine-3-carboxamide,
N—(N,N-dimethylsulfamoyl)-5-(2-(8-fluoro-2,3-dihydrobenzo[b][1,4]dioxin-6-yl)pyrrolidin-1-yl)pyrazolo[1,5-a]pyridine-3-carboxamide,
(R)—N—(N,N-dimethylsulfamoyl)-5-(2-(9-fluoro-3,4-dihydro-2H-benzo[b][1,4]dioxepin-7-yl)pyrrolidin-1-yl)pyrazolo[1,5-a]pyridine-3-carboxamide,
N-(tert-butylsulfonyl)-5-((2R,4S)-4-fluoro-2-(6-fluorobenzo[d][1,3]dioxol-4-yl)pyrrolidin-1-yl)pyrazolo[1,5-a]pyridine-3-carboxamide,
N—(N-ethyl-N-methylsulfamoyl)-5-((2R,4S)-4-fluoro-2-(6-fluorobenzo[d][1,3]dioxol-4-yl)pyrrolidin-1-yl)pyrazolo[1,5-a]pyridine-3-carboxamide,
(R)-5-(2-(2,5-difluorophenyl)pyrrolidin-1-yl)-N—(N-((1-(hydroxymethyl)cyclo butyl)methyl)-N-methylsulfamoyl)pyrazolo[1,5-a]pyridine-3-carboxamide,
(R)—N—(N-ethyl-N-methylsulfamoyl)-5-(2-(5-fluoro-2-((4-methyltetrahydro-2H-pyran-4-yl)oxy)phenyl)pyrrolidin-1-yl)pyrazolo[1,5-a]pyridine-3-carboxamide,
(R)—N-(tert-butylsulfonyl)-5-(2-(5-fluoro-2-((4-methyltetrahydro-2H-pyran-4-yl)oxy)phenyl)pyrrolidin-1-yl)pyrazolo[1,5-a]pyridine-3-carboxamide,
(R)-5-(2-(5-fluoro-2-((4-methyltetrahydro-2H-pyran-4-yl)oxy)phenyl)pyrrolidin-1-yl)-N-(isopropylsulfonyl)pyrazolo[1,5-a]pyridine-3-carboxamide,
N-(tert-butylsulfonyl)-4-fluoro-5-((2R,4S)-4-fluoro-2-(6-fluorobenzo[d][1,3]dioxol-4-yl)pyrrolidin-1-yl)pyrazolo[1,5-a]pyridine-3-carboxamide,
N-(tert-butylsulfonyl)-5-((2R,4S)-4-fluoro-2-(6-fluorobenzo[d][1,3]dioxol-4-yl)pyrrolidin-1-yl)pyrazolo[1,5-a]pyridine-3-carboxamide,
N—(N-ethyl-N-methylsulfamoyl)-5-((2R,4S)-4-fluoro-2-(6-fluorobenzo[d][1,3]dioxol-4-yl)pyrrolidin-1-yl)pyrazolo[1,5-a]pyridine-3-carboxamide,
N-(azetidin-1-ylsulfonyl)-4-fluoro-5-((2R,4S)-4-fluoro-2-(3-fluorophenyl)pyrrolidin-1-yl)pyrazolo[1,5-a]pyridine-3-carboxamide,
4-fluoro-5-((2R,4S)-4-fluoro-2-(3-fluorophenyl)pyrrolidin-1-yl)-N—(N-isobutyl-N-methylsulfamoyl)pyrazolo[1,5-a]pyridine-3-carboxamide,
N-(tert-butylsulfonyl)-5-((2R,4S)-2-(2,5-difluorophenyl)-4-fluoropyrrolidin-1-yl)-4-fluoropyrazolo[1,5-a]pyridine-3-carboxamide,
5-((2R,4S)-2-(2,5-difluorophenyl)-4-fluoropyrrolidin-1-yl)-4-fluoro-N-(isopropylsulfonyl)pyrazolo[1,5-a]pyridine-3-carboxamide,
5-((2R,4S)-2-(2,5-difluorophenyl)-4-fluoropyrrolidin-1-yl)-N—(N-ethyl-N-methylsulfamoyl)-4-fluoropyrazolo[1,5-a]pyridine-3-carboxamide,
5-((2R,4S)-2-(2,5-difluorophenyl)-4-fluoropyrrolidin-1-yl)-N—(N,N-dimethylsulfamoyl)-4-fluoropyrazolo[1,5-a]pyridine-3-carboxamide,
N-(azetidin-1-ylsulfonyl)-5-((2R,4S)-2-(2, 5-difluorophenyl)-4-fluoropyrrolidin-1-yl)-4-fluoropyrazolo[1,5-a]pyridine-3-carboxamide,
5-((2R,4S)-2-(2,5-difluorophenyl)-4-fluoropyrrolidin-1-yl)-4-fluoro-N—(N-isobutyl-N-methylsulfamoyl)pyrazolo[1,5-a]pyridine-3-carboxamide, or
5-((2R,4S)-2-(2,5-difluorophenyl)-4-fluoropyrrolidin-1-yl)-4-fluoro-N-sulfamoylpyrazolo[1,5-a]pyridine-3-carboxamide, or a pharmaceutically acceptable salt thereof, a pharmaceutically acceptable solvate thereof or a stereoisomer thereof.

19. The method of claim 18, wherein the compound having formula

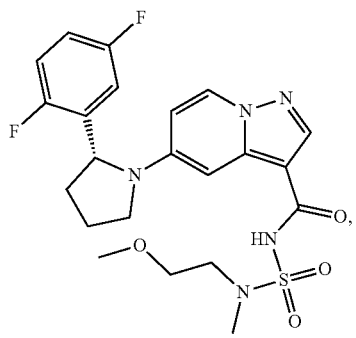

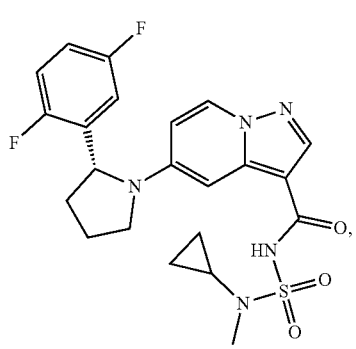

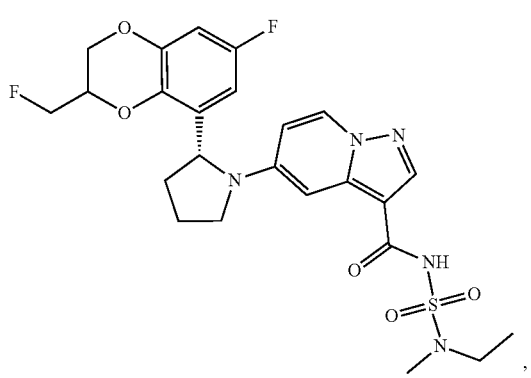

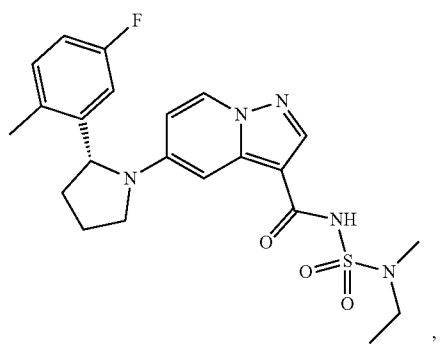

287
-continued
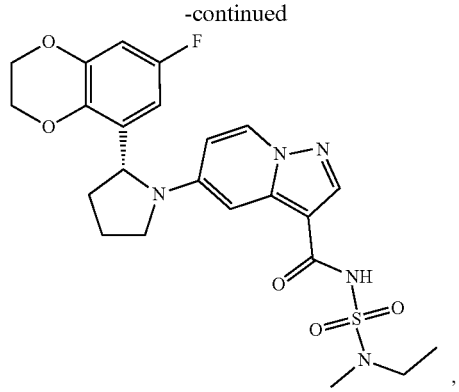
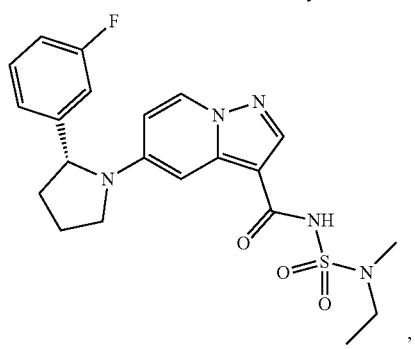
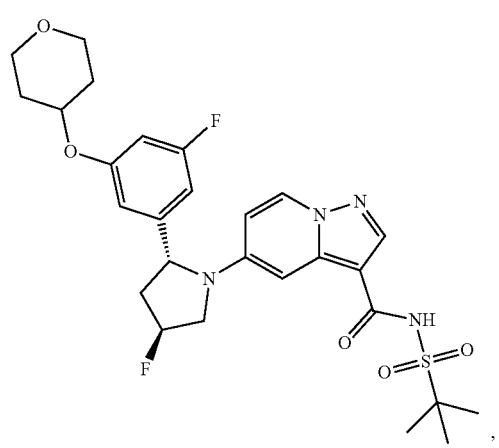
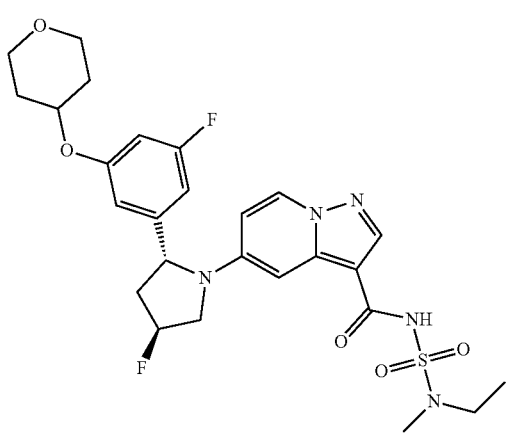
288
-continued
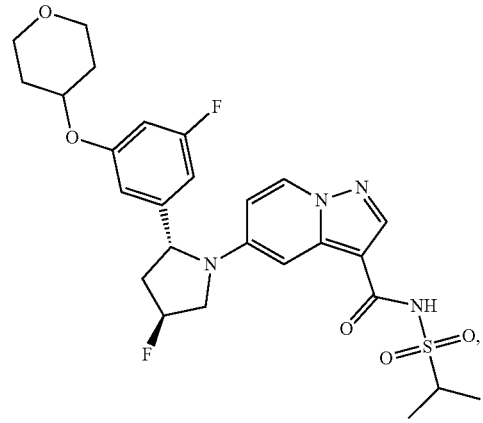
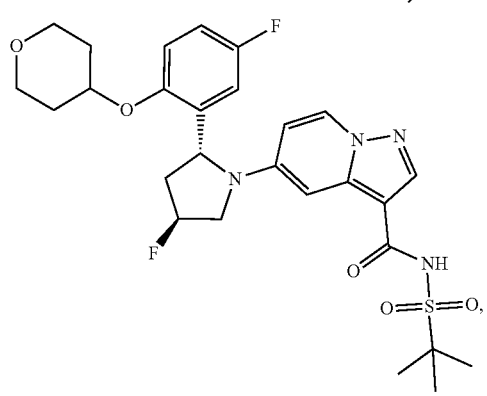
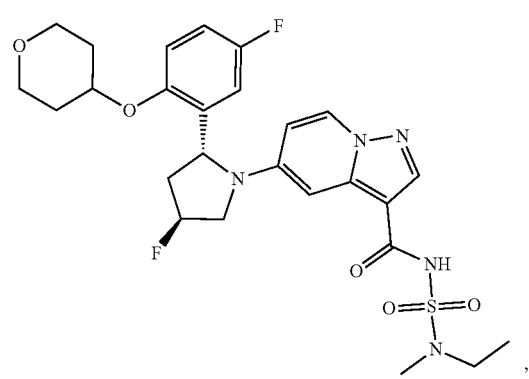
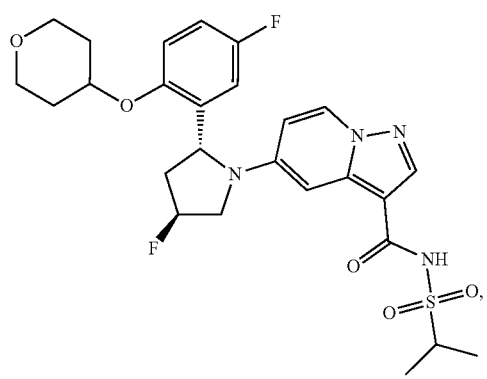

289
-continued
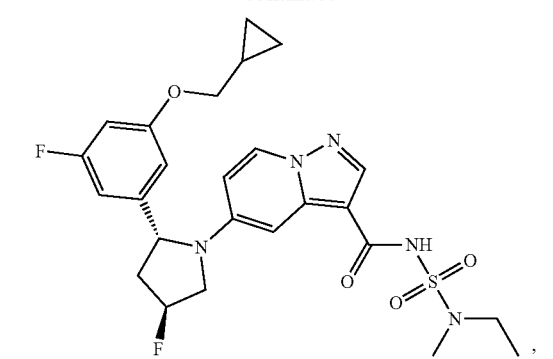
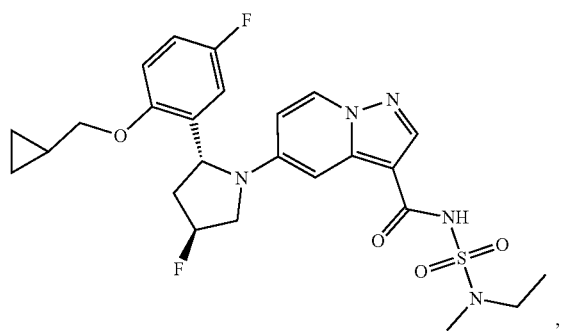
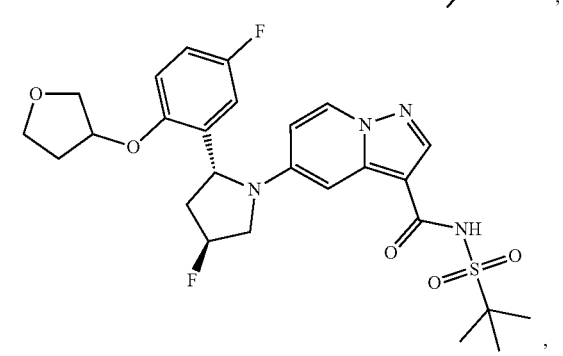
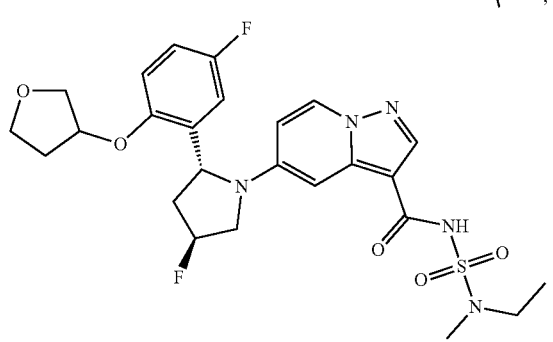
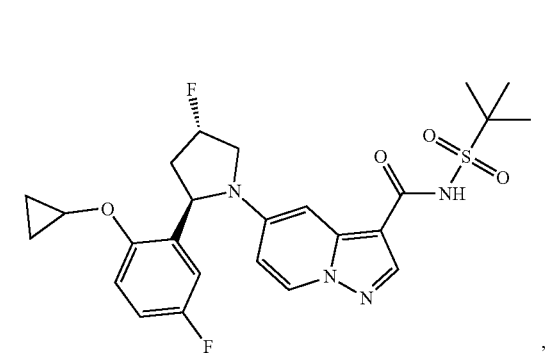
290
-continued
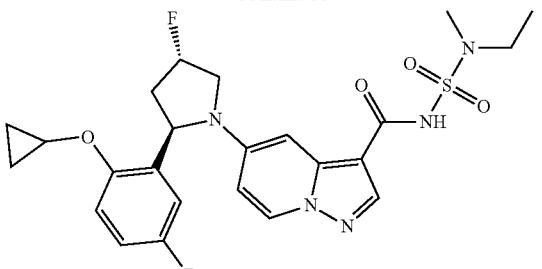
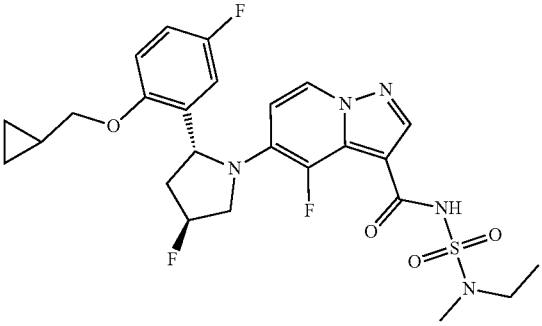
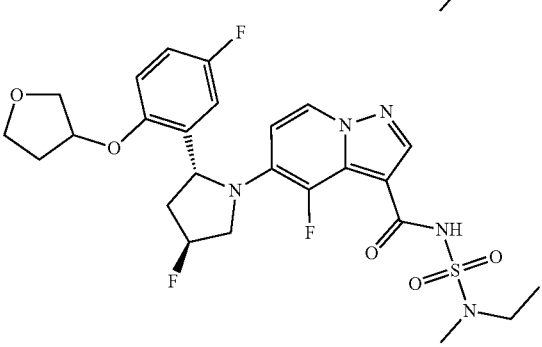
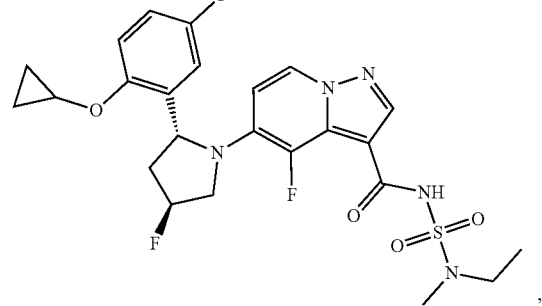
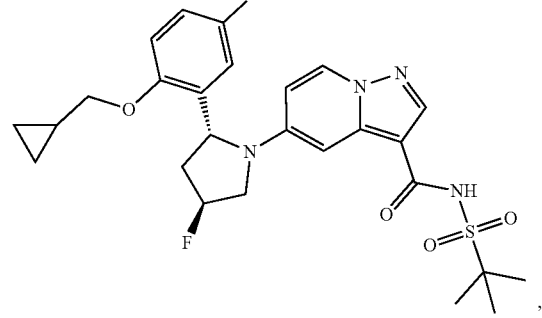

291
-continued
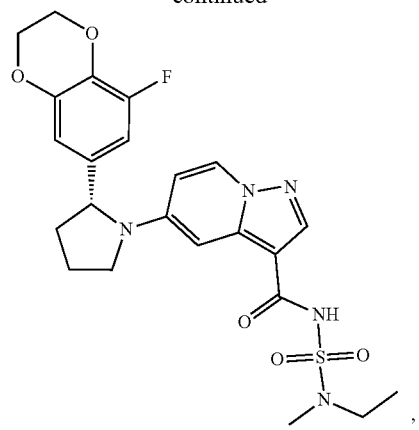
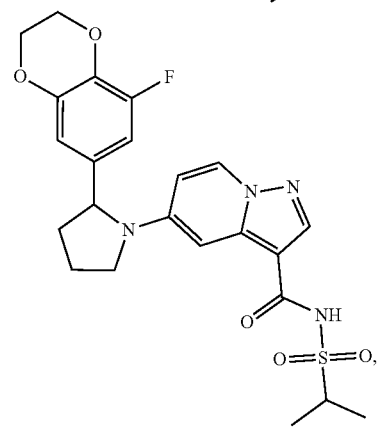
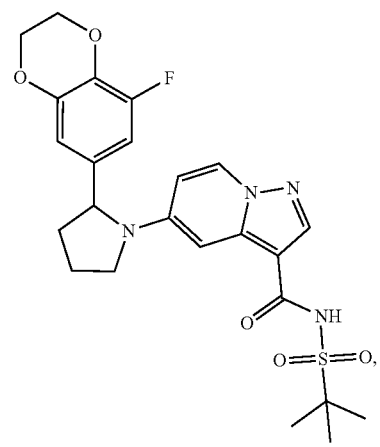
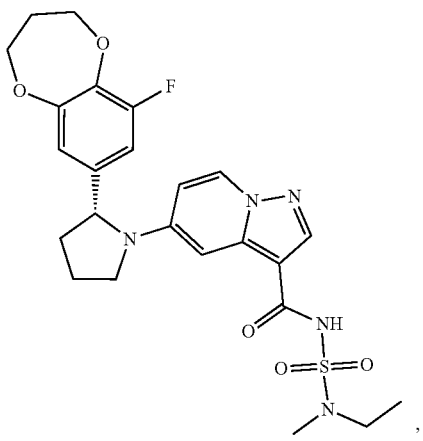
292
-continued
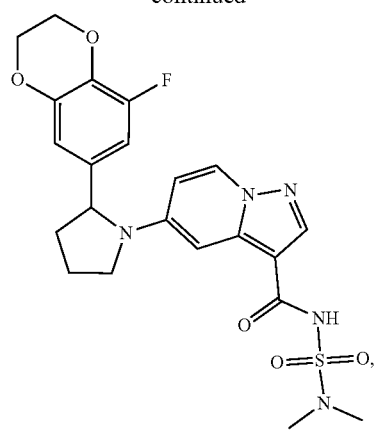
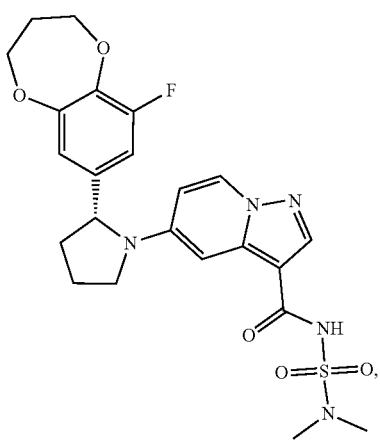
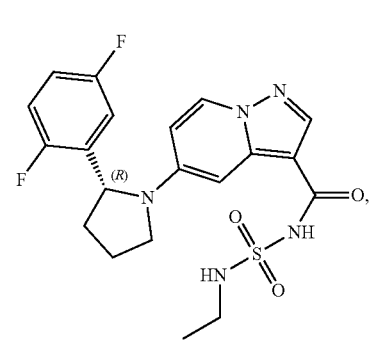
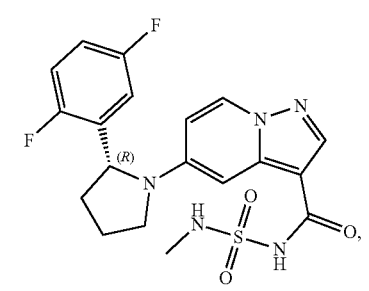

293
-continued
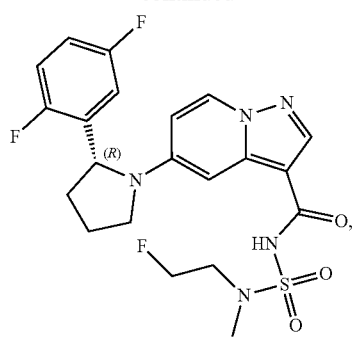
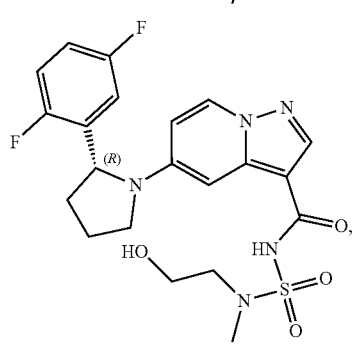
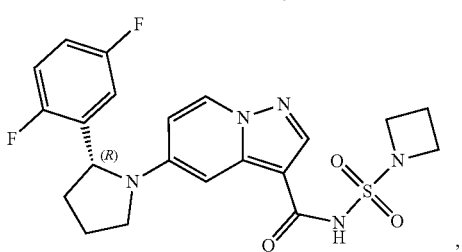
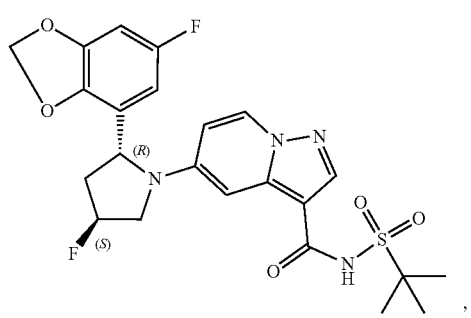
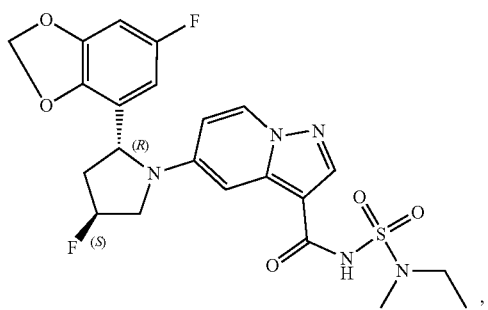
294
-continued
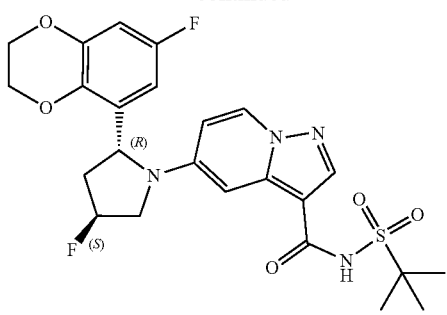
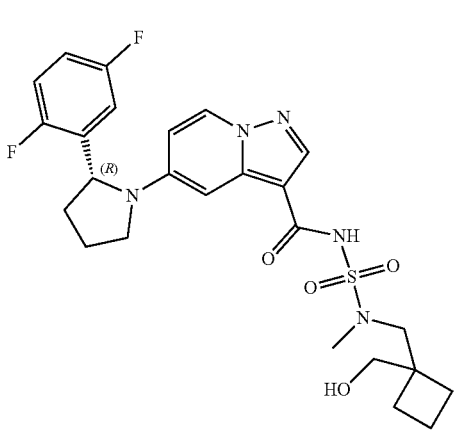
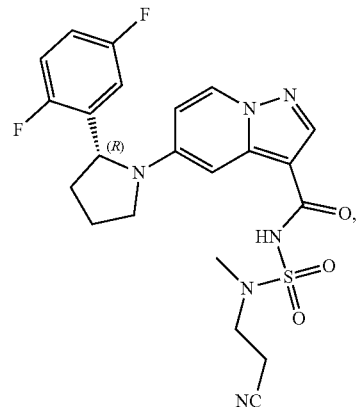
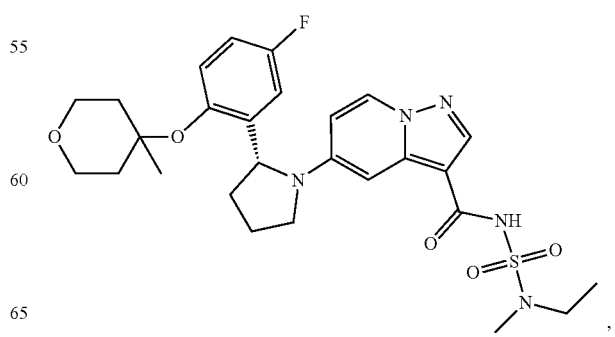

-continued
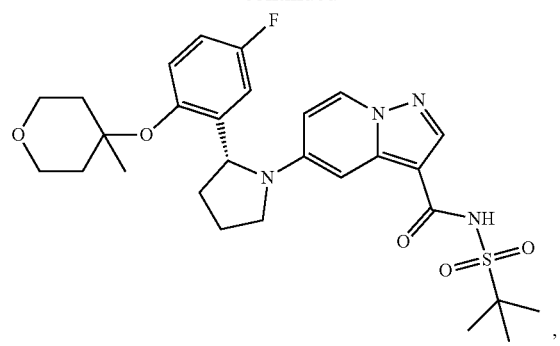
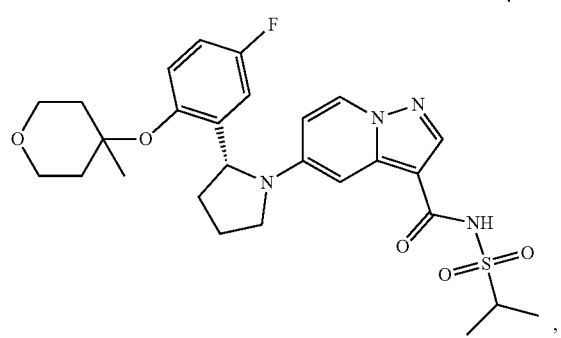
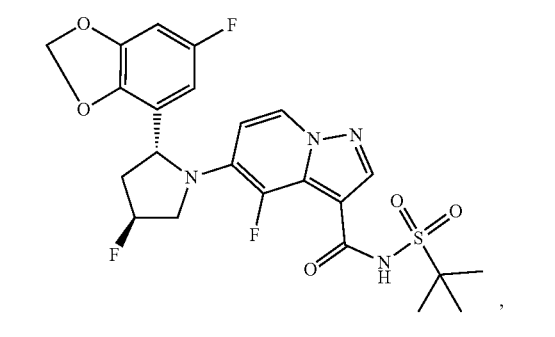
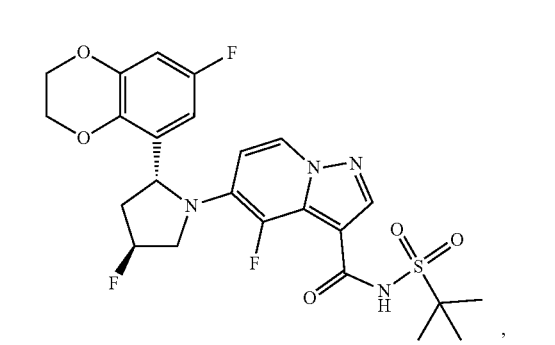
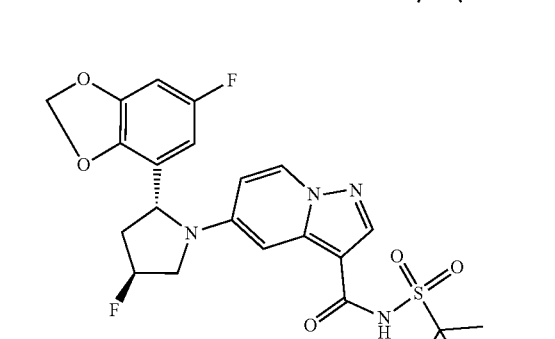
-continued
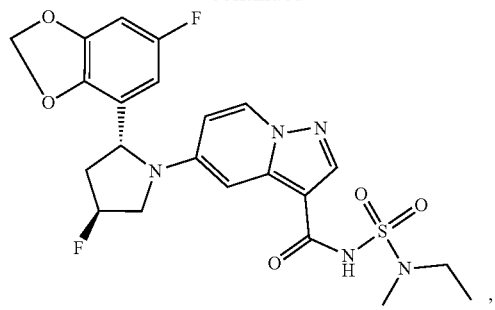
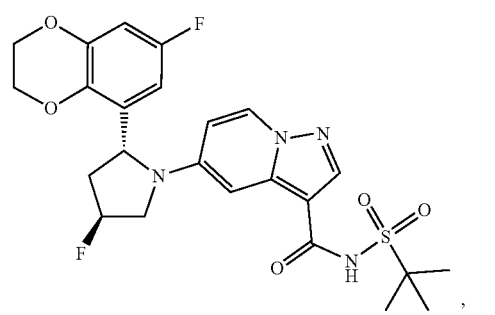
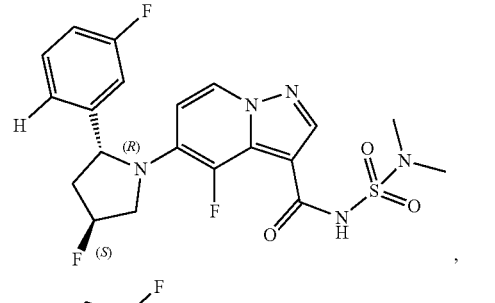
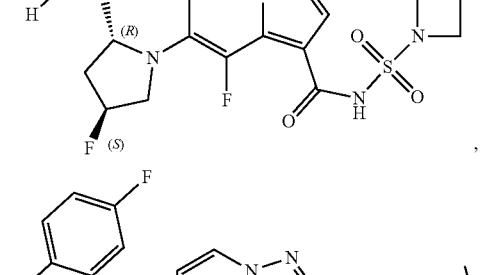
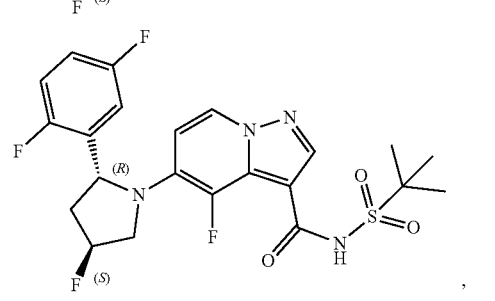

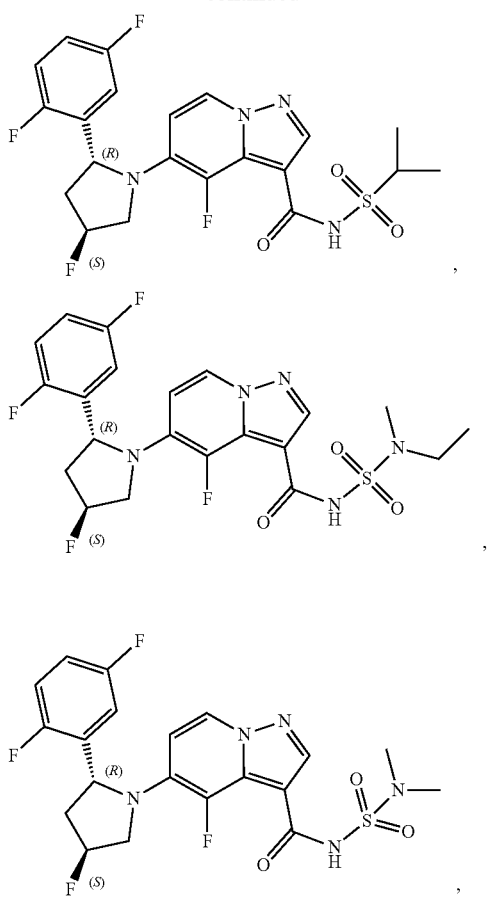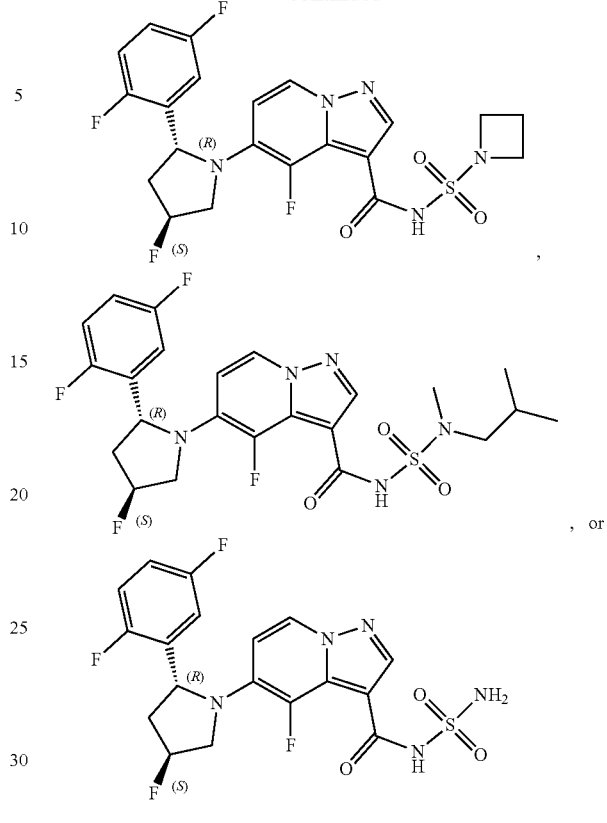
or a pharmaceutically acceptable salt thereof, or a pharmaceutically acceptable solvate thereof or a stereoisomer thereof.
* * * * *